(12) United States Patent
Freskgard et al.

(10) Patent No.: US 9,109,248 B2
(45) Date of Patent: *Aug. 18, 2015

(54) METHOD FOR THE SYNTHESIS OF A BIFUNCTIONAL COMPLEX

(75) Inventors: Per-Ola Freskgard, Norrköping (SE); Thomas Franch, Copenhagen (DK); Alex Haahr Gouliaev, Veksoe Sjaelland (DK); Mikkel Dybro Lundorf, Copenhangen (DK); Jakob Felding, Charlottenlund (DK); Eva Kampmann Olsen, Herlev (DK); Anette Holtmann, Ballerup (DK); Soeren Nyboe Jakobsen, Frederiksberg (DK); Christian Klarner Sams, Vaerloese (DK); Sanne Schroeder Glad, Ballerup (DK); Kim Birkebaek Jensen, Roedovre (DK); Henrik Pedersen, Bagsvaerd (DK)

(73) Assignee: Nuevolution A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/455,223

(22) Filed: Apr. 25, 2012

(65) Prior Publication Data

US 2013/0040823 A1   Feb. 14, 2013

Related U.S. Application Data

(63) Continuation of application No. 10/525,817, filed as application No. PCT/DK03/00739 on Oct. 30, 2003, now Pat. No. 8,206,901.

(60) Provisional application No. 60/486,199, filed on Jul. 11, 2003, provisional application No. 60/434,425, filed on Dec. 19, 2002, provisional application No. 60/422,167, filed on Oct. 30, 2002.

(30) Foreign Application Priority Data

Oct. 30, 2002 (DK) .................. 2002 01652
Dec. 19, 2002 (DK) .................. 2002 01955
Jul. 11, 2003  (DK) .................. 2003 01064

(51) Int. Cl.
  *C12Q 1/68* (2006.01)
  *C12N 15/10* (2006.01)

(52) U.S. Cl.
  CPC .......... *C12Q 1/6806* (2013.01); *C12N 15/1068* (2013.01); *C12Q 2521/101* (2013.01); *C12Q 2521/501* (2013.01)

(58) Field of Classification Search
  CPC .......... C12Q 1/6806; C12Q 2521/501; C12N 15/1068
  See application file for complete search history.

(56) References Cited

U.S. PATENT DOCUMENTS

| | | |
|---|---|---|
| 4,822,731 A | 4/1989 | Watson et al. |
| 5,047,519 A | 9/1991 | Hobbs, Jr. et al. |
| 5,432,272 A | 7/1995 | Benner |
| 5,449,613 A | 9/1995 | Dordick et al. |
| 5,451,503 A | 9/1995 | Hogan et al. |
| 5,473,060 A | 12/1995 | Gryaznov et al. |
| 5,474,796 A | 12/1995 | Brennan |
| 5,476,930 A | 12/1995 | Letsinger et al. |
| 5,503,805 A | 4/1996 | Sugerman et al. |
| 5,571,677 A | 11/1996 | Gryaznov |
| 5,571,903 A | 11/1996 | Gryaznov |
| 5,573,905 A | 11/1996 | Lerner et al. |
| 5,604,097 A | 2/1997 | Brenner |
| 5,635,400 A | 6/1997 | Brenner |
| 5,639,603 A | 6/1997 | Dower et al. |
| 5,643,722 A * | 7/1997 | Rothschild et al. .......... 435/6.13 |
| 5,654,413 A | 8/1997 | Brenner |
| 5,656,739 A | 8/1997 | Cubicciotti |
| 5,663,046 A | 9/1997 | Baldwin et al. |
| 5,665,975 A | 9/1997 | Kedar et al. |
| 5,681,943 A | 10/1997 | Letsinger et al. |
| 5,684,169 A | 11/1997 | Hamada et al. |
| 5,686,243 A | 11/1997 | Royer et al. |
| 5,708,153 A | 1/1998 | Dower et al. |
| 5,723,320 A | 3/1998 | Dehlinger |
| 5,723,598 A | 3/1998 | Lerner et al. |
| 5,739,386 A | 4/1998 | Holmes et al. |
| 5,741,643 A | 4/1998 | Gryaznov et al. |
| 5,763,175 A | 6/1998 | Brenner |
| 5,763,263 A | 6/1998 | Dehlinger |
| 5,770,358 A | 6/1998 | Dower et al. |
| 5,770,455 A | 6/1998 | Cargill et al. |
| 5,780,613 A | 7/1998 | Letsinger et al. |
| 5,789,162 A | 8/1998 | Dower et al. |
| 5,789,172 A | 8/1998 | Still et al. |

(Continued)

FOREIGN PATENT DOCUMENTS

| | | |
|---|---|---|
| DE | 196 46 372 | 6/1997 |
| DE | 196 42 751 | 4/1998 |

(Continued)

OTHER PUBLICATIONS

J. d'Angelo et al. Pathol. Biol. 2001; 49: 237-246.*

(Continued)

*Primary Examiner* — Angela M Bertagna
(74) *Attorney, Agent, or Firm* — Merchant & Gould P.C.

(57) ABSTRACT

Disclosed is a method for obtaining a bifunctional complex comprising a display molecule part and a coding part, wherein a nascent bifuntional complex comprising a chemical reaction site and a priming site for enzymatic addition of a tag is reacted at the chemical reaction site with one or more reactants, and provided with respective tag(s) identifying the reactant(s) at the priming site is using one or more enzymes.

141 Claims, 47 Drawing Sheets

(56) References Cited

U.S. PATENT DOCUMENTS

| | | |
|---|---|---|
| 5,795,976 A | 8/1998 | Oefner et al. |
| 5,804,563 A | 9/1998 | Still et al. |
| 5,817,795 A | 10/1998 | Gryaznov et al. |
| 5,824,471 A | 10/1998 | Mashal et al. |
| 5,830,658 A | 11/1998 | Gryaznov et al. |
| 5,840,485 A | 11/1998 | Lebl et al. |
| 5,843,650 A | 12/1998 | Segev |
| 5,843,701 A | 12/1998 | Gold et al. |
| 5,846,719 A | 12/1998 | Brenner et al. |
| 5,880,972 A | 3/1999 | Horlbeck |
| 5,942,609 A | 8/1999 | Hunkapiller |
| 5,948,648 A | 9/1999 | Khan et al. |
| 6,001,579 A | 12/1999 | Still et al. |
| 6,056,926 A | 5/2000 | Sugarman et al. |
| 6,060,596 A | 5/2000 | Lerner et al. |
| 6,090,912 A | 7/2000 | Lebl et al. |
| 6,096,875 A | 8/2000 | Khan et al. |
| 6,132,970 A | 10/2000 | Stemmer |
| 6,140,489 A | 10/2000 | Brenner |
| 6,140,493 A | 10/2000 | Dower et al. |
| 6,143,497 A | 11/2000 | Dower et al. |
| 6,143,503 A | 11/2000 | Baskerville et al. |
| 6,150,516 A | 11/2000 | Brenner et al. |
| 6,165,717 A | 12/2000 | Dower et al. |
| 6,165,778 A | 12/2000 | Kedar et al. |
| 6,172,214 B1 | 1/2001 | Brenner |
| 6,194,550 B1 | 2/2001 | Gold et al. |
| 6,197,555 B1 | 3/2001 | Khan et al. |
| 6,207,446 B1 | 3/2001 | Szostak et al. |
| 6,210,900 B1 | 4/2001 | Yamashita et al. |
| 6,232,066 B1 | 5/2001 | Felder et al. |
| 6,235,475 B1 | 5/2001 | Brenner et al. |
| 6,235,889 B1 | 5/2001 | Ulanovsky |
| 6,248,568 B1 | 6/2001 | Khan et al. |
| 6,274,385 B1 | 8/2001 | Hochlowski et al. |
| 6,287,765 B1 | 9/2001 | Cubicciotti et al. |
| 6,297,053 B1 | 10/2001 | Stemmer |
| 6,306,587 B1 | 10/2001 | Royer et al. |
| 6,352,828 B1 | 3/2002 | Brenner |
| 6,416,949 B1 | 7/2002 | Dower et al. |
| 6,429,300 B1 | 8/2002 | Kurz et al. |
| 6,479,264 B1 | 11/2002 | Louwrier |
| 6,503,759 B1 | 1/2003 | Still et al. |
| 6,514,736 B1 | 2/2003 | Erlich et al. |
| 6,537,776 B1 | 3/2003 | Short |
| 6,593,088 B1 | 7/2003 | Saito et al. |
| 6,613,508 B1 | 9/2003 | Ness et al. |
| 6,620,584 B1 | 9/2003 | Chee et al. |
| 6,620,587 B1 | 9/2003 | Taussig et al. |
| 6,780,981 B1 | 8/2004 | Southern et al. |
| 6,936,477 B2 | 8/2005 | Still et al. |
| 7,070,928 B2 | 7/2006 | Liu et al. |
| 7,223,545 B2 | 5/2007 | Liu et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,557,068 B2 | 7/2009 | Liu et al. |
| 7,704,925 B2 | 4/2010 | Gouliaev et al. |
| 7,727,713 B2 | 6/2010 | Pedersen et al. |
| 7,771,935 B2 | 8/2010 | Liu et al. |
| 7,915,201 B2 | 3/2011 | Franch et al. |
| 7,998,904 B2 | 8/2011 | Liu et al. |
| 8,206,901 B2 * | 6/2012 | Freskgard et al. ............ 435/6.1 |
| 2002/0048760 A1 | 4/2002 | Drmanac et al. |
| 2002/0055125 A1 | 5/2002 | Charych et al. |
| 2002/0072887 A1 | 6/2002 | Szalma et al. |
| 2002/0081714 A1 | 6/2002 | Jain et al. |
| 2002/0115068 A1 | 8/2002 | Tomlinson et al. |
| 2002/0127598 A1 | 9/2002 | Zhou et al. |
| 2002/0142335 A1 | 10/2002 | Strittmatter et al. |
| 2003/0004122 A1 | 1/2003 | Beigelman et al. |
| 2003/0050453 A1 | 3/2003 | Sorge |
| 2003/0113738 A1 | 6/2003 | Liu et al. |
| 2003/0182068 A1 | 9/2003 | Battersby et al. |
| 2003/0186233 A1 | 10/2003 | Chesnut et al. |
| 2004/0049008 A1 | 3/2004 | Pedersen et al. |
| 2004/0110213 A1 | 6/2004 | Namsaraev |
| 2004/0161741 A1 | 8/2004 | Rabani et al. |
| 2004/0185484 A1 | 9/2004 | Costa et al. |
| 2004/0191812 A1 | 9/2004 | Davydova et al. |
| 2004/0197845 A1 | 10/2004 | Hassibi et al. |
| 2004/0209282 A1 | 10/2004 | Ault-Riche et al. |
| 2005/0025766 A1 | 2/2005 | Liu et al. |
| 2005/0042669 A1 | 2/2005 | Liu et al. |
| 2005/0130173 A1 | 6/2005 | Leamon et al. |
| 2005/0142583 A1 | 6/2005 | Liu et al. |
| 2005/0158765 A1 | 7/2005 | Morgan et al. |
| 2005/0170376 A1 | 8/2005 | Liu et al. |
| 2006/0099592 A1 | 5/2006 | Freskgard et al. |
| 2006/0121470 A1 | 6/2006 | Pedersen |
| 2006/0234231 A1 | 10/2006 | Freskgard et al. |
| 2006/0246450 A1 | 11/2006 | Franch et al. |
| 2006/0269920 A1 | 11/2006 | Freskgard et al. |
| 2006/0292603 A1 | 12/2006 | Gouliaev et al. |
| 2007/0026397 A1 | 2/2007 | Freskgard et al. |
| 2007/0042401 A1 | 2/2007 | Morgan et al. |
| 2007/0224607 A1 | 9/2007 | Morgan et al. |
| 2008/0193983 A1 | 8/2008 | Gouliaev et al. |
| 2008/0305957 A1 | 12/2008 | Thisted et al. |
| 2009/0035824 A1 | 2/2009 | Liu et al. |
| 2009/0143232 A1 | 6/2009 | Pedersen et al. |
| 2009/0149347 A1 | 6/2009 | Liu et al. |
| 2009/0239211 A1 | 9/2009 | Freskgard et al. |
| 2009/0264300 A1 | 10/2009 | Franch et al. |
| 2010/0016177 A1 | 1/2010 | Pedersen et al. |
| 2011/0230419 A1 | 9/2011 | Lundorf et al. |
| 2012/0028812 A1 | 2/2012 | Freskgard et al. |

FOREIGN PATENT DOCUMENTS

| | | |
|---|---|---|
| EP | 0324616 | 7/1989 |
| EP | 0542770 | 5/1993 |
| EP | 0604552 | 2/1997 |
| EP | 0766826 | 4/1997 |
| EP | 0773227 | 5/1997 |
| EP | 0778280 | 6/1997 |
| EP | 0879219 | 11/1998 |
| EP | 0917494 | 5/1999 |
| EP | 0962527 | 12/1999 |
| EP | 0643778 | 5/2000 |
| EP | 0776330 | 2/2003 |
| EP | 1324045 | 7/2003 |
| EP | 0695305 | 8/2003 |
| EP | 1402024 | 3/2004 |
| EP | 1483585 | 12/2004 |
| EP | 1514938 | 3/2005 |
| EP | 1533385 | 5/2005 |
| EP | 1828381 | 9/2007 |
| EP | 1832567 | 9/2007 |
| EP | 2305808 | 4/2011 |
| JP | 05292967 | 11/1993 |
| JP | 08000268 | 1/1996 |
| WO | WO 90/05785 | 5/1990 |
| WO | WO 91/05058 | 4/1991 |
| WO | WO 91/19818 | 12/1991 |
| WO | WO 92/00091 | 1/1992 |
| WO | WO 92/02536 | 2/1992 |
| WO | WO 92/22875 | 12/1992 |
| WO | WO 93/31722 | 2/1993 |
| WO | WO9303172 | 2/1993 |
| WO | WO 93/06121 | 4/1993 |
| WO | WO 93/20242 | 10/1993 |
| WO | WO 94/08051 | 4/1994 |
| WO | WO 94/13623 | 6/1994 |
| WO | WO 94/24143 | 10/1994 |
| WO | WO 95/04160 | 2/1995 |
| WO | WO 95/06293 | 3/1995 |
| WO | WO 95/12608 | 5/1995 |
| WO | WO 96/03418 | 2/1996 |
| WO | WO 96/09316 | 3/1996 |
| WO | WO 96/11878 | 4/1996 |
| WO | WO 96/12014 | 4/1996 |
| WO | WO 96/24061 | 8/1996 |

(56) References Cited

FOREIGN PATENT DOCUMENTS

| | | |
|---|---|---|
| WO | WO 96/24847 | 8/1996 |
| WO | WO 96/35699 | 11/1996 |
| WO | WO 96/40201 | 12/1996 |
| WO | WO 96/41011 | 12/1996 |
| WO | WO 97/04131 | 2/1997 |
| WO | WO 97/11958 | 4/1997 |
| WO | WO 97/19039 | 5/1997 |
| WO | WO 97/27317 | 7/1997 |
| WO | WO 97/35198 | 9/1997 |
| WO | WO 98/01562 | 1/1998 |
| WO | WO 98/31700 | 7/1998 |
| WO | WO 98/47613 | 10/1998 |
| WO | WO 98/56904 | 12/1998 |
| WO | WO 98/58256 | 12/1998 |
| WO | WO 99/42605 | 8/1999 |
| WO | WO 99/51546 | 10/1999 |
| WO | WO 99/51773 | 10/1999 |
| WO | WO 99/64378 | 12/1999 |
| WO | WO 00/20639 | 4/2000 |
| WO | WO 00/21909 | 4/2000 |
| WO | WO 00/23456 | 4/2000 |
| WO | WO 00/23458 | 4/2000 |
| WO | WO 00/24882 | 5/2000 |
| WO | WO 00/32823 | 6/2000 |
| WO | WO 00/40695 | 7/2000 |
| WO | WO 00/47775 | 8/2000 |
| WO | WO 00/61755 | 10/2000 |
| WO | WO 01/00876 | 1/2001 |
| WO | WO 01/07657 | 2/2001 |
| WO | WO 01/07690 | 2/2001 |
| WO | WO 01/53539 | 7/2001 |
| WO | WO 01/56955 | 8/2001 |
| WO | WO 01/90414 | 11/2001 |
| WO | WO 02/03067 | 1/2002 |
| WO | WO 02/10186 | 2/2002 |
| WO | WO 02/34948 | 5/2002 |
| WO | WO 02/40664 | 5/2002 |
| WO | WO 02/074929 | 9/2002 |
| WO | WO 02/074978 | 9/2002 |
| WO | WO 02/083951 | 10/2002 |
| WO | WO 02/099078 | 12/2002 |
| WO | WO 02/102820 | 12/2002 |
| WO | WO 02/103008 | 12/2002 |
| WO | WO 03/025567 | 3/2003 |
| WO | WO 03/062417 | 7/2003 |
| WO | WO 03/076943 | 9/2003 |
| WO | WO 03/078050 | 9/2003 |
| WO | WO 03/078445 | 9/2003 |
| WO | WO 03/078446 | 9/2003 |
| WO | WO 03/078625 | 9/2003 |
| WO | WO 03/078626 | 9/2003 |
| WO | WO 03/078627 | 9/2003 |
| WO | WO 03/082901 | 10/2003 |
| WO | WO 03/106679 | 12/2003 |
| WO | WO 04/001042 | 12/2003 |
| WO | WO 2004/007529 | 1/2004 |
| WO | WO 2004/009814 | 1/2004 |
| WO | WO 2004/013070 | 2/2004 |
| WO | WO 2004/016767 | 2/2004 |
| WO | WO 2004/024929 | 3/2004 |
| WO | WO 2004/039825 | 5/2004 |
| WO | WO 2004/039962 | 5/2004 |
| WO | WO 2004/042019 | 5/2004 |
| WO | WO 2004/056994 | 7/2004 |
| WO | WO 2004/074429 | 9/2004 |
| WO | WO 2004/074501 | 9/2004 |
| WO | WO 2004/083427 | 9/2004 |
| WO | WO 2004/099441 | 11/2004 |
| WO | WO 2004/110964 | 12/2004 |
| WO | WO 2005/003778 | 1/2005 |
| WO | WO 2005/008240 | 1/2005 |
| WO | WO 2005/026387 | 3/2005 |
| WO | WO 2005/058479 | 6/2005 |
| WO | WO 2005/078122 | 8/2005 |
| WO | WO 2005/090566 | 9/2005 |
| WO | WO 2005/116213 | 12/2005 |
| WO | WO 2006/048025 | 5/2006 |
| WO | WO 2006/053571 | 5/2006 |
| WO | WO 2006/069063 | 6/2006 |
| WO | WO 2006/079061 | 7/2006 |
| WO | WO 2006/128138 | 11/2006 |
| WO | WO 2006/130669 | 12/2006 |
| WO | WO 2006/133312 | 12/2006 |
| WO | WO 2006/135654 | 12/2006 |
| WO | WO 2006/135786 | 12/2006 |
| WO | WO 2006/138560 | 12/2006 |
| WO | WO 2006/138666 | 12/2006 |
| WO | WO 2007/008276 | 1/2007 |
| WO | WO 2007/011722 | 1/2007 |
| WO | WO 2007/016488 | 2/2007 |
| WO | WO 2007/053358 A2 | 5/2007 |
| WO | WO 2007/062664 | 6/2007 |
| WO | WO 2007/124758 | 11/2007 |
| WO | WO 2008/014238 | 1/2008 |
| WO | WO 2008/036273 | 3/2008 |
| WO | WO 2008/054600 | 5/2008 |
| WO | WO 2009/018003 | 2/2009 |
| WO | WO 2009/077173 | 6/2009 |
| WO | WO 2009/152824 | 12/2009 |
| WO | WO 2011/127933 | 10/2011 |

OTHER PUBLICATIONS

1st Restriction requirement of Oct. 5, 2011 re U.S. Appl. No. 12/095,778.
2nd Restriction requirement of Jun. 27, 2012 re U.S. Appl. No. 12/095,778.
Examiner's amendment communication dated May 12, 2011 re U.S. Appl. No. 10/525,817.
Fiinal rejection dated Jan. 9, 2012 re U.S. Appl. No. 10/572,644.
Final rejection dated Feb. 6, 2012 in U.S. Appl. No. 10/523,006.
Final rejection of Dec. 22, 2012 re U.S. Appl. No. 10/539,288.
Issue notification dated Jun. 6, 2012 re U.S. Appl. No. 10/525,817.
Non final rejection of Sep. 21, 2012 re U.S. Appl. No. 10/539,288.
Non final rejection of Jul. 31, 2012 re U.S. Appl. No. 13/179,283.
Notice of Allowance dated Oct. 14, 2011 re U.S. Appl. No. 10/525,817.
Notice of Allowance dated Jan. 19, 2012 re U.S. Appl. No. 10/525,817.
Notice of Allowance dated Mar. 30, 2012 re U.S. Appl. No. 10/525,817.
Notice to file missing parts of May 11, 2012 re U.S. Appl. No. 13/455,223.
Office Action dated Sep. 17, 2012 in U.S. Appl. No. 12/330,709.
RCE filed Aug. 6, 2012 re U.S. Appl. No. 10/523,006.
RCE filed Jun. 9, 2012 re U.S. Appl. No. 10/572,644.
RCE filed Oct. 17, 2011 re U.S. Appl. No. 12/179,323.
RCE filed Aug. 20, 2012 re U.S. Appl. No. 10/539,288.
RCE filed Mar. 21, 2012 re U.S. Appl. No. 10/525,817.
Response to Notice to file missing parts of May 11, 2012 re U.S. Appl. No. 13/455,223 submitted Oct. 11, 2012.
Response to 1st Restriction Requirement of Oct. 5, 2011 U.S. Appl. No. 12/095,778 Mar. 5, 2012.
Response to 2nd Restriction Requirement of Jun. 27, 2012 re U.S. Appl. No. 12/095,778 submitted Dec. 27, 2012.
Response to non final rejection of Mar. 16, 2011 re U.S. Appl. No. 10/523,006 submitted Sep. 16, 2011.
Response to non final rejection of Apr. 25, 2011 re U.S. Appl. No. 10/539,288 submitted Oct. 25, 2011.
Response to Non final rejection of Jul. 31, 2012 re U.S. Appl. No. 13/179,283 submitted Jan. 30, 2013.
Response to Non final rejection of Mar. 31, 2011 re U.S. Appl. No. 10/572,644 submitted Sep. 30, 2011.
Response to restriction requirement of Apr. 24, 2012 re U.S. Appl. No. 13/179,283 submitted Jul. 23, 2012.
Restriction requirement of Apr. 24, 2012 re U.S. Appl. No. 13/179,283.
Abravaya et al. "Detection of point mutation with a modified ligase chain reaction (GAP-LCR)", *Nucleic Acids Research*, vol. 23, No. 4, 675-682 (1995).

(56) References Cited

OTHER PUBLICATIONS

Acinas et al. "PCR-Induced Sequence Artifacts and Bias: Insights from Comparison of Two 16S rRNA Clone Libraries Constructed from the same Sample", *Applied and Environmental Microbiology*, vol. 71, No. 12, 8966-8969, (2005).
Agarwal, et al. "Total Synthesis of the gene for an alanine transfer ribonucleic acid from yeast", Abstract only, *Nature*, 227, 27-34 (1970).
Anonymous. "Preparing Oligonucleotides for Antisensen Experiments", *Glen Research Report*, vol. 10, 3 (Dec. 1997 issue).
Anonymous. "Cytofectin GSV Transfection Protocol", *Glen Research Report*, vol. 10, 4-6 (Dec. 1997 issue).
Anonymous. "New Fluorescent Reagents—Tamra CPG, Fluorescein-dt", *Glen Research Report*, vol. 10, 7 (Dec. 1997 issue).
Anonymous. "Universal Support Replaces Individual Columns", *Glen Research Report*, vol. 10, 8 (Dec. 1997 issue).
Anonymous. "Q-Supports Reduce Cleavage Time to 2 Minutes", *Glen Research Report*, vol. 10, 9 (Dec. 1997 issue).
Anonymous. "5,6-Dihydro-Pyrimidines, Z-Phosphoramidites", *Glen Research Report*, vol. 10, 11 (Dec. 1997 issue).
Anonymous. "Non-enzymatic Ligation of Single-Stranded and Duplex DNA", *Glen Research Report*, vol. 10, 12 (Dec. 1997 issue).
Anonymous. "More Novel Monomers -4-Thio-dU, 5'-Amino-dT, 2'-F-Pyrimidines", *Glen Research Report*, vol. 10, 10 (Dec. 1997 issue).
Anonymous. "DCI—A Logical Alternative Aviator", *Glen Research Report*, vol. 10, No. 1 (1997).
Australian Patents Act 19909—Section 32 Regulation 3.6, (Request for a Determination of Dispute between Applicants) and 3.7 Applications to Commissioner for Declaration of an Eligible Person.—Not Date.
Baldwin, "Design, Synthesis and use of binary encoded synthetic chemical libraries", *Molecular Diversity*, 2, 81-88 (1996).
Baran et al. "Total Synthesis of Marine natural products without using protecting groups", Nature, vol. 446, 404-408 (2007).
Barany, "Genetic disease detection and DNA amplification using cloned thermostable ligase", Proc. Natl. Acad., vol. 88, 189-193 (1991).
Barany, F. "The ligase chain reaction in a PCR world", Genome Res. vol. 1, 5-16 (1991).
Barany, F. "The TaqI star reaction: strand preferences reveal hydrogen-bond donor and acceptor sites in canonical sequence recognition", *Gene* vol. 65 149-165 (1988).
Bayer, E. et al. "Liquid Phase Synthesis of Peptides", *Nature* vol. 237; 30 (Jun. 1972).
Bittker, et al. "Nucleic Acid Evolution and Minimization by Nonhomologous Random Recombination", *Nature Biotechnology* 20, 1024-1029 (2002).
Bonora, et al. "Large Scale, PEG-supported DNA Synthesis"; *Nucleosides & Nucleotides*, 10 (1-3), (1991).
Borman, "Combinatorial chemists focus on small molecules, molecular recognition, and automation", *Chemical & Engineering News*, Feb. 12, 1996.
Braasch, et al. "Locked nucleic acids (LNA): fine-tuning the recognition of DNA and RNA", *Elsevier, Chemistry & Biology*, 8, 1-7 (2001).
Brennan, et al. "Using T4 RNA Ligase with DNA Substrates", *Methods in enzymology*, vol. 100, pp. 38-52.
Broude, Natalie E. "Stem-loop oligonucleotides: a robust tool for molecule biology and biotechnology", *Trends in Biotechnology*, vol. 20, No. 6, Jun. 2002 (22-06) pp. 249-256.
Buller, F. et al., "Design and synthesis of a novel DNA-encoded chemical library using Diels-Alder cycloadditions", Bioorg Med Chem Lett 18, 5926 (2008).
Buller, F. et al. "Discovery of TNF inhibitors from an DNA-encoded chemical library based on Diels-Alder cycloaddition", Chem Biol 16, 1075 (2009).
Buller et al., "Drug Discovery with DNA-Encoded Chemical Libraries", Bioconjugate Chem., vol. 21 (9), pp. 1571-1580, (2010).

Bunin et al., "[26] Synthesis and Evaluation of 1, 4-Benzodiazepine Libraries," Mthods in Enzymology, vol. 267, pp. 448-465, (1996).
Bunin, et al. "The combinatorial synthesis and chemical and biological evaluation of a 1,4-benzodiazepine library", *Proc. Natl. Acad. Sci. USA*, vol. 91, pp. 4708-4712 (May 1994).
Buskirk, et al. "Engineering a Ligand-Dependent RNA Transcriptional Activator", Chem. Biol. 11, 1157-1163 (2004), This work is featured in a Research Highlight in Nature Methods 1, 6-7 (2004).
Canne et al. "Chemical Protein Synthesis by Solid Phase Ligation of Unprotected Peptide Segments", J. Am. Chem. Soc., 121, 8720-8727 (1999).
Chen, et al. "Enzyme Engineering for Nonaqueous Solvents: Random Mutagenesis to Enchance Activity of Subtilisin E in Polar Organic Media"; Bio/Technology 9, 1073-1077 (1991)—Abstract.
Chen, et al. "Enzymes in Nonaqueous Solvents; Applications in Carbohydrate and Peptide Preparation", *Methods in Biotechnology*, vol. 15, 373-374 (2001).
Chu et al. "Ligation of oligonucleotides to nucleic acids or proteins via disulfide bonds." *Nucleic Acids Research*. vol. 16. No. 9. pp. 3671-3691 (1998).
Clark et al. "Design, synthesis and selection of DNA-encoded small-molecule libraries", Nat Chem Biol 5, 647 (2009).
Clark, Matthew A. "Selecting chemicals: the emerging utility of DNA-encoded libraries", *Molecular Discovery Research*, GlaxoSmithKline, Waltham, MA, USA. Current Opinion in Chemical Biology (2010), 14(3), 396-403. Publisher: Elsevier B.V.
Colombo, R. et al. "Synthesis of leucin-enkephalin and methionineenkephalin . . . ", *Hoppe-Seyler's Z.Physiol.Chem*. vol. 363 (1981).
Cotton, et al. "Reactivity of cytosine and thymine in single-base-pair mismatches with hydroxylamine and osmium tetroxide and its application to the study of mutations", *Proc Natl Acad Sci* (US), 85, 4397-401 (1988).
Constantino, L et al. "Privileged structures as leads in medicinal chemistry", *Curr Med Chem* 13, 65, (2006).
Czarnik, A. W. "Encoding strategies in combinatorial chemistry", *Proc. Natl. Acad. Sci. USA*, vol. 94, pp. 12738-12739 (Nov. 1997).
Czarnik, et al. "Encoding methods for combinatorial chemistry", Current Opinion in Chemical Biology, vol. 1, ISS 1, p. 60-66 (Jun. 1997).
Degn, Hans, et al. "Enzyme Activity in Organic Solvent As a Function of Water Activity Determined by Membrane Inlet Mass Spectometry"; Biotechnology Techniques vol. 6; No. 2; pp. 161-164 (Mar./Apr. 1992).
Denapoli, et al. "PEG-supported Synthesis of Cyclic Oligodeoxyribonucleotides", Nucleosides & Nucleotides, vol. 12, No. 1 (1993).
"DNA Phosphoramidites & CPG's"; http://www.qualitysystems.com.tw/proligo/dna%20phosphoamidites%20&%20cpg's.htm Dec. 2, 2010.
"Dokl Akad Nauk SSSR", vol. 258, 1242-1245, Krynetskya NF Tumanov YV (1981).
Dolinnaya, et al. "Chemical ligation as a method for the assembly of double-stranded nucleic acids: Modifications and local structure studies", Russian Chemical Bulletin, vol. 45, No. 8 (1996).
Dolinnaya, et al. "Structural and kinetic aspects of chemical reactions in DNA duplexes. Information on DNA local structure obtained from chemical ligation data", Nucleic Acids Research, vol. 19, No. 11, 3073-3080 (1991).
Douglas, et al. "Polymer-supported solution synthesis of oligosaccharides", J. Am. Chem. Soc., vol. 113 (1991).
Drabovich, et al. "Selection of Smart Small-Molecule Ligands: The Proof of Principle", Analytical Chemistry, vol. 81, No. 1, 490-494 (2009).
Drews "Drug Discovery: A Historical Perspective", Science vol. 287, pp. 1960-1964 (2000).
Dreyer, et al. "Enzyme Catalysis in Nonaqueous Media: Past, Present and Future" in Patel (ed.), "Biocatalysis in the Pharmaceutical and Biotechnology Industries", 819-820 (2006).
Ecker, David J, et al. "Rational screening of oligonucleotide combinatorial libraries for drug discovery", Nucleic Acids Research, vol. 21, No. 8, pp. 1853-1856 (1993).

(56) References Cited

OTHER PUBLICATIONS

Fack, Fred, et al. "Heteroduplex mobility assay (HMA) pre-screening: An improved strategy for the rapid identification of inserts selected from phage-displayed peptide libraries", Molecular Diversity, vol. 5, No. 1; pp. 7-12 (2000).
Ficht, Simon, et al. "As Fast and Selective as Enzymatic Ligations: Upaired Nucleobases Increase the Selectivity of DNA-Controlled Native Chemical PNA Ligation"; ChemBioChem: vol. 6, Issue 11, pp. 2098-2103 (2005).
Fegan et al. "Rigid cyanine dye nucleic acid labels", Chem Commun May 7; (17) 2004-6 (2008).
Furka, et al. "Combinatorial Libraries by Portioning and Mixing", Combinatorial Chemistry & High Throughput Screening, 2, 105-122 (1999).
Gorin, et al. "Reactivity-Dependent PCR: Direct, Solution-Phase in Vitro Selection for Bond Formation", J. Am. Chem. Soc. 131, pp. 9189-9191 (2009).
Grange, et al. "Detection of point mutations in type I collagen by RNase digestion of RNA/RNA hybrids", Nucleic Acids Research 18: 4227-36 (1990).
Gruen, et al. "An in Vivo Selection System for Homing Endonuclease Activity", Nucleic Acids Research 30, e29 (2002).
Gumport, et al. "T4 RNA Ligase as a Nucleic Acids Synthesis and Modification Reagent", Elsevier North Holland, Inc., 314-345 (1981).
Guo, T. et al. "Preparation of Encoded Combinatorial Libraries for Drug Discovery", Methods in Molecular Biology, Combinatorial Library Methods and Protocols, pp. 23-39 (2002).
Hansen, M. "A Yoctoliter-scale DNA reactor for small-molecule evolution", J Am Chem Soc. 131, 1322 (2009).
Harada, et al. "Unexpected substrate specificity of T4 DNA ligase revealed by in vitro selection", Nucleic Acids Research, vol. 21, No. 10, 2287-2291 (1993).
Harada "In vitro selection of optimal DNS substrates for ligation by a water-soluble carbodiimide", J Mol Evol., 38, 6, 558-560 (1994).
Harada, et al. "In vitro selection of optimal DNA substrates for t4 RNA ligase", Proc. Natl. Acad. Sci. USA, vol. 90, pp. 1576-1579 (Feb. 1993).
Herpin, et al. "Synthesis of a 10000 member 1, 5-Benzodiazepine-2-one Library by the Directed Sorting Method", J. Comb. Chem., 2, 513-521 (2000).
Higgins, et al. "Addition of Oligonucleotides to the 5'-Terminus of DNA by T4 RNA Ligase", Nucleic Acids Research, 6(3): 1013-1024 (1979).
Higgins, et al. "DNA-joining Enzymes: A Review", Methods in Enzymology, vol. 68, pp. 50-71 (1979).
Hinton, et al. "T4 RNA Ligase Joins 2'-Deoxyribonucleoside 3', 5'-Bisphosphates to Oligodeoxyribonucleotides", Biochemistry vol. 17, No. 24, pp. 5091-5097 (1978).
Holmes, CP "Model Studies for New o-Nitrobenzyl Photolabile Linkers: Substituent Effects on the Rates of Photochemical Cleavage", J. Org. Chem. 62, 2370-2380 (1997).
Housby, Nicholas J, et al. "Fidelity of DNA ligation: a novel experimental approach based on the polymerisation of libraries of oligonucleotides", Nucleic Acids Research, vol. 26, No. 18, pp. 4259-4266 (1998).
Hsu "Detection of DNA point mutations with DNA mismatch repair enzymes" Carcinogenesis 15:1657-62 (1994).
Ito et al. Tag-reporter and Resin Capture + Release Strategy in Oligosaccharide Synthesis. Chemistry—A European Journal 8(14):3077-3084 (2002).
James, Kenneth D. et al. "The Fidelity of Template-Directed Oligonucleotide Ligation and the Inevitability of Polymerase Function", Origins of Life and Evolution of the Biosphere 29, 1999 Kluwer Academic Publishers; pp. 375-390.
Janda, Kim D. "Tagged versus untagged libraries: Methods for the generation and screening of combinatorial chemical libraries", Proc. Natl. Acad. Sci. USA, vol. 91, pp. 10779-10785 (Nov. 1994).
Jäschke, Andres, et al. "Evolution of DNA and RNA as catalysts for chemical reactions"; Current Opinion in Chemical Biology 4; pp. 257-262 (2000).
Jäschke, et al. "Synthesis and properties of oligodeoxyribonucleotide—polyethylene glycol conjugates", Nucleic Acids Research, vol. 22, No. 22, pp. 4810-4817 (1994).
Jones, et al. "Enzymes in organic synthesis 22. Effects of organic solvents on horse liver alcohol dehydrogense-catalyzed reduction"; Can. J. Chem. 60 pp. 335-338 (1982).
Kanagawa, Takahiro Bias and Artifacts in Multitemplate Polymerase Chain Reactions (PCR), Journal of Bioscience and Bioengineering, vol. 96, No. 4, pp. 317-323 (2003).
Kanan, et al. "Reaction Discovery Enabled by DNA-Templated Synthesis and In Vitro Selection", Supplementary Information, pp. 1-20.
Kerr, JM et al. "Encoded Combinatorial Peptide Libraries Containing Non-Natural Amino Acids", J. Am. Chem. Soc.115, 2529-2531 (1993).
Kinoshita, et al. "Enzymatic Synthesis of Code Regions for Encoded Combinatorial Chemistry", Nucleic Acids Symposium Series, 34: 201-202 (1995).
Kinoshita, Y. et al. "Strand ligation in a double-stranded DNA by T4 RNA ligase", Department of Functional Materials Science, Saitama University, Urawa, Japan. Chemistry Letters (9), 797-798 (1996).
Klibanov, Alexander M. "Why are enzymes less active in organic solvent than water?"; Trends in Biotechnology; vol. 15, Issue 3, 97-101; 1 (Mar. 1997)—Abstract.
Krishna, Sajja Hari "Developments and trends in enzyme catalysis in nonconventional media", Biotechnology Advances; vol. 20; Issues 3-4; pp. 239-267 (Nov. 2002)—Abstract.
Krug, et al. "Reversal of T4 RNA Ligase", Biochemistry vol. 21, No. 8, pp. 1858-1864 (1982).
Kurz, M. et al. "cDNA—protein fusions: covalent protein—gene conjugates for the in vitro selection of peptides and proteins", Chembiochem—A European Journal of Chemical Biology, Wiley VCH, Weinheim, DE, vol. 2, No. 9, Sep. 3, 2001, pp. 666-672, XP002332971, ISSN: 1439-4227.
Kurz, M., et al. "An efficient synthetic strategy for the preparation of nucleic acid-encoded peptide and protein libraries for in vitro evolution protocols". Fourth International Electron Conference on Synthetic Organic Chemistry (ECSOC-4), www.mdpi.org/ecsoc-4.htm, Sep. 1-30, 2000.
Lebl, Michal "Parallel Personal Comments on Classical" Papers in Combinatorial Chemistry, J. Comb. Chem. 1, pp. 3-24 (1999).
Lehman, I.R. "DNA ligase: Structure, Mechanism, and Function; The joining of DNA chains by DNA ligase is an essential component of DNA repair, replication, and recombination", Science vol. 186; pp. 790-797 (1974).
"Ligase", Answers.com: http://www.answers.com/topic/ligase, [accessed Dec. 10, 2009].
Lim, Carols S. et al. "Syntehsis of DNA Dumbbells: Chemical vs. Enzymatic Ligation of Self-Complementary Oligonucleotides", Abstract only, Nucleotides and Nucleic Acids; vol. 16, Issue 1 & 2; pp. 41-51 (Jan. 1997).
Lindström, Ulf M. et al. "An orthogonal oligonucleotide protecting group strategy that enables assembly of repetitive or highly structured DNAs"; Nucleic Acids Research 30(19), e101; 2002 Oxford University Press (Oct. 1, 2002).
Liu, D.R. "Development of Amplifiable and Evolvable Unnatural Molecules", website of Dr. D. R. Liu, publicly available Mar. 11, 2000. http://web.archive.org/web/20000311112631/http://evolve.havard.edu.
Liu, D.R. "The Chemistry and Chemical Biology of Molecular Evolution," website of Dr. D.R. Liu, publicly available Mar. 1, 2001. http://web.archive.org/web/20010301175107/http://evolve.havard edu.
Liu, D.R. "The Chemistry and Chemical Biology of Molecular Evolution," website of Dr. D.R. Liu, publicly available Oct. 15, 2003. http://web.archive.org/web/20031216020734/http://evolve.havard edu.
Liu, D.R. "The Chemistry and Chemical Biology of Molecular Evolution," website of Dr. D.R. Liu, publicly available Nov. 20, 2002. http://web.archive.org/web/20021129131743/http://evolve.havard edu.

(56) References Cited

OTHER PUBLICATIONS

Liu, D.R. "The Chemistry of Molecular Evolution," website of Dr. D.R. Liu, publicly available Oct. 15, 2000. http://web.archive.org/web/20001015144553/http://evolve.havard.edu.

Liu, W, et al. "Denaturing high performance liquid chromatography (DHPLC) used in the detection of germline and somatic mutations" Nucleic Acids Research. vol. 26. pp. 1396-1400 (1998).

Liu, D.R. "The Chemistry and Chemical Biology of molecular Evolution", Liu Group Research Summary from the website of Professor David R. Liu, obtained from the website in Feb. 2005.

Lobanov Trends in Biotechnology, vol. 20, No. 2, pp. 86-87 (Feb. 2002).

Lockhart, et al. "Expression monitoring by hybridization to high-density oligonucleotide arrays", Bio/Technology, Nature publishing co., New York, US, vol. 14, No. 13, p. 1675-1680 (Dec. 1, 1996).

Loughlin, Wendy A. "Biotransformations in organic synthesis"; Bioresource Technology 74, pp. 49-62 (2000).

Luebke, Kevin J. et al. "Nonenzymatic ligation of double-helical DNA by alternate-strand triple helix formation"; Nucleic Acids Research; vol. 20, No. 12; pp. 3005-3009 (1992).

MacLean, Derek, et al. "Encoded Combinatorial Chemistry: Synthesis and screening of a library of highly functionalized pyrrolidines", Proc. Natl. Acad. Sci. USA, vol. 94, pp. 2805-2810 (Apr. 1997).

Makara, Gergely M. et al. "Improving Success rates for lead generation using affinity binding technologies", Current Opinion in Biotechnology 16:666-673 (2005).

Magliery, et al. "Expanding the Genetic Code In Vitro and In Vivo", The Genetic Code and the Origin of Life, Ed. Ribas de Pouplana, L. Landes Bioscience, In Press (2004).

Mannocci, L. "DNA-Encoded affinity maturation libraries", Proc Natl Acad Sci USA 105, 17670 (2008).

Mannocci, Lucca "DNA-Encoded Chemical Libraries", Diss. ETH No. 18153 (2009).

Margulies, M. et al., "Genome sequencing in microfabricated high-density picolitre reactors", Nature 437, 376 (2005).

Mashal, et al. "Detection of mutations by cleavage of DNA heteroduplexes with bacteriophage resolvases", Nature Genetics 9:177-83 (1995).

Matsuda, et al. "Low Fidelity DNA Synthesis by Human DNA Polymerase-?", Nature, 404: 1011-1013 (Apr. 27, 2000).

Matsuura, K., et al. "Construction of glyco-clusters by self-organization of site-specifically glycosylated oligonucleotides and their cooperative amplification of lectin-recognition." Journal of the American Chemical Society, vol. 123, No. 2, pp. 357-358 (Jan. 17, 2001).

McCoy, et al. "T4 Ribonucleic Acid Ligase Joins Single-Strand Oligo(deoxyribonucleotides)", Biochemistry vol. 19, No. 4, 635-642 (1980).

McGregor, et al. "Interaction-Dependent PCR: Identification of Ligand-Target Pairs from Libraries of Ligands and Libraries of Targets in a Single Solution-Phase Experiment", J. Am. Chem. Soc. 132, pp. 15522-15524 (2010).

Melkko, Samu. et al. "Lead discovery by DNA-encoded chemical libraries", Drug Discovery Today, vol. 12, No. 11/12, pp. 465-471 (Jun. 2007).

Mendel, D. "Site-directed mutagenesis with an expanded genetic code." Annu. Rev. Biophys. Biomol. Struc. vol. 24, pp. 435-462. (1995).

Miller, Scott J. "DNA as a template for reaction discovery", Nature Biotechnology, vol. 22, No. 11, pp. 1378-1379 (Nov. 2004).

Mudrakovskaya, et al. "Solid-Phase Enzymatic Synthesis of Oligoribonucleotides", Bioorg Khim vol. 17, No. 6, pp. 469-472 (1991).

Mutter, M. et al. "Functionalized polyethylene glycols and polypeptides in organic synthesis and catalysis", Reactive Polymers, vol. 6, pp. 99-107 (1987).

Myers, et al. "Detection of single base substitutions by ribonuclease cleavage at mismatches in RNA:DNA duplexes". Science 230: 1242-6 (1985).

Nielsen "Combinatorial chemistry and automation", DDT, vol. 1, No. 11, pp. 458-460 (Nov. 1996).

Nishigaki, Koichi, et al. "Y-ligation: an efficient method for ligating single stranded DNAs and RNAs with T4 RNA ligase", Department of Functional Materials Science, Saitama University, Urawa, Japan. Molecular Diversity vol. 4(3), 187-190 (2000).

O'Donovan MC, et al. "Blind analysis of denaturing high-perfomance liquid chromatography as a tool for mutation detection", Genomics. 52:4449 (1998).

"Organic Chemistry", Wikipedia, [accessed Dec. 10, 2009]: http://en.wikipedia.org/wiki/organic_chemistry (10 pages).

"Orthogonal Protection Protecting Group", Wikipedia: http://en.Wikipedia.org/wiki/protecting_group#Orthogonal_protection [accessed Apr. 15, 2010].

Persichetti, et al. "Cross-Linked Enzyme Crystals (CLECs) of Thermolysin in the Synthesis of Peptides", Journal of the American Chemical Society, 117: 2732-2737 (1995).

Pochet, et al. "Solid-Supported Ligation Primer", Nucleic Acids Research, 16(4): 1619 (1988).

Polsky-Cynkin et al. "Use of DNA immobilized on platic and agarose supports to detect DNA by sandwich hybridization", Clin. Chem. 31(9): 1438-43 (Sep. 1985).

Porco, Jr. "Synthesis Undressed", Nature 446, 383-5 (Mar. 22, 2007).

Purmal, Andrei A., et al. "A new affinity reagent for the site-specific, covalent attachment of DNA to active-site nucleophiles: application to the EcoRl and Rsrl restriction and modification enzymes", Nucleic Acids Research; vol. 20, No. 14; Oxford University Press; pp. 3713-3719 (1992).

Robertson, Dan "Direct Evolution Process for Robust Enzyme Catalysis in Organic Solvents"; Report date: Sep. 1996. pp. 1-14.

Robinson "A Synthesis of Tropinone", Journal of the Chemical Society Transactions, vol. 111, pp. 762-768, (1917).

Romaniuk, et al. "Joining of RNA molecules with Rna ligase", Methods in Enzymology, vol. 100, pp. 52-59, (1983).

Saiki et al. "Genetic analysis of amplified DNA with immobilized sequence-specific oligonucleotide probes" PNAS 86(16): 6230-6234 (1989).

Sarmento, et al. "Cardosins A and B, Two New Enzymes Available for Peptide Synthesis", Journal of Molecular Catalysis B: Enzymatic, 5: 327-330 (1998).

Scheuermann, Jörg, et al. "DNA-encoded chemical libraries", Journal of Biotechnology 126 568-581 (2006).

Scheuermann, Jörg, et al. "DNA-encoded chemical libraries: A tool for drug discovery and for chemical biology", ChemBioChem 0000, 00, 1-8 (2010).

Schmidt, JG, et al., "Information transfer from peptide nucleic acids to RNA by template-directed syntheses", Nucleic Acids Res., vol. 25 (23), pp. 4792-4796 (Dec. 1, 1997).

Schmitz, et al. "Solid-Phase Enzymatic Synthesis of Oligonucleotides", Organic Letters, 1(11): 1729-1731 (1999).

Schoenleber, R.O. et al. "Photochemical release of amines by C,N-bond cleavage", Synlett 501-504 (2003).

Schultz, et al. "The Combinatorial Library: A Multifunctional Resource", Biotechnol. Prog. 12, 729-743 (1996).

Shabarova, et al. "Chemical ligation of DNA: the first non-enzymatic assembly of a biologically active gene", Nucl. Acids Res., 19:4247-51 (1991).

Sharifian, Hoda. "Errors induced during PCR amplification", May 30, 2010.

Shuman, Stewart. "DNA ligases: Progress and Prospects"; jbc.org/content/284/26/17365. full downloaded Feb. 10, 2009.

Snyder, T. "Ordered multistep synthesis in a single solution directed by DNA templates", Angew Chem Int Ed Engl 44, 7379 (2005).

Sokolova, N.I., et al. "Chemical reactions within DNA duplexes; Cyanogen bromide as an effective oligodeoxyribonucleotide coupling agent"; FEBS letters, vol. 232, No. 1, pp. 153-155 (May 1988).

Still, W. Clark "Career-In-Review (CIR)", BJ Wright, Synthesis Literacy Group, Columbia University Chemistry, Mar. 30, 2007.

Tabor, Stanley "DNA-ligases"; Current Protocols in Molecular Biology 3.14.1-3.14.4 (1987).

Takemori, Shigeki, et al. "Stabilization of Enzyme Activity by an Organic Solvent", Abstract only, Nature 215, 417-419 (Jul. 22, 1967).

(56) References Cited

OTHER PUBLICATIONS

Tan et al. "Natural-product inhibitors of human DNA ligase I", *Biochemical Journal* 314: 993-1000 (1996).
Tan, Derek S. et al. "Ligand discovery using encoded combinatorial libraries", *Current Opinion in Drug Discovery & Development*, 3(4), p. 439-53 (Jul. 2000).
Tessier, et al. "Ligation of Single-Stranded Oligodeoxyribonucleotides by T4 RNA Ligase", *Analytical Biochemistry* 158, 171-178 (1986).
Tse, B. "Translation of DNA into a library of 13,000 synthetic small-molecule macrocycles suitable for in vitro selection", *J Am Chem Soc* 130, 15611 (2008).
Unknown "Science & Technology: Concentrates", Chem. & Eng. News 82 [40] 31 (2004).
Uhlenbeck, et al. "T4 RNA Ligase", The Enzymes, vol. XV, pp. 31-58 (1982).
Vágner, et al. "Enzyme-mediated spatial segregation on individual polymeric support beads: Application to generation and screening of encoded combinatorial libraries", Proc. Natl. Acad. Sci. USA, vol. 93, pp. 8194-8199, (Aug. 1996).
Vaisman, et al. "Human DNA polymerase, promiscuous mismatch extension", JBC 276: 30615-30622 (2001).
Vratskikh, et al. "Solid-phase synthesis of oligoribonucleotides using T4 RNA ligase and T4 polynucleotide kinase", *Biochimie* 77, 227-232 (1995).
Wagner, et al. "Mutation detection using immobilized mismatch binding protein (MutS)" *Nucleic Acids Research* 22, 3944-3948 (1995).
Walder, JA., et al. "Complementary carrier Peptide Synthesis: General Strategy and Implications for Prebiotic Origin of Peptide Synthesis", Department of Chemistry, and Department of Biochemistry and Molecular Biology, Northwestern University, Evanston, Illinois 60201, vol. 76, No. 1, p. 51-55, (1979).
Wang, S., et al. "Circular RNA oligonucleotides. Synthesis, nucleic acid binding properties, and a comparison with circular DNAs"; *Nucleic Acids Research*, 1994, vol. 22, No. 12; Oxford University Press; pp. 2326-2333 (1994).
Washington, et al. "Mismatch extension ability of yeast and human DNA polymerase n", JBC 276: 2263-2266 (2001).
Weiss, et al. "Enzymatic Breakage and Joining of Deoxyribonucleic Acid, I. Repair of Single-Strand Breaks in DNA by an Enzyme System From *Escherichia coli* Infected With T4 Bacteriophage*" *PNAS* 57, (4): 1021-1028 (1967).
Whitesides, et al. "Enzymes as Catalysts in Organic Synthesis", *Aldrichimica Acta.*, vol. 16, No. 2, pp. 27-34, (1983).
Winzeler, et al. "Fluorescence-based expression monitoring using microarrays", *Methods Enzymol.* 306: 3-18 (1999).
Wong, Daphne M. et al. "Branch capture reactions: displacers derived from assymmetric PCR"; 1991 *Oxford University Press; Nucleic Acids Research*; vol. 19; No. 9; pp. 2251-2259 (1991).
Xu, Y, et al. "A Novel 5'-Iodonucleoside Allows Efficient Non-enzymatic Ligation of Single-Stranded and Duplex DNA", Abstract, Glen Research Catalog, Tetrahedron Letters 38:5595-5598 (1997).
Xu, Y, et al. "High sequence fidelity in a non-enzymatic DNA autoligation reaction", Nucleic Acids Research, vol. 27, No. 3; pp. 875-881 (1999).
Zhu, et al. A Primer-dependent Polymerase Function of *Pseudomonas aeruginosa* ATP-dependent DNA ligase (LigD). Journal of Biological Chemistry 280(1): 418-427 (2005).
Website of prof. David R. Liu, publicly available Apr. 23, 2003.
Website of prof. David R. Liu, publicly available Aug. 1, 2003.
Website of prof. David R. Liu, publicly available Aug. 2, 2002.
Website of prof. David R. Liu, publicly available Feb. 8, 2003.
Website of prof. David R. Liu, publicly available Feb. 10, 2004.
Website of prof. David R. Liu, publicly available Feb. 15, 2001.
Website of prof. David R. Liu, publicly available Dec. 16, 2003.
Website of prof. David R. Liu, publicly available Jun. 4, 2002.
Website of prof. David R. Liu, publicly available Jun. 6, 2003.
Website of prof. David R. Liu, publicly available Mar. 27, 2003.
Website of prof. David R. Liu, publicly available Mar. 31, 2001.
Website of prof. David R. Liu, publicly available Nov. 29, 2002.
Website of prof. David R. Liu, publicly available Nov. 30, 2001.
Website of prof. David R. Liu, publicly available Oct. 17, 2002.
Decision to Grant from European Application No. EP 02740409.4 dated Jul. 26, 2007.
European Office Action from European Application No. EP 02740409.4 dated Sep. 1, 2005.
Reply to European Office Action from European Application No. EP 02740409.4 dated Jun. 16, 2006.
Intent to Grant from European Application No. EP 02740409.4 printed Oct. 13, 2006.
Extended European Search Report from European Application No. 07114663.3 dated May 25, 2009.
Extended European Search Report from European Application No. 10 18 4311 dated Feb. 28, 2011.
International Preliminary Examination Report from PCT No. PCT/DK02/00419 dated Jan. 28, 2004.
International Search Report from PCT No. PCT/DK02/00419 dated Jun. 25, 2003.
Restriction Requirement from U.S. Appl. No. 10/175,539 mailed Apr. 6, 2005.
Response to Restriction Requirement from U.S. Appl. No. 10/175,539 mailed May 6, 2005.
Office Action (Non-Final Rejection) from U.S. Appl. No. 10/175,539 mailed May 13, 2005.
Response to Office Action (Non-Final Rejection) from U.S. Appl. No. 10/175,539 mailed Apr. 13, 2006.
Office Action (Non-Final Rejection) from U.S. Appl. No. 10/175,539 mailed May 14, 2007.
Response to Office Action (Non-Final Rejection) from U.S. Appl. No. 10/175,539 mailed Sep. 13, 2007.
Office Action (Final Rejection) from U.S. Appl. No. 10/175,539 mailed May 19, 2006.
Notice of Appeal from U.S. Appl. No. 10/175,539 dated Nov. 20, 2006.
Request for Continued Examination from U.S. Appl. No. 10/175,539 dated Feb. 20, 2007.
Office Action (Ex Parte Quayle Action) from U.S. Appl. No. 10/175,539 mailed Nov. 27, 2007.
Response to Ex Parte Quayle Action from U.S. Appl. No. 10/175,539 filed Feb. 27, 2008.
Notice of Allowance from U.S. Appl. No. 10/175,539 mailed May 30, 2008.
Issue Notification U.S. Appl. No. 10/175,539 issued Jun. 1, 2010.
Office Action (Non-Final Rejection) from U.S. Appl. No. 12/330,709 mailed Oct. 27, 2009.
Response to Office Action (Non-Final Rejection) from U.S. Appl. No. 12/330,709 filed Apr. 21, 2010.
Notice of Allowance from U.S. Appl. No. 12/330,709 mailed Mar. 3, 2011.
Request for Continued Examination and supplemental IDS from U.S. Appl. No. 12/330,709, filed Jun. 2, 2011.
Office Action from European Application No. 03709676.5 dated Feb. 23, 2005.
Reply to 1st Office Action from European Application No. 03709676.5 dated Jun. 30, 2005.
2nd Office Action from European Application No. 03709676.5 dated Aug. 26, 2005.
Reply to 2nd Office Action from European Application No. 03709676.5 dated Sep. 13, 2005.
3rd Office Action from European Application No. 03709676.5 dated Sep. 30, 2005.
Reply to 3rd Office Action from European Application No. 03709676.5 dated May 19, 2006.
Intent to Grant from European Application No. 03709676.5 dated Oct. 10, 2006.
Amendment after Intention to Grant from European Application No. 03709676.5 dated Nov. 16, 2007.
Decision to Grant from European Application No. 03709676.5 dated Oct. 23, 2008.
European Search Report from European Application No. 08 16 9346 mailed Apr. 13, 2010.

(56) References Cited

OTHER PUBLICATIONS

1st Office Action from European Application No. 08169346.7 mailed Apr. 19, 2011.
Response filed in European Application No. 08169346.7 mailed Mar. 23, 2011.
International Search Report for PCT Application No. PCT/DK03/00172 mailed Nov. 3, 2003.
Office Action (Non-Final) for U.S. Appl. No. 10/507,121 mailed Feb. 8, 2007.
Response to Office Action for U.S. Appl. No. 10/507,121 mailed Jun. 7, 2007.
Office Action (Final Rejection) for U.S. Appl. No. 10/507,121 mailed Sep. 7, 2007.
Request for Continued Examination and supplemental amendment for U.S. Appl. No. 10/507,121, filed Feb. 13, 2008.
Notice of Allowance for U.S. Appl. No. 10/507,121 mailed Mar. 20, 2008.
Issue Notification for U.S. Appl. No. 10/507,121 mailed Jul. 30, 2008.
Office Action (Non-Final) from U.S. Appl. No. 12/179,323 mailed Jan. 27, 2010.
Response to Office Action from U.S. Appl. No. 12/179,323, filed Jun. 24, 2010.
Office Action (Final Rejection) for U.S. Appl. No. 12/179,323 mailed Sep. 15, 2010.
Notice of Appeal from U.S. Appl. No. 12/179,323, filed Mar. 15, 2011.
1st Office Action from European Application No. 03766117.0 dated Mar. 24, 2009.
Reply to 1st Office Action from European Application No. 03766117.0 dated Jan. 8, 2010.
2nd Office Action from European Application No. 03766117.0 dated Feb. 16, 2010.
Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Application No. 03766117.0 dated Jun. 9, 2011.
International Search Report from PCT Application No. PCT/DK03/00516 mailed Feb. 18, 2004.
1st Restriction Requirement from U.S. Appl. No. 10/523,006 mailed Apr. 4, 2008.
Response to 1st Restriction Requirement from U.S. Appl. No. 10/523,006, filed Oct. 1, 2008.
2nd Restriction Requirement from U.S. Appl. No. 10/523,006 mailed Dec. 9, 2009.
Response to 2nd Restriction Requirement from U.S. Appl. No. 10/523,006, filed May 5, 2010.
3rd Restriction Requirement from U.S. Appl. No. 10/523,006 mailed Aug. 3, 2010.
Response to 3rd Restriction Requirement from U.S. Appl. No. 10/523,006, filed Feb. 1, 2011.
Office Action (Non-Final) from U.S. Appl. No. 10/523,006 mailed Mar. 16, 2011.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 6, 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
European Search Report for European Application No. 09 17 7376 dated Feb. 24, 2011.
International Search Report for PCT Application No. PCT/DK03/00921 Jun. 22, 2004.
Restriction Requirement for U.S. Appl. No. 10/539,288 mailed Aug. 2, 2010.
Response to Restriction Requirement for U.S. Appl. No. 10/539,288, filed Jan. 31, 2011.
Office Action (Non-Final) for U.S. Appl. No. 10/539,288 mailed Apr. 25, 2011.
1st Office Action for European Application No. 03729906.6 mailed May 17, 2006.
Reply to 1st Office Action for European Application No. 03729906.6 mailed Mar. 9, 2007.
2nd Office Action for European Application No. 03729906.6 mailed Sep. 22, 2009.
Reply to 2nd Office Action for European Application No. 03729906.6 mailed May 6, 2010.
International Search Report for PCT Application No. PCT/DK03/00417 mailed Feb. 10, 2004.
Restriction Requirement for U.S. Appl. No. 10/518,056 mailed Jan. 4, 2008.
Response to Restriction Requirement for U.S. Appl. No. 10/518,056, filed Jun. 2, 2008.
Office Action (Non-Final) for U.S. Appl. No. 10/518,056 mailed Oct. 8, 2008.
Reply to Office Action for U.S. Appl. No. 10/518,056, filed Feb. 17, 2009.
Office Action (Final Rejection) for U.S. Appl. No. 10/518,056 mailed May 27, 2009.
Notice of Appeal for U.S. Appl. No. 10/518,056 mailed Oct. 27, 2009.
Amendment After Appeal for U.S. Appl. No. 10/518,056, filed Nov. 17, 2009.
Advisory Action for U.S. Appl. No. 10/518,056 mailed Jan. 7, 2010.
Request for Continued Examination and IDS for U.S. Appl. No. 10/518,056, filed Mar. 22, 2010.
1st Office Action for European Application No. 04713515.7 mailed Oct. 19, 2006.
Reply to 1st Office Action for European Application No. 04713515.7 mailed Aug. 20, 2007.
2nd Office Action for European Application No. 04713515.7 mailed Mar. 31, 2008.
Reply to 2nd Office Action for European Application No. 04713515.7 mailed Dec. 5, 2008.
3rd Office Action for European Application No. 04713515.7 mailed Sep. 6, 2010.
Reply to 3rd Office Action for European Application No. 04713515.7 mailed Jun. 21, 2011.
International Search Report for PCT Application No. PCT/DK2004/000116 mailed Aug. 23, 2004.
Office Action (Non-Final) for U.S. Appl. No. 10/545,795 mailed Mar. 31, 2008.
Response filed for U.S. Appl. No. 10/545,795, filed Sep. 30, 2008.
Office Action for U.S. Appl. No. 10/545,795 mailed Jan. 27, 2009.
Notice of Appeal filed for U.S. Appl. No. 10/545,795, filed Jul. 27, 2009.
Amendment after Appeal for U.S. Appl. No. 10/545,795, filed Sep. 28, 2009.
Office Action (Advisory Action) for U.S. Appl. No. 10/545,795 mailed Sep. 29, 2009.
Request for Continued Examination and IDS for U.S. Appl. No. 10/545,79, filed Oct. 27, 2009.
Office Action (Non-Final) for U.S. Appl. No. 10/545,795 mailed Nov. 16, 2009.
Office Action (Non-Final) for U.S. Appl. No. 10/545,795 mailed Mar. 30, 2010.
Office Action (Interview Summary) for U.S. Appl. No. 10/545,795 mailed Jul. 30, 2010.
Response filed for U.S. Appl. No. 10/545,795, filed Aug. 30, 2010.

(56) References Cited

OTHER PUBLICATIONS

Office Action (Final rejection) for U.S. Appl. No. 10/545,795 mailed Feb. 1, 2011.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.
International Search Report for International Application No. PCT/DK2004/000117 mailed Aug. 19, 2004.
Restriction Requirement for U.S. Appl. No. 10/546,538 mailed Jul. 31, 2008.
Response to Restriction Requirement for U.S. Appl. No. 10/546,538, filed Dec. 24, 2008.
Office Action (Non-Final) for U.S. Appl. No. 10/546,538 mailed Jun. 10, 2009.
Response to Office Action for U.S. Appl. No. 10/546,538, filed Dec. 9, 2009.
Office Action (Final Rejection) for U.S. Appl. No. 10/546,538 mailed Jun. 8, 2010.
Response to Office Action (Notice of Appeal) for U.S. Appl. No. 10/546,538, filed Dec. 8, 2010.
Office Action (Communication re: Appeal) for U.S. Appl. No. 10/546,538 mailed Jul. 20, 2011.
1st Office Action for European Application No. 04722237.7 dated Mar. 2, 2006.
Reply to 1st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Amendment to Grant for European Application No. 04722237.7 dated Nov. 11, 2008.
Decision to Grant for European Application No. 04722237.7 dated Feb. 5, 2009.
European Search Report for European Application No. 09154197 mailed Sep. 15, 2010.
International Search Report for International Application No. PCT/DK2004/000195 mailed Dec. 27, 2004.
Restriction Requirement for U.S. Appl. No. 10/549,619 mailed Apr. 21, 2008.
Response to Restriction Requirement for U.S. Appl. No. 10/549,619, filed Sep. 22, 2008.
Office Action (Non-Final) for U.S. Appl. No. 10/549,619 mailed Apr. 28, 2009.
Response to Office Action for U.S. Appl. No. 10/549,619, filed Oct. 26, 2009.
Office Action (Interview Summary) for U.S. Appl. No. 10/549,619 mailed Mar. 3, 2010.
Amendment filed for U.S. Appl. No. 10/549,619, filed Oct. 21, 2010.
Notice of Allowance for U.S. Appl. No. 10/549,619 mailed Jul. 7, 2010.
Amendment After Allowance for U.S. Appl. No. 10/549,619, filed Oct. 6, 2010.
Issue Notification for U.S. Appl. No. 10/549,619 mailed Mar. 9, 2011.
Australian Application No. 2003273792.
Examination Report for Australian Application No. 2003273792 dated May 6, 2011.
Reply to 1st Office Action for European Application No. 03757752.5 dated Jan. 12, 2006.
Amendment after ESP for European Application No. 03757752.5 dated Feb. 14, 2006.
1st Office Action for European Application No. 03757752.5 dated Mar. 16, 2006.
2nd Office Action for European Application No. 03757752.5 dated Feb. 15, 2007.
Reply to 2nd Office Action for European Application No. 03757752.5 dated Aug. 15, 2007.
Summons for European Application No. 03757752.5 dated Aug. 11, 2008.
Letter for Oral Proceeding for European Application No. 03757752.5 dated Dec. 15, 2008.
Telephone Summary for European Application No. 03757752.5 dated Dec. 23, 2008.
Letter for Oral Proceeding for European Application No. 03757752.5 dated Jan. 2, 2009.
Oral Proceedings for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intent to Grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Office Action for Japanese Application No. 2005-501801 dated Apr. 6, 2010.
Office Action for Japanese Application No. 2005-501801 dated May 31, 2011.
International Search Report for International Application No. PCT/DK03/00739 mailed Aug. 30, 2004.
Restriction Requirement for U.S. Appl. No. 10/525,817 mailed May 9, 2007.
Response to Restriction Requirement for U.S. Appl. No. 10/525,817, filed Sep. 10, 2007.
Restriction Requirement for U.S. Appl. No. 10/525,817 mailed Nov. 28, 2007.
Response to Restriction Requirement for U.S. Appl. No. 10/525,817, filed Feb. 28, 2008.
Restriction Requirement for U.S. Appl. No. 10/525,817 mailed Jul. 7, 2009.
Response to Restriction Requirement for U.S. Appl. No. 10/525,817, filed Oct. 5, 2009.
Office Action (Non-Final) for U.S. Appl. No. 10/525,817 mailed Apr. 1, 2010.
Supplemental Office Action for U.S. Appl. No. 10/525,817 mailed Apr. 5, 2010.
Response filed for U.S. Appl. No. 10/525,817, filed Jul. 27, 2010.
Office Action (Non-Final) for U.S. Appl. No. 10/525,817 mailed Jan. 5, 2011.
Office Action (Interview Summary) for U.S. Appl. No. 10/525,817 mailed Jul. 1, 2011.
Response filed for U.S. Appl. No. 10/525,817, filed Jul. 5, 2011.
Restriction Requirement for U.S. Appl. No. 11/402,957 mailed Jun. 25, 2008.
Response to Restriction Requirement for U.S. Appl. No. 11/402,957, filed Aug. 25, 2008.
Office Action (Non-Final) for U.S. Appl. No. 11/402,957 mailed Nov. 28, 2008.
Response filed for U.S. Appl. No. 11/402,957, filed May 15, 2009.
Office Action (Non-Final) for U.S. Appl. No. 11/402,957 mailed Jul. 6, 2009.
Response filed for U.S. Appl. No. 11/402,957, filed Dec. 7, 2009.
Office Action (Final Rejection) for U.S. Appl. No. 11/402,957 mailed Feb. 16, 2010.
Response filed for U.S. Appl. No. 11/402,957, filed Jul. 28, 2010.
Notice of Appeal filed for U.S. Appl. No. 11/402,957, filed Aug. 16, 2010.
Notice of Allowance for U.S. Appl. No. 11/402,957 mailed Sep. 2, 2010.
Request for Continued Examination filed for U.S. Appl. No. 11/402,957, filed Dec. 2, 2010.

(56) References Cited

OTHER PUBLICATIONS

Second Notice of Allowance for U.S. Appl. No. 11/402,957 mailed Apr. 29, 2011.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to 2nd Office Action for European Application No. 04762850.8 dated Sep. 2, 2008.
Intent to Grant for European Application No. 04762850.8 dated Dec. 10, 2008.
Decision to Grant for European Application No. 04762850.8 dated Oct. 8, 2009.
Amendment after Grant for European Application No. 04762850.8 dated Jul. 17, 2009.
International Search Report for PCT/DK2004/000630 mailed Feb. 14, 2005.
Restriction Requirement for US U.S. Appl. No. 10/572,644 dated Feb. 4, 2009.
Response to Restriction Requirement for U.S. Appl. No. 10/572,644 dated Jul. 29, 2009.
Restriction Requirement for U.S. Appl. No. 10/572,644 dated Jul. 21, 2010.
Response to Restriction Requirement for U.S. Appl. No. 10/572,644, filed Jan. 19, 2011.
Office Action (Non-Final) for U.S. Appl. No. 10/572,644 dated Oct. 29, 2009.
Response to Office Action for U.S. Appl. No. 10/572,644, filed Apr. 28, 2010.
Office Action (Non-Final) for U.S. Appl. No. 10/572,644 dated Mar. 31, 2011.
1st Office Action for European Application No. 05715120.1 dated Apr. 12, 2007.
Reply to 1st Office Action for European Application No. 05715120.1 dated Feb. 1, 2008.
2nd Office Action for European Application No. 05715120.1 dated Mar. 25, 2008.
Reply to 2nd Office Action for European Application No. 05715120.1 dated Jan. 9, 2009.
Intent to Grant for European Application No. 05715120.1 dated May 7, 2009.
Amendment after Grant for European Application No. 05715120.1 dated Sep. 3, 2009.
Decision to Grant for European Application No. 05715120.1 dated Oct. 1, 2009.
International Search Report for International Application No. PCT/DK2005/000199 mailed Jan. 23, 2006.
Office Action for U.S. Appl. No. 10/593,868 mailed Mar. 30, 2009.
Response to Office Action for U.S. Appl. No. 10/593,868, filed Jul. 28, 2009.
Notice of Allowance for U.S. Appl. No. 10/593,868 mailed Nov. 16, 2009.
Amendment after Allowance for U.S. Appl. No. 10/593,868, filed Feb. 16, 2010.
Issue Notification for U.S. Appl. No. 10/593,868 mailed Apr. 7, 2010.
1st Office Action for European Application No. 05700655.3 dated Jun. 19, 2007.
Reply to 1st Office Action for European Application No. 05700655.3 dated Apr. 11, 2008.
2nd Office Action for European Application No. 05700655.3 dated Sep. 12, 2008.
Reply to 2nd Office Action for European Application No. 05700655.3 dated Jul. 9, 2009.
3rd Office Action for European Application No. 05700655.3 dated Aug. 12, 2009.
Reply to 3rd Office Action for European Application No. 05700655.3 dated Feb. 9, 2010.
Intent to Grant for European Application No. 05700655.3 dated Mar. 31, 2010.
Amendment after Grant for European Application No. 05700655.3 dated Nov. 11, 2010.
Decision to Grant for European Application No. 05700655.3 dated Dec. 2, 2010.
International Search Report for International Application No. PCT/DK2005/000106 mailed Sep. 12, 2005.
Restriction Requirement for U.S. Appl. No. 10/589,551 mailed Apr. 7, 2011.
1st Office Action for European Application No. 06818144.5 dated Dec. 11, 2008.
Reply to 1st Office Action for European Application No. 06818144.5 dated Oct. 30, 2009.
Intent to Grant for European Application No. 06818144.5 dated Feb. 23, 2010.
Amendment after Grant for European Application No. 06818144.5 dated Oct. 7, 2010.
Decision to Grant European Application No. 06818144.5 dated Nov. 5, 2010.
European Search Report for European Application No. 10 19 2716 mailed May 24, 2011.
Invitation to Identify Subject Matter for European Application No. 10 192 717.6 dated Jun. 1, 2011.
International Search Report for International Application No. PCT/DK2006/000685 mailed Jun. 14, 2007.
Communication pursuant to Rule 161(1) and 162 for European Application No. 09765460.2 dated Mar. 14, 2011.
Response to Rule 161(1) and 162 for European Application No. 09765460.2 dated Apr. 18, 2011.
International Search Report for International Application No. PCT/DK2009/050129 mailed Aug. 21, 2009.
Annex I: Vipergen Technology Paper—The YoctoReactor drug discovery technology platform. 2 pages.
Annex II: Vipergen Technology Paper—The YoctoReactor drug discovery technology platform. 2 pages. Aug. 2008.
Kahn, Jason. "DNA-ligases": http://adnadn.umd.edu/biochem/kahn/molmachines/replication/DNA%20ligase.htm downloaded Dec. 10, 2009.
Office Action in European application No. 07114663.3, dated Sep. 12, 2011.
Response to European Search Report in European application No. 10184311.8, dated Feb. 6, 2012.
Response to Office Action in European application No. 08169346.7, dated Feb. 10, 2012.
Office Action in European application No. 08169346.7, dated Feb. 24, 2012.
Annex to Office Action in European application No. 08169346.7, dated Feb. 24, 2012.
Response to Office Action in European application No. 09154197.9, dated Aug. 5, 2011.
Office Action in European application No. 09154197.9, dated Sep. 12, 2011.
Annex to Office Action in European application No. 09154197.9, dated Sep. 12, 2011.
European Search Report in European application No. 10183942.1, dated Feb. 6, 2012.
Communication re partial European Search Report in European application No. 10184069.2, dated Feb. 10, 2012.
Partial European Search Report in European application No. 10184069.2, dated Feb. 10, 2012.
Response to Invitation in European application No. 10192717.6, dated Aug. 5, 2011.
Communication re European Search Report in European application No. 10192717.6, dated Oct. 7, 2011.
Partial European Search Report in European application No. 10192717.6, dated Oct. 7, 2011.
Response to Partial European Search Report in European application No. 10192717.6, dated Dec. 8, 2011.
European Search Report in European application No. 10192717.6, dated Jan. 25, 2012.
European Search Opinion in European application No. 10192717.6, dated Jan. 25, 2012.

(56) References Cited

OTHER PUBLICATIONS

International Search Report in PCT/DK2011/000031, dated Aug. 23, 2011.
Opposition against EP 1558744 filed by Strawman Limited on Mar. 12, 2012.
Opposition against EP 1558744 filed HGF on Mar. 14, 2012.
Kinoshita et al. "Enzymatic synthesis of code regions for encoded combinatorial chemistry (ECC)." *Nucleic Acids Symposium Series* vol. 34: 1995. pp. 201-202.
Zhu et al. "A Primer-dependent Polymerase Function of *Pseudomonas aeruginosa* ATP-dependent DNA Ligase (LigD)." *J. of Bio. Chem.* vol. 280. No. 1. 2005. pp. 418-427.
Tan et al. "NAtrual-product inhibitors of human DNS ligase I." *Biochem. J.* vol. 314. 1996. pp. 993-1000.
Ito et al. "Tag-Reporter and Resin Capture ± Release Strategy in Oligosaccharide Synthesis." *Chem—A Euro. J.* vol. 8. No. 14. 2002. pp. 3077-3084.
Lim et al. "Synthesis of DNA dumbbells: chemical vs. enzymatic ligation of self-complementary oligonucleotides." *Nucleosides & Nucleotides* vol. 16 No. 1&2. 1997 pp. 41-51.
Schmitz et al. Solid-Phase Enzymatic Synthesis of Oligonucleotides. Organic Letters (1999) 1 (11): 1729-1731.
Pochet et al. "Solid-supported ligation primer." *Nucleic Acids Research* vol. 16. No. 4. 1988 pp. 1619.
Gryaznov et al. "Template controlled coupling and recombination of oligonucleotide blocks containing thiophosphoryl groups." *Nucleic Acids Research* vol. 21. No. 6. 1993 pp. 1403-1408.
Herpin et al. "Synthesis of a 10,000 Member 1,5-Benzodiazepine-2-one Library by the Directed Sorting Method." Journal of Combinatorial Chemistry vol. 2. 2000 pp. 513-521.
Braasch et al. Locked nucleic acid (LNA): ¢ne-tuning the recognition of DNA and RNA. Chemistry & Biology (2001) 8(1): 1-7.
Matsuda et al. "Low fdelity DNA synthesis by human DNA polymerase-n." Nature vol. 404. 2000 pp. 1011-1013.
Higgins et al. "Addition of oligonucleotides to the S'-tenninus of DNA by T4 RNA ligase." Nucleic Acids Research vol. 6. No. 3. 1979 pp. 1013-1024.
Barany, F. "Genetic disease detection and DNA amplification using cloned thermostable ligase." *Proceedings of the National Academy of Sciences*, USA vol. 88. 1991 pp. 189-193.
Canne et al. "Chemical Protein Synthesis by Solid Phase Ligation of Unprotected Peptide Segments." *Journal of the American Chemical Society* vol. 121. 1999 pp. 8720-8727.
Persichetti et al. "Cross-Linked Enzyme Crystals (CLECs) of Thermoly sin in the Synthesis of Peptides." *Journal of the American Chemical Society* vol. 117. 1995 pp. 2732-2737.
Sarmento et al. "Cardosins A and B, two new enzymes available for peptide synthesis." *Journal of Molecular Catalysis B: Enzymatic* vol. 5. 1998 pp. 327-330.
Brenner et al. "Encoded combinatorial chemistry." *Proceedings of the National Academy of Sciences*, USA vol. 89. 1992 pp. 5381-5383.
Abravaya et al. "Detection of point mutations with a modified ligase chain reaction (Gap-LCR)." *Nucleic Acids Research* vol. 23. No. 4. 1995 pp. 675-82.
Fredriksson et al. "Protein detection using proximity-dependent DNA ligation assays." *Nature Biotechnology* vol. 20. 2002 pp. 473-477.
Nemoto, N et al. "In vitro virus: bonding of mRNA bearing puromycin at the 3'-terminal end to the C-terminal end of its encoded protein on the ribosome in vitro." FEBS Lett. Sep. 8, 1997;414(2):405-8.
Roberts, RW et al. "RNA-peptide fusions for the in vitro selection of peptides and proteins". Proc Natl Acad Sci USA. Nov. 11, 1997;94(23):12297-302.
Kurz, M et al. "An efficient synthetic strategy for the preparation of nucleic acid-encoded peptide and protein libraries for in vitro evolution protocols" Fourth International Electronic Conference on Synthetic Organic Chemistry (ECSOC-4), www.mdpi.org/ecsoc-4.htm, Sep. 1-30, 2000.

Kurz, M et al. Psoralen photo-crosslinked mRNA-puromycin conjugates: a novel template for the rapid and facile preparation of mRNA-protein fusions. Nucleic Acids Res. Sep. 15, 2000;28(18):E83.
Keiler et al. "Role of a peptide tagging system in degradation of proteins synthesized from damaged messenger RNA". Science. Feb. 16, 1996;271(5251):990-3.
Benner, SA. "Expanding the genetic lexicon: incorporating non-standard amino acids into proteins by ribosome-based synthesis". Trends Biotechnol. May 1994;12(5):1 58-63.
Mendel, D."Site-directed mutagenesis with an expanded genetic code". Annu. Rev. Biophys. Biomol. Struc. 1995. 24:463-93.
Liu DR et al. "Engineering a tRNA and aminoacyl-tRNA synthetase for the site-specific incorporation of unnatural amino acids into proteins in vivo". Proc Natl Acad Sci USA. Sep. 16, 1997;94(19):10092-7.
Liu DR et al. "Progress toward the evolution of an organism with an expanded genetic code". Proc Natl Acad Sci USA. Apr. 27, 1999;96(9):4780-5.
Liu, R et al. "Optimized synthesis of RNA-protein fusions for in vitro protein selection". Methods Enzymol. 2000;318:268-93.
Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.
Ellman J.A., et al. " Biosynthetic method for introducing Unnatural Amino acids site specifically into proteins". Methods Enzymol. 202,301-336 (1992).
Jose Salas et al. "Biosynthetic Polydeoxynucleotides as Direct Templates for Polypeptide Synthesis". J. of Biological Chemistry, vol. 243, No. 6, 1968, p. 1012-1015.
Walder JA, Walder RY, Heller MJ, Freier SM, Letsinger RL, Klotz IM. "Complementary carrier peptide synthesis: general strategy and implications for prebiotic origin of peptide synthesis". Proc Natl Acad Sci USA. Jan. 1979;76(1):51-5.
Bruick et al. "Template-directed ligation of peptides to oligonucleotides" Chemistry and Biology, vol. 3, No. 1, Jan. 1996, p. 49-56.
Tamura K, Schimmel P. "Oligonucleotide-directed peptide synthesis in a ribosome- and ribozyme-free system". Proc Natl Acad Sci USA. Feb. 13, 2001:98(4):1393-7.
Lewis RJ, Hanawalt PC. "Ligation of oligonucleotides by pyrimidine dimers—a missing 'link' in the origin of life ?" 22;298(5872):393-6.
Liu J, Taylor JS. "Template-directed photoligation of oligodeoxyribonucleotides via 4-thiothymidine". Nucleic Acids Res. Jul. 1, 1998;26(13):3300-4.
Fujimoto et al. "Template-directed photoreversible ligation of deoxyoligonucleotides via 5-Vinyldeoxyuridine" J. Am. Soc. 2000, 122, 5646-5647.
Kenzo Fujimoto, Shigeo Matsuda, Naoki Ogawa, Masayuki Hayashi & Isao Saito "Template-directed reversible photocircularization of DNA via 5-vinyldeoxycytidine". Tetrahedron Letters 2000 , 41:33:6451-6454.
Kenzo Fujimoto, Naoki Ogawa, Masayuki Hayashi, Shigeo Matsuda & Isao Saito "Template directed photochemical synthesis of branched oligodeoxynucleotides via 5-carboxyvinyldeoxyuridine". Tetrahedron Letters 2000, 41:49:9437-40.
Letsinger et al. "Chemical Ligation of oligonucleotides in the presence and absence of a template". J. Amer. Chem. Soc. 1993, 115, 3808-9.
Gryaznov SM, Letsinger RL. "Template controlled coupling and recombination of oligonucleotide blocks containing thiophosphoryl groups". Nucleic Acids Res. Mar. 25, 1993:21(6):1403-8.
Gryaznov SM, Schultz R, Chaturvedi SK, Letsinger RL. "Enhancement of selectivity in recognition of nucleic acids via chemical autoligation". Nucleic Acids Res. Jun. 25, 1994;22(12):2366-9.
Herrlein MK, Letsinger RL. "Selective chemical autoligation on a double-stranded DNA template". Nucleic Acids Res. Nov. 25, 1994;22(23):5076-8.
Letsinger, RL; Wu, T; Elghanian, R "Chemical and photochemical ligation of oligonucleotide blocks". Nucleosides and nucleotides, 16(5&6), 643-652 (1997).

(56) References Cited

OTHER PUBLICATIONS

Visscher J, Schwartz AW "Template-directed synthesis of acyclic oligonucleotide analogues". J Mol Evol. Dec. 1988-Feb. 1989;28(1-2):3-6.
Visscher J, Bakker CG, van der Woerd R, Schwartz AW "Template-directed oligomerization catalyzed by a polynucleotide analog". Science. Apr. 21, 1989:244(4902):329-31.
Visscher J, van der Woerd R, Bakker CG, Schwartz AW. "Oligomerization of deoxynucleoside-bisphosphate dimers: template and linkage specificity". Orig Life Evol Biosph. 1989; 19(1):3-6.
Zhan, ZJ and Lynn, DG "Chemical Amplification through template-directed synthesis". J. Am. Chem. Soc. 1997, 119,12420-1.
Bruick RK, Koppitz M, Joyce GF, Orgel LE. "A simple procedure for constructing 5'-aminoterminated oligodeoxynucleotides in aqueous solution Nucleic Acids Res". Mar. 15, 1997;25(6):1309-10.
Albagli, D; Atta, RVA; Cheng, P; Huan, B and Wood, ML. "Chemical amplification (CHAMP) by a continuous, self-replicating oligonucleotide-based system" J. Am. Chem. Soc. 1999, 121, 6954-6955. Pub. on the web Jul. 14, 1999.
Xu, Y and Kool, E "Rapid and Selective selenium-mediated autoligation of DNA strands" J. Am. Chem. Soc. 2000, 122, 9040-1 Pub. on web Aug. 31, 2000.
Xu Y, Karalkar NB, Kool ET "Nonenzymatic autoligation in direct three-color detection of RNA and DNA point mutations". Nat Biotechnol. Feb. 2001;19(2):148-52.
Li X, Zhan ZY, Knipe R,Lynn DG. "DNA-catalyzed polymerization". J Am Chem Soc. Feb. 6, 2002;124(5):746-7.
Czlapinski, JL and Sheppard. TL. "Nucleic acid template-directed assembly of metallosalen-DNA conjugates". J Am Chem Soc. Sep. 5, 2001;123(35):8618-9 published on the web Aug. 10, 2001.
Leitzel JC, Lynn DG "Template-directed ligation: from DNA towards different versatile templates". Chem Rec. 2001; 1(1):53-62. Published online Jan. 30, 2001.
Schmidt JG, Nielsen PE, Orgel LE. "Information transfer from peptide nucleic acids to RNA by template-directed syntheses". Nucleic Acids Res. Dec. 1, 1997;25(23):4797-802.
Dower, WJ et al. "In vitro selection as a powerful tool for the applied evolution of proteins and peptides".Current Opinion in Chemical Biology, 2002, 6:390-398.
Brenner, S and Lerner, RA. "Encoded combinatorial chemistry" Proc. Natl. Acad. Sci. USA. vol. 89. p. 5381-5383, Jun. 1992.
Gartner, Z; Liu, DR "The generality of DNA-templated synthesis as a basis for evolving non-natural small molecules". J Am Chem Soc. Jul. 18, 2001;123(28):6961-3.
David Liu. "Expanding the reaction scope of DNA-templated synthesis Angew". Chem. Int. Ed. 2002, 41, No. 10 pp. 1796-1800. Published May 15, 2002.
Gartner, ZJ et al. "Multistep small-molecule synthesis programmed by DNA templates". J. Am. Chem. Soc. vol. 124. No. 35, 2002, 10304-10306.
Calderone. CT et al. "Directing otherwise incompatible reactions in a single solution by using DNA-templated organic synthesis". Angew Chem Int Ed, 2002, 41, No. 21. 4104-4108.
Bittker. JA; Phillips, KJ and Liu, DR "Recent advances in the in vitro evolution of nucleic acids". Curr Opin Chem Biol. Jun. 2002;6(3):367-74. Review. Pub. on the web Mar. 20, 2002.
Summerer, D and Marx, A "DNA-templated synthesis: more versatile than expected". Angew Chem Int Ed Engl. Jan. 4, 2002;41(1):89-90. Review.
Gartner, ZJ et al. "Two enabling architectures for DNA-templated organic synthesis". Angew. Chem Int. Ed. 2003, 42. No. 12, 1370-1375.
Rosenbaum, DM et al. "Efficient and sequence-specific DNA-templated polymerization of peptide nucleic acid aldehydes". J. Am. Chem. Soc. vol. 125. No. 46, 2003. 13924-13925.
Li, X et al. "Stereoselectivity in DNA-templated organic synthesis and its origins". J. Am. Chem. Soc. vol. 125, No. 34, 2003, 10188-10189.

Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994.
Otto, S et al. S "Recent developments in dynamic combinatorial chemistry". Current opinion in Chemical Biology 2002,6: 321-327.
Pavia, MR. "The Chemical generation of molecular diversity". http://www.netsci.org/Science/Combichem/feature01.html.
Braun, E, et al. "DNA-templated assembly and electrode attachment of a conducting silver wire". Nature, vol. 391, Feb. 19, 1998, 775-778.
Tanaka. K et al. "Synthesis of a novel nucleoside for alternative DNA base pairing through metal complexation" J. Org. Chem. 1999, 64, 5002-5003.
Beger. M et al. "Universal bases for hybridization. replication and chain termination". Nucleic acids research, Oxford University Press, vol. 28, No. 15, pub. Aug. 1, 2000, p. 2911-2914.
Weizman. H et al. "2.2'-Bipyridine ligandoside: a novel building block for modifying DNA with intra-duplex metal complexes". J. Am. Chem. Soc. 2001, 123, 3375-3376.
Frutos. AG et al. "Demonstration of a word design strategy for DNA computing on surfaces". Nucleic Acids Research, 1997. vol. 25, No. 23, 4748-4757.
Loweth. CJ et al. "DNA-based assembly of gold nanocrystals". Angew. Chem. Int. Ed. 1999, 38, No. 12, 1808-1812.
Elghanian, R et al. "Selective colorimetric detection of polynucleotides based on the distance-dependent optical properties of gold nanoparticles". Science, vol. 277, Aug. 22, 1997.
Storhoff, JJ and Mirkin. CA. "Programmed Materials Synthesis with DNA". Chem Rev. Jul. 14, 1999;99(7):1849-1862.
Mirkin CA. "Programming the assembly of two- and three-dimensional architectures with DNA and nanoscale inorganic building blocks". Inorg Chem. May 29, 2000;39(11):2258-72.
Waybright SM, Singleton CP, Wachter K, Murphy CJ, Bunz UH. "Oligonucleotide-directed assembly of materials: defined oligomers". J Am Chem Soc. Mar. 7, 2001;123(9):1828-33. Pub. on web Feb. 7, 2001.
Bruce Smith and Markus Krummenacker "DNA-guided assembly of proteins as a pathway to an assembler" (http//:www.wadsworth.org/albcon97/abstract/krummena.htm) The 1997 Albany Conference: Biomolecular Motors and Nanomachines.
DeWitt, SH et al. "Diversomers: an approach to nonpeptide, nonoligomeric chemical diversity". Proc. Natl. Acad. Sci, USA, vol. 90, pp. 6909-6913. Aug. 1993.
Nielsen, J et al. "Synthetic methods for the implementation of encoded combinatorial chemistry". J. Am. Chem. Soc. 1993,115,9812-9813.
Ohlmeyer. MHJ et al. "Complex synthetic chemical libraries indexed with molecular tags". Proc. Natl. Acad. Sci. USA, vol. 90, pp. 10922-10926. Dec. 1993, Chemistry.
Zuckermann, RN et al. "Discovery of nanomolar ligands for 7-transmembrane G-protein-coupled receptors from a diverse N-(substituted) glycine peptoid library". J. Med. Chem. 1994, 37, 2678-2685.
Luo, P et al. "Analysis of the structure and stability of a backbone-modified oligonucleotide: implications for avoiding product inhibition in catalytic template-directed synthesis". J. Am. Chem. Soc. 1998, 120, 3019-3031.
Luther, A et al. "Surface-promoted replication and exponential amplification of DNA analogues". Nature, vol. 396, Nov. 19, 1998, 245-248.
Klekota, B et al. "Selection of DNA-Binding Compounds via Multistage Molecular Evolution". Tetrahedron 55 (1999) 11687-11697.
Furlan, RLE et al. "Molecular amplification in a dynamic combinatorial library using non-covalent interactions". Chem. Commun., 2000, 1761-1762.
Ramstrom, O et al. "In situ generation and screening of a dynamic combinatorial carbohydrate library against concanavalinA". ChemBioChem, 2000,1, 41-48.
Cousins, GRL et al. "Identification and Isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.

(56) References Cited

OTHER PUBLICATIONS

Roberts. SI et al. "Simultaneous selection, amplification and isolation of a pseudo-peptide receptor by an immobilised N-methyl ammonium ion template". Chem. Commun., 2002. 938-939.
Furka, A "Combinatorial Chemistry: 20 years on . . . " Drug discovery today vol. 7, No. 1. p1-4, 2002.
Nielsen, J et al. "Synthetic Methods for the Implementation of Encoded Combinatorial Chemistry" J. Am. Chem. Soc., 1993, 115, 9812-9813.
Needels, CM et al. "Generation and screening of an oligonucleotide-encoded synthetic peptide library" Proc. Natl. Acad. Sci., USA, vol. 90, pp. 10700-10704. Nov. 1993, Chemistry.
Kerr, JM et al. "Encoded Combinatorial Peptide Libraries Containing Non-Natural Amino Acids" J. Am. Chem. Soc., USA. 1993, 115, 2529-2531.
Ohlmeyer, MHJ et al. "Complex synthetic chemical libraries indexed with molecular tags" Proc. Natl. Acad. Sci., USA. vol. 90, pp. 10922-10926, Dec. 1993, Chemistry.
Nestler, HP et al. "A general Method for Molecular Tagging of Encoded Combinatorial Chemistry Libraries" J. Org. Chem., 1994, 59, 4723-4724.
Baldwin, JJ et al. "Synthesis of a Small Molecule Combinatorial Library Encoded with Molecular Tags" J. Am. Chem. Soc. 1995, 117, 5588-5589.
Nikolaiev, v et al. "Peptide-Encoding for structure determination of nonsequenceable polymers within libraries synthesized and tested on solid-phase supports" Peptide Research, vol. 6, No. 3, 1993. pp. 161-170.
"The Nucleus", Jan. 2004, vol. LXXXII, No. 5, R. Grubina; "Summer Research Report: R. Grubina on DNA Templated Synthesis for Small Molecule Library", p. 10-14.
Nazarenko et al., "A closed tube format for amplification and detection of DNA based on energy transfer", Nucleic Acids Research, 1997, vol. 25, No. 12, p. 2516-2521.
Chan et al., "Intra-tRNA distance measurements for nucleocapsid protein-dependent tRNA unwinding during priming of HIV reverse transcription", PNAS vol. 96, p. 459-464, Jan. 1999.
DNA-templated synthesis as a basis for the evolution of synthetic molecules. Liu DR, Gartner ZJ, Kanan MW, Calderone CT, Abstracts of Papers of the American Chemical Society 225: 612-0RGN, Part 2, Mar. 2003.
Rodriguez et al., "Template-directed extension of a guanosine 5'-phosphate covalently attached to anoligodeoxycytidylate template", J Mol Evol (1991) 33:477-482.
Inoue et al, Oligomerization of (Guanosine 5'-phosphor)-2-methylimidazolide on Poly(C), J. Mol. Biol. (1982), 162, 201-217.
HC C. B. Chen et al., "Template-directed synthesis on Oligodeoxycytidylate and Polydeoxycytidylate templates" J. Mol. Biol. 1985,181. 271.
H. Rembold et al., "Single-strand regions of Poly(G) act as templates for oligo(C) synthesis", J. Mol. Evol. 1994, 38, 205.
T. Inoue et al., "A nonenzymatic RNA polymerase model", Science 1983, 219, p. 859-862.
O. L. Acevedo et al., "Non-enzymatic transcription of an oligonucleotide 14 residues long", J. Mol. Biol. 1987, 197, p. 187-193.
C. Bohler et al., "Template switching between PNA and RNA oligonucleotides", Nature 1995, 376, 578-581.
Acevedo et al., "Template-directed oligonucleotide ligation on hydroxylapatite", Nature vol. 321, Jun. 19, 1986, p. 790-792.
Piccirilli, "RNA seeks its maker", Nature vol. 376, Aug. 17, 1995, p. 548-549.
A. W. Schwartz et al., "Template-directed synthesis of novel, nucleic acid-like structures", Science 1985, 228, 585-7.
Halpin et al.: DNA display III. Solid-phase organic synthesis on unprotected DNA. PLoS Biol. Jul. 2004;2(7):E175. Epub Jun. 22, 2004.
Halpin et al.: DNA display II. Genetic manipulation of combinatorial chemistry libraries for small-molecule evolution. PLoS Biol. Jul. 2004;2(7):E174. Epub Jun. 22, 2004.
Halpin et al.: DNA display I. Sequence-encoded routing of DNA populations. PLoS Biol. Jul. 2004;2(7):E173. Epub Jun. 22, 2004.
"Highly Sensitive In Vitro Selections for DNA-Linked Synthetic Small Molecules with Protein Binding Affinity and Specificity", Doyon, J. B.; Snyder. T. M.; Liu, D. R. J. Am. Chem. Soc. 125, 12372-12373 (2003).
"Translation of DNA into Synthetic N-Acyloxazolidines", Li, X.; Gartner, Z. J.; Tse, B. N.; Liu, D. R., J. Am. Chem. Soc. 126, 5090-5092(2004).
"DNA-Templated Organic Synthesis: Nature's Strategy for Controlling Chemical Reactivity Applied to Synthetic Molecules", Li, X.; Liu, D. R., Angew. Chem. Int. Ed. 43, 4848-4870 (2004).
"DNA-Templated Organic Synthesis and Selection of a Library of Macrocycles" Gartner, Z. J.; Tse, B. N.; Grubina, R.; Doyon, J. B.; Snyder, T. M.; Liu, D. R., Science 305,1601-1605 (2004).
"Nucleic Acid-Templated Synthesis as a Model System for Ancient Translation",Calderone, C. T. and Liu, D. R., Curr. Opin. Chem. Biol. 8, 645-653 (2004).
"DNA-Templated Functional Group Transformations Enable Sequence-Programmed Synthesis Using Small-Molecule Reagents", Sakurai, K.; Snyder, T. M.; Liu, D. R. J., Am. Chem. Soc. 127, 1660-1661 (2005).
Translating DNA into synthetic Molecules, David R. Liu, PLoS Biology, Jul. 2004, vol. 2, Iss. 7, p. 905-6.
"The Development of Amplifiable and Evolvable Unnatural Molecules", David R. Liu, Harvard Univ. Cambridge MA Dept of Chemistry and Chemical Biology, Report dated Aug. 4, 2003 No. A104614, approved for public release.
Website of Prof. David R. Liu, publicly available Mar. 11, 2000.
Website of Prof. David R. Liu, publicly available Oct. 15, 2000.
Website of Prof. David R. Liu, publicly available Mar. 1, 2001.
Website of Prof. David R. Liu, publicly available Apr. 19, 2001.
Website of Prof. David R. Liu, publicly available Sep. 23, 2001.
Website of Prof. David R. Liu, publicly available Sep. 24, 2002.
Website of Prof. David R. Liu, publicly available Nov. 20, 2002.
Website of Prof. David R. Liu, publicly available Oct. 15, 2003.
Doyon, J.B et al. "Highly sensitive in vitro selections for DNA-linked synthetic small molecules with protein binding affinity and specificity", J. Am. Chem. Soc, Sep. 16, 2003.
Kanan, M.W et al. "Reaction discovery enabled by DNA-templated synthesis and in vitro selection", Nature, vol. 431, Sep. 30, 2004.
"Finding reactions in a haystack: Try'em all, see what works", Meeting American Chemical Society, Sep. 10, 2004, vol. 305, Science.
Fredriksson et al., "Protein detection using proximity-dependent DNA ligation assays", Nature Biotechnology, vol. 20, p. 473-477, May 2002.
Lowe et al., "Combinatorial Libraries for Studying Molecule Recognition", URL: http://www.iupac.org/svmposia/proceedings/phuket97/lowe.html, downloaded in Jun. 2005.
Czarnik et al., "Encoding methods for combinatorial chemistry", Current Opinion in Chemical Biology vol. 1, Iss 1, Jun. 1997, p. 60-66.
Battersby et al., "Optical encoding of micro-beads for gene screening: alternatives to micro-arrays", Drug Discovery Today, vol. 6, Supp 1, Jun. 1, 2001, p. 19-26.
Shchepinov et al., "Trityl tags for encoding in combinatorial synthesis", Tetrahedron 56 (2000) 2713-2724.
Geysen et al., "Combinatorial Compound Libraries for Drug Discovery: An Ongoing Challenge", Nature Reviews, Drug Discovery, vol. 2, Mar. 2003, p. 222-230.
Fujimoto, et al., "Template-directed photoreversible ligation of deoxyoligonucleotides via 5-Vinyldeoxyuridine", J. Am. Chem. Soc., vol. 122, pp. 5646-5647, 2000.
Gartner, et al., "Expanding the reaction scope of DNA-templated synthesis", Angew. Chem. Int. Ed., vol. 41, No. 10, pp. 1796-1800, 2002.
Giebel L.B.; et al; "Screening of cyclic peptide phage libraries identifies ligands that bind straptavidin with high affinities" Biochemistry, vol. 34, 1995; pp. 15430-15435.
Gryaznov, et al., "Chemical Ligation of oligonucleotides in the presence and absence of a template", J. Amer. Chem. Soc. , vol. 115, pp. 3808-3809, 1993.

(56) References Cited

OTHER PUBLICATIONS

Kanan, M.W et al. "Reaction discovery enabled by DNA-templated synthesis and in vitro selection", Nature, vol. 431, 2004, pp. 545-549.
Koivunen E. et al: "Phage libraries displaying cyclic peptides with different ring sizes: Ligand Specificities of the RGD-directed Integrins" Bio/Technology, Nature Publ. Co. NY, US; vol. 13, 1995; pp. 265-270.
Kurz, M., et al. Psoralen photo-crosslinked mRNA-puromycin conjugates: a novel template for the rapid and facile preparation of mRNA-protein fushion. Nucleic Acids Res. 2000; 28(18):E83.
Ladner R.C.; "Constrained peptides as binding entities." Trends in Biotechnology, Elsevier Publ.; Cambridge GB, vol. 13, 1995; pp. 426-430.
Millward; S.W. et al.; "A General Route for Post-Translational Cyclization of mRNA Display Libraries" Journal of the American Chemical Society, American Chemical Society Washington DC; US; vol. 127; 2005; pp. 14142-14143.
Millward; S.W. et al.; "Design of cyclic peptides that bind protein surfaces with antibody-like affinity" ACS Chemical Biology, American Chemical Society; Washington, DC, US vol. 2, No. 9; 2007; pp. 625-634.
Roberts, RW., et al. "RNA-peptide fusions for the in vitro selection of peptides and proteins.", Proc Natl Acad Sci USA. 1997; 94:12297-122302.
Response to Office Action in EP 07114663.3 dated Jul. 4, 2012.
2nd Office Action in EP 07114663.3 dated Jul. 23, 2012.
Response to Office Action in EP 07114663.3 dated May 17, 2013.
3rd Office Action in European patent application No. 07114663.3 dated Jun. 3, 2013.
EESR Office Action in EP 10184311.8 dated Mar. 19, 2012.
Response to 1st Office Action of Mar. 19, 2012 in EP 10184311.8 submitted Jan. 18, 2013.
2nd Office action dated Feb. 6, 2013 in EP 10184311.8.
Response to 2nd Office Action of Feb. 24, 2012 in EP 08169346.7 submitted Dec. 21, 2012.
3rd Office Action dated Jan. 29, 2013 in EP 08169346.7.
Response to 4th Office Action dated Jun. 9, 2011 in EP 03766117.0 submitted Mar. 14, 2012.
5th Office Action from European Application No. 03766117.0 dated May 31, 2012.
Office Action from European Application No. 03766117.0 dated Mar. 26, 2013.
Reply to first Office Action Reply to 1 st Office Action for European Application No. 04722237.7 dated Dec. 20, 2006.
Intention to grant Intent to Grant for European Application No. 04722237.7 dated Jan. 18, 2008.
Comm. 71(3) in European patent appliction No. 09154197.9 dated Aug. 7, 2012.
Decision to Grant dated Oct. 10, 2013 re European patent appliction No. 09154197.9.
Response to oppositions against EP 1558744 submitted Dec. 5, 2012.
Written submissions re EP 1558744 submitted Sep. 11, 2013 by proprietor.
Written submissions re EP 1558744 submitted Sep. 12, 2013 by opponent.
Response to ESR of Feb. 6, 2012 re European Patent Application No. 10183942.1 submitted Jan. 9, 2013.
1st Office Action for European Patent Application No. 10183942.1 dated Feb. 11, 2013.
Partial European Search Report dated Feb. 3, 2012.
European Search Report issued Jun. 6, 2012 re EP 10184069.2.
Response dated Apr. 12, 2013 to European Search Report issued in European Patent Application No. 10184069.2.
1st Office Action for European Patent Application No. 10184069.2 dated Jul. 3, 2013.
EESR Office Action in European patent application No. 10192716.8 dated Jul. 30, 2012.
EESR Office Action in European patent application No. 10192716.8 dated Jul. 3, 2013.
Invitation to identify subject matter for search Response to ESR dated Jan. 25, 2012 submitted Dec. 5, 2012.
Invitation to identify subject matter for search Office Action dated Jul. 16, 2013 re European patent application No. 10192717.6.
European Office Action from EP 09765460.2 dated May 7, 2012.
Response to office action re 09765460.2 submitted Feb. 22, 2013.
Communication pursuant to Rule 161(1) and 162 for European Application No. 11720372.9 dated Dec. 12, 2012.
Notice of Acceptance for Australian Application No. 2003273792 dated Jun. 22, 2011.
Response to OA dated Mar. 26, 2012 re Canadian patent application No. 2,544,153.
Office action of Aug. 20, 2012 re Canadian patent application No. 2,544,153.
Office Action in Chinese patent application No. 200380104764.5 dated Feb. 29, 2012.
Notice of Allowance of Sep. 3, 2012 re Chinese patent application No. 200380104764.5.
Office Action in Israeli patent application No. 207672 dated Jan. 15, 2012.
Barnes et al., "Recent developments in the encoding and deconvolution of combinatorial libraries", Current Opinions in Chemical Biology 2000, 4:346-350.
Chen et al., "Total Synthesis of Naturally Occurring Prostaglandin F2a on a Non-Cross-Linked Polystyrene Support", Tetrahedron Letters 39 (1998) 3943-3946.
Coe et al., "Solution-phase combinatorial chemistry", Molecular Diversity, 4: 31-38, 1999.
Dolle, "Comprehensive Survey of Combinatorial Library Synthesis: 2000", Journal of Combinatorial Chemistry, 2001, vol. 3, No. 6, pp. 477-517.
Dolle, "Comprehensive Survey of Combinatorial Library Synthesis: 2001", Journal of Combinatorial Chemistry, 2002, vol. 4, No. 5, pp. 369-418.
Dolle, "Comprehensive Survey of Combinatorial Library Synthesis: 2002", Journal of Combinatorial Chemistry, 2003, vol. 5, No. 6, pp. 693-753.
Furka et al., "General method for rapid synthesis of multicomponent peptide mixtures", Int. J. Peptide Protein Res., 37, 1991, 487-493.
Gallop et al., "Applications of Combinatorial Technologies to Drug Discovery. 1. Background and Peptide Combanitorial Libraries", Journal of Medicinal Chemistry, 1994, vol. 37, No. 9, pp. 1233-1251.
Guillen Schlippe et al., "In Vitro Selection of Highly Modified Cyclic Peptides That Act as Tight Binding Inhibitors", J. Am. Chem. Soc. 2012, 134, 10469-10477.
Han et al., "Liquid-phase combinatorial synthesis", Proc. Natl. Acad. Sci. USA, vol. 92, pp. 6419-6423, Jul. 1995.
www.wikipedia.org/wiki/DNA-encoded chemical library Oct. 2, 2012, pp. 1-12.
http://www2.umt.edu/medchem/teaching/medchem/mclect14.htm, Thompson C. M., Medicinal Chemistry, lecture 14, Pharmaceutical Sciences 621 & Chemistry 569, 2012.
Li et al., "Kinetics of RNA Degradation by specific base catalysis of transesterification involving the 2'-hydroxyl group", J. Am. Chem. Soc., 1999, 121, pp. 5364-5372.
Ma et al., "In Vitro Selection of Unnatural Cyclic Peptide Libraries via mRNA Display", Book Ribosome Display and Related Technologies, ch. 21, pp. 367-390, 2012.
MacLean et al., "Glossary of terms used in combinatorial chemistry", Pure Appl. Chem., vol. 71, No. 12, pp. 2349-2365, 1999.
Meier et al, "Combinatorial Methods, Automated Synthesis and High-Throughput Screening in Polymer Research: The Evolution Continues", Macromol. Rapid Commun. 2004, 25, 21-33.
Chorghade, "Drug discovery and development", 2006, ISBN-13: 978-0-471-39848-6, Published by John Wiley & Sons, Inc., Hoboken, New Jersey.
Needels et al., "Generation and screening of an oligonucleotide-encoded synthetic peptide library", Proc. Natl. Acad. Sci. USA, vol. 90, pp. 10700-10704, Nov. 1993.
Ni et al., "Versatile Approach to Encoding Combinatorial Organic Syntheses Using Chemically Robust Secondary Amine Tags", J. Med. Chem. 1996, 39, 1601-1608.

(56) References Cited

OTHER PUBLICATIONS

Nicolaou et al., "Radiofrequency Encoded Combinatorial Chemistry", Angew. Chem. Int. Ed. Engl., 1995, 34, No. 20, pp. 2289-2291.
Noren et al., "A general method for site-specific incorporation of unnatural aminoacids into protein", Science, American Association for the advancement of science, Washington, DC, vol. 244, 1989, pp. 182-188.
Starck et al., "The puromycin route to assess stereo- and regiochemical constraints on peptide bond formation in eukaryotic ribosomes", J. Am. Chem. Soc., 2003, 125, 8090-8091.
Studer et al., "Fluorous Synthesis: A Fluorous-Phase Strategy for Improving Separation Efficiency in Organic Synthesis", 1997, Science 275, pp. 823-826.
Terrett et al., "Combinatorial synthesis—The design of compound libraries and their application to drug discovery", Tetrahedron, 1995, vol. 51, No. 30., pp. 8135-8173.
Website: "Combinatorial chemistry", http://www.ukessays.co.uk/essays/chemistry/combinatorial-chemistry.php, Oct. 29, 2012, pp. 1-11.
Wermuth et al., "Glossary of terms used in medical chemistry", Pure & Appl. Chem, 1998, vol. 70, No. 5, pp. 1129-1143.
Ymane et al., "Discrimination between D- and L-Tyrosyl transfer ribonucleic acids in peptide chain elongation", Biochemistry, vol. 20, No. 25, Dec. 8, 1981, pp. 7059-7064.
Lipinski et al., "Experimental and computational approaches to estimate solubility and permeability in drug discovery and development settings", Adv. Drug Deliv. Rev., vol. 46, 2001, pp. 3-26.
Lipinski, "Lead- and drug-like compounds: the rule-of-five revolution", Drug Discovery Today: Technologies, vol. 1, No. 4, 2004, pp. 337-341.
Kleiner et al., "Small-molecule discovery from DNA-encoded chemical libraries", Chem. Soc. Rev., 2011, 40, pp. 5707-5717.
http://en.wikipedia.org/wiki/Scaffold_protein, 2013.
Balkenhohl et al., "Combinatorial synthesis of small organic molecules", Angew Chem Int. Ed Engl. 1996, 35, pp. 2288-2337.
Strachan, "Human Molecular Genetics", 2nd edition, textbook published by Wiley-Liss, 1999.
Bain et al., "Regioselective Ligation of Oligoribonucleotides using DNA Splints", Nucl. Acids Res., vol. 20, No. 16, 4372, 1992.
Boger & Goldberg "Chapter 10: Multi-step Solution Phase Combinatorial Synthesis" in Combinatorial Chemistry, ed. Hicham Fenniri, Oxford University Press (Oxford, England), 2000, pp. 303-326.
Cheng et al., "Novel Solution Phase Strategy for the Synthesis of Chemical Libraries Containing Small Organic Molecules", J. Am. Chem. Soc., vol. 118, 2567-2573, 1996.
Clark et al., "Design, Synthesis and Selection of DNA-encoded Small-molecule Libraries", Nat. Chem. Biol., vol. 5, No. 9, 647-772, 2009.
Curran, "Strategy-Level Separations in Organic Synthesis: From Planning to Practise", Angew. Chem. Int. Ed., vol. 37, 1174-1196, 1998.
Declaration by Dr. Dennis Benjamin (including curriculum vitae), 2013.
Frutos et al. "Enzymatic Ligation Reactions of DNA "Words" on Surfaces for DNA Computing", J. Am. Chem. Soc., vol. 120, No. 40, 10277-10282, 1998.
Gait, "Chapter 1: An Introduction to Modern Methods of DNA Synthesis": Van Boom & Wreesman, "Chapter 7: Chemical Synthesis of Small Oligoribonucleotides in solution"; and Beckett & Uhlenbeck, "Chapter 8: Enzymatic Synthesis of Oligoribonucleotides", in Oligonucleotide Synthesis: A Practical Approach, ed. M.J. Gait, IRL Press (Oxford, England and Washington, DC), 1984, pp. 1-22, 153-183, and 185-197.
Gartner et al., "Expanding the Reaction Scope of DNA-Templated Synthesis", Angew. Chem. Int. Ed., vol. 41, No. 10, 1796-1800, 2002.
Gartner et al., "Multistep Small-Molecule Synthesis Programmed by DNA Templates", J. Am. Chem. Soc., vol. 124, No. 35, 10304-10306 (including Supporting Information, pp. 1-4).
Glen Research Report, "Advances in RNA Synthesis and Structural Analysis", vol. 11, No. 2, Dec. 1998.
Harrison et al., "Synthesis and Hybridization Analysis of a Smal Library of Peptide-oligonucleotide Conjugates", Nucl. Acids Res., vol. 26, No. 13, 3136-3145, 1998.
Hausch et al., "Libraries of Multifunctional RNA Conjugates for the Selection of New RNA Catalysts", Bioconjugate Chem., vol. 8, 885-890, 1997.
Hill et al., "Diels-Alder Bioconjugation of Diene-Modified Oligonucleotides", J. Org. Chem., vol. 66, 5352-5358, 2001.
Itakura et al., "Expression in *Escherichia coli* of a Chemically Synthesized Gene for the Hormone Somatostatin", Science, vol. 198, 1056-1063, 1977.
Janda, "Tagged Versus Untagged Libraries: Methods for the Generation and Screening of Combinatorial Chemical Libraries," PNAS USA, vol. 91, 10779-10785, 1994.
Kelemen et al., "Hypersensitive Substrate for Ribonucleases", Nucl. Acids. Res., vol. 27, No. 18, 3696-3701, 1999.
Response to OA in Israeli patent application No. 207672 dated Jun. 14, 2012.
Office Action in Israeli patent application No. 207672 dated May 28, 2013.
Office Action in Israeli patent application No. 207673 dated Jan. 15, 2012.
Response to OA in Israeli patent application No. 207673 dated Jun. 14, 2012.
Office Action in Israeli patent application No. 207673 dated May 28, 2013.
Appeal filed for Indian patent application No. 178/MUMNP/2007 dated Nov. 15, 2011.
Office Action of Jul. 10, 2012 re Japanese Application No. 2010-226107.
Office Action of Jan. 29, 2013 re Japanese patent application No. 2010-226107.
Decision of dismissal of amendment dated Aug. 20, 2013 re Japanese patent application No. 2010-226107.
Non-final Rejection dated Oct. 13, 2005 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Supplemental response submitted Jun. 2, 2010 re U.S. Appl. No. 12/330,709.
Ex parte Quyale Action dated Jul. 27, 2010 re U.S. Appl. No. 12/330,709.
Response of Jan. 10, 2011 to Ex parte Quayle Action re U.S. Appl. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
Final rejection dated Oct. 28, 2013 re U.S. Appl. No. 12/330,709.
Non-final Rejection dated Jul. 3, 2013 re U.S. Appl. No. 12/179,323.
Response submitted Sep. 16, 2011 to non-final rejection re U.S. Appl. No. 10/523,006.
Response submitted Oct. 11, 2013 re U.S. Appl. No. 10/523,006.
Response after Non-final rejection submitted Oct. 25, 2011 re U.S. Appl. No. 10/539,288.
Notice of Appeal filed Jun. 18, 2012 re U.S. Appl. No. 10/539,288.
Response after Non-final rejection submitted Feb. 28, 2013 re U.S. Appl. No. 10/539,288.
Non-final rejection dated Apr. 16, 2013 re U.S. Appl. No. 10/539,288.
Response to Non-final rejection submitted Sep. 16, 2013 re U.S. Appl. No. 10/539,288.
Second amendment after Notice of Appeal submitted Sep. 28, 2009 re U.S. Appl. No. 10/545,795.
Advisory Action dated Oct. 21, 2009 re U.S. Appl. No. 10/545,795.
Interview summary dated Jul. 15, 2010 re U.S. Appl. No. 10/545,795.
Notice of Appeal filed Jul. 27, 2011 re U.S. Appl. No. 10/545,795.
Final rejection dated Apr. 11, 2013 re U.S. Appl. No. 13/179,283.
Notice of Appeal filed Sep. 11, 2013 re U.S. Appl. No. 13/179,283.

(56) References Cited

OTHER PUBLICATIONS

Response after Non-final Rejection submitted Oct. 26, 2009 re U.S. Appl. No. 10/549,619.
RCE dated Jul. 28, 2011 re U.S. Appl. No. 11/402,957.
Third Notice of Allowance dated Oct. 31, 2011 re U.S. Appl. No. 11/402,957.
RCE dated Dec. 12, 2011 re U.S. Appl. No. 11/402,957.
Preliminary amendment Nov. 21, 2012 re U.S. Appl. No. 11/402,957.
Non-final Rejection dated May 22, 2013 re U.S. Appl. No. 11/402,957.
Response to Non-final rejection submitted Sep. 23, 2013 re U.S. Appl. No. 11/402,957.
Response submitted Sep. 30, 2011 to Non final rejection re U.S. Appl. No. 10/572,644.
Notice of Appeal filed Jul. 6, 2012 re U.S. Appl. No. 10/572,644.
Response submitted Oct. 7, 2011 to Restriction Requirement re U.S. Appl. No. 10/589,551.
Non-final rejection dated Oct. 26, 2011 re U.S. Appl. No. 10/589,551.
Office Action dated Apr. 15, 2013 re U.S. Appl. No. 12/095,778.
Response dated May 15, 2013 to Restriction Requirement re U.S. Appl. No. 12/095,778.
Non-final rejection dated Oct. 8, 2013 re U.S. Appl. No. 12/095,778.
Adang et al., "The Contribution of Combinatorial Chemistry to Lead Generation: An Interim Analysis", Current Medicinal Chemistry, 2001, 8, 985-998.
Affleck, "Solutions for library encoding to create collections of discrete compounds", Current Opinion in Chemical Biology, 2001, 5:257-263.
Bain et al., "Biosynthetic site-specific incorporation of a non-natural amino acid into a polypeptide", J. Am. Chem. Soc., 1989, 111, 8013-8014.
Kempe et al., "Chemical and Enzymatic Biotin-labeling of Oligodeoxyribonucleotides", Nucl. Acids Res., vol. 13, No. 1, 45-57, 1985.
Kinoshita et al., "Enzymatic Synthesis of Sequencing Primers Based on a Library of Tetramers", Chem. Express, No. 2, 149-152, 1992.
Kinoshita et al., "Strand Ligation in a double-stranded DNA by T4 RNA Ligase", Chem. Lett., No. 9, 797-798, 1996.
Kitamura et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura et al., "Development of Systemic in vitro Evolution and Its Application to Generation of Peptide-Aptamer-Based Inhibitors of Cathepsin E", J. Mol. Biol., vol. 387, 1186-1198, 2009.
Moore et al. "Site-specific Modification of Pre-mRNA: the 2'-hydroxyl Groups at the Splice Sites", Science, vol. 256, No. 5059, 992-997, 1992.
Nielsen et al., "Synthetic Methods for the Implementation of Encoded Combinatorial Chemistry", J. Am. Chem. Soc., vol. 115, 9812-9813, 1993 with supplementary Materials (pp. 1-7).
Nielsen et al., "Toward Chemical Implementation of Encoded Combinatorial Libraries", Methods: A Companion to Meth: Enzymol., vol. 6, 361-371, 1994.
Roux, "Optimization and troubleshooting in PCR", PCR Methods Appl., vol. 4, No. 5, S185-S194, 1995.
Schmitz et al., "Solid-phase Enzymatic Synthesis of Oligonucleotides", Org. Lett., vol. 1, 1729-1731, 1999.
Seelig et al., "Site-specific Modification of Enzymatically Synthesized RNA: Transcription Initiation and Diels-Alder Reaction, " Tetrahed. Lett., vol. 38, 7729-7732, 1997.
Seo et al., "Click Chemistry to Construct Fluorescent Oligonucelotides for DNA Sequencing", J. Org. Chem., vol. 68, 609-612, 2003.
Sherlin et al., "Chemical and Enzymatic Synthesis of tRNAs for High-throughput Crystallization", RNA, vol. 7, 1671-1678, 2001.
Tabuchi et al., "An Efficient Ligation Method in the Making of an in vitro Virus for in vitro Protein Evolution," Biol., Proced. Online, vol. 4, No. 1, 49-54, 2002.
Verma et al., "Modified Oligonucleotides: Synthesis and Strategy for Users", Annu. Rev. Biochem., vol. 67, 99-134, 1998.
Woiwode et al., "Synthetic Compound Libraries Displayed on the Surface of Encoded Bacteriophage", Chem. Biol., vol. 847-858, Sep. 2003.
Wojczewski et al., "Fluorescent Oligonucleotides—Versatile Tools as Probes and Primers for DNA and RNA Analysis", Synlett, No. 10, 1667-1678, 1999.
Wong & Whitesides, "Enzymes in Synthetic Organic Chemistry", Tetrahedron Organic Chemistry Series Volume 12, Pergamon, Elsevier Science Lrd. (Oxford, England) 1994, pp. Xiii-xv, 1-40, and 329-334.
Zhang et al., "Solution-Phase Preparation of a 560-Compound Library of Individual Pure Mappicine Analogous by Fluorous Mixture Synthesis", J. Am. Chem. Soc., vol. 124, 10443-10450, 2002.
Barrio et al., "Synthesis of modified nucleoside 3', 5'-bisphophates and their incorporation into oligoribunucleotides with T4 RNA Ligase", Biochemistry, vol. 17, No. 11, 1978.
Chan et al., "Altered DNA ligase I activity in Bloom's syndrome cells", Nature, vol. 325, pp. 357-359 , 1987.
Cranston et al., "Studies on ribonucleic acid ligase", J.Biol.Chem., vol. 249, No. 23, pp. 7447-7456, 1974.
England et al., "Enzymatic oligoribonucleotide synthesis with T4 RNA ligase", American Chemical Society, 1978.
Gassen et al., "Synthesis by polymer-bound ribonuclease of the termination codons U-A-A, U-A-G, and U-G-A" Biochemical and biophysical research communications, vol. 44, No. 6, pp. 1410-1415, 1971.
Haseth et al., "Interaction of *Escherichia coli* host factor protein with oligoriboadenylates", Biochemistry, 19, pp. 6138-6446, 1980.
Hoffman et al., "Polynucleotide phosphorylase covalently bound to cellulose and its use in the preparation of homopolynucleotides", Biochemical and biophysical research communications, vol. 41, No. 3, pp. 710-714, 1970.
Kiebom, "Enzymes that do not work in organic solvents: Too polar substrates give too tight enzyme-product complexes", Recl. Trav. Chim. Pays-Bas, 107, pp. 347-348, 1988.
Middleton et al., "Synthesis and purification of oligoribonucleotides using T4 RNA ligase and reverse-phase chromatography", Analytical Biochemistry, 144, pp. 110-117, 1985.
Narang, "DNA synthesis", Tetrahedron, vol. 39, No. 1, pp. 3-22, 1983.
Neilson et al., "Synthesis of biologically active portions of an intercistronic region by use of a new 3'-phosphate incorporation method to protect 3'-OH and their binding to ribosomes", Eur. J. Biochem., 99, pp. 429-439, 1979.
Ochoa et al., "Enzymatic synthesis of polynucleotides", J.Biol. Chem., vol. 236, 12, pp. 3303-3311, 1961.
Willis et al., "DNA ligase I deficiency in Bloom's syndrome", Nature, vol. 325, pp. 355-357, 1987.
Balasubramanian, "Solid phase chemical technologies for combinatorial chemistry", J. Cell. Biochem. Suppl., 37, 2001, pp. 28-33.
Balasubramanian, "The science of chemical discovery: probing the unknown with new technologies", DDT, vol. 5, No. 12, Dec. 2000, pp. 533-534.
piercenet.com/method/avidin-biotin-interaction retrieved Nov. 5, 2013.
Schreiber, "The small-molecule approach to biology—Chemical genetics and diversity-oriented organic synthesis make possible the systematic exploration of biology", C&EN, Mar. 3, 2003, pp. 51-61.
Wills et al., "Recent developments in linker design and application", Current Opinion in Chemical Biology, 2003, 7, pp. 346-352.

\* cited by examiner

Figure 2.
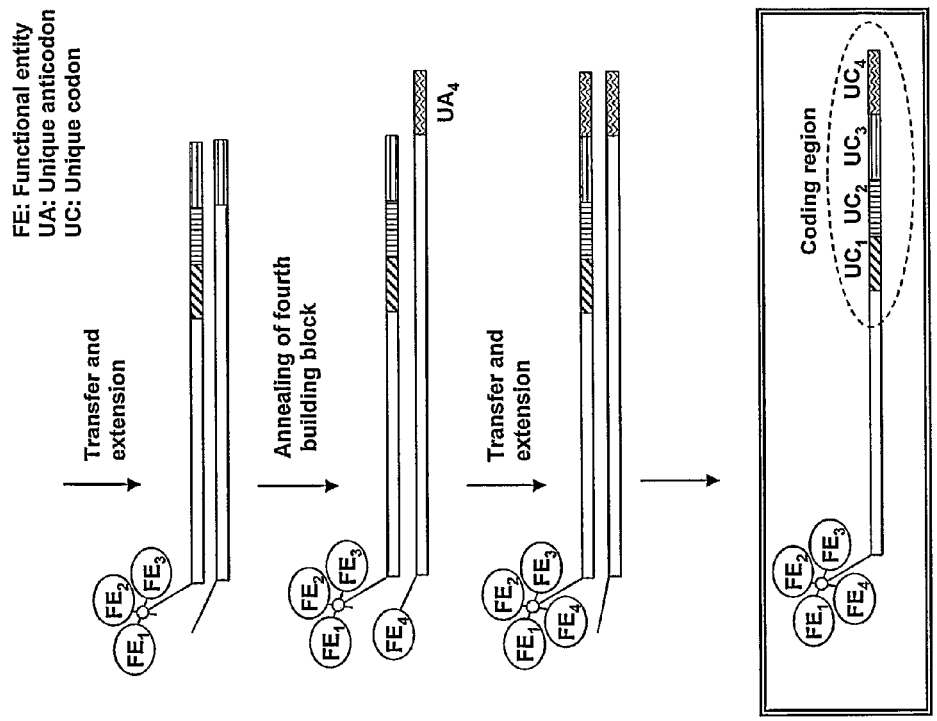
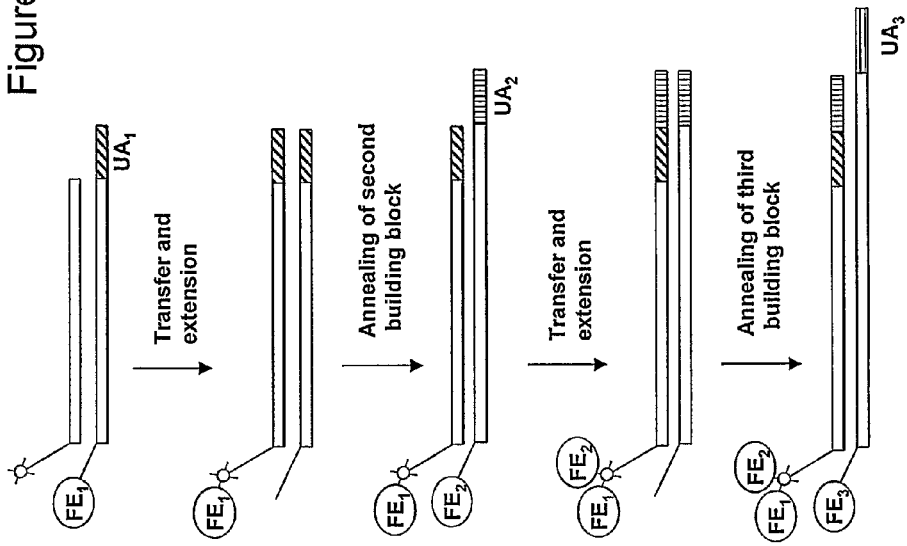

Figure 4.
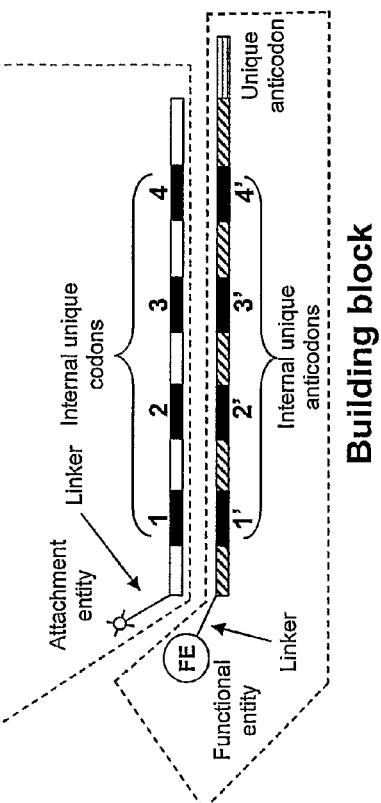
A
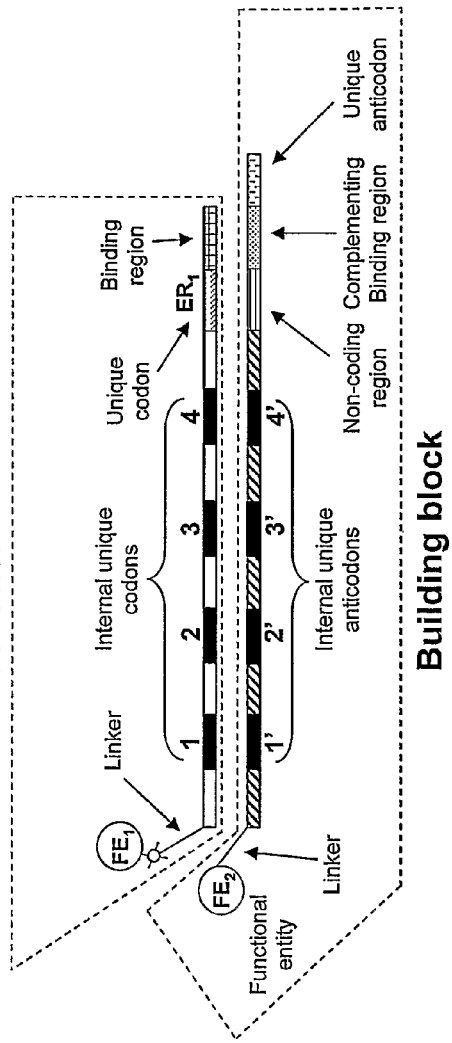
B

Fig. 15 Single encoding

Fig. 17 Double encoding

1 Enzymatic or chemical ligation
2 Single or double stranded enzymatic or chemical ligation

SEQUENCE LISTING

```
<160> NUMBER OF SEQ ID NOS: 166

<210> SEQ ID NO 1
<211> LENGTH: 5
<212> TYPE: PRT
<213> ORGANISM: Artificial Sequence
<220> FEATURE:
<223> OTHER INFORMATION: Artificially produced

<400> SEQUENCE: 1

Asp Asp Asp Asp Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Artificially produced
<220> FEATURE:
<221> NAME/KEY: MISC_FEATURE
<222> LOCATION: (7)..(7)
<223> OTHER INFORMATION: may be Gly or Ser (G or S)

<400> SEQUENCE: 2

Glu Asn Leu Tyr Phe Gln Xaa
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: Artificially produced

<400> SEQUENCE: 3

Leu Val Pro Ala Gly Ser
1               5

<210> SEQ ID NO 4
<211> LENGTH: 4
<212> TYPE: PRT
<213> ORGANISM: Artificial Sequence
<220> FEATURE:
<223> OTHER INFORMATION: Artificially produced

<400> SEQUENCE: 4

Ile Glu Gly Arg
1

<210> SEQ ID NO 5
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: modified_base
<222> LOCATION: (1)..(1)
<223> OTHER INFORMATION: Amino modifier C6 5'labelled identifier oligo,
      may be obtained from Glen research cat. # 10-1039-90

<400> SEQUENCE: 5
tcgtaacgac tgaatgacgt                                               20

<210> SEQ ID NO 6
<211> LENGTH: 6
<212> TYPE: PRT
<213> ORGANISM: Artificial Sequence
<220> FEATURE:
<223> OTHER INFORMATION: Artificially produced

<400> SEQUENCE: 6

Cys Phe Phe Lys Lys Lys
1               5

<210> SEQ ID NO 7
<211> LENGTH: 25
<212> TYPE: DNA
<213> ORGANISM: Artificial Sequence
<220> FEATURE:
<223> OTHER INFORMATION: Artificially produced
<220> FEATURE:
<221> NAME/KEY: modified_base
<222> LOCATION: (1)..(1)
<223> OTHER INFORMATION: biotin labelled
<220> FEATURE:
<221> NAME/KEY: modified_base
<222> LOCATION: (25)..(25)
<223> OTHER INFORMATION: thio-modifier C6 S-S labelled (obtainable from
      Glen Research, cat # 10-1936-90)

<400> SEQUENCE: 7
tgcagacgtc attcagtcgt tacga                                         25

<210> SEQ ID NO 8
```

```
<211> LENGTH: 21
<212> TYPE: DNA
<213> ORGANISM: Artificial Sequence
<220> FEATURE:
<223> OTHER INFORMATION: Artificially produced

<400> SEQUENCE: 8
gcacacatgc atgagcacac g                                       21

<210> SEQ ID NO 9
<211> LENGTH: 38
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (27)..(32)
<223> OTHER INFORMATION: N represents a nucleobase selected from A, G,
      T, and C.

<400> SEQUENCE: 9
cgtgtgtacg tactcgtgtg cgtgtgnnnn nntgacta                     38

<210> SEQ ID NO 10
<211> LENGTH: 50
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (27)..(32)
<223> OTHER INFORMATION: n represents inosine
<220> FEATURE:
<221> NAME/KEY: misc_feature
<222> LOCATION: (39)..(44)
<223> OTHER INFORMATION: n represents a nucleobase selected from A, G,
      T and C.

<400> SEQUENCE: 10
cgtgtgtacg tactcgtgtg cgtgtgnnnn nntgactann nnnntgcaac        50

<210> SEQ ID NO 11
<211> LENGTH: 62
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (27)..(32)
<223> OTHER INFORMATION: n represents inosine (I)
<220> FEATURE:
<221> NAME/KEY: misc_feature
<222> LOCATION: (39)..(44)
<223> OTHER INFORMATION: n represents inosine (I)
<220> FEATURE:
<221> NAME/KEY: misc_feature
<222> LOCATION: (51)..(56)
<223> OTHER INFORMATION: n represents a nucleobase selected from A, G,
      T and C.

<400> SEQUENCE: 11
cgtgtgtacg tactcgtgtg cgtgtgnnnn nntgactann nnnntgcaac nnnnnnactt    60
tg                                                            62

<210> SEQ ID NO 12
<211> LENGTH: 91
<212> TYPE: DNA
<213> ORGANISM: Artificial Sequence
```

```
<220> FEATURE:
<223> OTHER INFORMATION: Artificially produced
<220> FEATURE:
<221> NAME/KEY: misc_feature
<222> LOCATION: (27)..(32)
<223> OTHER INFORMATION: n represents inosine (I)
<220> FEATURE:
<221> NAME/KEY: misc_feature
<222> LOCATION: (39)..(44)
<223> OTHER INFORMATION: n represents inosine (I)
<220> FEATURE:
<221> NAME/KEY: misc_feature
<222> LOCATION: (51)..(56)
<223> OTHER INFORMATION: n represents inosine (I)
<220> FEATURE:
<221> NAME/KEY: misc_feature
<222> LOCATION: (63)..(68)
<223> OTHER INFORMATION: n represents a nucleobase selected from A, G, T
      and C.

<400> SEQUENCE: 12
cgtgtgtacg tactcgtgtg cgtgtgnnnn nntgactann nnnntgcaac nnnnnnactt    60
tgnnnnnnga attcggcaat acgcattacc g                                  91

<210> SEQ ID NO 13
<211> LENGTH: 38
<212> TYPE: DNA
<213> ORGANISM: Artificial Sequence
<220> FEATURE:
<223> OTHER INFORMATION: Artificially produced

<400> SEQUENCE: 13
cgtgtgtacg tactcgtgtg cgtgtgtcga tgtgacta                           38

<210> SEQ ID NO 14
<211> LENGTH: 38
<212> TYPE: DNA
<213> ORGANISM: Artificial Sequence
<220> FEATURE:
<223> OTHER INFORMATION: Artificially produced

<400> SEQUENCE: 14
gcacacatgc atgagcacac gcacacagct acactgat                           38

<210> SEQ ID NO 15
<211> LENGTH: 50
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (27)..(32)
<223> OTHER INFORMATION: n represents inosine (I)

<400> SEQUENCE: 15
cgtgtgtacg tactcgtgtg cgtgtgnnnn nntgactaca atcgtgcaac               50

<210> SEQ ID NO 16
<211> LENGTH: 50
<212> TYPE: DNA
<213> ORGANISM: Artificial Sequence
<220> FEATURE:
<223> OTHER INFORMATION: Artificially produced

<400> SEQUENCE: 16
gcacacatgc atgagcacac gcacacagct acactgatgt tagcacgttg               50

<210> SEQ ID NO 17
```

```
<211> LENGTH: 62
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (27)..(32)
<223> OTHER INFORMATION: n represents inosine (I)
<220> FEATURE:
<221> NAME/KEY: misc_feature
<222> LOCATION: (39)..(44)
<223> OTHER INFORMATION: n represents inosine (I)

<400> SEQUENCE: 17
cgtgtgtacg tactcgtgtg cgtgtgnnnn nntgactann nnnntgcaac ctctgtactt    60
tg                                                                  62

<210> SEQ ID NO 18
<211> LENGTH: 62
<212> TYPE: DNA
<213> ORGANISM: Artificial Sequence
<220> FEATURE:
<223> OTHER INFORMATION: Artificially produced

<400> SEQUENCE: 18
gcacacatgc atgagcacac gcacacagct acactgatgt tagcacgttg gagacatgaa    60
ac                                                                  62

<210> SEQ ID NO 19
<211> LENGTH: 91
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (27)..(32)
<223> OTHER INFORMATION: n represents inosine (I)
<220> FEATURE:
<221> NAME/KEY: misc_feature
<222> LOCATION: (39)..(44)
<223> OTHER INFORMATION: n represents inosine (I)
<220> FEATURE:
<221> NAME/KEY: misc_feature
<222> LOCATION: (51)..(56)
<223> OTHER INFORMATION: n represents inosine (I)

<400> SEQUENCE: 19
cgtgtgtacg tactcgtgtg cgtgtgnnnn nntgactann nnnntgcaac nnnnnnactt    60
tgtaagctga attcggcaat acgcattacc g                                  91

<210> SEQ ID NO 20
<211> LENGTH: 91
<212> TYPE: DNA
<213> ORGANISM: Artificial Sequence
<220> FEATURE:
<223> OTHER INFORMATION: Artificially produced

<400> SEQUENCE: 20
gcacacatgc atgagcacac gcacacagct acactgatgt tagcacgttg gagacatgaa    60
acattcgaca attcccgtta tgcgtaatgg c                                  91

<210> SEQ ID NO 21
<211> LENGTH: 91
<212> TYPE: DNA
<213> ORGANISM: Artificial Sequence
<220> FEATURE:
```

<223> OTHER INFORMATION: Artificially produced
<220> FEATURE:
<221> NAME/KEY: misc_feature
<222> LOCATION: (27)..(32)
<223> OTHER INFORMATION: n represents inosine (I)
<220> FEATURE:
<221> NAME/KEY: misc_feature
<222> LOCATION: (39)..(44)
<223> OTHER INFORMATION: n represents inosine (I)
<220> FEATURE:
<221> NAME/KEY: misc_feature
<222> LOCATION: (51)..(56)
<223> OTHER INFORMATION: n represents inosine (I)

<400> SEQUENCE: 21
cgtgtgtacg tactcgtgtg cgtgtgnnnn nntgactann nnnntgcaac nnnnnnactt    60
tgtaagctgt tatgggcaat acgcattacc g                                   91

<210> SEQ ID NO 22
<211> LENGTH: 71
<212> TYPE: DNA
<213> ORGANISM: Artificial Sequence
<220> FEATURE:
<223> OTHER INFORMATION: Artificially produced

<400> SEQUENCE: 22
gcacacagct acactgatgt tagcacgttg gagacatgaa acattcgaca attcccgtta    60
tgcgtaatgg c                                                         71

<210> SEQ ID NO 23
<211> LENGTH: 49
<212> TYPE: DNA
<213> ORGANISM: Artificial Sequence
<220> FEATURE:
<223> OTHER INFORMATION: Artificially produced

<400> SEQUENCE: 23
gcacacagct acactgatgt tagcacgttg gagacatgaa acattcgac                49

<210> SEQ ID NO 24
<211> LENGTH: 21
<212> TYPE: DNA
<213> ORGANISM: Artificial Sequence
<220> FEATURE:
<223> OTHER INFORMATION: Artificially produced

<400> SEQUENCE: 24
acctcagctg tgtatcgagc g                                              21

<210> SEQ ID NO 25
<211> LENGTH: 42
<212> TYPE: DNA
<213> ORGANISM: Artificial Sequence
<220> FEATURE:
<223> OTHER INFORMATION: Artificially produced

<400> SEQUENCE: 25
gcagtagcgg gcctcgtacg acctgttcgg ctactgccga gc                       42

<210> SEQ ID NO 26
<211> LENGTH: 9
<212> TYPE: DNA
<213> ORGANISM: Artificial Sequence
<220> FEATURE:
<223> OTHER INFORMATION: Artificially produced

<400> SEQUENCE: 26 ccgcatcgc                                                                                    9

<210> SEQ ID NO 27
<211> LENGTH: 21
<212> TYPE: DNA
<213> ORGANISM: Artificial Sequence
<220> FEATURE:
<223> OTHER INFORMATION: Artificially produced

<400> SEQUENCE: 27
tggagtcgac acatagctcg c                                                                      21

<210> SEQ ID NO 28
<211> LENGTH: 23
<212> TYPE: DNA
<213> ORGANISM: Artificial Sequence
<220> FEATURE:
<223> OTHER INFORMATION: Artificially produced

<400> SEQUENCE: 28
ggcgtagcgc atagcgcaat cgc                                                                    23

<210> SEQ ID NO 29
<211> LENGTH: 36
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: residue is bonded to an identifier with
      sequence PSN, wherein N = 5'-Amino-Modifier 5 (Glen research cat#
      10-1905-90), S = Spacer C3 CPG (Glen research cat# 20-2913-01),
      P =  PC Spacer Phosphoramidite (Glen research cat# 10-4913-90)

<400> SEQUENCE: 29
acctcagctg tgtatcgagc ggcagcgtta tcgtcg                                                      36

<210> SEQ ID NO 30
<211> LENGTH: 36
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: residue is bonded to an identifier with
      sequence PSN, wherein N = 5'-Amino-Modifier 5 (Glen research cat#
      10-1905-90), S = Spacer C3 CPG (Glen research cat# 20-2913-01),
      P =  PC Spacer Phosphoramidite (Glen research cat# 10-4913-90)

<400> SEQUENCE: 30
acctcagctg tgtatcgagc ggcagcagtg ccgtcg                                                      36

<210> SEQ ID NO 31
<211> LENGTH: 36
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: residue is bonded to an identifier with
      sequence PSN, wherein N = 5'-Amino-Modifier 5 (Glen research cat#
      10-1905-90), S = Spacer C3 CPG (Glen research cat# 20-2913-01),
      P =  PC Spacer Phosphoramidite (Glen research cat# 10-4913-90)

<400> SEQUENCE: 31

-continued acctcagctg tgtatcgagc ggcagcgcac acgtcg                                          36

<210> SEQ ID NO 32
<211> LENGTH: 36
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: residue is bonded to an identifier with
      sequence PSN, wherein N = 5'-Amino-Modifier 5 (Glen research cat#
      10-1905-90), S = Spacer C3 CPG (Glen research cat# 20-2913-01),
      P =  PC Spacer Phosphoramidite (Glen research cat# 10-4913-90)

<400> SEQUENCE: 32
acctcagctg tgtatcgagc ggcagcggat acgtcg                                          36

<210> SEQ ID NO 33
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (20)..(20)
<223> OTHER INFORMATION: Carboxy dT (Glen research cat# 10-1035-90)

<400> SEQUENCE: 33
cgctcgatac acagctgagg                                                            20

<210> SEQ ID NO 34
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (20)..(20)
<223> OTHER INFORMATION: carboxy dT (Glen research cat# 10-1035-90)

<400> SEQUENCE: 34
cgctcgatac acagctgagg                                                            20

<210> SEQ ID NO 35
<211> LENGTH: 25
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)

<400> SEQUENCE: 35

-continued tgctgataac cgacgnnnnn gctgc        25

<210> SEQ ID NO 36
<211> LENGTH: 14
<212> TYPE: DNA
<213> ORGANISM: Artificial Sequence
<220> FEATURE:
<223> OTHER INFORMATION: Artificially produced

<400> SEQUENCE: 36
tcgagcggca gcca        14

<210> SEQ ID NO 37

<400> SEQUENCE: 37

000        7

<210> SEQ ID NO 38
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90))

<400> SEQUENCE: 38
tgctgataac cgacgnnnnn gctgccgctc gatacacagc tgagg        45

<210> SEQ ID NO 39
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90)

<400> SEQUENCE: 39
tgctgtgtgc cgacgnnnnn gctgccgctc gatacacagc tgagg        45

<210> SEQ ID NO 40
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin

```
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90)

<400> SEQUENCE: 40
tgctggcact cgacgnnnnn gctgccgctc gatacacagc tgagg          45

<210> SEQ ID NO 41
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90)

<400> SEQUENCE: 41
tgctgtatcc cgacgnnnnn gctgccgctc gatacacagc tgagg          45

<210> SEQ ID NO 42
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (46)..(46)
<223> OTHER INFORMATION: Carboxy dT (Glen research cat# 10-1035-90)

<400> SEQUENCE: 42
tgctgcagcg cgacgnnnnn gctgccgctc gatacacagc tgagg          45

<210> SEQ ID NO 43
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90)
```

```
<400> SEQUENCE: 43
tgctgaccag cgacgnnnnn gctgccgctc gatacacagc tgagg           45

<210> SEQ ID NO 44
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90)

<400> SEQUENCE: 44
tgctggaaca cgacgnnnnn gctgccgctc gatacacagc tgagg           45

<210> SEQ ID NO 45
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90)

<400> SEQUENCE: 45
tgctgcaggt cgacgnnnnn gctgccgctc gatacacagc tgagg           45

<210> SEQ ID NO 46
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90)

<400> SEQUENCE: 46
tgctggctcg cgacgnnnnn gctgccgctc gatacacagc tgagg           45

<210> SEQ ID NO 47
<211> LENGTH: 45
```

```
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (46)..(46)
<223> OTHER INFORMATION: Carboxy dT (Glen research cat# 10-1035-90)

<400> SEQUENCE: 47
tgctggatac cgacgnnnnn gctgccgctc gatacacagc tgagg                45

<210> SEQ ID NO 48
<211> LENGTH: 45
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (16)..(20)
<223> OTHER INFORMATION: n represents inosine (I)
<220> FEATURE:
<221> NAME/KEY: misc_feature
<222> LOCATION: (45)..(45)
<223> OTHER INFORMATION: Carboxy dT (Glen research cat# 10-1035-90)

<400> SEQUENCE: 48
tgctgaggcc cgacgnnnnn gctgccgctc gatacacagc tgagg                45

<210> SEQ ID NO 49
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 49
tttagatggc agattcgaca taactgctgn nnnncgacgn nnnngctgcc gctcgataca   60
cagctgagg                                                          69

<210> SEQ ID NO 50
<211> LENGTH: 69
<212> TYPE: DNA
<213> ORGANISM: Artificial Sequence
```

```
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 50
tttagatggc agattcgact gtgctgctgn nnnncgacgn nnnngctgcc gctcgataca    60
cagctgagg                                                           69

<210> SEQ ID NO 51
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 51
tttagatggc agattcgacg cacttgctgn nnnncgacgn nnnngctgcc gctcgataca    60
cagctgagg                                                           69

<210> SEQ ID NO 52
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 52
```

```
tttagatggc agattcgact atcctgctgn nnnncgacgn nnnngctgcc gctcgataca    60
cagctgagg                                                           69

<210> SEQ ID NO 53
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 53
tttagatggc agattcgacc agcgtgctgn nnnncgacgn nnnngctgcc gctcgataca    60
cagctgagg                                                           69

<210> SEQ ID NO 54
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 54
tttagatggc agattcgaca ccagtgctgn nnnncgacgn nnnngctgcc gctcgataca    60
cagctgagg                                                           69

<210> SEQ ID NO 55
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
```

```
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 55
tttagatggc agattcgacg aacatgctgn nnnncgacgn nnnngctgcc gctcgataca      60
cagctgagg                                                              69

<210> SEQ ID NO 56
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 56
tttagatggc agattcgacc aggttgctgn nnnncgacgn nnnngctgcc gctcgataca      60
cagctgagg                                                              69

<210> SEQ ID NO 57
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 57
tttagatggc agattcgacg ctcgtgctgn nnnncgacgn nnnngctgcc gctcgataca      60
cagctgagg                                                              69

<210> SEQ ID NO 58
<211> LENGTH: 69
<212> TYPE: DNA
<213> ORGANISM: Artificial Sequence
```

```
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 58
tttagatggc agattcgacg atactgctgn nnnncgacgn nnnngctgcc gctcgataca      60
cagctgagg                                                             69

<210> SEQ ID NO 59
<211> LENGTH: 69
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' biotin
<220> FEATURE:
<221> NAME/KEY: misc_feature
<222> LOCATION: (30)..(34)
<223> OTHER INFORMATION: n represents inosine (I)
<220> FEATURE:
<221> NAME/KEY: misc_feature
<222> LOCATION: (40)..(44)
<223> OTHER INFORMATION: n represents inosine (I)
<220> FEATURE:
<221> NAME/KEY: misc_feature
<222> LOCATION: (69)..(69)
<223> OTHER INFORMATION: Carboxy dT (Glen research cat# 10-1035-90)

<400> SEQUENCE: 59
tttagatggc agattcgaca ggcctgctgn nnnncgacgn nnnngctgcc gctcgataca      60
cagctgagg                                                             69

<210> SEQ ID NO 60
<211> LENGTH: 15
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: CXS biotin

<400> SEQUENCE: 60
ttttagatgg cagat                                                      15

<210> SEQ ID NO 61
<211> LENGTH: 27
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
```

```
<222> LOCATION: (1)..(1)
<223> OTHER INFORMATION: biotin

<400> SEQUENCE: 61
aattccggaa catactagtc aacatga                                               27

<210> SEQ ID NO 62
<211> LENGTH: 36
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5'-terminal amino-group (Glen Research catalog
      # 10-1905-90) linked by a Spacer-PEG18 (Glen Research catalog
      # 10-1918-90) and a photocleavable (Glen Research catalog#10-4913)
      spacer

<400> SEQUENCE: 62
acctcagctg tgtatcgagc ggcagcggcc tcgtcg                                     36

<210> SEQ ID NO 63
<211> LENGTH: 19
<212> TYPE: DNA
<213> ORGANISM: Artificial Sequence
<220> FEATURE:
<223> OTHER INFORMATION: Artificially produced

<400> SEQUENCE: 63
tgtgcgacga ggccgctgc                                                        19

<210> SEQ ID NO 64
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 64
cacaagtacg aacgtgcatc agag                                                  24

<210> SEQ ID NO 65
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 65
tcctctctga tgcacgttcg tact                                                  24

<210> SEQ ID NO 66
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
```

```
<223> OTHER INFORMATION: 5' phosphate

<400> SEQUENCE: 66
cacatagtct cctccacttc catg                                              24

<210> SEQ ID NO 67
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 67
tcctcatgga agtggaggag acta                                              24

<210> SEQ ID NO 68
<211> LENGTH: 23
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 68
cacatacatc gttccagata ccg                                               23

<210> SEQ ID NO 69
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 69
tcctcatgga agtggaggag acta                                              24

<210> SEQ ID NO 70
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 70
cacatccagt gcaagactga acag                                              24

<210> SEQ ID NO 71
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
```

```
<223> OTHER INFORMATION: 5' phosphate

<400> SEQUENCE: 71
tcctctgttc agtcttgcac tgga                                              24

<210> SEQ ID NO 72
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 72
cacaagcatc actactctgt ctgg                                              24

<210> SEQ ID NO 73
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 73
tcctccagac agagtagtga tgct                                              24

<210> SEQ ID NO 74
<211> LENGTH: 48
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 74
aggacgagca ggacctggaa cctggtgcgt tcctccacca cgtctccg                    48

<210> SEQ ID NO 75
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 75
gcaccaggtt ccaggtcctg ctcg                                              24

<210> SEQ ID NO 76
<211> LENGTH: 48
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
```

<223> OTHER INFORMATION: 5' phosphate

<400> SEQUENCE: 76
aggactcgac cactgcaggt ggagctccgt tcctccacca cgtctccg     48

<210> SEQ ID NO 77
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 77
ggagctccac ctgcagtggt cgag     24

<210> SEQ ID NO 78
<211> LENGTH: 48
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 78
aggacgtgct tcctctgctg caccaccggt tcctccacca cgtctccg     48

<210> SEQ ID NO 79
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 79
cggtggtgca gcagaggaag cacg     24

<210> SEQ ID NO 80
<211> LENGTH: 48
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 80
aggacctggt gtcgaggtga gcagcagcgt tcctccacca cgtctccg     48

<210> SEQ ID NO 81
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)

```
<223> OTHER INFORMATION: 5' phosphate

<400> SEQUENCE: 81
gctgctgctc acctcgacac cagg                                              24

<210> SEQ ID NO 82
<211> LENGTH: 48
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 82
aggactcgac gaggtccatc ctggtcgcgt tcctccacca cgtctccg                    48

<210> SEQ ID NO 83
<211> LENGTH: 24
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 83
gcgaccagga tggacctcgt cgag                                              24

<210> SEQ ID NO 84
<211> LENGTH: 20
<212> TYPE: DNA
<213> ORGANISM: Artificial Sequence
<220> FEATURE:
<223> OTHER INFORMATION: Artificially produced

<400> SEQUENCE: 84
cggagacgtg gtggaggaac                                                   20

<210> SEQ ID NO 85
<211> LENGTH: 19
<212> TYPE: DNA
<213> ORGANISM: Artificial Sequence
<220> FEATURE:
<223> OTHER INFORMATION: Artificially produced

<400> SEQUENCE: 85
acctcagctg tgtatcgag                                                    19

<210> SEQ ID NO 86
<211> LENGTH: 88
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 86
cggcagctgc ctcgtcgcac atccagtgca agactgaata gaggactcga cgaggtccat       60
cctggtcgcg ttcctccacc acgtctcc                                          88
```

```
<210> SEQ ID NO 87
<211> LENGTH: 87
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' phosphate

<400> SEQUENCE: 87
cggcaggcct cgtcgcacat ccagtgcaag actgaacaga ggacctcgac gaggtccatc    60
ctggtcgcgt tcctccacca cgtctcc                                        87

<210> SEQ ID NO 88
<211> LENGTH: 90
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (23)..(23)
<223> OTHER INFORMATION: n represents c, g, t or a

<400> SEQUENCE: 88
cggcctcgtc gcacatcatt gcnacgactg aacaggagga ctcgacgagg tccatcctgt    60
ctgccggttc tctcaccaca ccagtctctc                                     90

<210> SEQ ID NO 89
<211> LENGTH: 88
<212> TYPE: DNA
<213> ORGANISM: Artificial Sequence
<220> FEATURE:
<223> OTHER INFORMATION: Artificially produced

<400> SEQUENCE: 89
cggcagcggt tcgtcgcac atccagtgca agactaacag aggacctcga cgagttccat    60
cctggtcgcg ttcctccacc acgtctcc                                       88

<210> SEQ ID NO 90
<211> LENGTH: 82
<212> TYPE: DNA
<213> ORGANISM: Artificial Sequence
<220> FEATURE:
<223> OTHER INFORMATION: Artificially produced

<400> SEQUENCE: 90
cgggcctcgt cgcacatcca gtgcaagact gaacagagga ctcgacgagg tccatcctgg    60
tcgcgttcct ccaccacgtt cc                                             82

<210> SEQ ID NO 91
<211> LENGTH: 83
<212> TYPE: DNA
<213> ORGANISM: Artificial Sequence
<220> FEATURE:
<223> OTHER INFORMATION: Artificially produced

<400> SEQUENCE: 91
cggcagcggc tcgtcgaca agcatcacta ctctgtctgg aggatcgagg tccatcctgg    60
tcgcgttcct ccaccacgtc tcc                                            83

<210> SEQ ID NO 92
```

```
<211> LENGTH: 88
<212> TYPE: DNA
<213> ORGANISM: Artificial Sequence
<220> FEATURE:
<223> OTHER INFORMATION: Artificially produced

<400> SEQUENCE: 92
cggcagcggc ctcgtcgcac atccagtgca agactgaaca gaggactcga cgaggtccat     60
cctggtcgcg ttcctccacc acgtctcc                                        88

<210> SEQ ID NO 93
<211> LENGTH: 87
<212> TYPE: DNA
<213> ORGANISM: Artificial Sequence
<220> FEATURE:
<223> OTHER INFORMATION: Artificially produced

<400> SEQUENCE: 93
cggcagcggc ctcgtcgcac atccagtgca agattgaaca gaggactcga cgaggtccat     60
cctggtcgcg ttcctccacc acgtctc                                         87

<210> SEQ ID NO 94
<211> LENGTH: 87
<212> TYPE: DNA
<213> ORGANISM: Artificial Sequence
<220> FEATURE:
<223> OTHER INFORMATION: Artificially produced

<400> SEQUENCE: 94
cggcagcggc ctcgtcgcac ttcagtgcaa gactgaacag aggactcgat gaaggtccat     60
cctggtcgcg ttcctccacc acgtctc                                         87

<210> SEQ ID NO 95
<211> LENGTH: 86
<212> TYPE: DNA
<213> ORGANISM: Artificial Sequence
<220> FEATURE:
<223> OTHER INFORMATION: Artificially produced

<400> SEQUENCE: 95
cggcagcggc ctcgtcgcac atccaggcaa gactgaacag aggactcgac gaggtccatc     60
ctggtcgcgt tcctccacca cgtctc                                          86

<210> SEQ ID NO 96
<211> LENGTH: 87
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (26)..(26)
<223> OTHER INFORMATION: n represents a, c, g or t

<400> SEQUENCE: 96
cggcagcggc ctcgtcgcac atagtnccct ccacttccat gaggactcga cgaggtccat     60
cctggtcgcg ttcctccacc acgtctc                                         87

<210> SEQ ID NO 97
<211> LENGTH: 87
<212> TYPE: DNA
<213> ORGANISM: Artificial Sequence
<220> FEATURE:
<223> OTHER INFORMATION: Artificially produced
```

-continued

```
<400> SEQUENCE: 97
cggcagcggc tcgtcgcac atccagtgca agactgaaca gaggactcga cgaggtccat    60
cctggtcgcg ttcctccacc acgtctc                                       87

<210> SEQ ID NO 98
<211> LENGTH: 86
<212> TYPE: DNA
<213> ORGANISM: Artificial Sequence
<220> FEATURE:
<223> OTHER INFORMATION: Artificially produced

<400> SEQUENCE: 98
cggcagcggc tcgttgcac atcagtgcaa gactgaacag aggactcgac gaggtccatc    60
ctggtcgcgt tcctccacca cgtctc                                        86

<210> SEQ ID NO 99
<211> LENGTH: 85
<212> TYPE: DNA
<213> ORGANISM: Artificial Sequence
<220> FEATURE:
<223> OTHER INFORMATION: Artificially produced

<400> SEQUENCE: 99
cggcagcggc tcgtcgcac atcagtgcaa gactgaacag aggctcgacg aggtccatcc    60
tggtcgcgtt cctccaccac gtctc                                         85

<210> SEQ ID NO 100
<211> LENGTH: 86
<212> TYPE: DNA
<213> ORGANISM: Artificial Sequence
<220> FEATURE:
<223> OTHER INFORMATION: Artificially produced

<400> SEQUENCE: 100
cggcagcggc tcgtcgcac atcagtgcaa gactgaacag aggactcgac gaggtccatc    60
ctggtcgcgt tcctccacca cgtctc                                        86

<210> SEQ ID NO 101
<211> LENGTH: 87
<212> TYPE: DNA
<213> ORGANISM: Artificial Sequence
<220> FEATURE:
<223> OTHER INFORMATION: Artificially produced

<400> SEQUENCE: 101
cggcagcggc tcgtcgcac atccagtgca agactgaaca gaggactcga cgaggtccat    60
cctggtcgcg ttcctccacc acgtctc                                       87

<210> SEQ ID NO 102
<211> LENGTH: 86
<212> TYPE: DNA
<213> ORGANISM: Artificial Sequence
<220> FEATURE:
<223> OTHER INFORMATION: Artificially produced

<400> SEQUENCE: 102
cggcagcggc tcgtcgcac atcagtgcaa gactgaacag aggactcgac gaggtccatc    60
ctggtcgcgt tcctccacca cgtctc                                        86

<210> SEQ ID NO 103
<211> LENGTH: 87
<212> TYPE: DNA
```

```
<213> ORGANISM: Artificial Sequence
<220> FEATURE:
<223> OTHER INFORMATION: Artificially produced

<400> SEQUENCE: 103
cggcagcggc ctcgtcgcac atccagtgca agactgaaca gaggactcga cgaggtccat    60
cctggtcgcg ttcctccacc acgtctc                                        87

<210> SEQ ID NO 104
<211> LENGTH: 21
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' amino C6 (Glen Research catalogue
      # 10-1906-90)
<220> FEATURE:
<221> NAME/KEY: misc_feature
<222> LOCATION: (21)..(21)
<223> OTHER INFORMATION: 3'Biotin

<400> SEQUENCE: 104
cgatggtacg tccaggtcgc a                                              21

<210> SEQ ID NO 105
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (20)..(20)
<223> OTHER INFORMATION: Amino-C2-dT-3'-PO4 (Glen research catalogue
      #10-1037-90)

<400> SEQUENCE: 105
gcgacctgga gcatccatcg                                                20

<210> SEQ ID NO 106
<211> LENGTH: 21
<212> TYPE: DNA
<213> ORGANISM: Artificial Sequence
<220> FEATURE:
<223> OTHER INFORMATION: Artificially produced

<400> SEQUENCE: 106
cgatggtacg tccaggtcgc a                                              21

<210> SEQ ID NO 107
<211> LENGTH: 15
<212> TYPE: DNA
<213> ORGANISM: Artificial Sequence
<220> FEATURE:
<223> OTHER INFORMATION: Artificially produced

<400> SEQUENCE: 107
atcgtgctgc gacct                                                     15

<210> SEQ ID NO 108
<211> LENGTH: 23
<212> TYPE: DNA
<213> ORGANISM: Artificial Sequence
<220> FEATURE:
<223> OTHER INFORMATION: Artificially produced
```

```
<400> SEQUENCE: 108
gcacgatatg tacgatacac tga                                              23

<210> SEQ ID NO 109
<211> LENGTH: 14
<212> TYPE: DNA
<213> ORGANISM: Artificial Sequence
<220> FEATURE:
<223> OTHER INFORMATION: Artificially produced

<400> SEQUENCE: 109
gtgccattca gtgt                                                        14

<210> SEQ ID NO 110
<211> LENGTH: 23
<212> TYPE: DNA
<213> ORGANISM: Artificial Sequence
<220> FEATURE:
<223> OTHER INFORMATION: Artificially produced

<400> SEQUENCE: 110
atggcactta atggttgtaa tgc                                              23

<210> SEQ ID NO 111
<211> LENGTH: 14
<212> TYPE: DNA
<213> ORGANISM: Artificial Sequence
<220> FEATURE:
<223> OTHER INFORMATION: Artificially produced

<400> SEQUENCE: 111
tgtatgcgca ttac                                                        14

<210> SEQ ID NO 112
<211> LENGTH: 21
<212> TYPE: DNA
<213> ORGANISM: Artificial Sequence
<220> FEATURE:
<223> OTHER INFORMATION: Artificially produced

<400> SEQUENCE: 112
gcatacaaat cgataatgca c                                                21

<210> SEQ ID NO 113
<211> LENGTH: 21
<212> TYPE: DNA
<213> ORGANISM: Artificial Sequence
<220> FEATURE:
<223> OTHER INFORMATION: Artificially produced

<400> SEQUENCE: 113
cgatggtacg tccaggtcgc a                                                21

<210> SEQ ID NO 114
<211> LENGTH: 21
<212> TYPE: DNA
<213> ORGANISM: Artificial Sequence
<220> FEATURE:
<223> OTHER INFORMATION: Artificially produced

<400> SEQUENCE: 114
gtgcattatc gatttgtatg c                                                21

<210> SEQ ID NO 115
<211> LENGTH: 20
<212> TYPE: DNA
```

<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' C6 amino modifier (Glen research cat# 10-1916-90) suitable for attachment of functional entities such as peptides, small molecules or polymers

<400> SEQUENCE: 115
ctatgcggac tgactggtac                                           20

<210> SEQ ID NO 116
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' C6 amino modifier (Glen research cat# 10-1916-90) suitable for attachment of functional entities such as peptides, small molecules or polymers

<400> SEQUENCE: 116
ctatgatgct taggcggtac                                           20

<210> SEQ ID NO 117
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' C6 amino modifier (Glen research cat# 10-1916-90) suitable for attachment of functional entities such as peptides, small molecules or polymers

<400> SEQUENCE: 117
ctatgtaccg tacgtggtac                                           20

<210> SEQ ID NO 118
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' C6 amino modifier (Glen research cat# 10-1916-90) suitable for attachment of functional entities such as peptides, small molecules or polymers

<400> SEQUENCE: 118
ctatgaatgc tagctggtac                                           20

<210> SEQ ID NO 119
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' C6 amino modifier (Glen research cat# 10-1916-90) suitable for attachment of functional entities such as peptides, small molecules or polymers

<400> SEQUENCE: 119
ctatggattg cgcgtggtac                                        20

<210> SEQ ID NO 120
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' C6 amino modifier (Glen research cat#
      10-1916-90) suitable for attachment of functional entities such as
      peptides, small molecules or polymers

<400> SEQUENCE: 120
ctatgccact attagggtac                                        20

<210> SEQ ID NO 121
<211> LENGTH: 40
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: joined to photocleavable linker (Glen research
      cat#10-4913-90) which is linked to 5'-biotin (Glen research
      Cat#10-1953-95)

<400> SEQUENCE: 121
tataggatcc gtaccagtca gtccgcatag gaattctagt                  40

<210> SEQ ID NO 122
<211> LENGTH: 40
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: joined to photocleavable linker (Glen research
      cat#10-4913-90) which is linked to 5'-biotin (Glen research
      Cat#10-1953-95)

<400> SEQUENCE: 122
tataggatcc gtaccgccta agcatcatag gaattctagt                  40

<210> SEQ ID NO 123
<211> LENGTH: 40
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: joined to photocleavable linker (Glen research
      cat#10-4913-90) which is linked to 5'-biotin (Glen research
      Cat#10-1953-95)

<400> SEQUENCE: 123
tataggatcc gtaccacgta cggtacatag gaattctagt                  40

<210> SEQ ID NO 124

```
<211> LENGTH: 40
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: joined to photocleavable linker (Glen research
      cat#10-4913-90) which is linked to 5'-biotin (Glen research
      Cat#10-1953-95)

<400> SEQUENCE: 124
tataggatcc gtaccagcta gcattcatag gaattctagt                              40

<210> SEQ ID NO 125
<211> LENGTH: 40
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: joined to photocleavable linker (Glen research
      cat#10-4913-90) which is linked to 5'-biotin (Glen research
      Cat#10-1953-95)

<400> SEQUENCE: 125
tataggatcc gtaccacgcg caatccatag gaattctagt                              40

<210> SEQ ID NO 126
<211> LENGTH: 40
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: joined to photocleavable linker (Glen research
      cat#10-4913-90) which is linked to 5'-biotin (Glen research
      Cat#10-1953-95)

<400> SEQUENCE: 126
tataggatcc gtaccctaat agtggcatag gaattctagt                              40

<210> SEQ ID NO 127
<211> LENGTH: 15
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: joined to photocleavable linker (Glen research
      cat#10-4913-90) which is linked to 5'-biotin (Glen research
      Cat#10-1953-95)

<400> SEQUENCE: 127
tataggatcc gtacc                                                         15

<210> SEQ ID NO 128
<211> LENGTH: 15
<212> TYPE: DNA
<213> ORGANISM: Artificial Sequence
<220> FEATURE:
<223> OTHER INFORMATION: Artificially produced

<400> SEQUENCE: 128
```
actagaattc ctatg                                                        15

<210> SEQ ID NO 129
<211> LENGTH: 7
<212> TYPE: PRT
<213> ORGANISM: Artificial Sequence
<220> FEATURE:
<223> OTHER INFORMATION: Artificially produced

<400> SEQUENCE: 129

Gly Arg Gly Asp Ser Pro Cys
1               5

<210> SEQ ID NO 130
<211> LENGTH: 7
<212> TYPE: PRT
<213> ORGANISM: Artificial Sequence
<220> FEATURE:
<223> OTHER INFORMATION: Artificially produced

<400> SEQUENCE: 130

Gly Arg Ala Asp Ser Pro Cys
1               5

<210> SEQ ID NO 131
<211> LENGTH: 7
<212> TYPE: PRT
<213> ORGANISM: Artificial Sequence
<220> FEATURE:
<223> OTHER INFORMATION: Artificially produced

<400> SEQUENCE: 131

Gly Arg Gly Glu Ser Pro Cys
1               5

<210> SEQ ID NO 132
<211> LENGTH: 7
<212> TYPE: PRT
<213> ORGANISM: Artificial Sequence
<220> FEATURE:
<223> OTHER INFORMATION: Artificially produced

<400> SEQUENCE: 132

Gly Asp Gly Arg Ser Pro Cys
1               5

<210> SEQ ID NO 133
<211> LENGTH: 4
<212> TYPE: PRT
<213> ORGANISM: Artificial Sequence
<220> FEATURE:
<223> OTHER INFORMATION: Artificially produced

<400> SEQUENCE: 133

Cys Lys Lys Lys
1

<210> SEQ ID NO 134
<211> LENGTH: 6
<212> TYPE: PRT
<213> ORGANISM: Artificial Sequence
<220> FEATURE:
<223> OTHER INFORMATION: Artificially produced

<400> SEQUENCE: 134

Cys Phe Phe Lys Lys Lys
1               5

-continued

```
<210> SEQ ID NO 135
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' C6 amino modifier (Glen research cat#
      10-1039-90) suitable for attachment of functional entities such as
      peptides, small molecules or polymers

<400> SEQUENCE: 135
ctatgcggac tgactggtac                                                 20

<210> SEQ ID NO 136
<211> LENGTH: 20
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 5' C6 amino modifier (Glen research cat#
      10-1039-90) suitable for attachment of functional entities such as
      peptides, small molecules or polymers
<220> FEATURE:
<221> NAME/KEY: misc_feature
<222> LOCATION: (7)..(14)
<223> OTHER INFORMATION: n represents G, A, T or C

<400> SEQUENCE: 136
ctatgannnn nnnncggtac                                                 20

<210> SEQ ID NO 137
<211> LENGTH: 40
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(3)
<223> OTHER INFORMATION: phosphorothioate

<400> SEQUENCE: 137
tataggatcc gtaccagtca gtccgcatag gaattctagt                           40

<210> SEQ ID NO 138
<211> LENGTH: 40
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(3)
<223> OTHER INFORMATION: phosphorothioate
<220> FEATURE:
<221> NAME/KEY: misc_feature
<222> LOCATION: (17)..(24)
<223> OTHER INFORMATION: n represents A, T, C or G.

<400> SEQUENCE: 138
tataggatcc gtaccgnnnn nnnntcatag gaattctagt                           40

<210> SEQ ID NO 139
<211> LENGTH: 15
<212> TYPE: DNA
```

```
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(3)
<223> OTHER INFORMATION: phosphorothioate

<400> SEQUENCE: 139
tataggatcc gtacc                                                      15

<210> SEQ ID NO 140
<211> LENGTH: 15
<212> TYPE: DNA
<213> ORGANISM: Artificial Sequence
<220> FEATURE:
<223> OTHER INFORMATION: Artificially produced

<400> SEQUENCE: 140
actagaattc ctatg                                                      15

<210> SEQ ID NO 141
<211> LENGTH: 71
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (47)..(51)
<223> OTHER INFORMATION: n represents inosine (I)

<400> SEQUENCE: 141
acctcagctg tgtatcgagc ggcagccccc ccgtcgcccc ccagcannnn ngtcgaatct     60
gccatctaaa a                                                          71

<210> SEQ ID NO 142
<211> LENGTH: 60
<212> TYPE: DNA
<213> ORGANISM: Artificial Sequence
<220> FEATURE:
<223> OTHER INFORMATION: Artificially produced

<400> SEQUENCE: 142
cctgtagcat cactccatgt tgaacgtaga tgcaagtacc ttttagatgg cagattcgac     60

<210> SEQ ID NO 143
<211> LENGTH: 20
<212> TYPE: DNA
<213> ORGANISM: Artificial Sequence
<220> FEATURE:
<223> OTHER INFORMATION: Artificially produced

<400> SEQUENCE: 143
cgctcgatac acagctgagt                                                 20

<210> SEQ ID NO 144
<211> LENGTH: 70
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (46)..(50)
<223> OTHER INFORMATION: n represents inosine (I)

<400> SEQUENCE: 144
```

```
acctcagctg tgtatcgagc ggcagccccc cgtcgccccc cagcannnnn gtcgaatctg    60
ccatctaaaa                                                           70
```

<210> SEQ ID NO 145
<211> LENGTH: 40
<212> TYPE: DNA
<213> ORGANISM: Artificial Sequence
<220> FEATURE:
<223> OTHER INFORMATION: Artificially produced

<400> SEQUENCE: 145

```
cctgtagcat cactccatgt ttttagatgg cagattcgac                          40
```

<210> SEQ ID NO 146
<211> LENGTH: 21
<212> TYPE: DNA
<213> ORGANISM: Artificial Sequence
<220> FEATURE:
<223> OTHER INFORMATION: Artificially produced

<400> SEQUENCE: 146

```
cgctcgatac acagctgagt t                                              21
```

<210> SEQ ID NO 147
<211> LENGTH: 71
<212> TYPE: DNA
<213> ORGANISM: Artificial Sequence
<220> FEATURE:
<223> OTHER INFORMATION: Artificially produced

<400> SEQUENCE: 147

```
acctcagctg tgtatcgagc ggcagccccc ccgtcgcccc ccagcacccc cgtcgaatct    60
gccatctaaa a                                                         71
```

<210> SEQ ID NO 148
<211> LENGTH: 60
<212> TYPE: DNA
<213> ORGANISM: Artificial Sequence
<220> FEATURE:
<223> OTHER INFORMATION: Artificially produced

<400> SEQUENCE: 148

```
cctgtagcat cactccatgt tgaacgtaga tgcaagtacc ttttagatgg cagattcgac    60
```

<210> SEQ ID NO 149
<211> LENGTH: 21
<212> TYPE: DNA
<213> ORGANISM: Artificial Sequence
<220> FEATURE:
<223> OTHER INFORMATION: Artificially produced

<400> SEQUENCE: 149

```
cgctcgatac acagctgagg t                                              21
```

<210> SEQ ID NO 150
<211> LENGTH: 71
<212> TYPE: DNA
<213> ORGANISM: Artificial Sequence
<220> FEATURE:
<223> OTHER INFORMATION: Artificially produced

<400> SEQUENCE: 150

```
acctcagctg tgtatcgagc ggcagccccc ccgtcgcccc ccagcacccc cgtcgaatct    60
gccatctaaa a                                                         71
```

<210> SEQ ID NO 151
<211> LENGTH: 39
<212> TYPE: DNA
<213> ORGANISM: Artificial Sequence
<220> FEATURE:
<223> OTHER INFORMATION: Artificially produced

<400> SEQUENCE: 151
cctgtagcat cactccatgt tttagatggc agattcgac                                  39

<210> SEQ ID NO 152
<211> LENGTH: 21
<212> TYPE: DNA
<213> ORGANISM: Artificial Sequence
<220> FEATURE:
<223> OTHER INFORMATION: Artificially produced

<400> SEQUENCE: 152
cgctcgatac acagctgagg t                                                      21

<210> SEQ ID NO 153
<211> LENGTH: 22
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: photo cleavable spacer (Glen Research Products
      cat# 10-4913), linked to LH193 (Diisopropyl-phosphoramidous acid
      2-cyano-ethyl ester
      2-[2-(2-{2-[2-(2-{[(4-methoxy-phenyl)-diphenyl-methyl]-amino}-eth

<400> SEQUENCE: 153
cagcttggac accacgtcat ac                                                     22

<210> SEQ ID NO 154
<211> LENGTH: 84
<212> TYPE: DNA
<213> ORGANISM: Artificial Sequence
<220> FEATURE:
<223> OTHER INFORMATION: Artificially produced

<400> SEQUENCE: 154
gctagagacg tggtggagga agtcttccta gaagctggat atcaccacat ctctagcagc           60
tagtatgacg tggtgtccaa gctg                                                  84

<210> SEQ ID NO 155
<211> LENGTH: 84
<212> TYPE: DNA
<213> ORGANISM: Artificial Sequence
<220> FEATURE:
<223> OTHER INFORMATION: Artificially produced

<400> SEQUENCE: 155
gctagagacg tggtggagga agtcttccta gaagctggat atcaggtctt ctgtcttctt           60
ccgtatgacg tggtgtccaa gctg                                                  84

<210> SEQ ID NO 156
<211> LENGTH: 84
<212> TYPE: DNA
<213> ORGANISM: Artificial Sequence
<220> FEATURE:
<223> OTHER INFORMATION: Artificially produced

<400> SEQUENCE: 156

```
gctagagacg tggtggagga agtcttccta gaagctggat atcttcagtt ctcgactcct    60
gagtatgacg tggtgtccaa gctg                                           84
```

<210> SEQ ID NO 157
<211> LENGTH: 84
<212> TYPE: DNA
<213> ORGANISM: Artificial Sequence
<220> FEATURE:
<223> OTHER INFORMATION: Artificially produced

<400> SEQUENCE: 157

```
gctagagacg tggtggagga agtcttccta gaagctggat atctgacgtg ttgacgtaca    60
cagtatgacg tggtgtccaa gctg                                           84
```

<210> SEQ ID NO 158
<211> LENGTH: 21
<212> TYPE: DNA
<213> ORGANISM: Artificial Sequence
<220> FEATURE:
<223> OTHER INFORMATION: Artificially produced

<400> SEQUENCE: 158

```
gtcagagacg tggtggagga a                                              21
```

<210> SEQ ID NO 159
<211> LENGTH: 18
<212> TYPE: DNA
<213> ORGANISM: Artificial Sequence
<220> FEATURE:
<223> OTHER INFORMATION: Artificially produced
<220> FEATURE:
<221> NAME/KEY: misc_feature
<222> LOCATION: (1)..(1)
<223> OTHER INFORMATION: 6-FAM-

<400> SEQUENCE: 159

```
tccagcttct aggaagac                                                  18
```

<210> SEQ ID NO 160
<211> LENGTH: 6
<212> TYPE: PRT
<213> ORGANISM: Artificial Sequence
<220> FEATURE:
<223> OTHER INFORMATION: Artificially produced

<400> SEQUENCE: 160

Met Gly Asx Asn Phe Gln
1               5

<210> SEQ ID NO 161
<211> LENGTH: 22
<212> TYPE: DNA
<213> ORGANISM: Artificial Sequence
<220> FEATURE:
<223> OTHER INFORMATION: Artificially produced

<400> SEQUENCE: 161

```
cagcttggac accacgtcat ac                                             22
```

<210> SEQ ID NO 162
<211> LENGTH: 30
<212> TYPE: DNA
<213> ORGANISM: Artificial Sequence
<220> FEATURE:
<223> OTHER INFORMATION: Artificially produced

```
<400> SEQUENCE: 162
gtcatactag ctgctagaga tgtggtgata                                        30

<210> SEQ ID NO 163
<211> LENGTH: 28
<212> TYPE: DNA
<213> ORGANISM: Artificial Sequence
<220> FEATURE:
<223> OTHER INFORMATION: Artificially produced

<400> SEQUENCE: 163
catacggaag aagacagaag acctgata                                          28

<210> SEQ ID NO 164
<211> LENGTH: 29
<212> TYPE: DNA
<213> ORGANISM: Artificial Sequence
<220> FEATURE:
<223> OTHER INFORMATION: Artificially produced

<400> SEQUENCE: 164
tcatactcag gagtcgagaa ctgaagata                                         29

<210> SEQ ID NO 165
<211> LENGTH: 28
<212> TYPE: DNA
<213> ORGANISM: Artificial Sequence
<220> FEATURE:
<223> OTHER INFORMATION: Artificially produced

<400> SEQUENCE: 165
catactgtgt acgtcaacac gtcagata                                          28

<210> SEQ ID NO 166
<211> LENGTH: 25
<212> TYPE: DNA
<213> ORGANISM: Artificial sequence
<220> FEATURE:
<223> OTHER INFORMATION: Artificially produced

<400> SEQUENCE: 166
tcgtaacgac tgaatgacgt ctgct                                             25
```

METHOD FOR THE SYNTHESIS OF A BIFUNCTIONAL COMPLEX

This application is a Continuation of U.S. Ser. No. 10/525,817, filed 15 Sep. 2005, which is a National Stage of PCT/DK2003/000739 filed 30 Oct. 2003, now U.S. Pat. No. 8,206,901, which claims the benefit of U.S. provisional application Ser. No. 60/422,167, filed 30 Oct. 2002, U.S. provisional application Ser. No. 60/434,425, filed 19 Dec. 2002, U.S. provisional application Ser. No. 60/486,199, filed 11 Jul. 2003, Serial No. PA 2002 01652, filed 30 Oct. 2002, Serial No. PA 2002 01955 filed 19 Dec. 2002, and Serial No. PA 2003 01604 filed 11 Jul. 2003 in Denmark, and which applications are hereby incorporated by reference in their entirety. To the extent appropriate, a claim of priority is made to each of the above disclosed applications. All patent and non-patent references cited in these patent applications, or in the present application, are hereby incorporated by reference in their entirety.

TECHNICAL FIELD OF THE INVENTION

The present invention relates to a method for obtaining a bifunctional complex comprising display molecule part and a coding part. The invention also relates to a method for generation of a library of bifunctional complexes, a method for identifying a display molecule having a preselected property.

BACKGROUND

Approaches have been developed that allow the synthetic encoding of polypeptides and other biochemical polymers. An example of this approach is disclosed in U.S. Pat. No. 5,723,598, which pertains to the generation of a library of bifunctional molecules. One part of the bifunctional complex is the polypeptide and the other part is an identifier oligonucleotide comprising a sequence of nucleotides which encodes and identifies the amino acids that have participated in the formation of the polypeptide. Following the generation of the library of the bifunctional molecules, a partitioning with respect to affinity towards a target is conducted and the identifier oligonucleotide part of the bifunctional molecule is amplified by means of PCR. Eventually, the PCR amplicons are sequenced and decoded for identification of the polypeptides that have affinity towards the target. The library of bifunctional complexes is produced by a method commonly known as split-and-mix. The method implies that a linker molecule is divided into spatial separate compartments and reacted with a specific amino acid precursor at one terminus in each compartment and appended a nucleic acid tag which codes for this specific amino acid precursor at the other terminus by an orthogonal chemical reaction. Subsequently, the content of the various compartments are collected (mixed) and then again split into a number of compartments for a new round of alternating reaction with amino acid precursor and nucleotide tag. The split-and-mix method is continued until the desired length of polypeptide is reached.

This prior art method is constrained in its application because there must be compatible chemistries between the two alternating synthesis procedures for adding a chemical unit as compared to that for adding a nucleotide or oligonucleotide sequence. According to the prior art, the problem of synthesis compatibility is solved by the correct choice of compatible protecting groups as the alternating polymers are synthesised, and by the correct choice of methods for deprotection of one growing polymer selectively while the other growing polymer remains blocked.

Halpin and Harbury have in WO 00/23458 suggested another approach, wherein the molecules formed are not only identified but also directed by the nucleic acid tag. The approach is also based on the split-and-mix strategy to obtain combinatorial libraries using two or more synthetic steps. A plurality of nucleic acid templates are used, each having at one end a chemical reactive site and dispersed throughout the stand a plurality of codon regions, each of said codon regions in turn specifying different codons. The templates are separated by hybridisation of the codons to an immobilised probe and subsequently each of the strands is reacted at the chemical reaction sites with specific selected reagents. Subsequently, all the strands are pooled and subjected to a second partitioning based on a second codon region. The split-and-mix method is conducted an appropriate number of times to produce a library of typically between $10^3$ and $10^6$ different compounds. The method has the disadvantage that a large number of nucleic acid templates must be provided. In the event a final library of $10^6$ different compounds is desired, a total of $10^6$ nucleic acid templates must be synthesised. The synthesis is generally cumbersome and expensive because the nucleic acids templates must be of a considerable length to secure a sufficient hybridisation between the codon region and the probe.

In WO 02/074929 a method is disclosed for the synthesis of chemical compounds. The compounds are synthesised by initial contacting a transfer unit comprising an anti-codon and a reactive unit with a template having a reactive unit associated therewith under conditions allowing for hybridisation of the anti-codon to the template and subsequently reacting the reactive units. Also this method suffers from the disadvantage that a large number of nucleic acid templates initially must be provided.

The prior art methods using templates suffer from the disadvantage that encoding is dependent upon the recognition between the anti-codon and the template. The hybridisation between two oligonucleotides can occur in the event there is a sufficient complementarity between these. Occasionally, the hybridisation will occur even though a complete match between the oligonucleotides is not present. The effect is, in the event a plurality of transfer units are present then sometimes the codon sequence of the template does not correspond to the reactive unit actually reacted. This undesired effect is even more pronounced when the formation of library is intended because a plurality of templates and building blocks are supposed to find each other in the reaction media. When the hybridisation step is not completely correct, molecules will be generated that are encoded by the incorrect codons on the template. This will have two major effects on the selection process performed on the library. First, templates with a codon combination encoding for binding ligands will be lost in the selection process. Secondly, and may be more important, templates with a codon combination encoding for non-binding ligands will be enriched.

In an aspect of the present invention it is an object to provide a non-template dependent method for obtaining an encoded molecule, said method allowing for versatile chemistries to be applied in the formation of the encoded molecule, because the application of compatible orthogonal protection groups in the alternating formation of the encoded molecule and oligonucleotide tag can be avoided. The present invention in a preferred aspect intends to improve on the error prone hybridisation method previous suggested in the codon recognition process. Furthermore, it is an object of the invention to reduce non-specific reaction products formed. Thus, in an aspect of the present invention, the present method has an inherent proof-reading facility securing that the phenotype is accurately encoded by the genotype.

In some embodiments the bifunctional complex comprises codons of different lengths.

In some embodiments, instead of using enzymatic addition of a tag, the tag is chemically connected to the priming site of a tag applying a guiding oligonucleotide complementing an end of the tag and a part of the bifunctional complex comprising the priming site, such that the ends abut each other.

SUMMARY OF THE INVENTION

The present invention relates to a method for obtaining a bifunctional complex comprising a display molecule part and a coding part, wherein a nascent bifunctional complex comprising a chemical reaction site and a priming site for enzymatic addition of a tag is reacted at the chemical reaction site with one or more reactants, and provided with respective tag(s) identifying the reactant(s) at the priming site using one or more enzymes.

Enzymes are in general substrate specific, entailing that the enzymatic addition of a tag to the priming site is not likely to interfere with the display molecule being formed. Thus, the application of protection groups on the coding part as well as the nascent display molecule can be avoided for this reason. However, it may be desired for other reasons to protect the growing display molecule. Enzymes are available having an activity in aqueous and organic media. The vast majority of enzymes, however, have a higher activity in an aqueous media compared to an organic media. Therefore, prior to or subsequent to the providing of the tag it may be desired to change the media in order to obtain applicable conditions for the reaction of the reactant at the chemical reaction site.

Generally, the display molecule part is formed by more than a single round of reaction between one or more reactants and the chemical reaction site. In a certain aspect of the invention, the nascent bifunctional complex reacted with one or more reactants and provided with respective tag(s) is reacted further one or more times with one or more reactant(s) and is provided with respective identifying tag(s) to produce a reaction product as one part of the bifunctional complex and an identifying part comprising tags which codes for the identity of the reactants which have participated in the formation of the reaction product.

In a certain aspect of the invention, a round or cycle of reaction implies that a single reactant is reacted with the chemical reaction site and that a respective tag identifying the reactant is provided at the priming site for enzymatic addition. In another aspect of the invention, a round of reaction implies that multiple reactants are reacted at the chemical reaction site and that tags identifying one or more, but not necessarily all, reactants are provided at the priming site for enzymatic addition. The reaction at the chemical reaction site and the addition of tags may occur in any order, i.e. the reaction may occur subsequent to, simultaneously with, or previous to the tag addition. The choice of order may among other things be dependent on the enzyme type, the reaction conditions, and the type of reactant.

The nascent bifunctional complex comprises a chemical reaction site and a priming site for enzymatic addition of a tag. Optionally, the nascent bifunctional complex also comprises a linking moiety, which connects the chemical reaction site with the priming site. The linking moiety may serve various purposes, such as distancing the priming site from the chemical reaction site sufficient from each other to allow an enzyme to perform the tag addition and provide for a hybridisation region. In an aspect of the invention, the linking moiety is a nucleic acid sequence. The length of the oligonucleotide is preferably suitable for hybridisation with a complementing oligonucleotide, i.e. the number of nucleotides in the linking moiety is suitably 8 or above. In a certain embodiment, the linking moiety is attached to the chemical reaction site via a spacer comprising a selectively cleavable linker to enable a detachment of the display molecule from the coding part in a step subsequent to the formation of the final bifunctional complex. A nascent bifunctional complex is also referred to as a growing complex and specifies an initial or intermediate complex to be processed according to the method of the present invention. An intermediate complex designates an initial complex that has been subjected to one or more rounds of reactant reaction and tag addition.

The chemical reaction site may comprise a single or multiple reactive groups capable of reacting with one or more reactants. In a certain aspect the chemical reaction site comprises a scaffold having one or more reactive groups attached. Examples of suitable reactive groups include amine, carboxylic acid, thio, aldehyde, and hydroxyl groups. Examples of scaffolds include benzodiazepines, steroids, hydantiones, piperasines, diketopiperasines, morpholines, tropanes, cumarines, qinolines, indoles, furans, pyrroles, oxazoles, amino acid precursors, and thiazoles. Furthermore, the reactive groups of the chemical reaction site may be in a pro-form that has to be activated before a reaction with the reactant can take place. As an example, the reactive groups can be protected with a suitable group, which needs to be removed before a reaction with the reactant can proceed. A display molecule in the present description with claims indicates a chemical reaction site that has been reacted with one or more reactants.

The reactants of the present invention include free reactants as well as reactants which comprises a functional entity and a nucleic acid sequence. The free reactant participates in the reaction with the chemical reaction site and may give rise to a chemical structure of the final display molecule. A functional entity attached to a nucleic acid may be referred to herein as a building block and specifies a chemical entity in which the functional entity is capable of being reacted at the chemical reaction site. In a certain aspect of the invention, the functional entity is detached from the nucleic acid part and transferred to the chemical reaction site. The oligonucleotide of the building block may or may not hold information as to the identity of the functional entity. In a certain embodiment of the present invention, the reactant is a building block comprising an oligonucleotide sufficient complementary to the linking moiety to allow for hybridisation, a transferable functional entity, and an anti-codon identifying the functional entity. The free reactant is generally not attached to a nucleic acid unless a nucleic acid component is intended in the final display molecule. The free reactant may have any chemical structure and preferably comprises a reactive group or a precursor therefore, which will enable a reaction with a chemical reaction site. Examples of reactive groups include hydroxyl groups, carboxylic acid groups, thiols, isocyanates, amines, esters, and thioesters. Optionally, a further reactant occurs to mediate a connection between the free reactant and the chemical reaction site. The functional entity of a building block resembles the free reactant as far as the requirement for reaction with the chemical reaction site concerns. In addition, however, it is in most instances necessary to cleave the connection between the functional entity and the nucleic acid following the reaction. Optionally, the reaction and cleavage may occur in a single step. Various types of building blocks are disclosed in detail below. In a certain aspect of the invention, the free reactant or the functional entity do not include a nucleotide.

The coding part of the nascent bifunctional complex is formed by addition of at least one tag to a priming site using one or more enzymes. Further tags may be attached to a previous tag so as to produce a linear or branched identifier. As long as at least one tag of the identifier is attached by an enzymatic catalysed reaction, further tags may be provided using chemical means or enzymatic means at the discretion of the experimenter. In a certain embodiment of the invention, all tags are provided using an enzymatic catalysed reaction. A tag suitably comprises recognition units, i.e. units which may be recognized by recognition groups. The recognition unit possess an ability to carry information so as to identify a reactant. A variety of different kinds of recognition exist in nature. Examples are antibodies, which recognise an epitope, proteins which recognise another protein, mRNA which recognise a protein, and oligonucleotides which recognise complementing oligonucleotide sequences. Generally, it is preferred that the tag is a sequence of nucleotides.

The coding part of the bifunctional complex is in a preferred aspect of the invention amplifiable. The capability of being amplified allows for the use of a low amount of bifunctional complex during a selection process. In the event, the tag is a protein, the protein may be amplified by attaching the mRNA which has encoded the synthesis thereof, generating the cDNA from the mRNA and subjecting said mRNA to a translation system. Such system is disclosed in WO 98/31700, the content of which is incorporated herein by reference. An alternative method for amplifying a protein tag is to use phage displayed proteins. In general, however, the tag is a sequence of nucleotides, which may be amplified using standard techniques like PCR. When two or more tags are present in a linear identifying oligonucleotide, said oligonucleotide generally consist of a certain kind of backbone structure, so as to allow an enzyme to recognise the oligonucleotide as substrate. As an example the back bone structure may be DNA or RNA.

The priming site of a nascent bifunctional complex is capable of receiving a tag. The chemical identity of the priming site depends among other things on the type of tag and the particular enzyme used. In the event the tag is a polynucleotide, the priming site generally comprises a 3'-OH or 5'-phosphate group of a receiving nucleotide, or functional derivatives of such groups. Enzymes which may be used for enzymatic addition of a tag to the priming site include an enzyme selected from polymerase, ligase, and recombinase, and a combination of these enzymes.

The reaction between the chemical reaction site and the one or more reactants may take place under suitable conditions that favours the reaction. In some aspects of the invention, the reaction is conducted under hybridisation conditions, i.e. an annealing between two complementing oligonucleotides remains during the reaction conditions. In other aspects of the invention, the reaction is conducted under denaturing conditions to allow for suitable condition for the reaction to occur. In the event, the coding part of the growing complex comprises an oligonucleotide; said oligonucleotide is in an aspect of the invention in a double stranded form during the reaction to reduce the likelihood of side reactions between components of the oligonucleotide and reactants.

The tag identifying a reactant can be added to the priming site using any appropriate enzyme. In a certain embodiment, a tag is provided at the priming site of the nascent bifunctional complex utilizing an enzymatic extension reaction. The extension reaction may be performed by a polymerase or a ligase or a combination thereof. The extension using a polymerase is suitably conducted using an anti-tag oligonucleotide as template. The anti-tag oligonucleotide is annealed at the 3' end of the oligonucleotide part of the nascent bifunctional complex with a single stranded overhang comprising an anti-codon, which identifies the reactant. The anti-codon of the anti-tag can be transcribed to the identifier part using a polymerase and a mixture of dNTPs. Alternatively, a ligase is used for the addition of the tag using one or more oligonucleotides as substrates. The ligation can be performed in a single stranded or a double stranded state depending on the enzyme used. In general it is preferred to ligate in a double stranded state, i.e. oligonucleotides to be ligated together are kept together by a complementing oligonucleotide, which complements the ends of the two oligonucleotides.

Examples of suitable enzymes include DNA polymerase, RNA polymerase, Reverse Transcriptase, DNA ligase, RNA ligase, Taq DNA polymerase, Pfu polymerase, Vent polymerase, HIV-1 Reverse Transcriptase, Klenow fragment, or any other enzyme that will catalyze the incorporation of complementing elements such as mono-, di- or polynucleotides. Other types of polymerases that allow mismatch extension could also be used, such for example DNA polymerase η (Washington et al., (2001) JBC 276: 2263-2266), DNA polymerase ι (Vaisman et al., (2001) JBC 276: 30615-30622), or any other enzyme that allow extension of mismatched annealed base pairs. In another aspect, when ligases are used, suitable examples include Taq DNA ligase, T4 DNA ligase, T4 RNA ligase, T7 DNA ligase, and E. coli DNA ligase. The choice of the ligase depends to a certain degree on the design of the ends to be joined together. Thus, if the ends are blunt, T4 RNA ligase may be preferred, while a Taq DNA ligase may be preferred for a sticky end ligation, i.e. a ligation in which an overhang on each end is a complement to each other.

The tag added to the priming site of the nascent bifunctional complex holds information as to the reactant. In the present invention with claims, the information relating to the reactant will be termed codon. Apart from a combination of the nucleotides coding for the identity of the reactant, a tag may comprise further nucleotides. In a certain aspect of the invention, a tag comprises a framing sequence. The framing sequence may serve various purposes, such as an annealing region for anti-tags and/or as a sequence informative of the point in time of the synthesis history the associated reactant has reacted.

The association between the codon and the identity of the reactant may vary dependent on the desired output. In a certain embodiment, the codon is used to code for several different reactants. In a subsequent identification step, the structure of the display molecule can be deduced taking advantage of the knowledge of the different attachment chemistries, steric hindrance, deprotection of orthogonal protection groups, etc. In another embodiment, the same codon is used for a group of reactants having a common property, such as a lipophilic nature, molecular weight, a certain attachment chemistry, etc. In a preferred embodiment however, the codon is unique, i.e. a similar combination of nucleotides does not identify another reactant. In a practical approach, for a specific reactant, only a single combination of nucleotides is used. In some aspects of the invention, it may be advantageous to use several different codons for the same reactant. The two or more codons identifying the same reactant may carry further information related to different reaction conditions. In another aspect of the invention, a single codon specifies two or more reactants.

In one aspect of the invention, each bifunctional complex is prepared by simultaneous or sequentially tagging and reaction of reactant as illustrated in the scheme below:

Capital letters represent reactant or chemical reaction site. Lower case letters represent tags.

A scaffold "X" is linked to a tag "x". A reactant is linked to "X" e.g. "A" and so is a tag for that fragment e.g. "a". Suitably, the tag is unique.

The coding part of the eventually formed bifunctional complex will contain all the codons. The sequence of each of the codons is used to decipher the structure of the reactants that have participated in the formation of the displayed molecule, i.e. the reaction product. The order of the codons can also be used to determine the order of incorporation of the reactants. This may be of particular interest when a linear polymer is formed, because the exact sequence of the polymer can be determined by decoding the encoding sequence. Usually, to facilitate the decoding step, a constant or binding region is transferred to the bifunctional complex together with the codon. The constant region may contain information about the position of the related reactant in the synthesis pathway of the display molecule.

The invention also relates to a method for identifying a display molecule having a preselected property, comprising the steps of: subjecting the library produced according to the method indicated above to a condition, wherein a display molecule or a subset of display molecules having a predetermined property is partitioned from the remainder of the library, and identifying the display molecule(s) having a preselected function by decoding the coding part of the complex.

The above method, generally referred to as selection, involves that a library is subjected to a condition in order to select display molecules having a property which is responsive to this condition. The condition may involve the exposure of the library to a target. The bifunctional complexes having an affinity towards this target may be partitioned form the remainder of the library by removing non-binding complexes and subsequent eluting under more stringent conditions the complexes that have bound to the target. Alternatively, the coding part of the bifunctional complex can be cleaved from the display molecule after the removal of non-binding complexes and the coding part may be recovered and decoded to identify the display molecule.

It is possible to perform a single or several rounds of selection against a specific target with a subsequently amplification of the selected variants. These obtained variants are then separately tested in a suitable assay. The selection condition can be stringent and specific to obtain binding molecules in one selection rounds. It may be advantageously to perform the method using a single round of selection because the number and diversity of the potential binders are larger compared to procedures using further selections where potential binders may be lost. In another embodiment the selection procedure involves several round of selection using increasing stringency conditions. Between each selection an amplification of the selected complex may be desirable.

The coding part can be amplified using PCR with primers generating two unique cut-sites. These cut-sites can be used for multimerization of the coding region by cloning into a suitable vector for sequencing. This approach will allow simultaneously sequencing of many encoding regions. Alternatively, the PCR product is directly cloned into a suitable vector using for example TA cloning. In still another approach the identity of the display molecule is established by applying the PCR product to a suitable microarray.

It is within the capability of the skilled person in the art to construct the desired design of an oligonucleotide. When a specific annealing temperature is desired it is a standard procedure to suggest appropriate compositions of nucleic acid monomers and the length thereof. The construction of an appropriate design may be assisted by software, such as Vector NTI Suite or the public database at the internet address .http://www.nwfsc.noaa.gov/protocols/oligoTMcalc. The conditions which allow hybridisation of two oligonucleotides are influenced by a number of factors including temperature, salt concentration, type of buffer, and acidity. It is within the capabilities of the person skilled in the art to select appropriate conditions to ensure that the contacting between two oligonucleotides is performed at hybridisation conditions. The temperature at which two single stranded oligonucleotides forms a duplex is referred to as the annealing temperature or the melting temperature. The melting curve is usually not sharp indicating that the annealing occurs over a temperature.

The present invention may be conducted in two basic modes. A first mode uses a reactant in which a codon or anti-codon covalently is connected to the functional entity which it identifies. A second mode uses a reactant which is not covalently attached to a codon or anti-codon. The tag is provided at the priming site of the bifunctional complex by an entity separate from the reactant. When more than a single round is carried out, the first and the second mode can be combined in any order. When a library of different bifunctional complexes is to be generated, the two modes are conducted in accordance with two different approaches. A library produced using the first mode can be conducted in a single vessel, which herein will be referred to as a one-pot synthesis, whereas a library produced according to the second mode requires a split-and-mix synthesis, i.e. the reaction and tag addition must be carried out in separate compartments for each complex. In a certain embodiment of the invention, one or more tags coding for two or more reactants, respectively, are provided prior to or subsequent to the reaction involving the two or more reactants and the chemical reaction site.

Mode 1:

The present invention relates in a first mode to a method for encoding the identity of a chemical entity transferred to a bifunctional complex, said method comprising the steps of
a) providing a nascent bifunctional complex comprising a reactive group and an oligonucleotide identifier region,
b) providing a building block comprising an oligonucleotide sufficient complementary to the identifier region to allow for hybridisation, a transferable functional entity, and an anti-codon identifying the functional entity,
c) mixing the nascent bifunctional complex and the building block under hybridisation conditions to form a hybridisation product,
d) transferring the functional entity of the building block to the nascent bifunctional complex through a reaction involving the reactive group of the nascent bifunctional complex, and
e) enzymatically extending the oligonucleotide identifier region to obtain a codon attached to the bifunctional complex having received the chemical entity.

The method of the invention involves the incorporation of a codon for the functional entity transferred to the complex. The incorporation of the codon is performed by extending over an anticodon of the building block using an appropriate enzyme, i.e. an enzyme active on nucleic acids. The transcription of the encoding region can be accomplished by an enzyme, such as a polymerase or a ligase. In general, it is preferred to use enzymes which are specific toward the substrate and the end-product to obtain an as accurate as possible transcription of the anti-codon. A high degree of specificity is generally available for nucleic acid active enzymes because a non-specific activity could destroy the ability of the living cells to survive. Especially preferred enzymes according to the present invention are polymerases with proof-reading activity for accurate encoding but preservation of the upstream nucleobases.

The enzymatic extension may occur subsequent to or simultaneously with the transfer of the functional entity or even prior to the transfer. However, in general it is preferred to perform the extension step subsequent to the transfer step to avoid any possible interaction between the enzyme and the functional entity.

As the enzyme will perform extension only when the identifier region and the complementing identifier region has hybridised to each other to form a double helix, it is secured that the functional entity and the reactive group has been in close proximity when the complex is provided with a codon. Compared to the hybridisation method previously suggested, the present invention has the advantage that complexes provided with functional entities through a non-directed reaction will not be provided with a codon. Thus, false positive molecules may easily be detected due to the absence of a codon.

The invention also relates to a method for obtaining a bifunctional complex composed of a display molecule part and a coding part, wherein the method for encoding the identity of a chemical entity transferred to a bifunctional complex further comprises step f) separating the components of the hybridisation product and recovering the complex.

The invention may be performed by transferring only a single functional entity and the corresponding codon to the nascent bifunctional complex. However, in general it is preferred to build a display molecule composed of two of more functional entities. Thus, in a preferred aspect of the invention a method is devised for obtaining a bifunctional complex composed of a display molecule part and a coding part, said display molecule part being the reaction product of functional entities and the reactive group of the initial complex, wherein steps c) to f) are repeated as appropriate. In the final cycle of the preparation of the bifunctional complex, step f) may be dispensed with, notably in cases in which a double stranded identifier oligonucleotide is obtained because a double stranded nucleic acid usually is more stable compared to a corresponding single stranded oligonucleotide. The identifier oligonucleotide may also become double stranded by an extension process in which a primer is annealed to the 3"end of the oligonucleotide and extended using a suitable polymerase. The double strandness may be an advantage during subsequent selection processes because a single stranded nucleic acid may perform interactions with a biological target, in a way similar to aptamers. In the repetition of the cycle, the produced bifunctional complex in a previous cycle, i.e. a nascent bifunctional complex that has received a functional entity and a codon, is used as the nascent bifunctional complex in the next cycle of functional entity transfer and codon incorporation.

The oligonucleotides used according to the present method are of a reasonable extent. Thus, the long pre-made templates suggested in the prior art (in WO 00/23458 it is suggested to use oligonucleotides of at least 220 and preferably 420 nucleotides) are generally avoided.

The invention also relates to a method for generating a library of bifunctional complexes, comprising the steps of:
a) providing one or more different nascent bifunctional complexes comprising a reactive group and an oligonucleotide identifier region,
b) providing a plurality of different building blocks, each comprising an oligonucleotide sufficient complementary to an identifier region to allow for hybridisation, a transferable functional entity, and an anti-codon identifying the functional entity,
c) mixing nascent bifunctional complexes and plurality of building blocks under hybridisation conditions to form hybridisation products,
d) transferring functional entities of the building blocks to the nascent bifunctional complexes through a reaction involving the reactive group of the nascent bifunctional complex,
e) enzymatically extending the oligonucleotide identifier regions to obtain codons attached to the bifunctional complexes having received the chemical entities,
f) separating the components of the hybridisation products and recovering the complexes,
g) repeating steps c) to f) one or more times, as appropriate.

A disadvantage associated with the hybridisation technique suggested in the prior art becomes apparent when the formation of libraries are considered. Even though two double stranded oligonucleotides have the same number of nucleotides it is by no means ensured that they will possess the same melting temperature. This is at least partly due to the fact that different number of hydrogen bondings are involved for different base pairs (the C-G pair involves three hydrogen bondings and the A-T base pair involves two hydrogen bondings). Thus, establishing a temperature for the annealing of various building blocks to a template will be a compromise between avoiding mismatching and ensuring sufficient annealing. The present invention aims at avoiding this disadvantage by providing, in a preferred embodiment of the invention, an identifier region having a similar affinity towards all building blocks.

In the event, more than one identifier sequence is used, e.g. when more than one kind of reactive group or scaffolds are present, a building block occasionally may be mis-annealed thereto. However, the transferred functional entity will actually be correctly encoded on the complex through the extension process. This approach resembles the arrangement Nature is using: Allowing mis-incorporation of bases at the DNA level (compare to mismatch annealing of building blocks) to obtain diversification but insisting on correct encoding for the phenotype (compare to the extension of the right codon on the complex).

The annealing between the identifier and the building block can either be a random process or be guided by the sequences in the identifier region and the complementing identifier region. A random process can be achieved by using the same sequence in all identifier regions and the complementing identifier regions. Thus a mixture of identifiers and building blocks will anneal randomly or simi-randomly and create unique combinations of functional entities. Alternatively, a random or simi-random process can be achieved by using universal bases at positions of the building block opposing nucleobases of the identifier that codes for the identity of a particular scaffold or reactive group. The sequences of the identifier oligonucleotides and the building block oligonucleotides may be optimized such that it is assured that the sequences in a library involved in the annealing process will assemble at an equal degree of annealing regardless of which functional entity that is attached to the building block. Thus, there will be no or diminished bias in the selection procedure due to different annealing properties for specific building blocks. In addition, the similarities in the annealing process in each annealing step and for each hybridisation product in a library will make sure the functional entity is presented equally for the reactive group/scaffold. This will provide optimal conditions for the transfer step.

The nascent bifunctional complex comprises an oligonucleotide identifier region and a reactive group. The reactive group may be connected to the oligonucleotide through a cleavable linker allowing for the separation of the final reaction product from the oligonucleotide. A single reactive group may be present or multiple reactive groups may be present as a part of a scaffold. The scaffold may be attached to the oligonucleotide through a cleavable linker to allow for subsequent separation of the reacted scaffold. The reactive groups may be selected from any groups capable of receiving a functional entity. Examples of suitable reactive groups include amine, carboxylic, thio, and hydroxyl groups. Furthermore, the reactive group of the nascent bifunctional complex may be in a pro-form that has to be activated before the method of the invention is initiated. A nascent bifunctional complex is also referred to as a growing complex and specifies an initial or intermediate complex to be further processed according to the present invention.

The number of nucleotides in the identifier region of the identifier molecule is determined from how strong and specific the annealing should be between the identifier and building block. A stronger and more specific annealing process is generally obtained with a longer nucleotide sequence. Normally about 10-20 nucleotides is sufficient to achieve specific and efficient annealing. However, in some aspects of the invention the range can be from 2-1000, most preferably between 15-30 nucleotides.

The identifier region may in certain embodiments comprise information about the identity of the reactive group or the scaffold of the nascent bifunctional complex. Such scaffold codon is generally at a position distanced from the scaffold to allow for the formation of a stable double helix at the part comprising the functional entity to be transferred and the scaffold. The scaffold codon may have any length but is generally selected with the same length as the codons specifying the functional entities. The rear part of the identifier region is generally provided with a constant or binding sequence. The binding sequence when annealed to a suitable part of the building block provides for a substrate for the enzyme to perform the extension.

The building block comprises an oligonucleotide sufficient complementary to at least a part of the identifier region to allow for hybridisation. The oligonucleotide of the building block may not completely be complementary to the identifier, that is, one or more mismatches may be allowed but it must be assured that the building block is able to anneal to the identifier region. For the sake of simplicity, the part of the building block oligonucleotide capable of annealing to the identifier will be referred to as the complementing identifier region. In the present description with claims, the term hybridisation is to be understood as the process of attaching two single stranded oligonucleotides to each other such that a hybridisation product is formed.

The building block comprises also an anticodon region made of oligonucleotides. The anti-codon identifies the identity of the functional entity of the building block. In a certain embodiment, the same anticodon is used to code for several different functional entities. In a subsequent identification step, the structure of the display molecule can be deduced taking advantage of the knowledge of different attachment chemistries, steric hindrance, deprotection of orthogonal protection groups, etc. In another embodiment, the same anticodon is used for a group of function entities having a common property, such as a lipophilic nature, a certain attachment chemistry etc. In a preferred embodiment, however, the anti-codon is unique i.e. a similar combination of nucleotides does not appear on another building block carrying another functional entity. In a practical approach, for a specific functional entity, only a single combination of nucleotides is used. In some aspects of the invention, it may be advantageous to use several anti-codons for the same functional entity, much in the same way as Nature uses up to six different anti-codons for a single amino acid. The two or more anti-codons identifying the same functional entity may carry further information related to different reaction conditions.

The individual anti-codons may be distinguished from another anti-codon in the library by only a single nucleotide. However, to facilitate a subsequent decoding process it is in general desired to have two or more mismatches between a particular anticodon and any other anti-codon appearing on the various building blocks. As an example, if a codon/anti-codon length of 5 nucleotides is selected, more than 100 nucleotide combinations exist in which two or more mismatches appear. For a certain number of nucleotides in the codon, it is generally desired to optimize the number of mismatches between a particular codon/anticodon relative to any other codon/anticodon appearing in the library.

The coupling of the functional entity to the complementary identifier region can be done with suitable coupling reactions. Any coupling reaction or combination of such reactions known in the art can be used as appropriate as readily recognized by those skilled in the art. The functional entity linked to the complementary identifier region is a molecule, which preferably comprises at least one reactive group that allows linkage to the reactive group of the identifier.

The sequence of the anticodon identifies the functional entity attached in the same building block. This anticodon sequence is either directly included in the building block sequence or is attached to a pre-existing building block using a polymerase or a ligase for example. In a certain embodiment, as disclosed in detail in example 7, complementing identifier regions, termed carrier oligos in the example, are initially loaded with the various functional entities. Each of the loaded carrier oligoes is subsequently ligated to an anti-codon oligo using a splint oligo to assemble the two oligonucleotides. The ligation reaction serves to connect the functional entity to be transferred with an anticodon specifying the structure of the functional entity. The anti-codon oligo may be designed in various ways. Normally, a region that allows for the annealing of the splint is included in the design. However, some ligases like the T4 RNA ligase, does not require a stretch of double stranded DNA. Therefore, the splint and the part of the anti-codon oligo annealing to the splint can be dispensed with in some embodiments. In the event the identifier region comprises a codon coding for the identity of the scaffold, the anti-codon oligo comprises a stretch of universal bases, like inosines. The universal bases may be dispensed with if a region complementing a binding region on the identifier region is included downstream. The latter embodiment normally will entail that a part of the identifier loops out. The complementing binding region is normally selected such that a polymerase is capable of recognizing a formed double helix with a binding region of the nascent bifunctional molecule as a substrate. The anti-codon is suitably positioned at the 5' side of the complementing binding region so it can be transferred to the nascent complex by an extension reaction. Suitably, the complementing binding region is designed such that it is possible to identify the position of the particular codon in the sequence of codons appearing on the eventual bifunctional complex.

The anticodon sequence is transcribed to the identifier through an extension process to form the codon on the identifier molecule. This may be carried out by any state of the art method including, but not limited to, a polymerase extension reaction. A polymerase extension reaction usually requires the presence of sufficient polymerase activity together with each of the four natural nucleotide tri-phosphates (ATP, CTP, GTP, and TTP) in a suitable buffer. Thus, the sequence of a particular anticodon is only transferred to the identifier as a codon when the building block and the identifier molecule has annealed and allow reaction to take place between the functional entity and the recipient reactive group.

The four natural nucleotides can encode for $4^N$ variants where N is the length of the codon. For example, if the unique codon is 5 nucleotides in length, the number of possible encoding for different functional entities is 1024. The codons can also be design using a sub-set of the four natural nucleotides in each position. This can be useful in combination with the use of universal nucleobases. The anticodon in each building block is coding for the functional entity in the same building block. This sequence may in an aspect of the invention be incorporated by PCR of the complementing identifier region with a functional entity primer and an anticodon primer.

The functional entity of the building block serves the function of being a precursor for the structural entity eventually incorporated into the displayed molecule. Therefore, when in the present application with claims it is stated that a functional entity is transferred to a nascent bifunctional complex it is to be understood that not necessarily all the atoms of the original functional entity is to be found in the eventually formed display molecule. Also, as a consequence of the reactions involved in the connection, the structure of the functional entity can be changed when it appears on the nascent display molecule. Especially, the cleavage resulting in the release of the functional entity may generate a reactive group which in a subsequent step can participate in the formation of a connection between a nascent display molecule and a functional entity.

The functional entity of the building block preferably comprises at least one reactive group capable of participating in a reaction which results in a connection between the functional entity of the building block and the identifier carrying the reactive group. The number of reactive groups which appear on the functional entity is suitably one to ten. A functional entity featuring only one reactive group is used i.a. in the end positions of polymers or scaffolds, whereas functional entities having two reactive groups are suitable for the formation of the body part of a polymer or scaffolds capable of being reacted further. Two or more reactive groups intended for the formation of connections, are typically present on scaffolds. A scaffold is a core structure, which forms the basis for the creation of multiple variants. The variant forms of the scaffold are typically formed through reaction of reactive groups of the scaffold with reactive groups of other functional entities, optionally mediated by fill-in groups or catalysts. The functional entities to be connected to the scaffold may contain one, two or several reactive groups able to form connections. Examples of scaffold include steroids, hydantions, benzodiazepines, etc.

The reactive group of the building block may be capable of forming a direct connection to a reactive group of the identifier or the reactive group of the building block may be capable of forming a connection to a reactive group of the identifier through a bridging fill-in group. It is to be understood that not all the atoms of a reactive group are necessarily maintained in the connection formed. Rather, the reactive groups are to be regarded as precursors for the structure of the connection.

After or simultaneously with the formation of the connection a cleavage is performed to transfer the functional entity to the identifier. The cleavage can be performed in any appropriate way. In an aspect of the invention the cleavage involves usage of a reagent or and enzyme. The cleavage results in a transfer of the functional entity to the nascent bifunctional complex or in a transfer of the complex to the functional entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the functional entity of the building block or the nascent display molecule is a leaving group of the reaction. In some aspects of the invention, it is preferred to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above. In other aspects of the invention, it is preferred to conduct separate cross-linkage and cleavage steps because the stepwise approach allows for mastering each sub steps and for a reduction in the likelihood for non-specific transfer.

Preferably, at least one linker remains intact after the cleavage step. The at least one linker will link the nascent display molecule to the encoding region. In case the method essentially involves the transfer of functional entities to a scaffold or an evolving polymer, the eventually scaffolded molecule or the polymer may be attached with a selectively cleavable linker. The selectively cleavable linker is designed such that it is not cleaved under conditions which result in a transfer of the functional entity to the nascent template-directed molecule.

The cleavable linkers may be selected from a large plethora of chemical structures. Examples of linkers includes, but are not limited to, linkers having an enzymatic cleavage site, linkers comprising a chemical degradable component, and linkers cleavable by electromagnetic radiation. Cleavable linkers of particular interest are currently linkers that can be cleaved by light. A suitable example includes an o-nitro benzyl group positioned between the display molecule and the identifier region.

The building blocks used in the method according to the present invention may be designed in accordance with the particular entities involved in the building block. As an example, the anti-codon may be attached to the complementing identifier region with a polyethylene glycol (PEG) linker and the functional entity may be directly attached to said complementing identifier region. In another and preferred example, the anti-codon, complementing identifier region and the functional entity is a contiguous linear oligonucleotide. In a certain embodiment of the invention, the building block is designed such that a part of the identifier loops out. The loop out of the identifier usually occurs because the building block oligo does not anneal to the entire length of the identifier. Usually, the building block is designed such that it is able to anneal to at least the identifier region of the bifunctional complex and to a binding region at the rear part of the identifier. The complementing identifier region and the anticodon may be directly connected through a single linkage, connected through a PEG linker of a suitable length, or a sequence of nucleobases which may or may not comprise nucleobases complementing the various codons and binding region on the identifier. In a certain embodiment of the invention, the building block is designed only to anneal to a binding region, usually at an end of the identifier opposing the end having attached the display molecule. In an aspect of the invention the building block and/or the nascent identifier are composed of two or more separate nucleotides, which are able to hybridise to each other to form the hybridisation complex. The gaps between the oligonucleotides may be filled with suitable nucleotide using an appropriate enzyme activity, such as a polymerase and a ligase, to produce a coherent identifier and or building block.

The attachment of the functional entity to the complementing identifier region is usually conducted through a linker. Preferably the linker connects the functional entity with the complementing identifier region at a terminal nucleotide or a nucleotide 1 or two nucleotides down the oligonucleotide. The attachment of the functional entity can be at any entity available for attachment, i.e. the functional entity can be attached to a nucleotide of the oligonucleotide at the nucleobase, or the back bone. In general, it is preferred to attach the functional entity at the phosphor of the internucleoside linkage or at the nucleobase.

In a certain aspect of the invention, the reactive group of the functional entity is attached to the linker oligonucleotide. The reactive group is preferably of a type which is able to create a connection to the nascent display molecule by either direct reaction between the respective reactive groups or by using a suitable fill-in group. The reactive group coupling the functional entity with the linker is preferably cleaved simultaneously with the establishment of the connection. The functional entity may in some cases contain a second reactive group able to be involved in the formation of a connection in a subsequent cycle. The second reactive group may be of a type which needs activation before it is capable of participating in the formation of a connection.

In the event two or more functional entities are to be transferred to the complex, the codons may be separated by a constant region or a binding region. One function of the binding region may be to establish a platform at which the polymerase can bind. Depending on the encoded molecule formed, the identifier may comprise further codons, such as 3, 4, 5, or more codons. Each of the further codons may be separated by a suitable binding region. Preferably, all or at least a majority of the codons of the identifier are separated from a neighbouring codon by a binding sequence. The binding region may have any suitable number of nucleotides, e.g. 1 to 20.

The binding region, if present, may serve various purposes besides serving as a substrate for an enzyme. In one setup of the invention, the binding region identifies the position of the codon. Usually, the binding region either upstream or downstream of a codon comprises information which allows determination of the position of the codon. In another setup, the binding regions have alternating sequences, allowing for addition of building blocks from two pools in the formation of the library. Moreover, the binding region may adjust the annealing temperature to a desired level.

A binding region with high affinity can be provided by incorporation of one or more nucleobases forming three hydrogen bonds to a cognate nucleobase. Examples of nucleobases having this property are guanine and cytosine. Alternatively, or in addition, the binding region may be subjected to backbone modification. Several backbone modifications provides for higher affinity, such as 2'-O-methyl substitution of the ribose moiety, peptide nucleic acids (PNA), and 2'-4'O-methylene cyclisation of the ribose moiety, also referred to as LNA (Locked Nucleic Acid).

The identifier may comprise flanking regions around the codons. The flanking region can encompass a signal group, such as a fluorophor or a radio active group to allow for detection of the presence or absence of a complex or the flanking region may comprise a label that may be detected, such as biotin. When the identifier comprises a biotin moiety, the identifier may easily be recovered.

The flanking regions can also serve as priming sites for amplification reactions, such as PCR. Usually, the last cycle in the formation of the bifunctional complex includes the incorporation of a priming site. The identifier region of the bifunctional complex is usually used for another priming site, thereby allowing for PCR amplification of the coding region of the bifunctional complex.

It is to be understood that when the term identifier is used in the present description and claims, the identifier may be in the sense or the anti-sense format, i.e. the identifier can comprise a sequence of codons which actually codes for the molecule or can be a sequence complementary thereto. Moreover, the identifier may be single-stranded or double-stranded, as appropriate.

The design of the part of the complementing identifier region or the building block oligonucleotide in general which comprises one or more anti-codons preceding the active anti-codon can be random or simi-random and one or more mismatches with the identifier region may be allowed. However, especially when a library is contemplated, it may be advantageous to incorporate in a region complementing a preceding codon one or more non-specific base-pairing nucleobases. Non-specific base-pairing nucleobases are bases which, when attached to a backbone, are able to pair with at least two of the five naturally occurring nucleobases (C, T, G, A, and U). Preferably, the base pairing between the two or more natural nucleobases and the non-specifically base-pairing nucleobase occur essentially iso-enegically, i.e. the bonds formed have a strength of the same order. The term "non-specifically base-pairing nucleobase" is used herein interchangeably with the term "universal base".

In natural tRNA, the nucleobase inosine is found. Inosine has the ability to hybridise non-specifically with three of the nucleobases, i.e. cytosine, thymine, and adenine. Inosine and examples of other synthetic compounds having the same ability of non-specifically base-pairing with natural nucleobases are depicted below Examples of Universal Bases

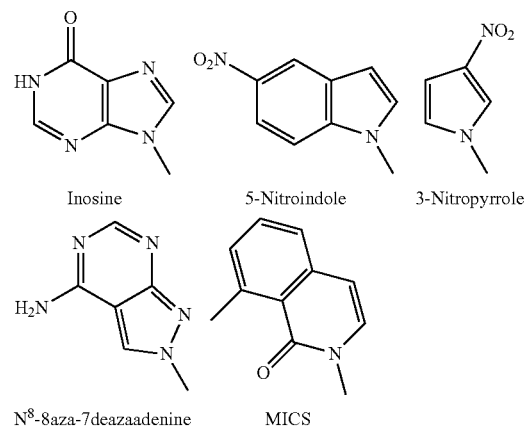

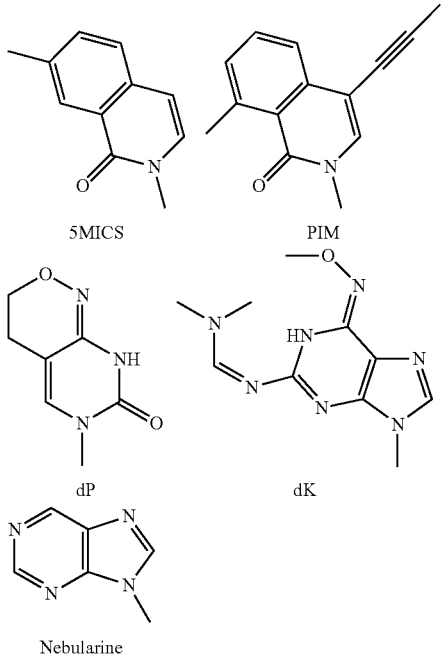

The use of universal bases in the present method has an advantage in the generation of a library because the nucleobases of previously transferred codons can be matched with universal bases on the complementing region of the building block. The complementing of a spent codon with a sequence of universal bases allows for the use of the same building block for a variety of growing bifunctional complexes.

The encoding by extension principle can also be used using a three-strand procedure. Each step involves a library of assembly platform molecules hybridised to a functional entity carrier (FIG. 7). The assembly platform comprise a fixed sequence (complementing identifier region) that binds equally well to all or a subset of identifier molecule through the identifier region. Alternatively, this complementing identifier sequence can also be random or simi-random to increase the diversity of the library as this would allow for the use of different scaffold molecules. The assembly platform also contains a unique anticodon region with a specific sequence. This specific sequence will anneal to the unique codon region in the carrier, thus forming a building block in which the transferable functional entity is coupled to a unique anticodon by hybridisation. The sequence of the unique anticodon and the unique anticodon region is linked allowing a direct coupling between these two sequences. This coupling is for example obtained when the assembly platform is synthesized.

The unique anticodon can either be identical to the unique anticodon region or a shorter or longer sequence. However, a prerequisite though is that these two sequences (the unique anticodon and the unique anticodon region) are linked to each other, e.g. through the complementing identifier region and, optionally, the connection region. The sequence of the unique anticodon can be used to decode the unique anticodon region. This will obtain the unique codon region which codes for the functional entity. The connecting region is optionally a sequence that can be varied to obtain optimal reactivity between functional entity and the attachment entity. If polymers are created using this system, the connecting region could be extended through the assembling cycles.

The formation of identifier-displayed molecules by the three-strand assembly principle is performed in sequential steps. Each individual step involves annealing of the carrier and the identifier molecules to the assembly platform. After the annealing step, two important events take place: 1) the reaction between the attachment entity and the functional entity to accomplish transfer of the functional entity to the identifier molecule, and 2) the extension of the unique codon sequence into the identifier molecule using the unique anticodon sequence on the assembly platform as the reading sequence. The formation of a library of bifunctional complexes according to the invention can be performed using a solid support for the platform molecule as shown in FIGS. 9 and 10. This allow a sequential transfer where each library of assembly platform molecules, with different addition of the non-coding region and complementing binding region dependent of which specific step, is immobilized in separate vials and a library of identifier and building block molecules is supplied. After the annealing-reaction/transfer-extension steps, the library is removed (e.g. with elevated temperature) and transferred to another vial with an immobilized assembly platform library (with an additional non-coding and complementing binding region) to allow the next step in the process.

Mode 2:

The present invention discloses in a second mode of the invention, a method for generating a complex comprising a display molecule part and a coding part, wherein a nascent bifunctional complex comprising a chemical reaction site and a priming site for enzymatic addition of a tag is reacted at the chemical reaction site with one or more reactants and provided at the priming site with respective tags identifying the one or more reactants using one or more enzymes.

The lack of a covalent link between the reactive part and the coding part of the building block implies that a library is to be produced by a split-and-mix strategy. In a first step a nascent bifunctional complex is dispensed in one or more separate compartment and subsequently exposed to a reactant in each compartment, which reacts at the chemical reaction site, and an agent which provides the tag identifying said reactant at the priming site. The agent providing the tag includes an enzyme and a substrate therefore. In a certain embodiment of the invention, the tag is provided by extending over an anticodon using a polymerase. In another embodiment of the invention, the tag is provided at the priming site by ligation of a codon oligonucleotide, which holds information as to the identity of the reactant.

When the enzyme is a polymerase, the substrate is usually a blend of triphosphate nucleotides selected from the group comprising dATP, dGTP, dTTP, dCTP, rATP, rGTP, rTTP, rCTP, rUTP. Substrates for ligases are oligo- and polynucleotides, i.e. nucleic acids comprising two or more nucleotides. An enzymatic ligation may be performed in a single or double stranded fashion. When a single stranded ligation is performed, a 3' OH group of a first nucleic acid is ligated to a 5' phosphate group of a second nucleic acid. A double stranded ligation uses a third oligonucleotide complementing a part of the 3' end and 5' end of the first and second nucleic acid to assist in the ligation. Generally, it is preferred to perform a double stranded ligation.

In some embodiments of the invention, a combination of polymerase transcription and ligational coupling is used. As an example, a gap in an otherwise double stranded nucleic acid may be filled-in by a polymerase and a ligase can ligate the extension product to the upstream oligonucleotide to produce a wholly double stranded nucleic acid.

Mode 2 is conducted in separate compartments for each reaction, as discussed above. Thus, the addition of a tag occurs without competing nucleic acids present and the likelihood of cross-encoding is reduced considerable. The enzymatic addition of a tag may occur prior to, subsequent to, or simultaneous with the reaction. In some aspects of the invention, it is preferred to add the tag to the nascent bifunctional complex prior to the reaction, because it may be preferable to apply conditions for the reaction which are different form the conditions used by the enzyme. Generally, enzyme reactions are conducted in aqueous media, whereas the reaction between the reactant and the chemical reaction site for certain reactions is favoured by an organic solvent. An appropriate approach to obtain suitable condition for both reactions is to conduct the enzyme reaction in an aqueous media, lyophilize and subsequent dissolve or disperse in a media suitable of the reaction at the chemical reactive site to take place. In an alternative approach, the lyophilization step may be dispensed with as the appropriate reaction condition can be obtained by adding a solvent to the aqueous media. The solvent may be miscible with the aqueous media to produce a homogeneous reaction media or immiscible to produce a bi-phasic media.

The reactant according to the second mode may be a free reactant or a zipper building block. A free reactant is not attached to a code identifying another part of the reactant. In most cases, a free reactant comprises a chemical structure comprising one, two or more reactive groups, which can react with the chemical reaction site. A zipper building block is a functional entity which is attached to a chemical entity that binds in the vicinity of the chemical reaction site. The binding chemical entity may be an oligonucleotide which hybridises to a linking moiety of the nascent bifunctional complex prior to the reaction. The hybridisation event will increase the proximity between the functional entity and the chemical reaction site, thereby reducing the possibility of side reactions and promote the reaction due to a high local concentration.

The nascent bifunctional complex is constructed having the encoding method in mind. Thus, if a polymerase is used for the encoding, a region of hybridisation is usually provided in the linker moiety. The region of hybridisation will allow for a binding region of a complementing oligonucleotide comprising an anti-codon to hybridise to the nascent bifunctional complex. The binding region serves as a binding site for a polymerase, which then may produce an extension product using the anti-codon oligonucleotide as template. When a ligase is used for the encoding, the priming site of the nascent bifunctional complex comprises one or more nucleotides which the ligase may consider as a substrate. In a single stranded ligation an oligonucleotide present in the media and bearing information as to the identity of the reactive group will be ligated to the nascent bifunctional molecule. A double stranded ligation requires the priming site of the nascent bifunctional complex to be able to hybridise to a complementing oligonucleotide prior to ligation. Suitably, the priming site comprises one, two, or more nucleotides, to which a complementing oligonucleotide can hybridise. The complementing oligonucleotide hybridise in the other end to the codon oligonucleotide, which holds the information of a particular reactant.

The linker moiety of the nascent bifunctional complex may comprise information relating to the identity of the chemical reaction site. In an applicable approach, the linker moiety comprises a codon informative of the identity of the chemical reaction site.

The oligonucleotides bearing the information on the pertinent reactant, may, apart from the combination of nucleotides identifying the reactant, comprise flanking regions. The flanking regions may serve as binding regions capable of hybridising to the nascent bifunctional complex. The binding region may be designed so as to hybridise promiscuous to more than a single nascent bifunctional complex. Alternatively, the binding region on the coding oligonucleotide is capable of being ligated to a binding region the nascent bifunctional complex using a splint oligonucleotide as mediator.

The invention may be performed by reacting a single reactant with the nascent bifunctional complex and add the corresponding tag. However, in general it is preferred to build a display molecule comprising the reaction product of two of more reactants. Thus, in a certain aspect of the invention a method is devised for obtaining a bifunctional complex composed of a display molecule part and a coding part, said display molecule part being the reaction product of reactants and the chemical reaction site of the initial complex. In an aspect of the invention, two alternating parallel syntheses are performed so that the tag is enzymatical linked to the nascent bifunctional complex in parallel with a reaction between a chemical reaction site and a reactant. In each round the addition of the tag is followed or preceded by a reaction between reactant and the chemical reaction site. In each subsequent round of parallel syntheses the reaction product of the previous reactions serves as the chemical reaction site and the last-incorporated tag provides for a priming site which allows for the enzymatical addition a tag. In other aspects of the invention, two or more tags are provided prior to or subsequent to reaction with the respective reactants.

The coding part comprising all the tags may be transformed to a double stranded form by an extension process in which a primer is annealed to the 3' end of the oligonucleotide and extended using a suitable polymerase. The double strandness may be an advantage during subsequent selection processes because a single stranded nucleic acid may perform interactions with a biological target in a way similar to aptamers.

In a certain aspect of mode 2 a method is devised for generating a library of bifunctional complexes comprising a display molecule part and a coding part. The method comprises the steps of providing in separate compartments nascent bifunctional complexes, each comprising a chemical reaction site and a priming site for enzymatic addition of a tag and performing in any order reaction in each compartment between the chemical reaction site and one or more reactants, and addition of one or more respective tags identifying the one or more reactants at the priming site using one or more enzymes.

The nascent bifunctional complexes in each compartment may be identical or different. In the event the nascent bifunctional complex differs at the chemical reaction site, the nascent bifunctional complex suitable comprises a codon identifying the structure of the chemical reaction site. Similar, the reactants applied in each compartment may be identical or different as the case may be. Also, the reaction conditions in each compartment may be similar or different.

Usually, it is desired to react the complex with more than a single reactant. In a certain aspect of the invention, the content of two or more compartments are pooled together and subsequently split into an array of compartments for a new round of reaction. Thus, in any round subsequent to the first round, the end product of a preceding round of reaction is used as the nascent bifunctional complex to obtain a library of bifunctional complexes, in which each member of the library comprises a reagent specific reaction product and respective tags which codes for the identity of each of the reactants that have participated in the formation of the reaction product. Between each round of reaction the content of the compartments is in an aspect of the invention mixed together and split into compartments again. In other aspects of the invention the content of a compartment is after having received a codon but before a reaction has occurred divided into further compartments in which a further codon is received and a reaction occurs with the two reactants that have been encoded. In another aspect of the invention, more than two codons are encoded before a reaction between chemical reaction site and reactants are allowed to take place. In the alternative, two or more reactions are allowed to occur before an encoding with the respective tags is initiated.

The individual codons may be distinguished from another codon in the library by only a single nucleotide. However, to facilitate a subsequent decoding process it is in general desired to have two or more differences between a particular codon and any other codon. As an example, if a codon/anticodon length of 5 nucleotides is selected, more than 100 nucleotide combinations exist in which two or more differences appear. For a certain number of nucleotides in the codon, it is generally desired to optimize the number of differences between a particular codon/anticodon relative to any other codon/anticodon appearing in the library. An oligonucleotide codon may comprise any suitable number of nucleotides, such as from 2 to 100, 3 to 50, 4 to 20 or 5 to 15 nucleotides.

The reactant can be a free reactant or a zipper building block. The reactant serves the function of being a precursor for the structural entity eventually incorporated in to the displayed molecule part. There structure of a reactant may after reaction with a chemical reaction site become changed in a subsequent round. In the event the reactant is a zipper building block, a cleavage of the linkage between the functional entity and the oligonucleotide is normally conducted after reaction. An exception is in the final round, in which the cleavage can be dispensed with. The cleavage can occur subsequent to or simultaneously with the reaction with the chemical reaction site. The cleavage may generate a reactive group which in a subsequent step can participate in the formation of a connection between the nascent display molecule and a reactant.

The free reactant or the functional entity of the zipper building block preferably comprises at least one reactive group capable of participating in a reaction which results in a connection to the chemical reaction site of the nascent bifunctional molecule. The number of reactive groups which appear on the free reactant and the functional entity is suitably one to ten. A free reactant or a functional entity featuring only one reactive group is used i.a. in the end positions of polymers or scaffolds, whereas functional entities having two reactive groups are suitable for the formation of the body part of a polymer or scaffolds capable of being reacted further. Two or more reactive groups intended for the formation of connections, are typically present on scaffolds. A scaffold is a core structure, which forms the basis for the creation of multiple variants. The variant forms of the scaffold are typically formed through reaction of reactive groups of the scaffold with reactive groups of other reactants, optionally mediated by fill-in groups or catalysts. The functional entities or free reactants to be connected to the scaffold may contain one, two or several reactive groups able to form connections. Examples of scaffolds include steroids, hydantions, benzodiazepines, etc.

The reactive group of the free reactant or the functional entity attached to a nucleic acid comprising a zipper region, i.e. a region promiscuously binding to a linking moiety of the nascent bifunctional complex, may be capable of forming a direct connection to a reactive groups of the chemical reactive site or the reactant may be capable of forming a connection to a reactive group of the chemical reactive site through a bridging fill-in group. It is to be understood that not all the atoms of the reactive groups are necessarily maintained in the connection formed. Rather the reactive groups are to be regarded as precursors for the structure of the connection.

When a zipper building block is used, a cleavage may be performed after or simultaneously with the formation of the connection between the chemical reaction site and the functional entity. The cleavage can be performed in any appropriate way. In an aspect of the invention the cleavage involves usage of a reagent or enzyme. The cleavage results in a transfer of the functional entity to the nascent bifunctional complex or in a transfer of the complex to the functional entity of the zipper building block. In some cases it may be advantageous to introduce new chemical groups as consequence of the cleavage. The new chemical groups may be used for further reaction in a subsequent cycle, either directly or after having been activated. In other cases it s desirable that no trace of the linker remains after the cleavage. In some aspects of the invention it may not be desired to cleave on or more chemical bonds. As an example, it may be desirable to maintain the connection between the zipper domain and the functional entity in the last round.

In some aspects of the invention, the connection and the cleavage is conducted as a simultaneous reaction, i.e. either the functional entity of the zipper building block or the chemical reactive site of the nascent bifunctional complex is a leaving group of the reaction. In some aspects of the invention, it is preferred to design the system such that the cleavage occurs simultaneously because this will reduce the number of steps and the complexity. The simultaneous connection and cleavage can also be designed such that either no trace of the linker remains or such that a new chemical group for further reaction is introduced, as described above. In other aspects of the invention, it is preferred to conduct separate cross-linking and cleavage steps because the stepwise approach allows for mastering each sub step and for a reduction of the likelihood of non-specific transfer.

The attachment of the functional entity to the oligonucleotide comprising a zipping domain is usually conducted through a linker. Preferably the linker connects the functional entity with the oligonucleotide at a terminal nucleotide or a nucleotide 1 or two nucleotides down the oligonucleotide. The attachment of the functional entity can be at any entity available for attachment, i.e. the functional entity can be attached to a nucleotide of the oligonucleotide at the nucleobase, or the back bone. In general, it is preferred to attach the functional entity at the phosphor of the internucleoside linkage or at the nucleobase.

In a certain aspect of the invention, the reactive group of the functional entity is attached to the oligonucleotide, optionally through a suitable spacer. The reactive group is preferably of a type which is able to create a connection to the nascent display molecule by either direct reaction between the respective reactive groups or by using a suitable fill-in group. The reactive group coupling the functional entity with the oligonucleotide is preferably cleaved simultaneously with the establishment of the connection. The functional entity may in some cases contain a second reactive group able to be involved in the formation of a connection in a subsequent cycle. The second reactive group may be of a type which needs activation before it is capable of participating in the formation of a connection.

Preferably at least one linker remains intact after the cleavage step. The at least one linker will link the display molecule to the coding part, i.e. the part comprising the one or more tags identifying the various reactant that have participated in the formation of the display molecule. It may be desired to connect the display molecule part to the coding part of the bifunctional complex through a space comprising a selectively cleavable linker. The selectively cleavable linker is designed such that it is not cleaved under conditions which result in a transfer of a function entity to the chemical reaction site.

The cleavable linkers may be selected from a large plethora of chemical structures. Examples of linkers includes, but are not limited to, linkers having an enzymatic cleavage site, linkers comprising a chemical degradable component, and linkers cleavable by electromagnetic radiation. Cleavable linkers of particular interest are currently linkers that can be cleaved by light. A suitable example includes an o-nitro benzyl group positioned between the display molecule and the coding part of the bifunctional complex.

In the event two or more reactants are reacted with the chemical reactive site, the codons of the coding part may be separated by a constant region or a binding region. One function of the binding region may be to establish a platform at which an enzyme, such as polymerase or ligase can recognise as a substrate. Depending on the encoded molecule formed, the identifier may comprise further codons, such as 3, 4, 5, or more codons. Each of the further codons may be separated by a suitable binding region. Preferably, all or at least a majority of the codons of the identifier are separated from a neighbouring codon by a binding sequence. The binding region may have any suitable number of nucleotides, e.g. 1 to 20.

The binding region, if present, may serve various purposes besides serving as a substrate for an enzyme. In one setup of the invention, the binding region identifies the position of the codon. Usually, the binding region either upstream or downstream of a codon comprises information which allows determination of the position of the codon. In another setup, the binding regions have alternating sequences, allowing for addition of building blocks from two pools in the formation of the library. Moreover, the binding region may adjust the annealing temperature to a desired level.

A binding region with high affinity can be provided by incorporation of one or more nucleobases forming three hydrogen bonds to a cognate nucleobase. Examples of nucleobases having this property are guanine and cytosine. Alternatively, or in addition, the binding region may be subjected to backbone modification. Several backbone modifications provides for higher affinity, such as 2'-O-methyl substitution of the ribose moiety, peptide nucleic acids (PNA), and 2'-4'O-methylene cyclisation of the ribose moiety, also referred to as LNA (Locked Nucleic Acid).

The identifier may comprise flanking regions around the codons. The flanking region can encompass a signal group, such as a fluorophor or a radio active group to allow for detection of the presence or absence of a complex or the flanking region may comprise a label that may be detected, such as biotin. When the identifier comprises a biotin moiety, the identifier may easily be recovered.

The flanking regions can also serve as priming sites for amplification reactions, such as PCR. Usually, the last cycle in the formation of the bifunctional complex includes the incorporation of a priming site. A region of the bifunctional complex close to the display molecule, such as a nucleic acid sequence between the display molecule and the codon coding for the scaffold molecule, is usually used for another priming site, thereby allowing for PCR amplification of the coding region of the bifunctional complex.

Combination of Mode 1 and Mode 2:

In a certain aspect of the invention, mode 1 and mode 2 described above is combined, i.e. different reactants are used in different rounds. Also within mode 1 and mode 2 different building blocks may be used in different rounds.

In the formation of a library it may be advantageous to use a combination of a one-pot synthesis strategy (mode 1) and a split-and-mix strategy (mode 2), because each of mode 1 and mode 2 has its virtues. The one-pot strategy offers the possibility of having the reactive groups in close proximity prior to reaction, thus obtaining a high local concentration and the convenience of having a single container. The split- and mix strategy offers the possibility of having a free reactant and non-hybridising reaction conditions, providing for versatile reactions. It may be appropriate to refer to FIG. 15 in which various single encoding enzymatic methods are shown. A split-and-mix synthesis strategy is generally used for reactants not having a covalent link between the reactant/functional entity and the codon/anti-codon, i.e. free reactants and zipper building blocks. A one-pot synthesis strategy is generally used for reactants in which a covalent link exist between the functional entity and the codon/anti-codon identifying said functional entity, i.e. the E2 building blocks, loop building blocks, and the N building blocks.

In a certain embodiment of the invention an intermediate library of bifunctional complexes is generated using a one-pot synthesis strategy. This intermediate library is subsequently used for the generation of a final library by a split-and-mix synthesis. The intermediate library may be generated using a single round or multiple rounds of one-pot synthesis and the final library may be produced applying a single or multiple rounds of split-and-mix. The use of a split-and-mix synthesis in the last round of library generation offers the possibility of using a reaction media not compatible with maintenance of a hybridisation, e.g. high ionic strength or organic solvents, for the final reactant.

In another embodiment an intermediate library is produced using a split and mix synthesis strategy. The intermediate library is used for the generation of a final library using a one-pot synthesis strategy. The intermediate library may be produced using a single or multiple rounds of split-and-mix synthesis and the final library may be manufactured applying one or more rounds of one-pot synthesis. The one-pot synthesis in the final round provide for a close proximity between the growing encoded molecule and the functional entity. The close proximity results in a high local concentration promoting the reaction even for reactants having a relatively low tendency to react.

Multiple Encoding

Multiple encoding implies that two or more codons are provided in the identifier prior to or subsequent to a reaction between the chemical reactive site and two or more reactants. Multiple encoding has various advantages, such allowing a broader range of reactions possible, as many compounds can only be synthesis by a three (or more) component reaction because an intermediate between the first reactant and the chemical reactive site is not stable. Other advantages relates to the use of organic solvents and the availability of two or more free reactants in certain embodiments.

Thus in a certain aspect of the invention, it relates to a method for obtaining a bifunctional complex comprising a display molecule part and a coding part, wherein the display molecule is obtained by reaction of a chemical reactive site with two or more reactants and the coding part comprises tag(s) identifying the reactants.

In a certain aspect of the invention, a first reactant forms an intermediate product upon reaction with the chemical reactive site and a second reactant reacts with the intermediate product to obtain the display molecule or a precursor thereof. In another aspect of the invention, two or more reactants react with each other to form an intermediate product and the chemical reactive site reacts with this intermediate product to obtain the display molecule or a precursor thereof. The intermediate product can be obtained by reacting the two or more reactants separately and then in a subsequent step reacting the intermediate product with the chemical reactive site. Reacting the reactants in a separate step provide for the possibility of using conditions the tags would not withstand. Thus, in case the coding part comprises nucleic acids, the reaction between the reactant may be conducted at conditions that otherwise would degrade the nucleic acid.

The reactions may be carried out in accordance with the scheme shown below. The scheme shows an example in which the identifying tags for two reactants and the chemical reactive site (scaffold) attached to the chemical reaction site are provided in separate compartments. The compartments are arranged in an array, such as a microtiter plate, allowing for any combination of the different acylating agents and the different alkylating agents.

Starting Situation:

|  | Alkylating agents | | | |
|---|---|---|---|---|
| Acylating agents | A | B | C | ... |
| 1 | Tagx11-X | Tagx12-X | Tagx13-X | ... |
| 2 | Tagx21-X | Tagx22-X | Tagx23-X | ... |
| 3 | Tagx31-X | Tagx32-X | Tagx33-X | ... |
| ... | ... | ... | ... | ... |

X denotes a chemical reaction site such as a scaffold.

The two reactants are either separately reacted with each other in any combination or subsequently added to each compartment in accordance with the tags of the coding part or the reactants may be added in any order to each compartment to allow for a direct reaction. The scheme below shows the result of the reaction.

Plate of Products

|  | Alkylating agents | | | |
|---|---|---|---|---|
| Acylating agents | A | B | C | ... |
| 1 | Tagx11-XA1 | Tagx12-XB1 | Tagx13-XC1 | ... |
| 2 | Tagx21-XA2 | Tagx22-XB2 | Tagx23-XC2 | ... |
| 3 | Tagx31-XA3 | Tagx32-XB3 | Tagx33-XC3 | ... |
| ... | ... | ... | ... | ... |

As an example XA2 denotes display molecule XA2 in its final state, i.e. fully assembled from fragments X, A and 2.

The coding part comprising the two or more tags identifying the reactants, may be prepared in any suitable way either before or after the reaction. In one aspect of the invention, each of the coding parts are synthesised by standard phosphoramidite chemistry. In another aspect the tags are pre-prepared and assembled into the final coding part by chemical or enzymatic ligation.

Various possibilities for chemical ligation exist. Suitable examples include that a) a first oligonucleotide end comprises a 3'-OH group and the second oligonucleotide end comprises a 5'-phosphor-2-imidazole group. When reacted a phosphodiester internucleoside linkage is formed, b) a first oligonucleotide end comprising a phosphoimidazolide group and the 3'-end and a phosphoimidazolide group at the 5'-and. When reacted together a phosphodiester internucleoside linkage is formed, c) a first oligonucleotide end comprising a 3'-phosphorothioate group and a second oligonucleotide comprising a 5'-iodine. When the two groups are reacted a 3'-O—P(=O)(OH)—S-5' internucleoside linkage is formed, and d) a first oligonucleotide end comprising a 3'-phosphorothioate group and a second oligonucleotide comprising a 5'-tosylate. When reacted a 3'-O—P(=O)(OH)—S—5' internucleoside linkage is formed.

Suitably, the tags operatively are joined together, so that as to allow a nucleic acid active enzyme to recognize the ligation area as substrate. Notably, in a preferred embodiment, the ligation is performed so as to allow a polymerase to recognise the ligated strand as a template. Thus, in a preferred aspect, a chemical reaction strategy for the coupling step generally includes the formation of a phosphodiester internucleoside linkage. In accordance with this aspect, method a) and b) above are preferred.

In another aspect, when ligases are used for the ligation, suitable examples include Taq DNA ligase, T4 DNA ligase, T7 DNA ligase, and E. coli DNA ligase. The choice of the ligase depends to a certain degree on the design of the ends to be joined together. Thus, if the ends are blunt, T4 DNA ligase may be preferred, while a Taq DNA ligase may be preferred for a sticky end ligation, i.e. a ligation in which an overhang on each end is a complement to each other.

In a certain aspect of the invention enzymatic encoding is preferred because of the specificity enzymes provide. FIG. 17 discloses a variety of methods for enzymatically encoding two or more reactants in the coding part of the bifunctional molecule. The choice of encoding method depends on a variety of factors, such as the need for free reactants, the need for proximity, and the need for convenience. The enzymatic double encoding methods shown on FIG. 17 may easily be expanded to triple, quarto, etc. encoding.

In accordance with a certain embodiment functional entities are attached to identifying tags, and each functional entity carries one or more reactive groups. All the functional entities react with each other to generate the final product containing as many tags as functional entities. The tags may be combined into a single coding part, usually an oligonucleotide through an intermolecular reaction or association followed by cleavage of two of the linkers, as shown below:

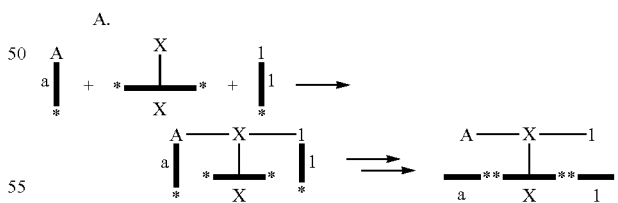

Bold lines represent tags. Thin lines represent linkers or bonds. "*" denotes a priming site. In some aspects of the invention X is regarded as the chemical reactive site.

In one aspect of the above embodiment the tags are of oligonucleotides, which combine through chemical ligation or enzyme catalysed ligation.

Alternatively, the tags are coupled prior to the reaction of the functional entities. In that process the functional entities will be cleaved from their tags or cleaved afterwards. E.g.

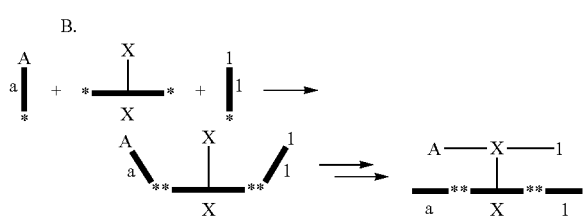

An embodiment of the above schematic representation comprises, when the tags are nucleotides, the combination of tags through chemical ligation or enzyme catalysed ligation.

Example 9 illustrates a multi component reaction in which triple encoding is used. Thus after the reaction of three free reactants with a chemical reactive site, the coding part is provided with three identifying tags by enzymatic ligation.
Building Blocks Capable of Transferring Functional Entities.

The following sections describe the formation and use of exemplary building blocks capable of transferring a functional entity to a reactive group of a bifunctional complex. A bold line indicates an oligonucleotide.
A. Acylation Reactions
General Route to the Formation of Acylating Building Blocks and the Use of these:

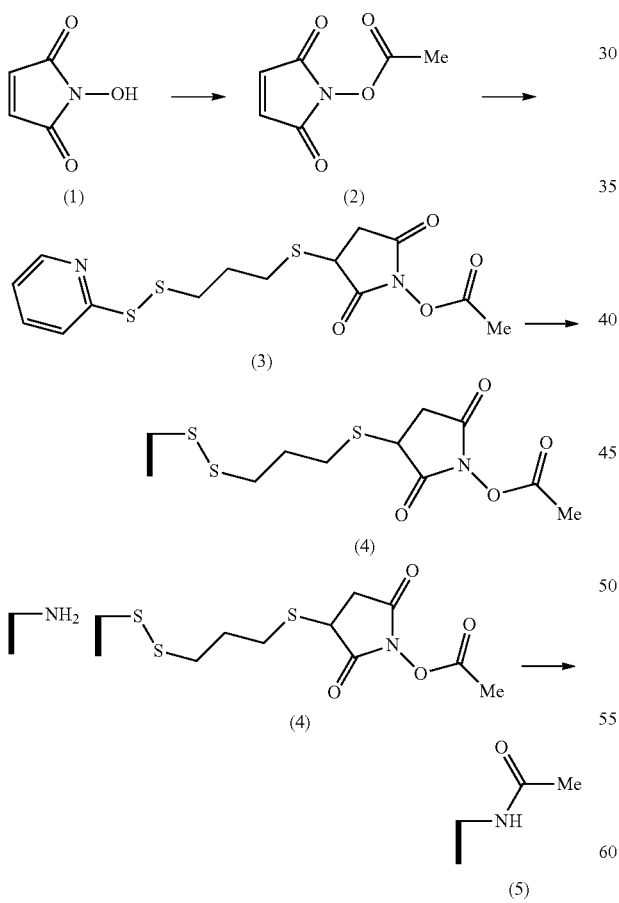

N-hydroxymaleimide (1) may be acylated by the use of an acylchloride e.g. acetylchloride or alternatively acylated in e.g. THF by the use of dicyclohexylcarbodiimide or diisopropylcarbodiimide and acid e.g. acetic acid. The intermediate may be subjected to Michael addition by the use of excess 1,3-propanedithiol, followed by reaction with either 4,4'-dipyridyl disulfide or 2,2'-dipyridyl disulfide. This intermediate (3) may then be loaded onto an oligonucleotide carrying a thiol handle to generate the building block (4). Obviously, the intermediate (2) can be attached to the oligonucleotide using another linkage than the disulfide linkage, such as an amide linkage and the N-hydroxymaleimide can be distanced from the oligonucleotide using a variety of spacers.

The building block (4) may be reacted with an identifier oligonucleotide comprising a recipient amine group e.g. by following the procedure: The building block (4) (1 nmol) is mixed with an amino-oligonucleotide (1 nmol) in hepes-buffer (20 μL of a 100 mM hepes and 1 M NaCl solution, pH=7.5) and water (39 uL). The oligonucleotides are annealed together by heating to 50° C. and cooling (2° C./second) to 30° C. The mixture is then left o/n at a fluctuating temperature (10° C. for 1 second then 35° C. for 1 second), to yield the product (5).

In more general terms, the building blocks indicated below is capable of transferring a chemical entity (CE) to a recipient nucleophilic group, typically an amine group. The bold lower horizontal line illustrates the building block and the vertical line illustrates a spacer. The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold

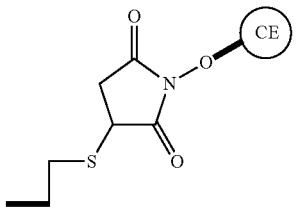

Another building block which may form an amide bond is

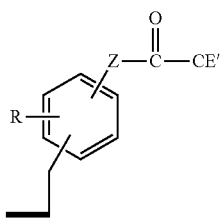

R may be absent or NO$_2$, CF$_3$, halogen, preferably Cl, Br, or I, and Z may be S or O. This type of building block is disclosed in Danish patent application No. PA 2002 0951 and US provisional patent application filed 20 Dec. 2002 with the title "A building block capable of transferring a functional entity to a recipient reactive group". The content of both patent application are incorporated herein in their entirety by reference.

A nucleophilic group can cleave the linkage between Z and the carbonyl group thereby transferring the chemical entity —(C=O)—CE' to said nucleophilic group.

B. Alkylation

General Route to the Formation of Alkylating/Vinylating Building Blocks and Use of these:

Alkylating building blocks may have the following general structure:

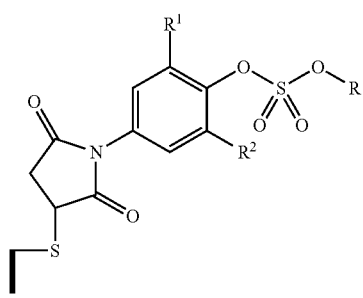

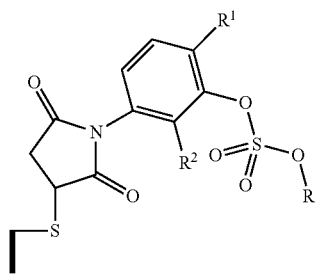

$R^1$ = H, Me, Et, iPr, Cl, $NO_2$
$R^2$ = H, Me, Et, iPr, Cl, $NO_2$ $R^1$ and $R^2$ may be used to tune the reactivity of the sulphate to allow appropriate reactivity. Chloro and nitro substitution will increase reactivity. Alkyl groups will decrease reactivity. Ortho substituents to the sulphate will due to steric reasons direct incoming nucleophiles to attack the R-group selectively and avoid attack on sulphur.

An example of the formation of an alkylating building block and the transfer of a functional entity is depicted below:

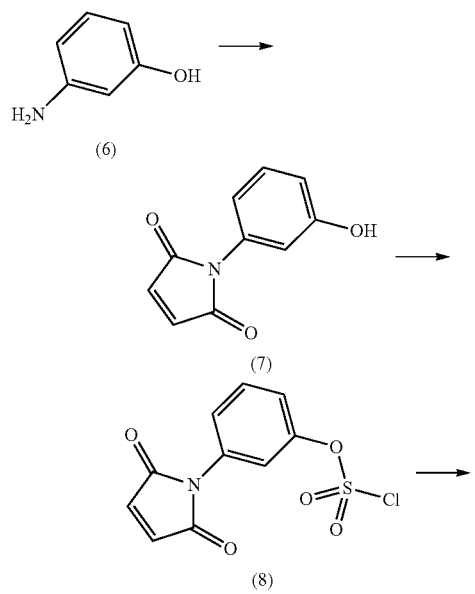

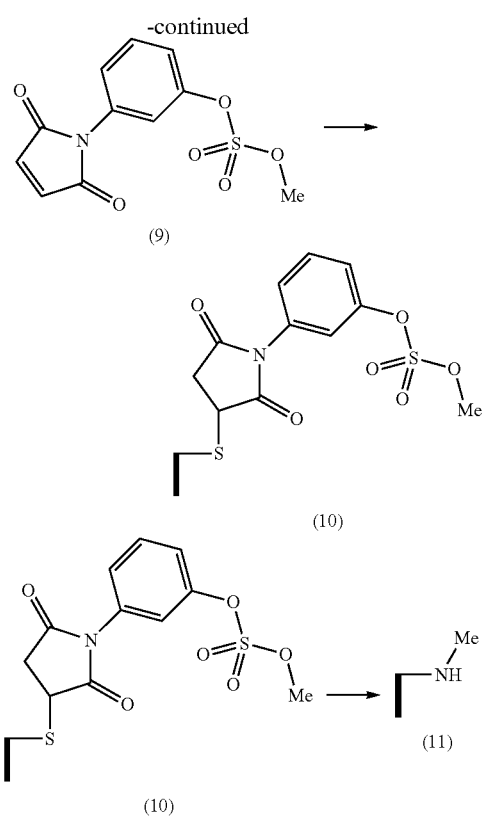

3-Aminophenol (6) is treated with maleic anhydride, followed by treatment with an acid e.g. $H_2SO_4$ or $P_2O_5$ and heated to yield the maleimide (7). The ring closure to the maleimide may also be achieved when an acid stable O-protection group is used by treatment with $Ac_2O$, with or without heating, followed by O-deprotection. Alternatively reflux in $Ac_2O$, followed by O-deacetylation in hot water/dioxane to yield (7). Further treatment of (7) with $SO_2Cl_2$, with or without triethylamine or potassium carbonate in dichloromethane or a higher boiling solvent will yield the intermediate (8), which may be isolated or directly further transformed into the aryl alkyl sulphate by the quench with the appropriate alcohol, in this case MeOH, whereby (9) will be formed.

The organic moiety (9) may be connected to an oligonucleotide, as follows: A thiol carrying oligonucleotide in buffer 50 mM MOPS or hepes or phosphate pH 7.5 is treated with a 1-100 mM solution and preferably 7.5 mM solution of the organic building block (9) in DMSO or alternatively DMF, such that the DMSO/DMF concentration is 5-50%, and preferably 10%. The mixture is left for 1-16 h and preferably 2-4 h at 25° C. to give the alkylating agent in this case a methylating building block (10).

The reaction of the alkylating building block (10) with an amine bearing nascent bifunctional complex may be conducted as follows: The bifunctional complex (1 nmol) is mixed the building block (10) (1 nmol) in hepes-buffer (20 µL of a 100 mM hepes and 1 M NaCl solution, pH=7.5) and water (39 uL). The oligonucleotides are annealed to each other by heating to 50° C. and cooled (2° C./second) to 30° C. The mixture is then left o/n at a fluctuating temperature (10° C. for 1 second then 35° C. for 1 second), to yield the methylamine reaction product (11).

In more general terms, a building block capable of transferring a chemical entity to a receiving reactive group forming a single bond is

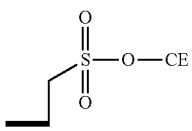

The receiving group may be a nucleophile, such as a group comprising a hetero atom, thereby forming a single bond between the chemical entity and the hetero atom, or the receiving group may be an electronegative carbon atom, thereby forming a C—C bond between the chemical entity and the scaffold.

C. Vinylation Reactions

A vinylating building block may be prepared and used similarly as described above for an alkylating building block. Although instead of reacting the chlorosulphonate (8 above) with an alcohol, the intermediate chlorosulphate is isolated and treated with an enolate or O-trialkylsilylenolate with or without the presence of fluoride. E.g.

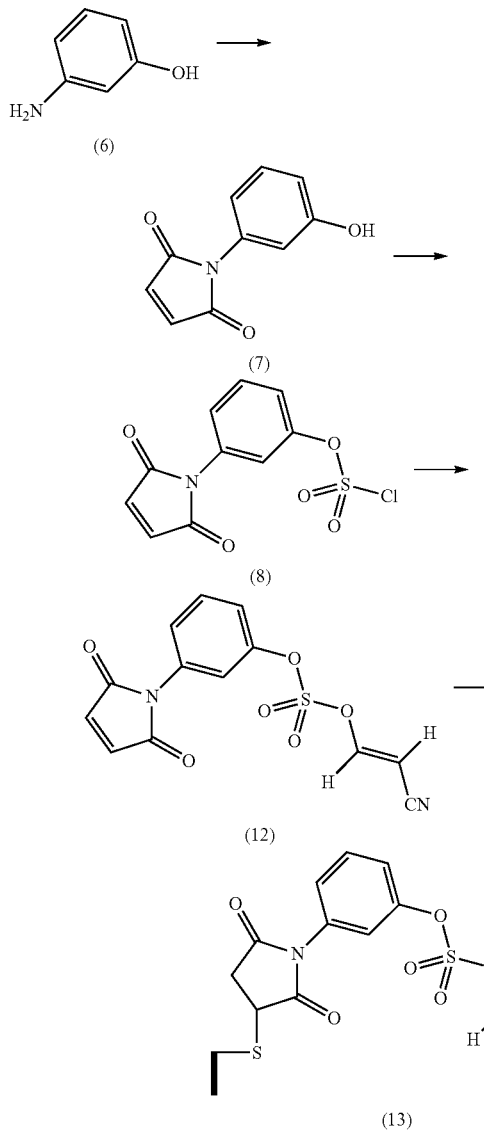

Formation of an Exemplary Vinylating Building Block (13):

The thiol carrying oligonucleotide in buffer 50 mM MOPS or hepes or phosphate pH 7.5 is treated with a 1-100 mM solution and preferably 7.5 mM solution of the organic moiety (12) in DMSO or alternatively DMF, such that the DMSO/DMF concentration is 5-50%, and preferably 10%. The mixture is left for 1-16 h and preferably 2-4 h at 25° C. to give the vinylating building block (13).

The sulfonylenolate (13) may be used to react with amine carrying scaffold to give an enamine (14a and/or 14b) or e.g. react with a carbanion to yield (15a and/or 15b). E.g.

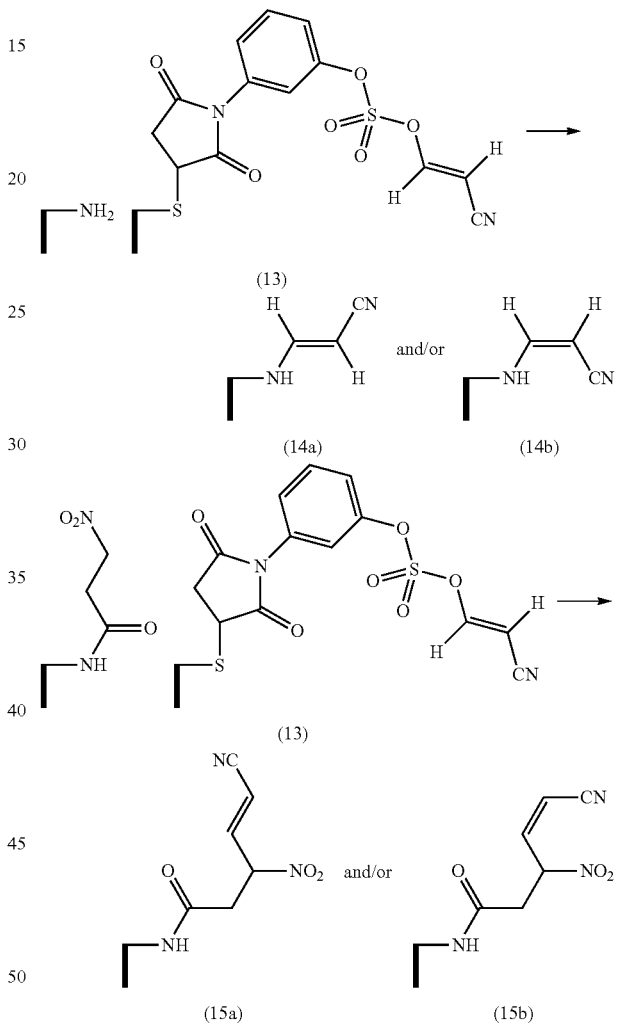

The reaction of the vinylating building block (13) and an amine or nitroalkyl carrying identifier may be conducted as follows:

The amino-oligonucleotide (1 nmol) or nitroalkyl-oligonucleotide (1 nmol) identifier is mixed with the building block (1 nmol) (13) in 0.1 M TAPS, phosphate or hepes-buffer and 300 mM NaCl solution, pH=7.5-8.5 and preferably pH=8.5. The oligonucleotides are annealed to the template by heating to 50° C. and cooled (2° C./second) to 30° C. The mixture is then left o/n at a fluctuating temperature (10° C. for 1 second then 35° C. for 1 second), to yield reaction product (14a/b or 15a/b). Alternative to the alkyl and vinyl sulphates described above may equally effective be sulphonates as e.g. (31) (however with R" instead as alkyl or vinyl), described below, prepared from (28, with the phenyl group substituted by an alkyl group) and (29), and be used as alkylating and vinylating agents.

Another building block capable of forming a double bond by the transfer of a chemical entity to a recipient aldehyde group is shown below. A double bond between the carbon of the aldehyde and the chemical entity is formed by the reaction.

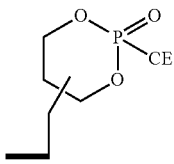

The above building block is comprised by the Danish patent application No. DK PA 2002 01952 and the US provisional patent application filed 20 Dec. 2002 with the title "A building block capable of transferring a functional entity to a recipient reactive group forming a C=C double bond". The content of both patent applications are incorporated herein in their entirety by reference.

D. Alkenylidation Reactions

General Route to the Formation of Wittig and HWE Building Blocks and Use of these:

Commercially available compound (16) may be transformed into the NHS ester (17) by standard means, i.e. DCC or DIC couplings. An amine carrying oligonucleotide in buffer 50 mM MOPS or hepes or phosphate pH 7.5 is treated with a 1-100 mM solution and preferably 7.5 mM solution of the organic compound in DMSO or alternatively DMF, such that the DMSO/DMF concentration is 5-50%, and preferably 10%. The mixture is left for 1-16 h and preferably 2-4 h at 25° C. to give the phosphine bound precursor building block (18). This precursor building block is further transformed by addition of the appropriate alkylhalide, e.g. N,N-dimethyl-2-iodoacetamide as a 1-100 mM and preferably 7.5 mM solution in DMSO or DMF such that the DMSO/DMF concentration is 5-50%, and preferably 10%. The mixture is left for 1-16 h and preferably 2-4 h at 25° C. to give the building block (19). As an alternative to this, the organic compound (17) may be P-alkylated with an alkylhalide and then be coupled onto an amine carrying oligonucleotide to yield (19).

An aldehyde carrying identifier (20), may be formed by the reaction between the NHS ester of 4-formylbenzoic acid and an amine carrying oligonucleotide, using conditions similar to those described above. The identifier (20) reacts with (19) under slightly alkaline conditions to yield the alkene (21).

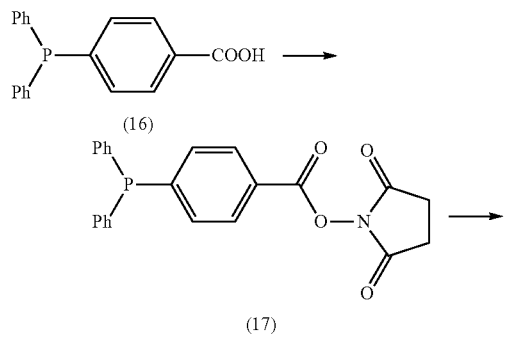

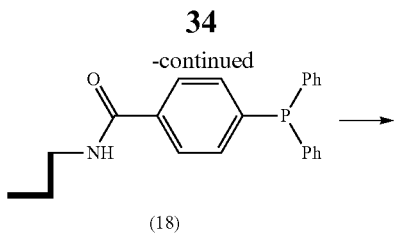

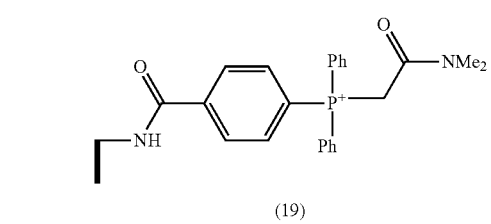

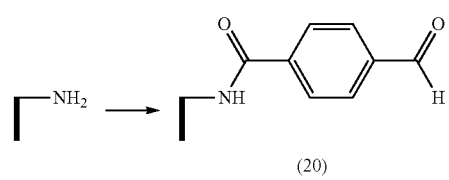

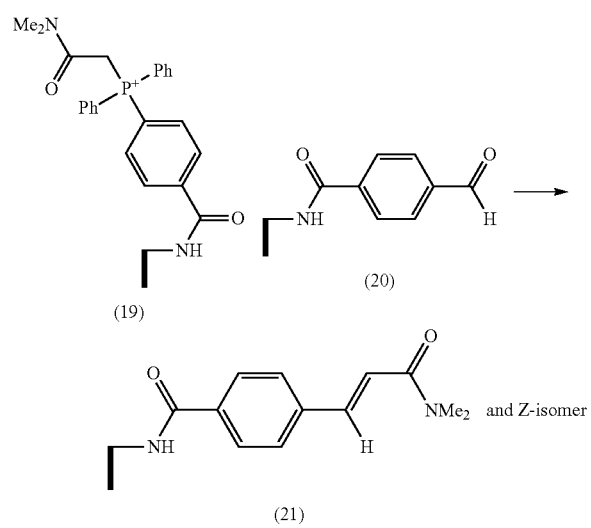

The reaction of monomer building blocks (19) and identifier (20) may be conducted as follows: The identifier (20) (1 nmol) is mixed with building block (19) (1 nmol) in 0.1 M TAPS, phosphate or hepes-buffer and 1 M NaCl solution, pH=7.5-8.5 and preferably pH=8.0. The reaction mixture is left at 35-65° C. preferably 58° C. over night to yield reaction product (21).

As an alternative to (17), phosphonates (24) may be used instead. They may be prepared by the reaction between diethylchlorophosphite (22) and the appropriate carboxy carrying alcohol. The carboxylic acid is then transformed into the NHS ester (24) and the process and alternatives described above may be applied. Although instead of a simple P-alkylation, the phosphite may undergo Arbuzov's reaction and generate the phosphonate. Building block (25) benefits from the fact that it is more reactive than its phosphonium counterpart (19).

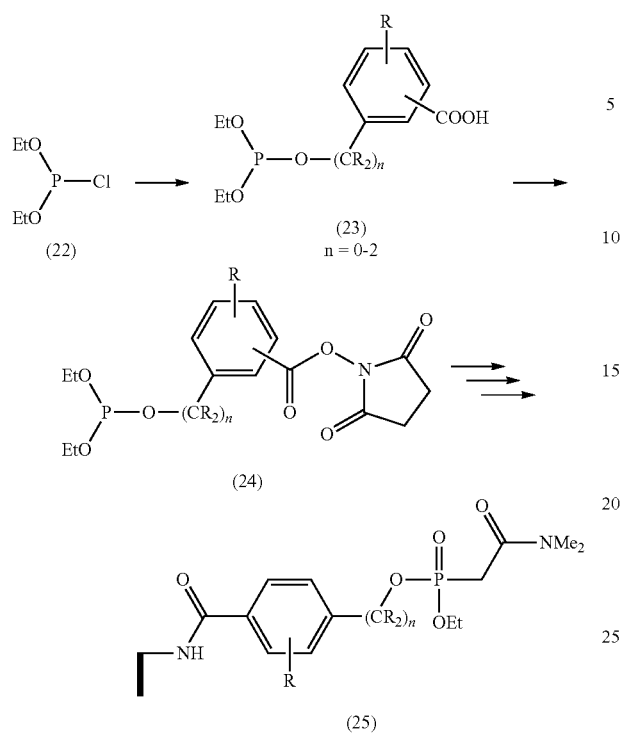

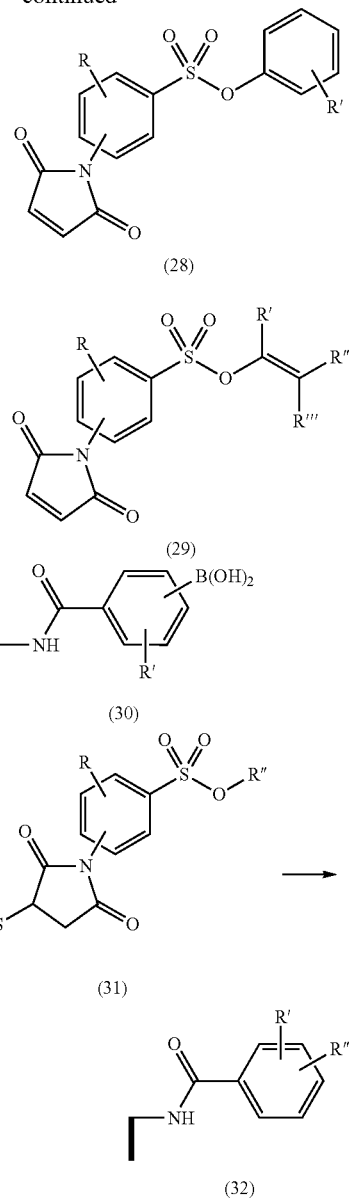

R''' = aryl, hetaryl or vinyl

E. Transition Metal Catalyzed Arylation, Hetaylation and Vinylation Reactions Electrophilic building blocks (31) capable of transferring an aryl, hetaryl or vinyl functionality may be prepared from organic compounds (28) and (29) by the use of coupling procedures for maleimide derivatives to SH-carrying oligonucleotides described above. Alternatively to the maleimide the NHS-ester derivatives may be prepared from e.g. carboxybenzensulfonic acid derivatives, be used by coupling of these to an amine carrying oligonucleotide. The R-group of (28) and (29) is used to tune the reactivity of the sulphonate to yield the appropriate reactivity.

The transition metal catalyzed cross coupling may be conducted as follows: A premix of 1.4 mM $Na_2PdCl_4$ and 2.8 mM $P(p-SO_3C_6H_4)_3$ in water left for 15 min was added to a mixture of the identifier (30) and building block (31) (both 1 nmol) in 0.5 M NaOAc buffer at pH=5 and 75 mM NaCl (final [Pd]=0.3 mM). The mixture is then left o/n at 35-65° C. preferably 58° C., to yield reaction product (32).

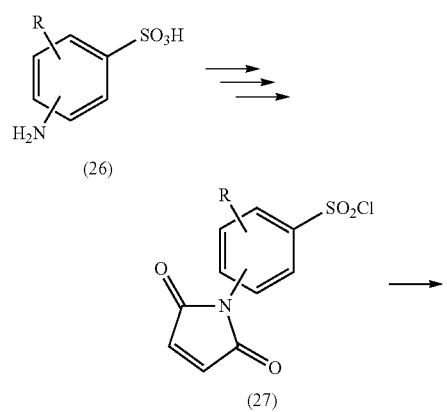

Corresponding nucleophilic monomer building blocks capable of transferring an aryl, hetaryl or vinyl functionality may be prepared from organic compounds of the type (35). This is available by estrification of a boronic acid by a diol e.g. (33), followed by transformation into the NHS-ester derivative. The NHS-ester derivative may then be coupled to an oligonucleotide, by use of coupling procedures for NHS-ester derivatives to amine carrying oligonucleotides described above, to generate building block type (37). Alternatively, maleimide derivatives may be prepared as described above and loaded onto SH-carrying oligonucleotides.

The transition metal catalyzed cross coupling is conducted as follows:

A premix of 1.4 mM $Na_2PdCl_4$ and 2.8 mM $P(p-SO_3C_6H_4)_3$ in water left for 15 min was added to a mixture of the identifier (36) and the building block (37) (both 1 nmol) in 0.5 M NaOAc buffer at pH=5 and 75 mM NaCl (final [Pd]=0.3 mM). The mixture is then left o/n at 35-65° C. preferably 58° C., to yield template bound (38).

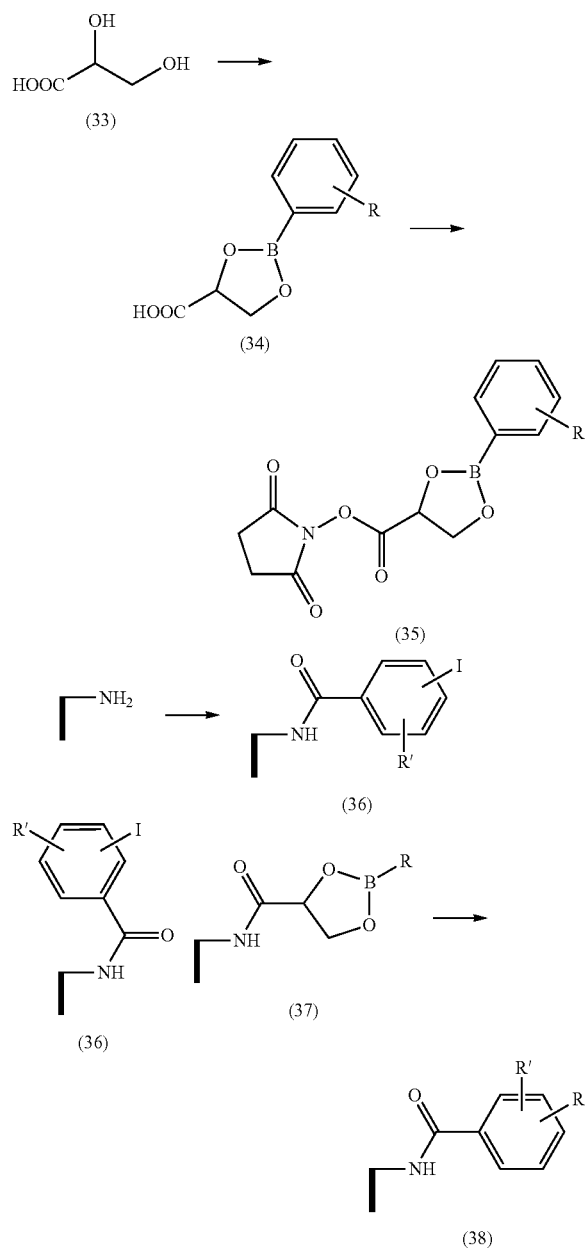

R = aryl, hetaryl or vinyl

F. Reactions of Enamine and Enolether Monomer Building Blocks

Building blocks loaded with enamines and enolethers may be prepared as follows:

For Z=NHR(R=H, alkyl, aryl, hetaryl), a 2-mercaptoethylamine may be reacted with a dipyridyl disulfide to generate the activated disulfide (40), which may then be condensed to a ketone or an aldehyde under dehydrating conditions to yield the enamine (41). For Z=OH, 2-mercaptoethanol is reacted with a dipyridyl disulfide, followed by O-tosylation (Z=OTs). The tosylate (40) may then be reacted directly with an enolate or in the presence of fluoride with a O-trialkylsilylenolate to generate the enolate (41). The enamine or enolate (41) may then be coupled onto an SH-carrying oligonucleotide as described above to give the building block (42).

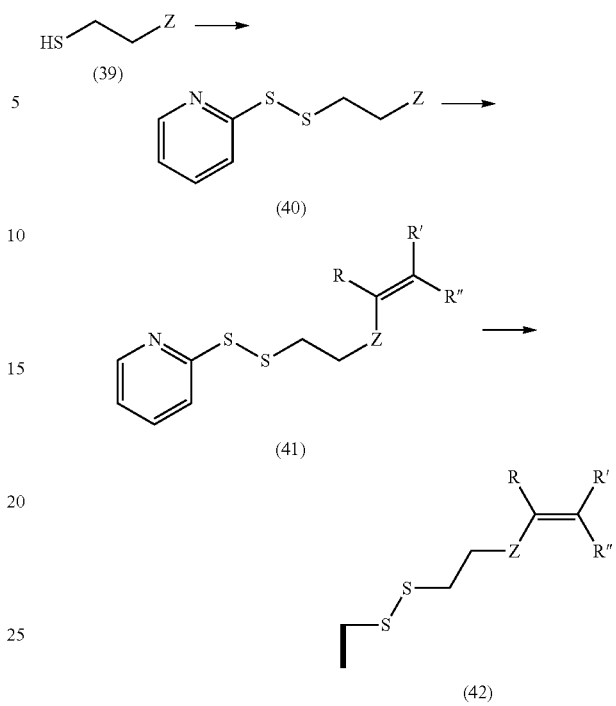

The building block (42) may be reacted with a carbonyl carrying identifier oligonucleotide like (44) or alternatively an alkylhalide carrying oligonucleotide like (43) as follows: The building block (42) (1 nmol) is mixed with the identifier (43) (1 nmol) in 50 mM MOPS, phosphate or hepes-buffer buffer and 250 mM NaCl solution, pH=7.5-8.5 and preferably pH=7.5. The reaction mixture is left at 35-65° C. preferably 58° C. over night or alternatively at a fluctuating temperature (10° C. for 1 second then 35° C. for 1 second) to yield reaction product (46), where Z=O or NR. For compounds where Z=NR slightly acidic conditions may be applied to yield product (46) with Z=O.

The building block (42) (1 nmol) is mixed with the identifier (44) (1 nmol) in 0.1 M TAPS, phosphate or hepes-buffer buffer and 300 mM NaCl solution, pH=7.5-8.5 and preferably pH=8.0. The reaction mixture is left at 35-65° C. preferably 58° C. over night or alternatively at a fluctuating temperature (10° C. for 1 second then 35° C. for 1 second) to yield reaction product (45), where Z=O or NR. For compounds where Z=NR slightly acidic conditions may be applied to yield product (45) with Z=O.

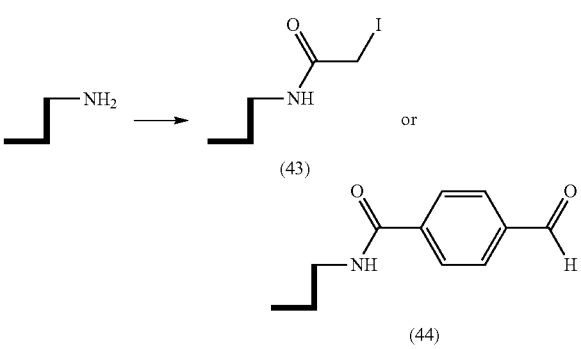

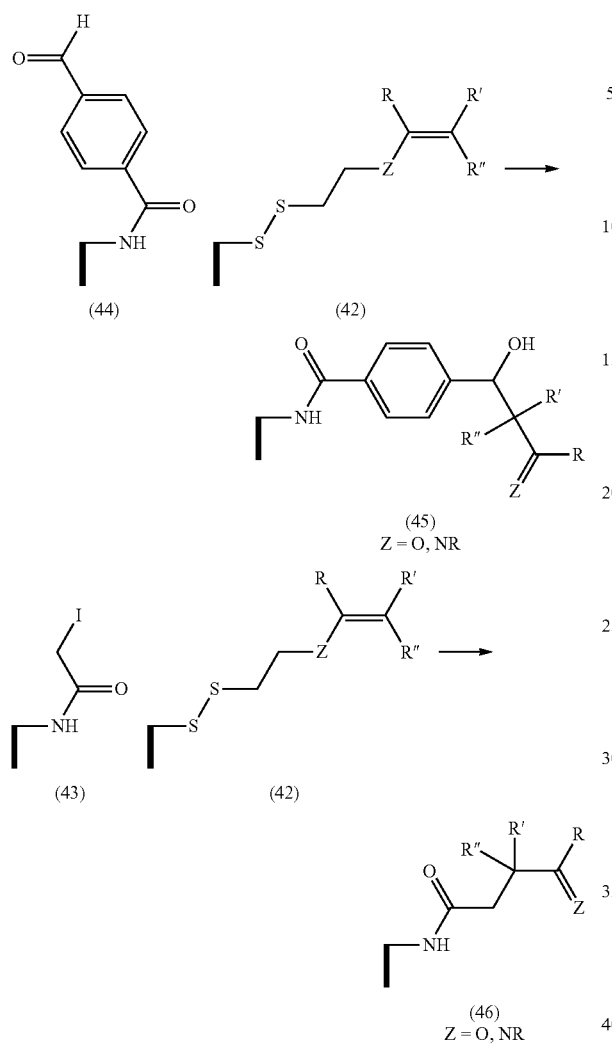
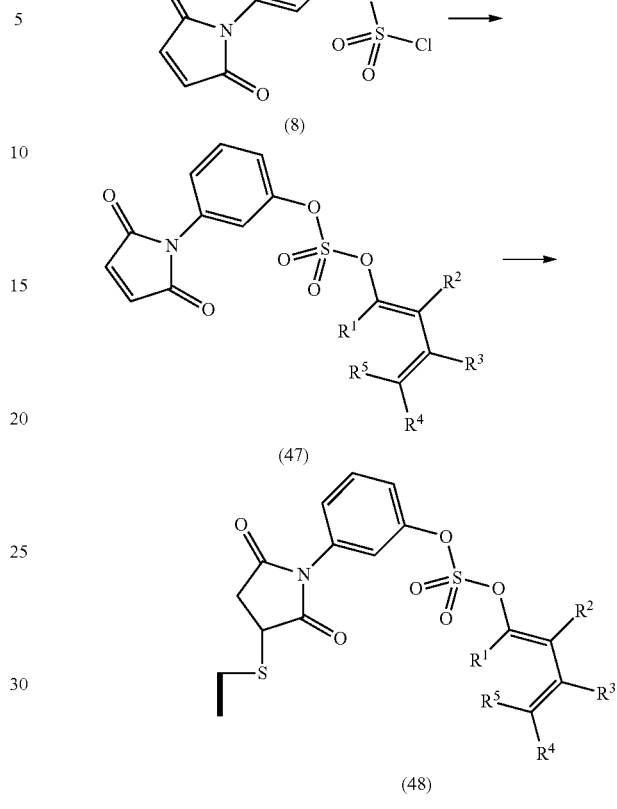

Enolethers type (13) may undergo cycloaddition with or without catalysis. Similarly, dienolethers may be prepared and used, e.g. by reaction of (8) with the enolate or trialkyl-silylenolate (in the presence of fluoride) of an α,β-unsaturated ketone or aldehyde to generate (47), which may be loaded onto an SH-carrying oligonucleotide, to yield monomer building block (48).

The diene (49), the ene (50) and the 1,3-dipole (51) may be formed by simple reaction between an amino carrying oligonucleotide and the NHS-ester of the corresponding organic compound. Reaction of (13) or alternatively (31, R"=vinyl) with dienes as e.g. (49) to yield (52) or e.g. 1,3-dipoles (51) to yield (53) and reaction of (48) or (31, R"=dienyl) with enes as e.g. (50) to yield (54) may be conducted as follows:

The building block (13) or (48) (1 nmol) is mixed with the identifier (49) or (50) or (51) (1 nmol) in 50 mM MOPS, phosphate or hepes-buffer buffer and 2.8 M NaCl solution, pH=7.5-8.5 and preferably pH=7.5. The reaction mixture is left at 35-65° C. preferably 58° C. over night or alternatively at a fluctuating temperature (10° C. for 1 second then 35° C. for 1 second) to yield template bound (52), (53) or (54), respectively.

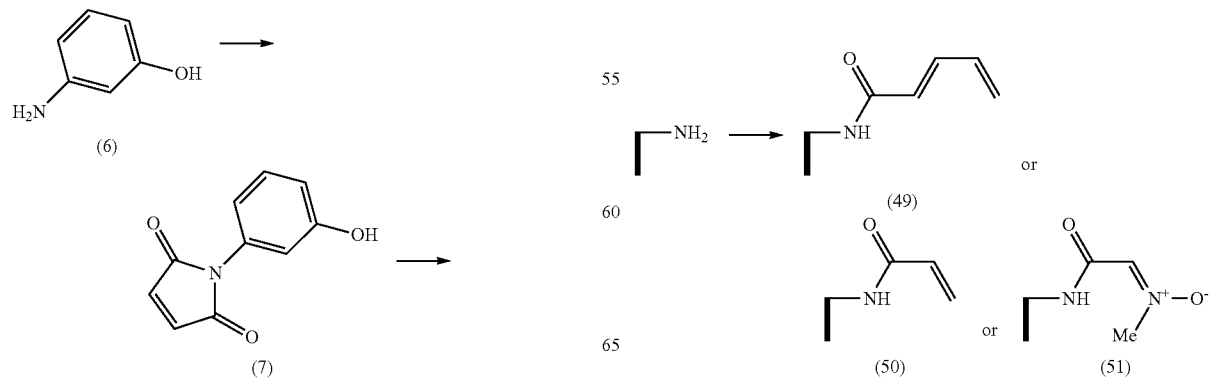

step can be optimized. A suitable building block for this two step process is illustrated below:

Initially, a reactive group appearing on the functional entity precursor (abbreviated FEP) reacts with a recipient reactive group, e.g. a reactive group appearing on a scaffold, thereby forming a cross-link. Subsequently, a cleavage is performed, usually by adding an aqueous oxidising agent such as $I_2$, $Br_2$, $Cl_2$, $H^+$, or a Lewis acid. The cleavage results in a transfer of the group HZ-FEP- to the recipient moiety, such as a scaffold.

In the above formula

Z is O, S, $NR^4$

Q is N, $CR^1$

P is a valence bond, O, S, $NR^4$, or a group $C_{5-7}$arylene, $C_{1-6}$alkylene, $C_{1-6}$O-alkylene, $C_{1-6}$S-alkylene, $NR^1$-alkylene, $C_{1-6}$alkylene-O, $C_{1-6}$alkylene-S option said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, B is a group comprising D-E-F, in which D is a valence bond or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, E is, when present, a valence bond, O, S, $NR^4$, or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, F is, when present, a valence bond, O, S, or $NR^4$, A is a spacing group distancing the chemical structure from the complementing element, which may be a nucleic acid, $R^1$, $R^2$, and $R^3$ are independent of each other selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, FEP is a group selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and Cross-Link Cleavage Building Blocks It may be advantageous to split the transfer of a chemical entity to a recipient reactive group into two separate steps, namely a cross-linking step and a cleavage step because each $R^5$ is selected independently from —$N_3$, —CNO, —C(NOH)$NH_2$, —NHOH, —NHN$HR^6$, —C(O)$R^6$, —Sn$R^6{}_3$, —B(O$R^6$)$_2$, —P(O)(O$R^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COO$R^6$, —CO$R^E$, —CN, —OSi$R^6{}_3$, —O$R^6$ and —N$R^6{}_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, —$NO_2$, —$R^3$, —O$R^3$, —Si$R^3{}_3$ $R^9$ is =O, —F, —Cl, —Br, —I, —CN, —$NO_2$, —O$R^6$, —N$R^6{}_2$, —N$R^6$—C(O)$R^8$, —N$R^6$—C(O)O$R^8$, —S$R^6$, —S(O)$R^6$, —S(O)$_2R^6$, —COO$R^6$, —C(O)N$R^6{}_2$ and —S(O)$_2$N$R^6{}_2$.

In a preferred embodiment Z is O or S, P is a valence bond, Q is CH, B is $CH_2$, and $R^1$, $R^2$, and $R^3$ is H. The bond between the carbonyl group and Z is cleavable with aqueous $I_2$.

Cleavable Linkers

A cleavable linker may be positioned between the target and a solid support or between the potential drug candidate and the identifier region or any other position that may ensure a separation of the nucleic acid sequence comprising the codons from successful complexes from non-specific binding complexes. The cleavable linker may be selectively cleavable, i.e. conditions may be selected that only cleave that particular linker.

The cleavable linkers may be selected from a large plethora of chemical structures. Examples of linkers includes, but are not limited to, linkers having an enzymatic cleavage site, linkers comprising a chemical degradable component, linkers cleavable by electromagnetic radiation.

Examples of Linkers Cleavable by Electromagnetic Radiation (Light)

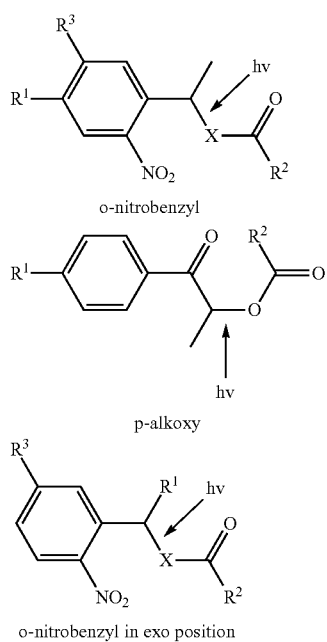

For more details see Holmes C P. J. Org. Chem. 1997, 62, 2370-2380

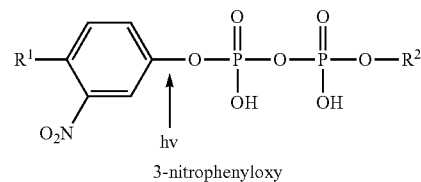

3-nitrophenyloxy

For more details see Rajasekharan Pillai, V. N. Synthesis. 1980, 1-26

Dansyl Derivatives:

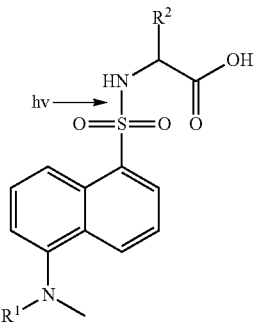

For more details see Rajasekharan Pillai, V. N. Synthesis. 1980, 1-26

Coumarin Derivatives

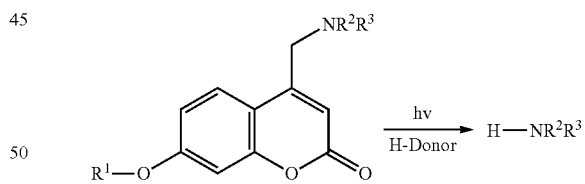

For more details see R. O. Schoenleber, B. Giese. Synlett 2003, 501-504

$R^1$ and $R^2$ can be either of the potential drug candidate and the identifier, respectively. Alternatively, $R^1$ and $R^2$ can be either of the target or a solid support, respectively.

$R^3$=H or $OCH_3$

If X is O then the product will be a carboxylic acid

If X is NH the product will be a carboxamide

One specific example is the PC Spacer Phosphoramidite (Glen research catalog #10-4913-90) which can be introduced in an oligonucleotide during synthesis and cleaved by subjecting the sample in water to UV light (~300-350 nm) for 30 seconds to 1 minute.

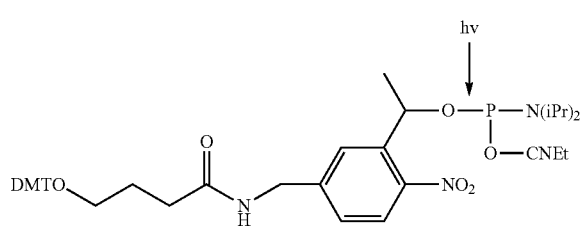

DMT = 4,4'-Dimethoxytrityl
iPr = Isopropyl
CNEt = Cyanoethyl

The above PC spacer phosphoamidite is suitable incorporated in a library of complexes at a position between the indentifier and the potential drug candidate. The spacer may be cleaved according to the following reaction.

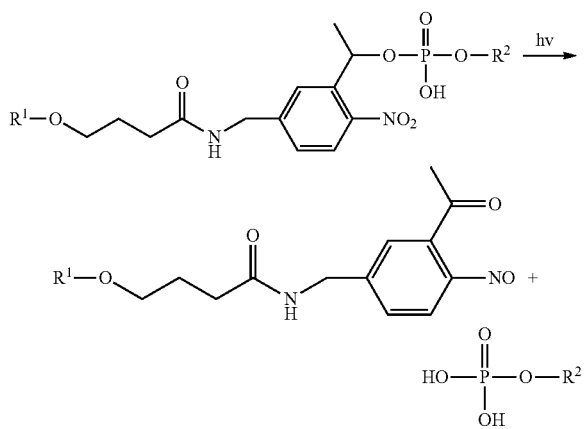

$R^1$ and $R^2$ can be either of the encoded molecule and the identifying molecule, respectively. In a preferred aspect $R^2$ is an oligonucleotide identifier and the $R^1$ is the potential drug candidate. When the linker is cleaved a phosphate group is generated allowing for further biological reactions. As an example, the phosphate group may be positioned in the 5"end of an oligonucleotide allowing for an enzymatic ligation process to take place.

Examples of Linkers Cleavable by Chemical Agents:

Ester linkers can be cleaved by nucleophilic attack using e.g. hydroxide ions. In practice this can be accomplished by subjecting the target-ligand complex to a base for a short period.

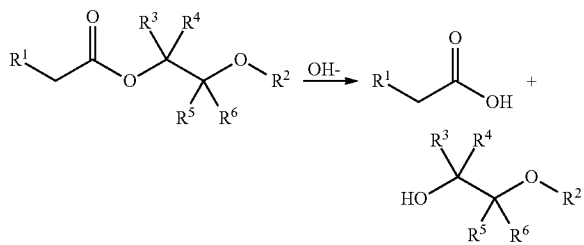

$R^1$ and $R^2$ can be the either of be the potential drug candidate or the identifier, respectively. $R^{4-6}$ can be any of the following: H, CN, F, $NO_2$, $SO_2NR_2$.

Disulfide linkers can efficiently be cleaved/reduced by Tris (2-carboxyethyl) phosphine (TCEP). TCEP selectively and completely reduces even the most stable water-soluble alkyl disulfides over a wide pH range. These reductions frequently required less than 5 minutes at room temperature. TCEP is a non-volatile and odorless reductant and unlike most other reducing agents, it is resistant to air oxidation. Trialkylphosphines such as TCEP are stable in aqueous solution, selectively reduce disulfide bonds, and are essentially unreactive toward other functional groups commonly found in proteins.

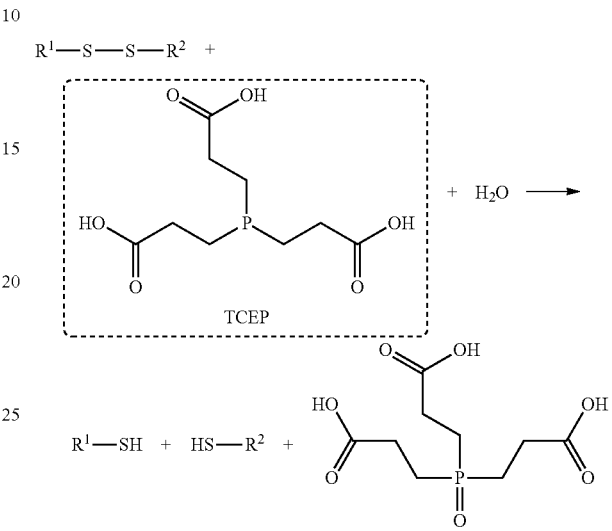

More details on the reduction of disulfide bonds can be found in Kirley, T. L. (1989), Reduction and fluorescent labeling of cyst(e)ine-containing proteins for subsequent structural analysis, *Anal. Biochem.* 180, 231 and Levison, M. E., et al. (1969), Reduction of biological substances by water-soluble phosphines: Gamma-globulin. *Experentia* 25, 126-127.

Linkers Cleavable by Enzymes

The linker connecting the potential drug candidate with the identifier or the solid support and the target can include a peptide region that allows a specific cleavage using a protease. This is a well-known strategy in molecular biology. Site-specific proteases and their cognate target amino acid sequences are often used to remove the fusion protein tags that facilitate enhanced expression, solubility, secretion or purification of the fusion protein.

Various proteases can be used to accomplish a specific cleavage. The specificity is especially important when the cleavage site is presented together with other sequences such as for example the fusion proteins. Various conditions have been optimized in order to enhance the cleavage efficiency and control the specificity. These conditions are available and know in the art.

Enterokinase is one example of an enzyme (serine protease) that cut a specific amino acid sequence. Enterokinase recognition site is Asp-Asp-Asp-Asp-Lys (DDDDK) (SEQ ID No: 1), and it cleaves C-terminally of Lys. Purified recombinant Enterokinase is commercially available and is highly active over wide ranges in pH (pH 4.5-9.5) and temperature (4-45° C.).

The nuclear inclusion protease from tobacco etch virus (TEV) is another commercially available and well-characterized proteases that can be used to cut at a specific amino acid sequence. TEV protease cleaves the sequence Glu-Asn-Leu-Tyr-Phe-Gln-Gly/Ser (ENLYFQG/S) (SEQ ID NO:2) between Gln-Gly or Gln-Ser with high specificity.

Another well-known protease is thrombin that specifically cleaves the sequence Leu-Val-Pro-Arg-Gly-Ser (LVPAGS) (SEQ ID NO: 3) between Arg-Gly. Thrombin has also been used for cleavage of recombinant fusion proteins. Other sequences can also be used for thrombin cleavage; these sequences are more or less specific and more or less efficiently cleaved by thrombin. Thrombin is a highly active protease and various reaction conditions are known to the public.

Activated coagulation factor FX (FXa) is also known to be a specific and useful protease. This enzyme cleaves C-terminal of Arg at the sequence Ile-Glu-Gly-Arg (IEGR) (SEQ ID NO: 4). FXa is frequently used to cut between fusion proteins when producing proteins with recombinant technology. Other recognition sequences can also be used for FXa.

Other types of proteolytic enzymes can also be used that recognize specific amino acid sequences. In addition, proteolytic enzymes that cleave amino acid sequences in an un-specific manner can also be used if only the linker contains an amino acid sequence in the complex molecule.

Other type of molecules such as ribozymes, catalytically active antibodies, or lipases can also be used. The only prerequisite is that the catalytically active molecule can cleave the specific structure used as the linker, or as a part of the linker, that connects the encoding region and the displayed molecule or, in the alternative the solid support and the target.

A variety of endonucleases are available that recognize and cleave a double stranded nucleic acid having a specific sequence of nucleotides. The endonuclease Eco RI is an example of a nuclease that efficiently cuts a nucleotide sequence linker comprising the sequence GAATTC also when this sequence is close to the nucleotide sequence length. Purified recombinant Eco RI is commercially available and is highly active in a range of buffer conditions. As an example the Eco RI is working in in various protocols as indicted below (NEBuffer is available from New England Biolabs):
NEBuffer 1: [10 mM Bis Tris Propane-HCl, 10 mM $MgCl_2$, 1 mM dithiothreitol (pH 7.0 at 25° C.)],
NEBuffer 2: [50 mM NaCl, 10 mM Tris-HCl, 10 mM $MgCl_2$, 1 mM dithiothreitol (pH 7.9 at 25° C.)],
NEBuffer 3: [100 mM NaCl, 50 mM Tris-HCl, 10 mM $MgCl_2$, 1 mM dithiothreitol (pH 7.9 at 25° C.)],
NEBuffer 4: [50 mM potassium acetate, 20 mM Tris-acetate, 10 mM magnesium acetate, 1 mM dithiothreitol (pH 7.9 at 25° C.)].
Extension buffer: mM KCl, 20 mM Tris-HCl(Ph 8.8 at 25° C.), 10 mM $(NH_4)_2SO_4$, 2 mM $MgSO_4$ and 0.1% Triton X-100, and 200 μM dNTPs.
Nucleotides The nucleotides used in the present invention may be linked together in a sequence of nucleotides, i.e. an oligonucleotide. Each nucleotide monomer is normally composed of two parts, namely a nucleobase moiety, and a backbone. The back bone may in some cases be subdivided into a sugar moiety and an internucleoside linker.

The nucleobase moiety may be selected among naturally occurring nucleobases as well as non-naturally occurring nucleobases. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudo-isocytosine, 2-hydroxy-5-methyl-4-triazolopyridine, isocytosine, isoguanine, inosine and the "non-naturally occurring" nucleobases described in Benner et al., U.S. Pat. No. 5,432, 272. The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases.

Examples of suitable specific pairs of nucleobases are shown below:

Natural Base Pairs

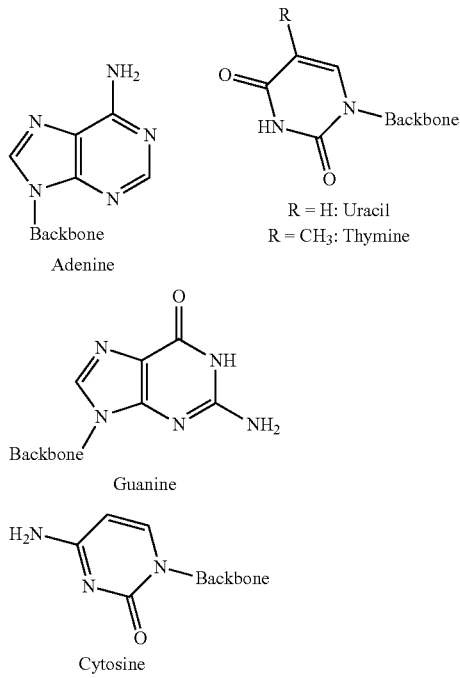

Synthetic Base Pairs

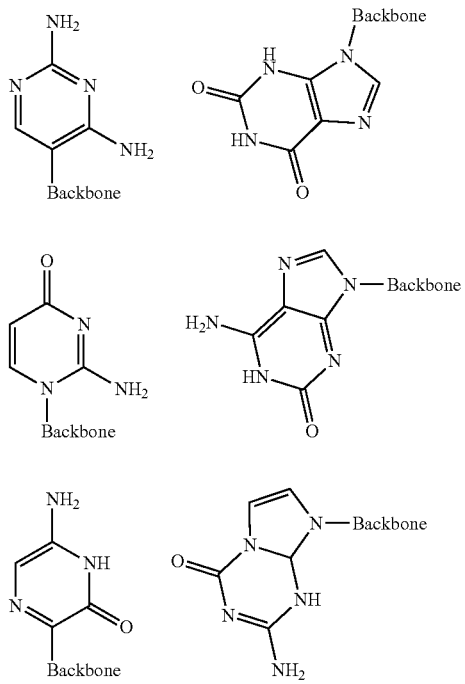

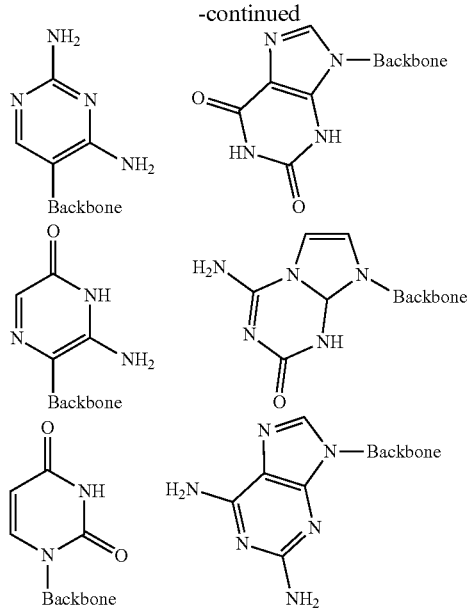
Synthetic purine bases pairring with natural pyrimidines
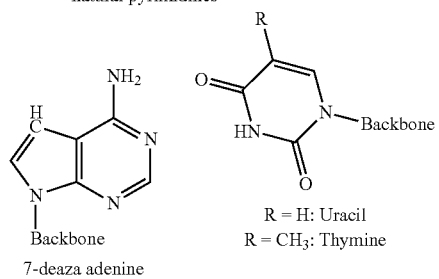
R = H: Uracil
R = CH₃: Thymine
7-deaza adenine
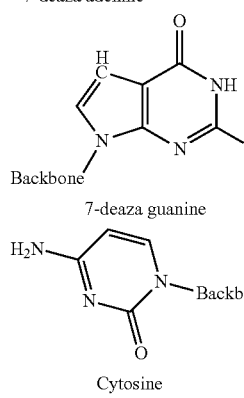
7-deaza guanine
Cytosine
Suitable examples of backbone units are shown below (B denotes a nucleobase):
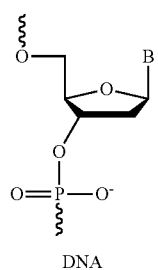
DNA
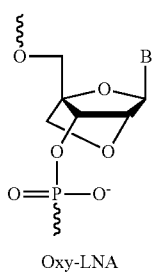
Oxy-LNA
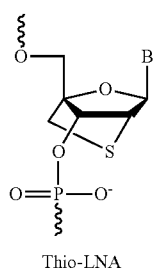
Thio-LNA
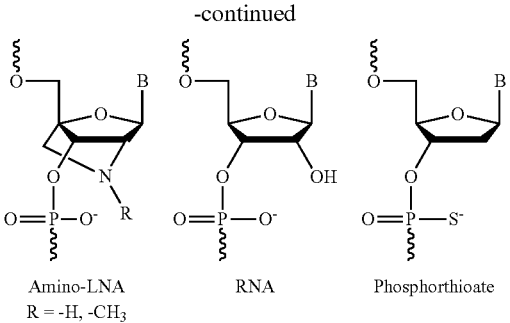
Amino-LNA
R = -H, -CH₃
RNA
Phosphorthioate
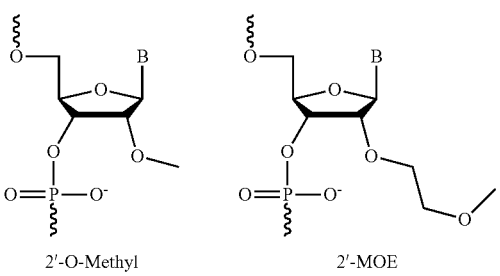
2'-O-Methyl
2'-MOE
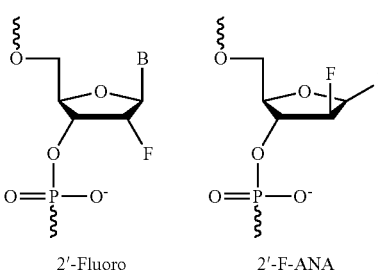
2'-Fluoro
2'-F-ANA
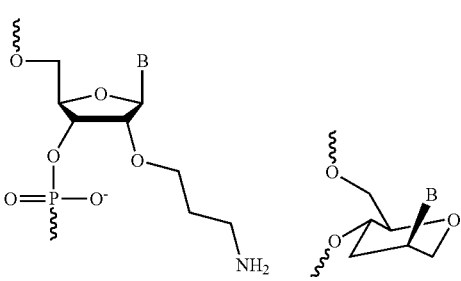
2'-AP
HNA
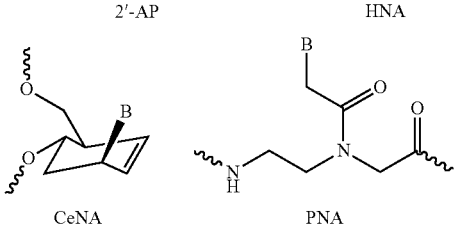
CeNA
PNA
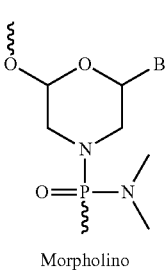
Morpholino
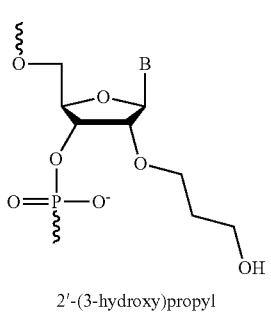
2'-(3-hydroxy)propyl

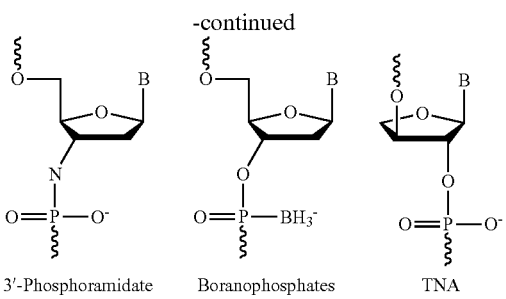

3'-Phosphoramidate    Boranophosphates    TNA

The sugar moiety of the backbone is suitably a pentose but may be the appropriate part of an PNA or a six-member ring. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose or 2-deoxyribose. The internucleoside linkage may be the natural occurring phosphodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine.

Selection

Once the library has been formed in accordance with the methods disclosed herein, one must screen the library for chemical compounds having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor. In addition to libraries produced as disclosed herein above, libraries prepared in accordance with method A and B below, may be screened according to the present invention.

A. Display molecules can be single compounds in their final "state", which are tagged individually and separately. E.g. single compounds may individually be attached to a unique tag. Each unique tag holds information on that specific compound, such as e.g. structure, molecular mass etc.

B. A display molecule can be a mixture of compounds, which may be considered to be in their final "state". These display molecules are normally tagged individually and separately, i.e. each single compound in a mixture of compounds may be attached to the same tag. Another tag may be used for another mixture of compounds. Each unique tag holds information on that specific mixture, such as e.g. spatial position on a plate.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-1 0 converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA2, red blood cells, glioblastomas, fibrin clots, PBMCs, hCG, lectins, selectins, cytokines, ICP4, complement proteins, etc.

The upper limit for the strength of the stringency conditions is the disintegration of the complex comprising the displayed molecule and the encoding region. Screening conditions are known to one of ordinary skill in the art.

Complexes having predetermined desirable characteristics can be partitioned away from the rest of the library while still attached to a nucleic acid identifier tag by various methods known to one of ordinary skill in the art. In one embodiment of the invention the desirable products are partitioned away from the entire library without chemical degradation of the attached nucleic acid such that the identifier nucleic acids are amplifiable. The part of the identifier comprising the codons may then be amplified, either still attached to the desirable chemical compound or after separation from the desirable chemical compound.

In a certain embodiment, the desirable display molecule acts on the target without any interaction between the coding sequences attached to the desirable display compound and the target. In one embodiment, the desirable chemical compounds bind to the target followed by a partition of the complex from unbound products by a number of methods. The methods include plastic binding, nitrocellulose filter binding, column chromatography, filtration, affinity chromatography, centrifugation, and other well known methods for immobilizing targets.

Briefly, the library is subjected to the partitioning step, which may include contact between the library and a column onto which the target is bound. All identifier sequences which do not encode for a reaction product having an activity towards the target will pass through the column. Additional undesirable chemical entities (e.g., entities which cross-react with other targets) may be removed by counter-selection methods. Desirable complexes are bound to the column and can be eluted by changing the conditions of the column (e.g., salt, etc.) or the identifier sequence associated with the desirable chemical compound can be cleaved off and eluted directly.

In a certain embodiment, the basic steps involve mixing the library of complexes with the immobilized target of interest. The target can be attached to a column matrix or microtitre wells with direct immobilization or by means of antibody binding or other high-affinity interactions. In another embodiment, the target and displayed molecules interact without immobilisation of the target. Displayed molecules that bind to the target will be retained on this surface, while nonbinding displayed molecules will be removed during a single or a series of wash steps. The identifiers of complexes bound to the target can then be separated by cleaving the physical connection to the synthetic molecule. It may be considered advantageously to perform a chromatography step after of instead of the washing step. After the cleavage of the physical link between the synthetic molecule and the identifier, the identifier may be recovered from the media and optionally amplified before the decoding step.

In traditional elution protocols, false positives due to suboptimal binding and washing conditions are difficult to circumvent and may require elaborate adjustments of experimental conditions. However, an enrichment of more than 100 to 1000 is rarely obtained. The selection process used in example 7 herein alleviates the problem with false positive being obtained because the non-specific binding complexes to a large extent remain in the reaction chamber. The experiments reported herein suggest that an enrichment of more than 107 can be obtained.

Additionally, chemical compounds which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group, or similar activated chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

Inherent in the present method is the selection of chemical entities on the basis of a desired function; this can be extended to the selection of small molecules with a desired function and specificity. Specificity can be required during the selection process by first extracting identifiers sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

Enrichment

The present invention also relates to a method for determining the identity of a chemical entity having a preselected property, comprising the steps of:

i) generating a tagged library of chemical entities by appending unique identifier tags to chemical entities, ii) subjecting the library to a condition, wherein a chemical entity or a subset of chemical entities having a predetermined property is partitioned from the remainder of the library, iii) recovering an anti-tag from the partitioned library, said anti-tag being capable of interacting with the unique identifier tag in a specific manner, and iv) identifying the chemical entity/ies having a preselected function by decoding the anti-tag.

The tag is appended the chemical entity by a suitable process. Notably, each chemical entity is appended a tag by a reaction involving a chemical reaction between a reactive group of the chemical entity and a reactive group of the tag, such as method A and B of the selection section. The attachment of the chemical entity may be directly or through a bridging molecule part. The molecule part may be any suitable chemical structure able to connect the chemical entity to the tag.

The anti-tag has the ability to interact with the unique identifier tag in a specific manner. The chemical structure of the anti-tag is to a large extent dependant on the choice of unique tag. As an example, if the unique tag is chosen as an antibody, the anti-tag is selected as the epitope able to associate with the antibody. In general, it is preferred to use an anti-tag comprising a sequence of nucleotides complementary to a unique identifier tag.

The method may be performed without amplification in certain embodiments. However, when larger libraries are intended, it is in general preferred to use an anti-tag which is amplifiable. Anti-tags comprising a sequence of nucleotides may be amplified using standard techniques like PCR. In the event the anti-tag is a protein, the protein may be amplified by attaching the mRNA which has encoded the synthesis thereof, generating the cDNA from the mRNA and subjecting said mRNA to a translation system. Such system is described in WO 98/31700 the content of which is incorporated herein by reference. An alternative method for amplifying a protein tag is to use phage-displayed proteins.

In the event the tag as well as the anti-tag is a sequence of nucleic acids, a tag:anti-tag hybrid may be formed prior to the subjecting the library to partitioning conditions or subsequent to the partitioning step. In some embodiments of the invention it is preferred to form the tag:anti-tag hybrid prior to the partition step in order to make the appended nucleotide sequence inert relative to the system as it is well known that certain sequences of nucleotides can bind to a target or catalyse a chemical reaction.

The oligonucleotide anti-tag may be formed in a variety of ways. In one embodiment of the invention, the anti-tag is formed as an enzymatic extension reaction. The extension comprises the initial annealing of a primer to the unique identifier tag and subsequent extension of the primer using a polymerase and dNTPs. Other types of extension reactions may also be contemplated. As an example ligases may be used to create the primer starting from di- or trinucleotide substrates and the extension may be performed using a suitable polymerase.

It may be desirable to recover the anti-tag at various steps during the process. To this end it is preferred in some aspects of the invention to provide the primer provided with a handle capable of binding to a suitable affinity partner. An arsenal of different handles and affinity partners are available to the skilled person in the art. The most widely used handle is biotin, which in general are also preferred according to the present invention. Biotin binds to the affinity partner streptavidin or avidin. A standard technique in the laboratory is to recover a biochemical entity having attached a biotin using a solid phase covered with streptavidin. Suitably, the solid phase is a bead which may be separated from the liquid after the binding action by rotation or a magnetic field in case the solid bead comprises magnetic particles.

In other aspects of the present invention, the anti-tag is provided as a separate oligonucleotide. The separate oligonucleotide may be produced using standard amidite synthesis strategies or may be provided using other useful methods. It is in general preferred to provide the oligonucleotide by synthesis, at least in part, because the biotin amidite is easily incorporated in a nascent oligonucleotide strand. Following the addition of an oligonucleotide anti-tag to a liquid comprising chemical entities tagged with complementing oligonucleotide tags a double stranded library is formed as a hybridisation product between the unique identifier tag and the anti-tag oligonucleotide.

As mentioned above, the anti-tag oligonucleotide may be provided with a handle, such as biotin, capable of binding to an affinity partner, such as streptavidin or avidin.

Following the addition of the anti-tag oligonucleotides to the tagged chemical entities, some of the oligonucleotides present in the media may not find a partner. In one aspect of the invention it is preferred that oligonucleotides not hybridised to a cognate unique identifier and/or anti-tag are transformed into a double helix. In other aspects of the invention single stranded oligonucleotides are degraded prior to step ii) to avoid unintended interference.

The handle may be used to purify the library prior to or subsequent to the partitioning step. In some embodiments of the invention, the purification step is performed prior to the partitioning step to reduce the noise of the system. In another aspect the handle is used to purify the partitioned library subsequent to step ii) in order to recover a double stranded product which may be amplified.

The library is subjected to a condition in order to select chemical entities having a property which is responsive to this condition. The condition may involve the exposure of the library to a target and partitioning the chemical entities having an affinity towards this target. Another condition could be subjecting the library to a substrate and partitioning chemical entities having a catalytical activity relative to this substrate.

The anti-tag can be formed subsequent to the partitioning step. In an aspect of the invention, the single stranded nucleotide serving as a tag is made double stranded while the chemical entity is attached to the target of an affinity partitioning. Optionally, in a repeated temperature cycle, a plurality of anti-tags may be formed as extension products using the tag as template. In another aspect of the invention, the chemical entity bearing the single stranded oligonucleotide is detached from the target and a complementing anti-tag is subsequently prepared.

In the event the anti-tag comprises a handle, this handle can be used to purify the partitioned library. The recovery of the anti-tag is then performed by melting off said anti-tag from a partitioned double stranded library. Optionally, the amount of anti-tags may be multiplied by conventional amplification techniques, such as PCR.

The method according to the invention can be performed using a single partitioning step. Usually, it is preferred, however, to use more than one partitioning step in order to select the candidate having the desired properties from a large library. Thus, the recovered anti-tags may be mixed with the initial library or a subset thereof and the steps of partitioning (step ii)) and recovery (step iii)) may is repeated a desired number of times. Optionally, single stranded moieties in the mixture may be degraded or removed or made inert as described above.

Generally, the partitioned library obtained in step ii) is subjected to one or more further contacting steps using increasing stringency conditions. The stringency conditions may be increased by increasing the temperature, salt concentration, acidity, alkalinity, etc.

In one embodiment of the invention, the partitioned library is not subjected to intermediate process steps prior to a repeated contacting step. Especially, the partitioned library is not subjected to intermediate amplification of the anti-tag. This embodiment may be of advantage when relatively small libraries are used.

The method of the invention terminates with a decoding step, that is a step in which the identity of the chemical entity or entities are deciphered by an analysis of the anti-tag. When the anti-tag is an oligonucleotide, the decoding step iv) may be performed by sequencing an anti-tag nucleotide. Various methods for sequencing are apparent for the skilled person, including the use of cloning and exposure to a microarray. The tags contain recognizing groups such as e.g. nucleotide sequence(s), epitope(s) a.o. The tags carries information of the entity to which it is attached, such as e.g. entity structure, mass, spatial position (plate information) etc. The tags may be composed of monoclonal antibodies, peptides, proteins, oligonucleotides, DNA, RNA, LNA, PNA, natural peptides, unnatural peptides, polymeric or oligomeric hydrazino aryl and alkyl carboxylic acids, polymeric or oligomeric aminoxy aryl and alkyl carboxylic acids, peptoids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da).

In one preferred embodiment, entities consist of small non-polymeric molecules (molecular weight <1000 Da). Small molecules are generally the compounds of interest in the quest for drug oral candidates. Especially, small molecules not occurring in Nature are of interest in the drug discovery process and in one aspect of the present invention the method are designed to select a oral drug candidate. A variety of drug candidate libraries are available on the market. The drug candidates of the library usually comprise a reactive group or a group which can be altered into a reactive group. In one preferred aspect of the present invention each of the members of the drug candidate library is appended a nucleic acid tag via said reactive group of the library member and a reactive group on the nucleic acid. Preferably, the nucleic acid is an oligonucleotide.

In another aspect of the invention, entities consist of large non-polymeric molecules (molecular weight >1000 Da). In still another embodiment, entities consist of polymeric molecules.

The tags and anti-tags may be composed of RNA linked to monoclonal antibodies, proteins, LNA, PNA, natural polypeptides, unnatural polypeptides, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da).

Alternatively, anti-tags may be composed of DNA linked to monoclonal antibodies, proteins, LNA, PNA, natural polypeptides, unnatural polypeptides, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Alternatively, anti-tags are just composed of oligonucleotides, DNA or RNA. In a preferred embodiment, anti-tags are composed of DNA. In another preferred embodiment anti-tags are composed of RNA.

Anti-tags which are linked to DNA or RNA are also encoded by the DNA/RNA linked to them, e.g. phage displayed or polysome displayed antibodies, peptides or proteins, and via DNA-templated synthesis of anti-tags, where the DNA encode the synthesis of the anti-tag, which is linked to its DNA during its synthesis.

Each chemical compound or group of compounds may be associated with a tag through formation of a covalent or non-covalent bond. For covalent bond formation, tagging may involve, but is not limited to, the formation of a cycloaddition product, an alkylation product, an arylation product, an acylation product, an amide bond, a carboxylic ester bond, a sulfonamide bond, a disulfide bond, an S-alkyl bond, an NR-alkyl bond, an O-alkyl bond, an aryl-vinyl bond, an alkyne-vinyl bond, an oxime bond, an imine bond, a bicyclic product, a trizole, a hexene, a 7-Oxa-bicyclo[2.2.1]hept-2-ene derivative, a 7-Aza-bicyclo[2.2.1]hept-2-ene derivative or a 7-Methyl-7-aza-bicyclo[2.2.1]hept-2-ene. Non-covalent bonds may involve, but are not limited to, attachment via e.g. hydrogen bonding, van der Waals interactions, pi-stacking or through hybridization. Hybridization may be between complementary strands of DNA, RNA, PNA or LNA or mixtures thereof. In such case both the tag and the chemical compound carries such a strand complementary to each other. The tagged entity, compound or mixture of compounds may be transformed into a new tagged entity, e.g. by transformation of the entity or by transformation of the tag. The transformation may be caused by either chemical or physical transformations such e.g. addition of reagents (e.g. oxidizing or reducing agents, pH adjustment a.o.) or subjection to UV-irradiation or heat.

The complex between tags and anti-tags may be formed on individually tagged entities immediately after tagging. Alternatively, after mixing individually tagged entities, either before or after the optionally use of library purification, or either before or after library enrichment for specific properties.

When tags and anti-tags are composed of nucleotides the complex consists of a double stranded nucleotide, e.g. duplex DNA or hybrids DNA/RNA.

The purification handle (denoted "@") may be connected to the anti-tag. The purification handle contains a recognizing group(s) such as e.g. nucleotide sequence(s), epitopes, reactive groups, high affine ligands a.o. The purification handles may be composed of monoclonal antibodies, peptides, proteins, DNA, RNA, LNA, PNA, natural peptides, unnatural peptides, polymeric or oligomeric hydrazine aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Purification handles may e.g. be a nucleotide sequence, biotin, streptavidin, avidin, "his-tags", mercapto groups or disulfide/activated disulfide groups. The purification handle may be part of the anti-tag, e.g. in the case the anti-tag is nucleotide based or e.g. antibodies where part of the antibody may serve as epitop for another antibody (e.g. immobilized antibody which serve as purification filter).

Purification filters contains components which associate, interact or react with purification handles whereby a complex is formed. This complex allows separation of non-complexed tagged entities and complexed tagged entities. The purification filter contains a recognizing group(s) such as e.g. nucleotide sequence(s), epitopes, reactive groups, high affine ligands a.o. The purification filter may be composed of monoclonal antibodies, peptides, proteins, DNA, RNA, LNA, PNA, natural peptides, unnatural peptides, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Purification filters may e.g. be a nucleotide sequence, biotin, strepdavidin, avidin, "his-tags", mercapto groups or disulfide/activated disulfide groups.

The library is probed and enriched for properties. Properties may be affinity, catalytic activity or membrane penetrating capability a.o.

Amplification may use PCR or RTPCR techniques. Anti-tags are amplifiable in some aspects of the invention. Anti-tags may be separated from tags by use of physical or chemical means, such as e.g. UV-irradiation, heat, pH-adjustment, use of salt solutions a.o.

Isolated tagged entities may be identified either trough their tag or anti-tag. Identification may be accomplished by cloning of anti-tags and sequencing their DNA/RNA or through mass analysis of either tagged entities or anti-tags or complexes of anti-tags/tagged entities.

The library of tagged entities may involve $10$-$10^{20}$ or $10$-$10^{14}$ or $10$-$10^2$ or $10$-$10^3$ or $10^2$-$10^3$ or $10^2$-$10^4$ or $10^3$-$10^6$ or $10^3$-$10^8$ or $10^3$-$10^{10}$ or $10^3$-$10^{14}$ or $10^5$-$10^6$ or $10^5$-$10^8$ or $10^5$-$10^{10}$ or $10^5$-$10^{14}$ or $10^8$-$10^{14}$ or $10^{14}$-$10^{20}$ entities.

Library complexes of tagged entities and anti-tags may be enriched for properties prior to purification by use of purification handle and purification filter or after purification.

The term unique, when used together with sequences of nucleotides, implies that at least one of the nucleobases and/or backbone entities of the sequence does not appear together with different chemical entities. Preferably, a specific sequence is unique due to fact that no other chemical entities are associated with the same sequence of nucleobases.

Once the library has been formed, one must screen the library for chemical compounds having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-1 0 converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA2, red blood cells, glioblastomas, fibrin clots, PBMCs, hCG, lectins, selectins, cytokines, ICP4, complement proteins, etc.

The stringency conditions under which the library are screened are normally limited to such condition that maintain the hybridisation between the identifier tag and the anti-tag. High stringency conditions may be applied, however, followed by a renewed synthesis or attachment of the anti-tag. Screening conditions are known to one of ordinary skill in the art.

Chemical compounds having predetermined desirable characteristics can be partitioned away from the rest of the library while still attached to a nucleic acid identifier tag by various methods known to one of ordinary skill in the art. In one embodiment of the invention the desirable products are partitioned away from the entire library without chemical degradation of the attached nucleic acid such that the identifier nucleic acids are amplifiable. The identifier tag may then be amplified, either still attached to the desirable chemical compound or after separation from the desirable chemical compound.

In the most preferred embodiment, the desirable chemical compound acts on the target without any interaction between the tag attached to the desirable chemical compound and the target. In one embodiment, the desirable chemical compounds bind to the target and the bound tag-desirable chemical compound-target complex can be partitioned from unbound products by a number of methods. The methods include nitrocellulose filter binding, column chromatography, filtration, affinity chromatography, centrifugation, and other well known methods.

Briefly, the library is subjected to the partitioning step, which may include contact between the library and a column onto which the target is bound. All tags which have not formed hybridisation products with a chemical entity-tag aggregate or those tags associated with undesirable chemical entities will pass through the column. Additional undesirable chemical entities (e.g., entities which cross-react with other targets) may be removed by counter-selection methods. Desirable complexes are bound to the column and can be eluted by changing the conditions of the column (e.g., salt, etc.) or the tag associated with the desirable chemical compound can be cleaved off and eluted directly.

Additionally, chemical compounds which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

Inherent in the present method is the selection of chemical entities on the basis of a desired function; this can be extended to the selection of small molecules with a desired function and specificity. Specificity can be required during the selection process by first extracting identifier sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

Following the selection procedure, anti-tags are recovered. The recovery may be performed by subjecting the selected complexes to stringency conditions which will detach the anti-tag sequences from the identifier tag. In the event the tag and the anti-tag are nucleic acids, the stringency conditions may be increased by increasing the temperature gradually until the two strands of the double helix are melted apart. Further copies of anti-tag sequences may be provided by extension of the identifier sequences using a suitable primer and a polymerase. In the alternative, the recovered anti-tag sequence and/or the identifier sequence tag may be subjected to PCR to form a double stranded product. The strands comprising the sequence that complements at least a part of a unique identifier sequence are subsequently isolated.

The selected chemical entity may be attached to the target during the extension or amplification or may be detached from the target. In one aspect of the invention, it is preferred that the target is immobilised and the chemical compound remain attached to the target during the extension or amplification, to allow for easy recovery of the extension or amplification product by simple elution. In another aspect the selected chemical entities are separated from the unique identifier sequences, prior to, simultaneous with or subsequent to the recovery of the enrichment sequences.

In order to recover the desired anti-tag sequences, it may be appropriate to provide the native as well as the amplified, if present, anti-tag sequences with one part of a molecular affinity pair. The one part of a molecular affinity pair is also referred to herein as a handle. The anti-tags may then be recovered by using the other part of the molecular affinity pair attached to a solid phase, which is possible to isolate. The essential property of the molecular affinity pair is that the two parts are capable of interacting in order to assemble the molecular affinity pair. In the biotechnological field a variety of interacting molecular parts are known which can be used as the molecular affinity pair. Examples include, but are not restricted to protein-protein interactions, protein-polysaccharide interactions, RNA-protein interactions, DNA-DNA interactions, DNA-RNA interactions, RNA-RNA interactions, biotin-streptavidin interactions, enzyme-ligand interactions, antibody-ligand interaction, protein-ligand interaction, etc.

A suitable molecular affinity pair is biotin-streptavidin. The anti-tag sequences can be provided with biotin, e.g. by using a primer attached to a biotin moiety in the amplification or extension step and contacting the biotin tagged anti-tag sequence with beads coated with streptavidin.

After the recovery of the anti-tag sequences, these are contacted with the initial library or a fraction thereof and an enriched library is allowed to be formed by the hybridisation of the anti-tag sequences to the cognate sequence of the unique identifier tag.

The method according to the invention may be repeated one or more times. In a second round of the method, the part of the single stranded library not recognized by an anti-tag sequence may be cleared from the reaction media or the remaining part of the single stranded library may remain in admixture with the enrich library. In general, it is not necessary to separate the remaining part of the single stranded library from the media before the enriched double stranded library is subjected to a second contact with the target because conditions for the preselected function usually are more stringent than the first round, wherefore the members of the single stranded library presumably will not bind to the target. However, to reduce the noise of the system, it may be useful at some events to withdraw from the media the members of the single stranded initial library not mated with an anti-tag sequence. If the anti-tag sequences are provided with one part of a molecular affinity pair, like biotin, the chemical compounds of interest can be extracted from the media by treatment with immobilized streptavidin, e.g beads coated with streptavidin.

As mentioned above, the conditions for performing the second or further selection step is generally more stringent than in the first or preceding step. The increasing stringency conditions in sequential selection rounds provide for the formation of a sub-library of chemical compounds which is narrowed with respect to the number but enriched with respect to the desired property.

In the present description with claims, the terms nucleic acid, oligonucleotide, oligo, and nucleotides are used frequently. The terms nucleotide, nucleotide monomer, or mononucleotides are used to denote a compound normally composed of two parts, namely a nucleobase moiety, and a backbone. The back bone may in some cases be subdivided into a sugar moiety and an internucleoside linker. Mononucleotides may be linked to each other to form a oligonucleotide. Usually, the mononucleotides are linked through an internucleoside linkage. The term nucleic acid covers mononucleotides as well as oligonucleotides. Usually, however, the term denotes an oligonucleotide having from 2 to 30 mononucleotides linked together through internucleoside linkers.

Determining the Coding Part of the Bifunctional Complex

The coding part of the identifier sequence present in the isolated bifunctional molecules or the separated identifier oligonucleotides is determined to identify the chemical entities that participated in the formation of the display molecule. The synthesis method of the display molecule may be established if information on the functional entities as well as the point in time they have been incorporated in the display molecule can be deduced from the identifier oligonucleotide. It may be sufficient to get information on the chemical structure of the various chemical entities that have participated in the display molecule to deduce the full molecule due to structural constraints during the formation. As an example, the use of different kinds of attachment chemistries may ensure that a chemical entity on a building block can only be transferred to a single position on a scaffold. Another kind of chemical constrains may be present due to steric hindrance on the scaffold molecule or the functional entity to be transferred. In general however, it is preferred that information can be inferred from the identifier sequence that enable the identification of each of the chemical entities that have participated in the formation of the encoded molecule along with the point in time in the synthesis history the chemical entities have been incorporated in the (nascent) display molecule.

Although conventional DNA sequencing methods are readily available and useful for this determination, the amount and quality of isolated bifunctional molecule may require additional manipulations prior to a sequencing reaction.

Where the amount is low, it is preferred to increase the amount of the identifier sequence by polymerase chain reaction (PCR) using PCR primers directed to primer binding sites present in the identifier sequence.

In addition, the quality of the isolated bifunctional molecule may be such that multiple species of bifunctional molecules are co-isolated by virtue of similar capacities for binding to the target. In cases where more than one species of bifunctional molecule are isolated, the different isolated species must be separated prior to sequencing of the identifier oligonucleotide.

Thus in one embodiment, the different identifier sequences of the isolated bifunctional complexes are cloned into separate sequencing vectors prior to determining their sequence by DNA sequencing methods. This is typically accomplished by amplifying all of the different identifier sequences by PCR as described herein, and then using a unique restriction endonuclease sites on the amplified product to directionally clone the amplified fragments into sequencing vectors. The cloning and sequencing of the amplified fragments then is a routine procedure that can be carried out by any of a number of molecular biological methods known in the art.

Alternatively, the bifunctional complex or the PCR amplified identifier sequence can be analysed in a microarray. The array may be designed to analyse the presence of a single codon or multiple codons in an identifier sequence.

Synthesis of Nucleic Acids

Oligonucleotides can be synthesized by a variety of chemistries as is well known. For synthesis of an oligonucleotide on a substrate in the direction of 3' to 5', a free hydroxy terminus is required that can be conveniently blocked and deblocked as needed. A preferred hydroxy terminus blocking group is a dimexothytrityl ether (DMT). DMT blocked termini are first deblocked, such as by treatment with 3% dichloroacetic acid in dichloromethane (DCM) as is well known for oligonucleotide synthesis, to form a free hydroxy terminus.

Nucleotides in precursor form for addition to a free hydroxy terminus in the direction of 3' to 5' require a phosphoramidate moiety having an aminodiisopropyl side chain at the 3' terminus of a nucleotide. In addition, the free hydroxy of the phosphoramidate is blocked with a cyanoethyl ester (OCNET), and the 5' terminus is blocked with a DMT ether. The addition of a 5' DMT-, 3' OCNET-blocked phosphoramidate nucleotide to a free hydroxyl requires tetrazole in acetonitrile followed by iodine oxidation and capping of unreacted hydroxyls with acetic anhydride, as is well known for oligonucleotide synthesis. The resulting product contains an added nucleotide residue with a DMT blocked 5' terminus, ready for deblocking and addition of a subsequent blocked nucleotide as before.

For synthesis of an oligonucleotide in the direction of 5' to 3', a free hydroxy terminus on the linker is required as before. However, the blocked nucleotide to be added has the blocking chemistries reversed on its 5' and 3' termini to facilitate addition in the opposite orientation. A nucleotide with a free 3' hydroxyl and 5' DMT ether is first blocked at the 3' hydroxy terminus by reaction with TBS-Cl in imidazole to form a TBS ester at the 3' terminus. Then the DMT-blocked 5' terminus is deblocked with DCA in DCM as before to form a free 5' hydroxy terminus. The reagent (N,N-diisopropylamino)(cyanoethyl) phosphonamidic chloride having an aminodiisopropyl group and an OCNET ester is reacted in tetrahydrofuran (THF) with the 5' deblocked nucleotide to form the aminodiisopropyl-, OCNET-blocked phosphonamidate group on the 5' terminus. Thereafter the 3' TBS ester is removed with tetrabutylammonium fluoride (TBAF) in DCM to form a nucleotide with the phosphonamidate-blocked 5' terminus and a free 3' hydroxy terminus. Reaction in base with DMT-Cl adds a DMT ether blocking group to the 3' hydroxy terminus.

The addition of the 3' DMT-, 5' OCNET-blocked phosphonamidated nucleotide to a linker substrate having a free hydroxy terminus then proceeds using the previous tetrazole reaction, as is well known for oligonucleotide polymerization. The resulting product contains an added nucleotide residue with a DMT-blocked 3' terminus, ready for deblocking with DCA in DCM and the addition of a subsequent blocked nucleotide as before.

BRIEF DESCRIPTION OF THE FIGURES

FIG. 2 shows the principle of encoding by extension

FIG. 4 shows the components of the identifier and the building block with internal codons

FIG. 31 shows two gels reported in example 13.

DETAILED DESCRIPTION OF THE FIGURES

Figure 1:
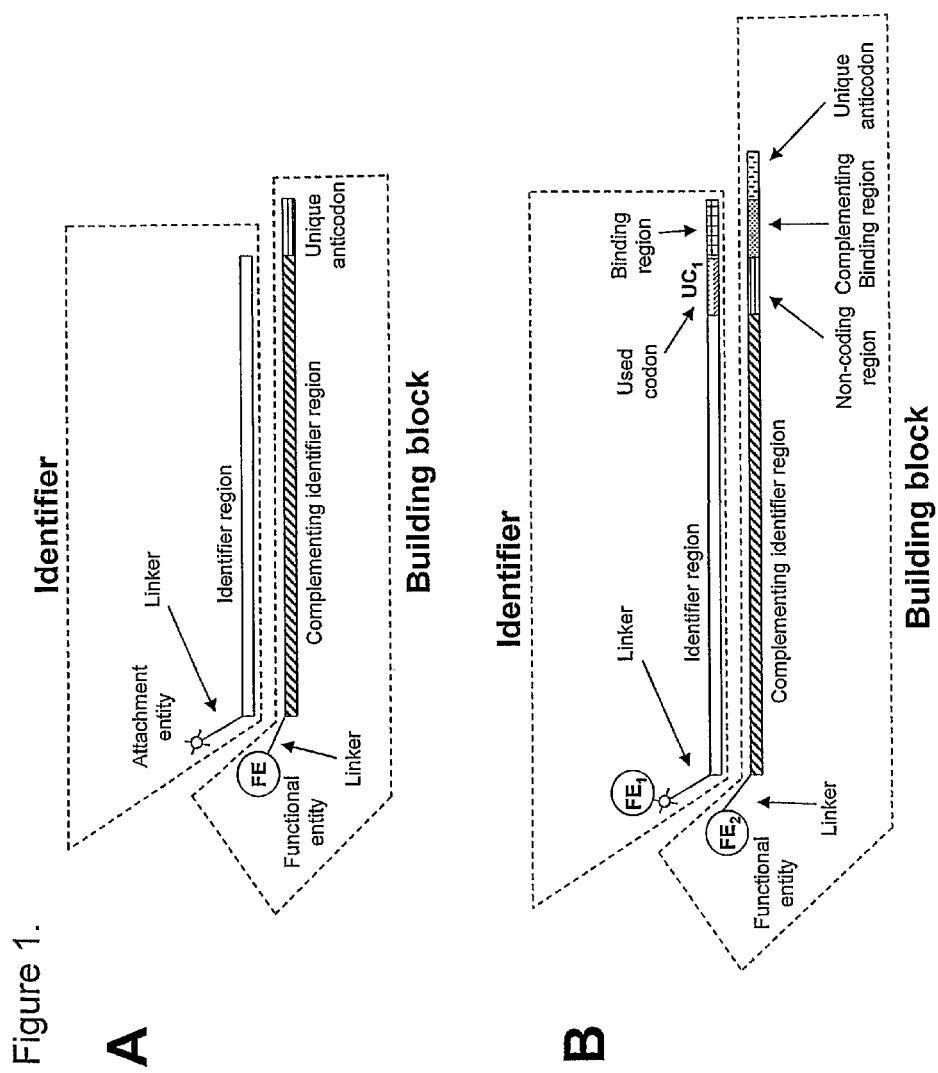
FIG. 1 shows the components of the identifier and the building block

FIG. 1 discloses in panel A a hybridisation product between a nascent bifunctional complex and a building block. The nascent bifunctional complex, for short the Identifier, comprises an attachment entity connected to an oligonucleotide identifier region by a linker moiety. The attachment entity may be a single recipient reactive group having been adapted to receive a functional entity or may be a scaffold structure comprising one or more recipient reactive groups. In panel A the attachment entity is indicated as a scaffold having four reactive groups capable of receiving functional entities.

The building block comprises a functional entity attached to an oligonucleotide which is sufficiently complementary to the identifier region to allow for a hybridisation product to be formed. The functional entity is able to be transferred to the attachment entity through a chemical reaction. The complementing identifier region further comprises a unique codon at the 3' or 5' end thereof. The unique codon identifies the functional entity in an unequivocal way.

Following the formation of the hybridisation product between the identifier and the building block, the functional entity and the unique anti-codon are transferred to the identifier. In an aspect of the invention, the linker connecting the functional entity and the complementing identifier region is cleaved simultaneously with the reaction with the attachment entity resulting in a transfer of the functional entity to the attachment entity. Prior to, simultaneously with or subsequent to the transfer, the transcription of the codon occurs.

The transcription is performed by an enzyme capable of polymerisation or oligomerisation of oligonucleotides using a template oligonucleotide to form a complementary stand. Usually a polymerase, such as the Pfu polymerase is used together with suitable dNTPs, i.e. a mixture of ATP, CTP, GTP, and TTP, to form the unique codon as an extension of the identifier strand using the unique anti-codon of the building block as template.

FIG. 1, panel B illustrates a typical setup for a second transfer of functional entity. The identifier has been provided with a first functional entity and has been extended by a codon. Furthermore, the codon also comprises a binding region as an extension of the codon. The binding region is usually a constant region transferred to the identifier in the first transfer cycle by the first building block. The identifier forms a hybridisation product with a second building block. The second building block comprises a second functional entity connected to an oligonucleotide sufficient complementary to the identifier region of the identifier to allow for a hybridisation. A part of the complementing identifier region comprises a non-coding region and a region complementing the binding region. The non-coding region opposes the codon transferred in the first cycle and the complementing binding region is complementary to the binding region to allow for a hybridisation which is sufficiently strong for an enzyme to bind to the helix. A second unique anti-codon is attached to the complementary binding region and identifies the second functional entity. The second codon is transferred to the identifier using the second anti-codon as template in the same manner as described above for the first codon.

FIG. 2 illustrates four cycles of functional entity and codon transfer. In the first cycle, a hybridisation product is formed between the identifier and building block. The hybridisation product ensures that the functional entity and the scaffold are brought into close spatial proximity, thus increasing the probability that a reaction will take place. The formation of a duplex between the two oligonucleotides also provides a binding region for a polymerase. In the presence of a polymerase, a mixture of dNTPs and a suitable puffer such as an aqueous solution containing 20 mM HEPES-KOH, 40 mM KCl and 8 mM $MgCl_2$ and a pH adjusted to 7.4, the unique anti-codon ($UA_1$) is transferred to the identifier as a codon.

After the transfer of functional entity and codon, respectively, the spent building block is separated from the identifier by increasing the stringency. Usually, the stringency is increased by a increasing the temperature, changing the pH or by increasing the ionic strength. After the rupture of the duple helix structure, the identifier is recovered. In one aspect of the invention the identifier is immobilized to ease the separation from the spent building block. In another aspect the spent building block is degraded chemically or enzymatically. Following the recovery of the identifier a new cycle can be initiated by contacting the identifier with a further building block.

The final product after four cycles of transfer is a bifunctional complex, which comprises a reaction product at one end and an encoding region at the other. The reaction product comprises constituents from the transferred functional entities and the initial scaffold. The encoding region comprises a genetic code for which entities that have been transferred in which order. Thus, the synthetic history may be decoded from the encoding region.

Figure 3:
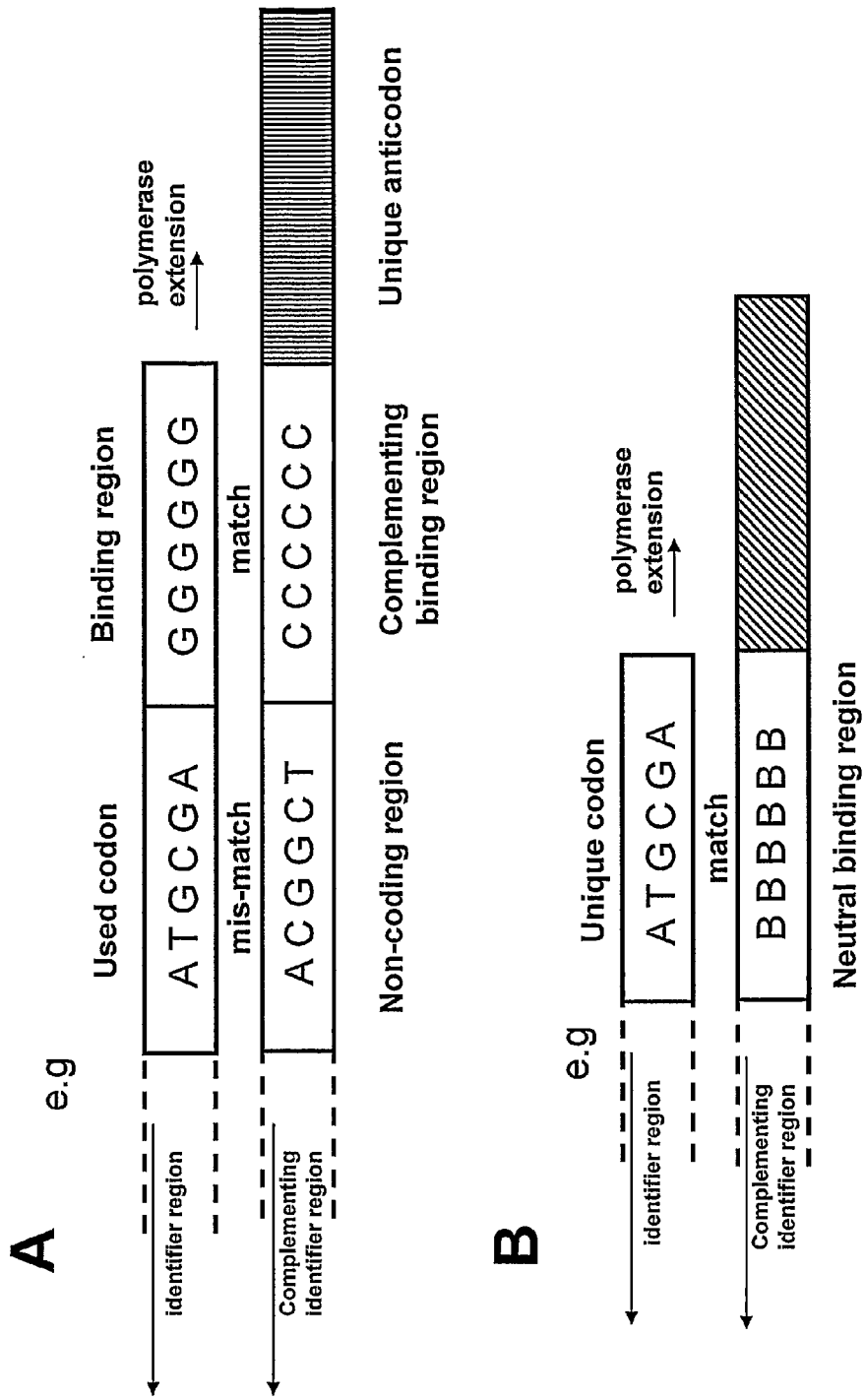
FIG. 3 shows the extension region of the building block

FIG. 3 shows examples of the design of the coding area. Panel A, depicts a detailed view of an example of a design according to FIG. 1, panel B. The unique codon transferred in a first cycle is opposed by a partly mis-matching region. To compensate for the decrease in affinity a binding region is following the codon. The binding region is opposed by a matching complementary binding region of the building block.

In FIG. 3, panel B the unique codon incorporated in a first cycle is opposed by a second building block having incorporated in the complementing identifier region a neutral binding region. The neutral binding region is not capable of discriminating between varieties of unique codons, but is able to show some kind of affinity towards the each of the codons. Usually, the neutral binding region comprises one or more universal bases and more preferred the neutral binding region comprises a sequence of universal bases opposing at least a part of the codon region on the identifier.

FIG. 4 shows a hybridisation product between an identifier and a building block wherein the identifier has internal codons and the building block has corresponding anti-codons. The identifier region and the complementing identifier region can also contain specific unique codons and anti-codons, respectively.

The use of internal codons is of particular importance when several rounds of selection are anticipated, especially when the encoded molecule is formed from a PCR product of a previous round. The internal anti-codons in the building block may completely or partly match the identifier sequence or may comprise one or more universal bases to provide for affinity but not for specificity. The role of the internal unique codons is only to guide the annealing between the identifier molecule and the building block molecule. The correct encoding is taken care of by the unique codons which are created in the extension process. These unique codons are passed on to the next generation of molecules and used to decode the synthetic history of the displayed molecules. This system will not be totally dependent on an accurate encoding function by the internal unique codons in order to pass the correct genotype to the next generation of identifier molecules.

In panel A the hybridisation product provides for a spatial proximity between the functional entity and the attachment entity, thus increasing the probability that a reaction occurs. The unique codon templates the codon on the identifier sequence by an enzymatic extension reaction. In panel B a binding region is introduced between each unique coding sequence to provide for affinity of the two strands to each other even though one or more mis-matching bases appear in the codon:non-coding domain of a previously used codon.

Figure 5:
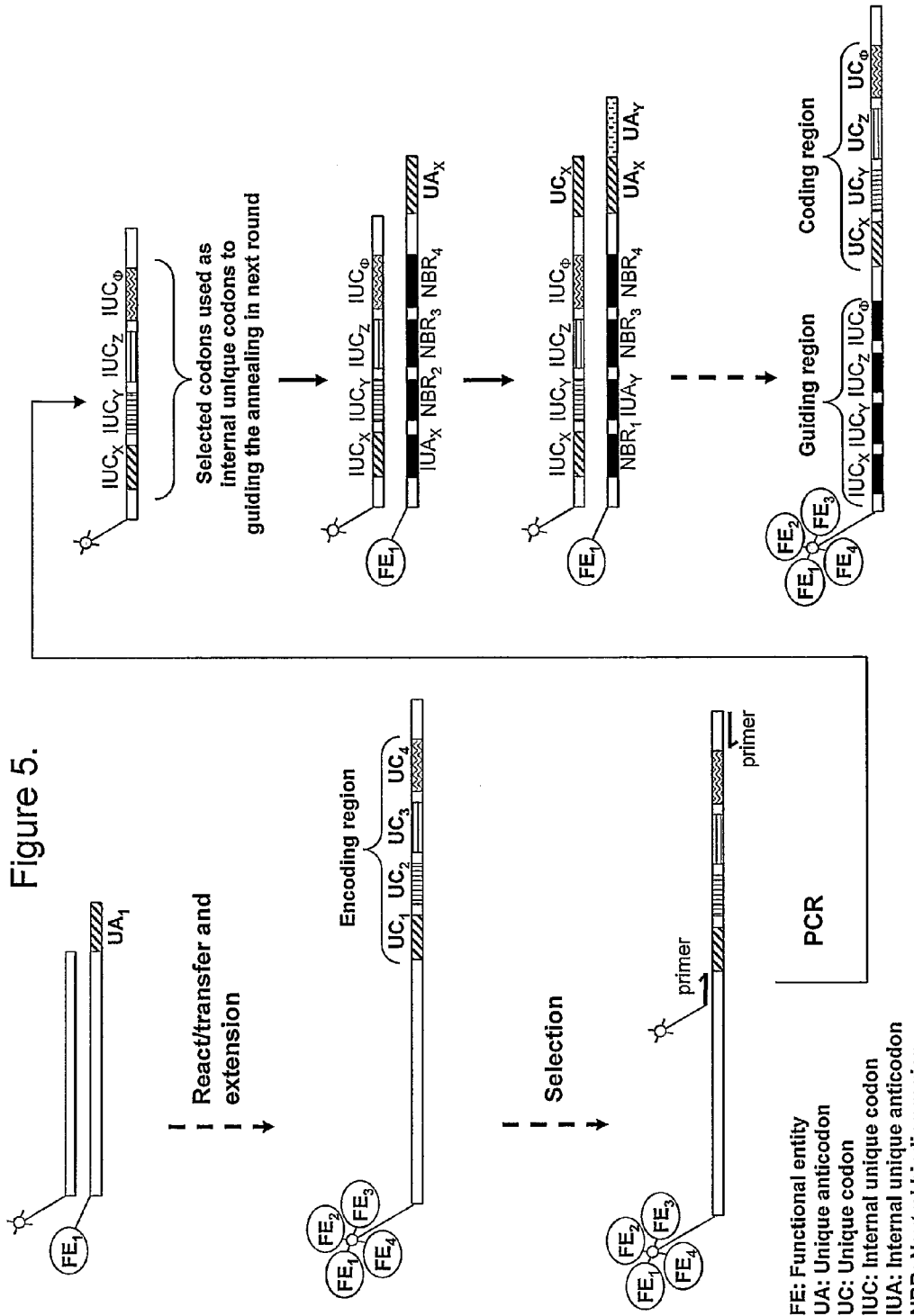
FIG. 5 shows the principle of encoding by extension with specific annealing

FIG. 5 shows an embodiment useful when an amplification step is involved between selections. Initially, a library of complexes is produced as depicted in FIG. 2. The library of the complexes may be subjected to a selection process. The selection process may involve presenting the display molecule on the complex to a target and subsequent selecting the display molecules which shows a desired interaction with the target. It may be advantageously to use relatively mild conditions during the selection process, to obtain a sub-library. The sub-library may be decoded to obtain information on the synthetic history for the entire sub-library. However, it is usually preferred to reduce the sub-library further before a decoding is performed.

The sub-library may be reduced by subjecting it to the target again and use more stringent conditions. However, to obtain a higher number of each of the members of the sub-library before a second selection, it is generally preferred to amplify the complex. Thus, a primer which is loaded with a scaffold is initially annealed to a primer site at one end of the encoding region. Subsequently a transcript is formed. A reverse primer is preferably present to obtain a duple stranded PCR product having a scaffold attached thereto.

This PCR is the basis for the generation of en amplification of the sub-library. The identifier sequence is segregated into a number of internal unique codons, abbreviated IUC in the drawing. The number of the IUCs corresponds to the number of functional entities participating in the formation of the display molecule. The sequence of the IUCs expresses the identity of the individual functional entities and the order of the IUCs indicates the order of reaction of the functional entities. Preferably, a primer region is presented adjacent to the sequence of IUCs to allow for a later amplification of the nucleic acid sequence.

The sub-library is contacted with a plurality of building blocks comprising a transferable functional entity and an internal unique anti-codon (IUA) complementary to at least one of the IUCs. The complementing identifier region is provided with sufficient complementarity to provide for a hybridisation with the oligonucleotide identifier region. In a preferred embodiment the IUCs not identifying a functional entity to be transferred is opposed in the complementary identifier region with a neutral binding region. As mentioned above the neutral binding region may comprise universal bases, i.e. bases that have the ability to be paired with two or more of the naturally occurring nucleobases. Adjacent to the region comprising specific base-pairing sequences and non-specific base-pairing sequences, i.e. the complementary identifier region is a unique anticodon (UA). The UA comprises the same information as the IUA of the complementing identifier region, typically the UA and the IUA has the same sequence on nucleotides.

The transfer step and the reaction step are conducted in several cycles as described above to form a bifunctional complex. In FIG. 5 four cycles are performed, however, it will be appreciated that less than cycles, such as 3 or 2 cycles can be performed to produce a reaction product comprising constituent from 3 or 2 functional entities respectively. Also more, than four cycles may be performed, such as 5 to 20 to form a more diverse library of display molecules. The complexes resulting form the cycles are a reaction product between the functional entities and the scaffold, and an oligonucleotide. The oligonucleotide can be divided into a guiding region, that is, the region that guided the annealing of the individual building blocks, and an encoding region, which comprises the unique codons which have been transferred from the building blocks to the identifier.

Using the above encoding method, allows for the amplification of more and more focused sub-libraries to obtain a sufficient amount of material to allow decoding.

Figure 6:
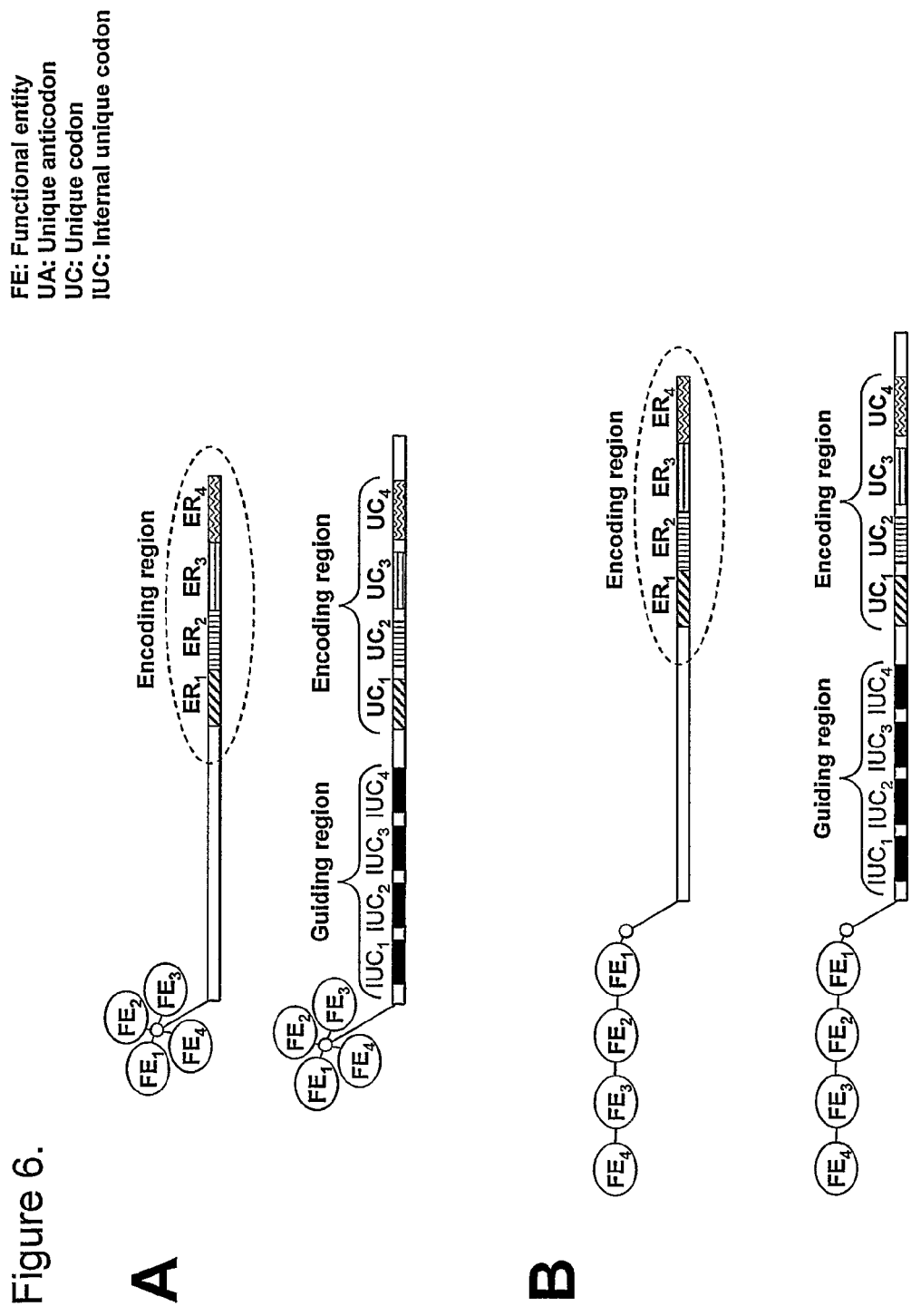
FIG. 6 shows the encoding of scaffolded and polymer molecules

The encoding method shown in FIG. 6 can create both monomer and polymer encoded molecules. Panel A: Complex reaction products can be created using an attachment entity which has reacted with multiple functional entities. Panel B: Polymers can be created using one attachment entity with one reactive group allowing attachment with a functional entity having at least two reactive groups.

Figure 7:
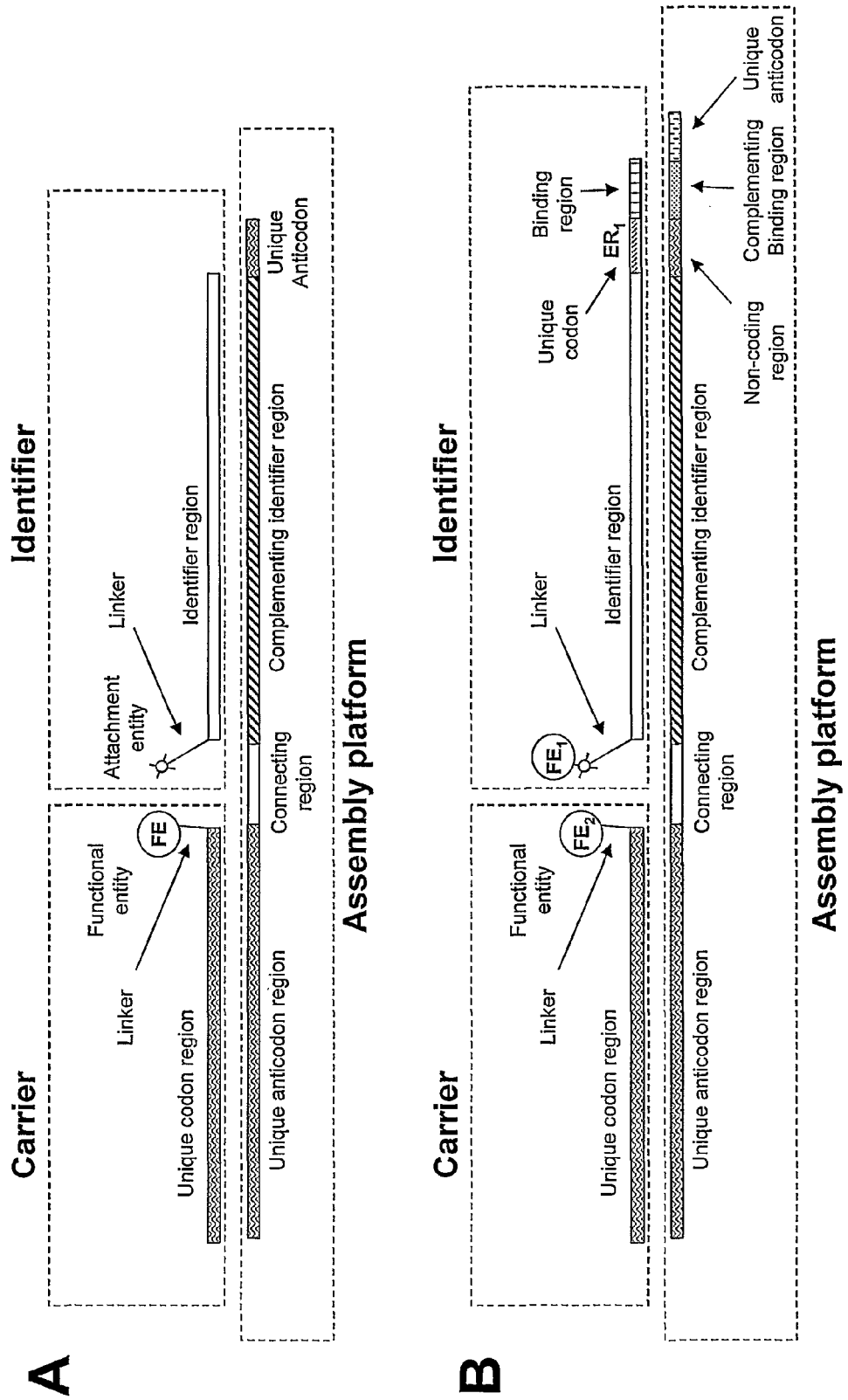
FIG. 7 shows the encoding by extension using three-strand assembly principle

FIG. 7 illustrates a three strand assembly procedure for the encoding by extension principle. A: The identifier and building block can be assembled on an assembly platform. This assembly platform contains a unique anticodon region and a unique anticodon where these two elements are directly linked through their sequences. There may be a connecting region linking the unique anticodon region together with the complementing identifier region. B: Describes all the components of the identifier, building block and the assembly platform used in the consecutive reaction, where the identifier also contain a unique codon and a binding region and the assembly platform also contains a non-coding region and a complementing binding region.

Figure 8:
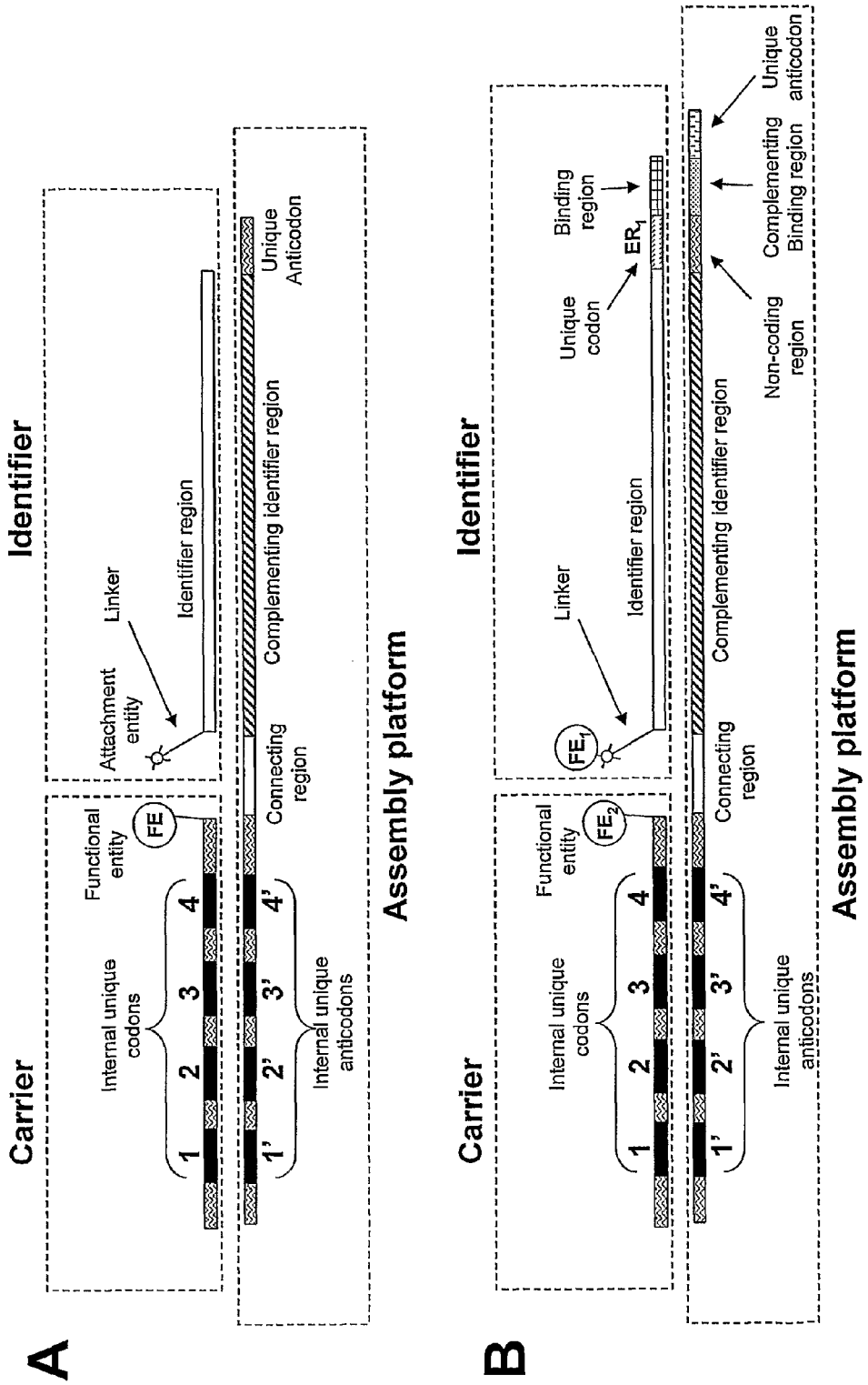
FIG. 8 shows encoding by extension using three-strand assembly principle with specific annealing

In FIG. 8 it is shown that internal codons can also be used for the three-strand assembly principle. This will be useful when selection will be performed in multiple rounds with intermediate amplification steps.

In FIG. 8A the identifier comprises an attachment entity whereas in FIG. 8B it comprises $FE_1$. Also, in FIG. 8B the identifier comprises a unique codon $ER_1$, and a binding region, whereas in FIG. 8A it does not. Also, in FIG. 8B the assembly platform comprises a non-coding region and a complementing binding region between the complementing identifier region and the unique anticodon, whereas in FIG. 8A it does not.

Figure 9:
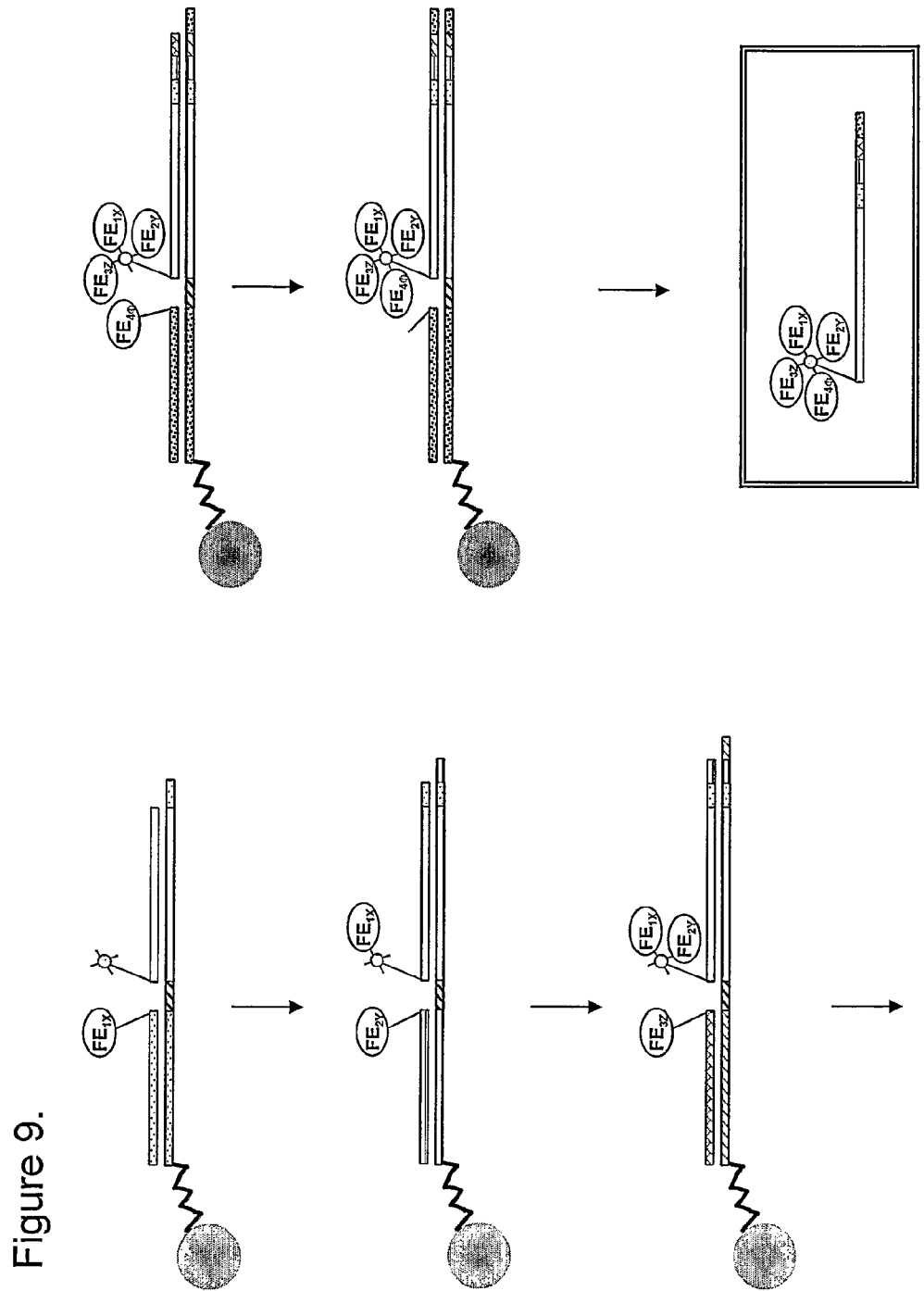
FIG. 9 shows the synthesis of three-strand identifier-displayed molecules using a solid-phase approach.

FIG. 9 shows a solid-phase three-strand displayed-molecule synthesis. The assembly platform molecule is attached to a solid support to allow sequential attachment of building blocks to the attachment entity. Different libraries of assembly platform molecules, which is extended with suitable non-coding regions and complementing binding regions, can be used in each step in separate vials. This will allow the use of identical building block and identifier molecules in each step.

Figure 10:
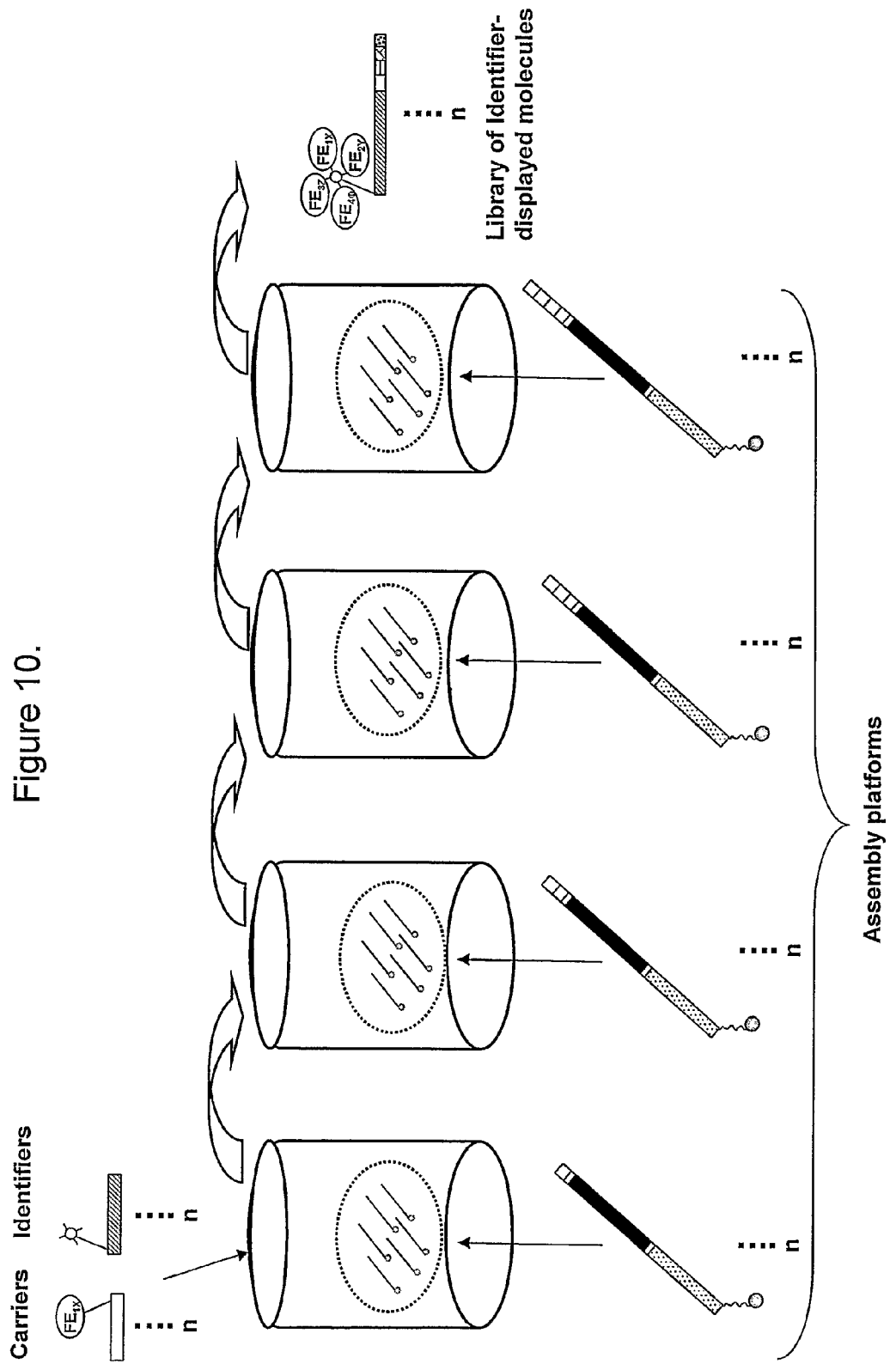
FIG. 10 shows the sequential reaction/extension using platform assembly.

FIG. 10 shows the sequential transfer/extension using the assembly platform principle. Each well contains a library of platform molecules. The platform molecule is extended with one unique anticodon in the subsequent wells. A library of identifier and building block molecule is added to the first well which allows specific annealing and transfer of functional entities. The reaction mixture is the transferred to the next wells which finally generates the identifier-displayed library.

Figure 11:
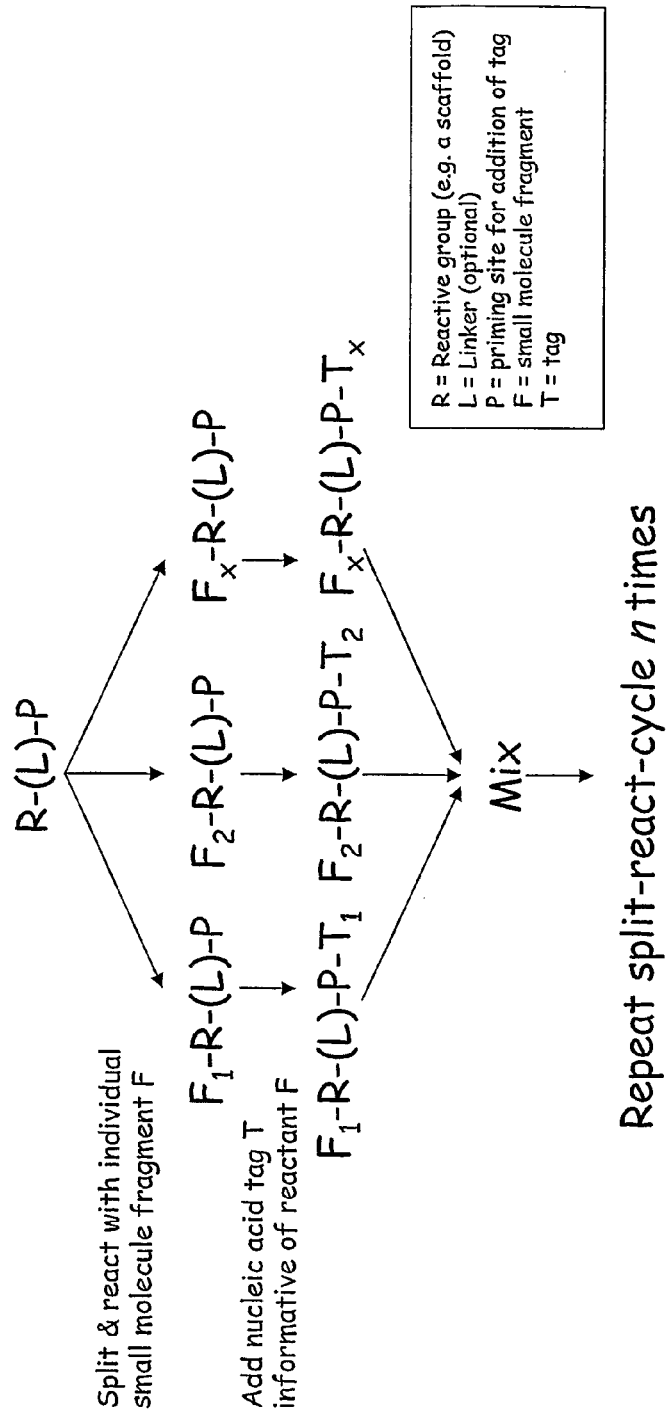
FIG. 11 discloses a general scheme for alternating parallel synthesis of a combinatorial library.

FIG. 11 discloses a general scheme for alternating parallel synthesis of combinatorial libraries. In a first step a nascent bifunctional molecule is provided. The nascent bifunctional molecule comprises as one part of the molecule a reactive group, which may appear on a chemical scaffold, and some times referred to herein as a chemical reactive site. Another part of the bifunctional molecule comprises a priming site for addition of a tag. The priming site may be a 3'-OH group or a 5'-phosphate group of a nucleotide in case the tag is a nucleotide. The chemical reactive site and the priming site may optionally be spaced by a linking group. In the event that the linking group is resent it may be a nucleotide or a sequence of nucleotides. The spacing entity may further comprise a hydrophilic linker, such as a polyethylene or polypropylene, to distance the chemical reactive site from the nucleotide. Also comprised in the linking moiety may be a selective cleavable linker that allows the experimenter to separate the display molecule from the coding part.

The nascent bifunctional molecule is divided into a plurality of compartments, usually wells of a microtiter plate or similar equipment that allow easy handling of multiple spatially separated containers. Each of the compartments is reacted with a specific small molecule fragment, also referred to herein as a reactant. Thus, in a first compartment, the nascent bifunctional molecule is reacted with a first small molecule fragment ($F_1$), in a second compartment; the nascent bifunctional molecule is reacted with a second small molecule fragment ($F_2$), etc. The number of compartments may in principle be indefinite, however, for practical reasons; the number is usually between 5 and 5000, such as 10 and 500. In each of the compartments the small molecule fragments may be identical or different as the case may be. In each compartment, one, two, or more reactants may participate in the reaction. After the reaction between the drug fragment and the nascent bifunctional molecule has occurred in each compartment, a tag is added, said tag identifying the small molecule fragment. In certain aspects of the invention, the tag is a nucleic acid. Thus, in the first compartment, a first nucleic acid tag ($T_1$) is added to the priming site of the reaction product, in the second compartment, a second nucleic acid tag ($T_2$) is added to the priming site of the second reaction product, etc. Various methods for enzymatic encoding are contemplated and discussed herein. Following the enzymatic addition of the tags in each of the compartments, the contents of the compartments are collected.

In a second round the mixture of bifunctional molecules is split into compartments again. The number of compartments of the second round need not be the same as the number of compartments in the first round. In each compartment the products of the previous round serves as the nascent bifunctional molecule. Thus, a reactive group appearing on the reaction product between the scaffold and the small molecule fragment of the first round is reacted with one or more small molecule fragments of the second round. Thus, in a first compartment, the mixed reaction products of the first round are reacted with a first small molecule fragment ($F_1$), in a second compartment, the mixed reaction products of the first round are reacted with a second small molecule fragment ($F_2$), etc. The small molecule fragments $F_1, F_2, \ldots F_X$ of the second round may be identical or different from the small molecule fragments used in the first round.

After the reactions have been allowed to occur, a tag specifying the small molecule fragment is added. The tag added in the first round usually comprises a priming site that can be used for addition of the tag in the second round so as to produce a linear identifier comprising the tags. In the first compartment, the reacted product is added a first tag which identifies the reactant of the second round that has reacted with the reactive reaction site of the nascent bifunctional molecule; in a second compartment, the product reacted with the second small molecule fragment of the second round is added the tag identifying said reactant, etc. Following the addition of the tags in each compartment, the content of the compartments are mixed in a common pool. The split-reaction-combining cycle can be repeated an appropriate number of times to obtain a library of bifunctional molecules comprising a display molecule part and a coding part. The library may be used in a selection process disclosed elsewhere herein.

Above, the general principle for split-and-mix is disclosed, in which the reaction of the small molecule fragment and the chemical reaction site occurs prior to the encoding step. Obviously, the events can occur in the reverse order or simultaneously.

Figure 12:
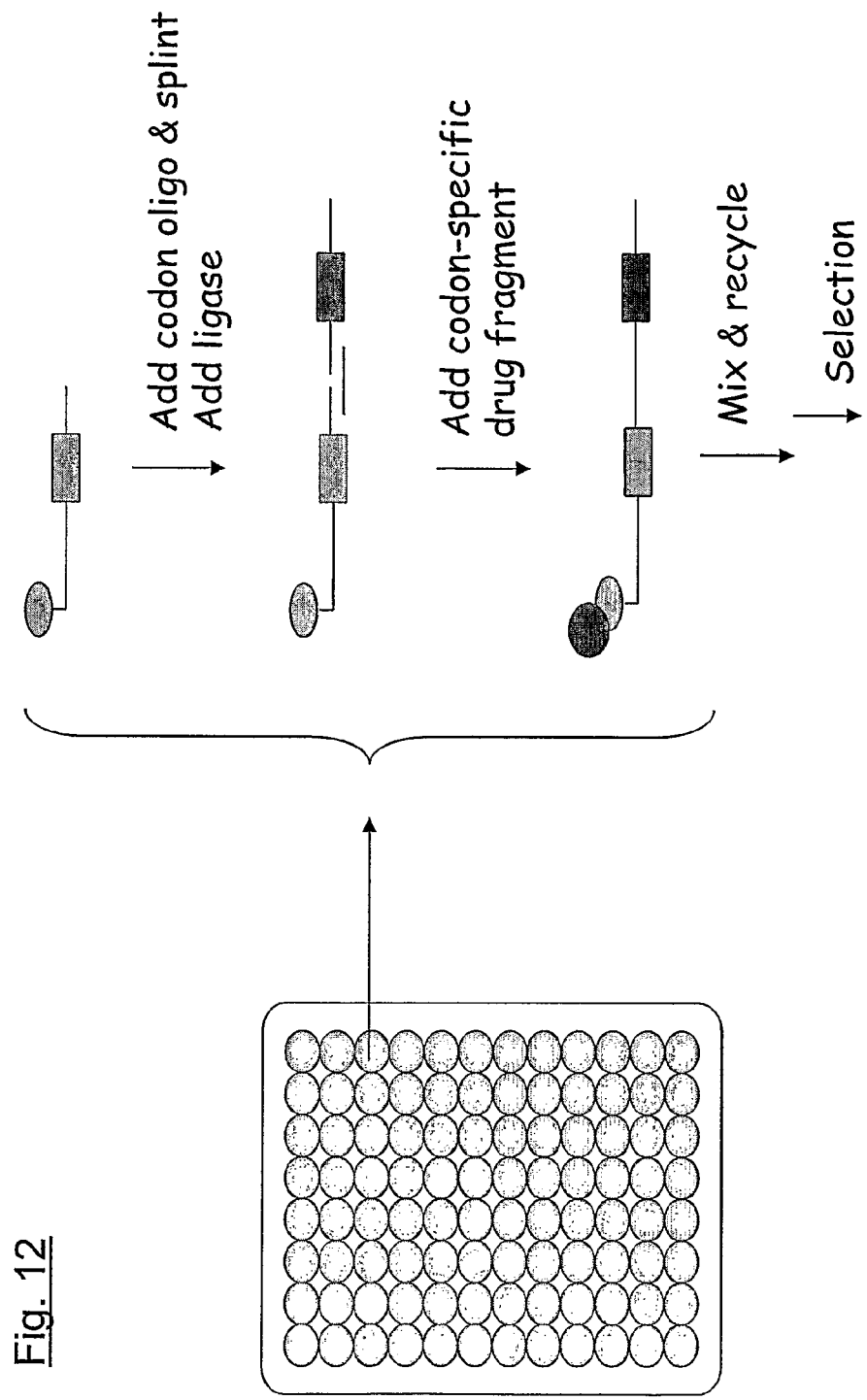
FIG. 12 discloses an encoding method using ligational encoding and a free reactant.

FIG. 12 schematically shows a 96 well microtiter plate to the left. In each well or in a selected number of wells, the process to the right occurs. Initially, a bifunctional molecule is provided. The bifunctional molecule comprise a chemical reaction site (oval) attached to a codon (rectangle) through a linker (line). To the left of the codon a binding region is provided. Next, a codon oligonucleotide and a splint oligonucleotide are added. The codon oligonucleotide is provided with a codon and flanking binding regions. The splint is designed with sequences complementing the binding region of the nascent bifunctional molecule and a binding region of the codon oligonucleotide such that the ends abut each other under hybridisation conditions. The nascent bifunctional complex, the splint and the codon oligonucleotide forms a hybridisation product under appropriate conditions. A ligase is added to couple the codon oligo to the nascent bifunctional complex. In a second step, a drug fragment, i.e. a reactant, is added and conditions providing for a reaction with the chemical reaction site is instituted.

Then the content of each well is combined and, optionally, divided into a range of wells again for a second round of reaction and encoding. In final step, the combined contents of the wells are used in a selection or partition step, as disclosed herein.

Figure 13:
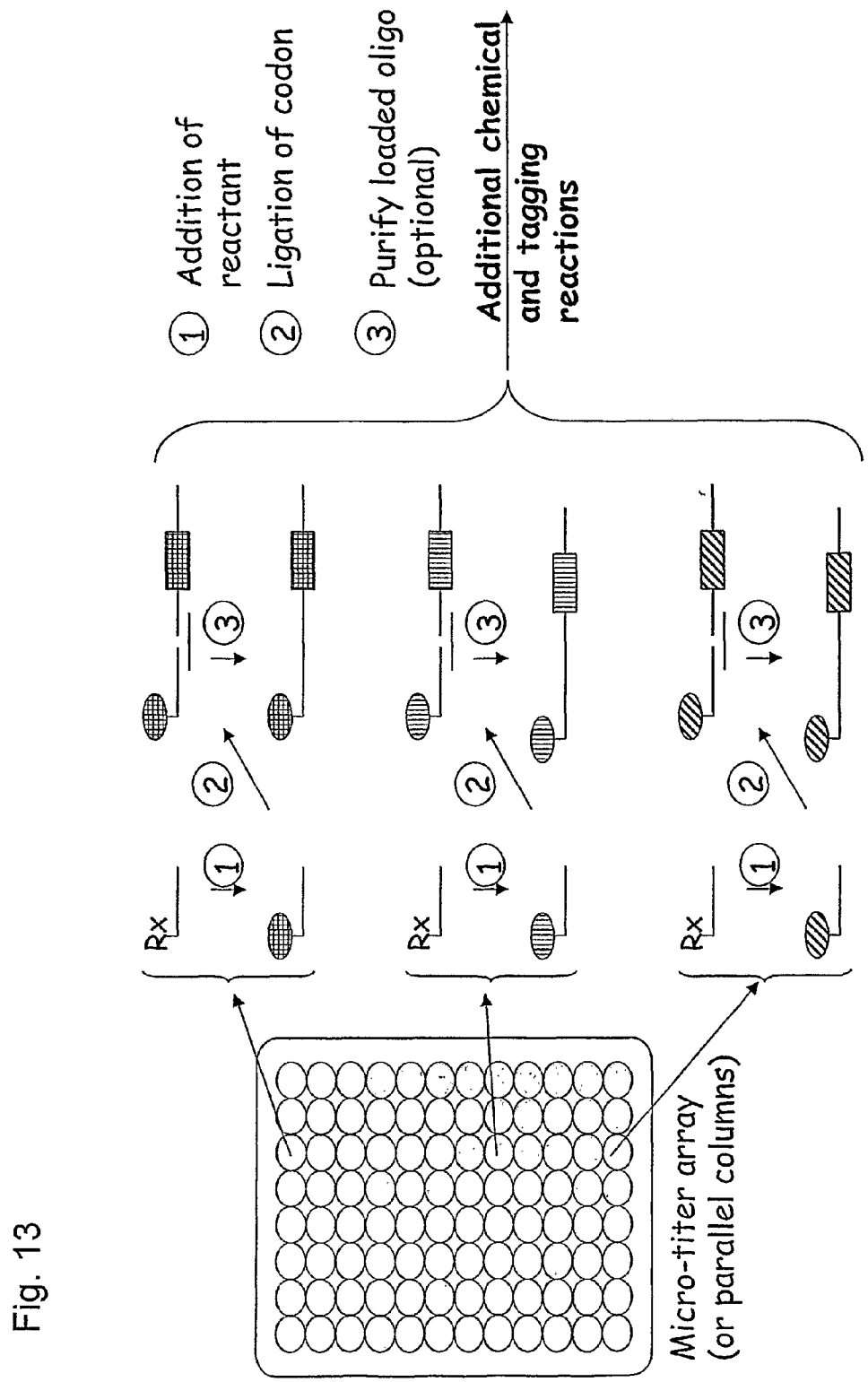
FIG. 13 discloses a library generating method in which a reaction is followed be an encoding step.

FIG. 13 outlines an embodiment with the encoding and reaction step reversed compared to the embodiment shown in FIG. 12. In a variety of wells a nascent bifunctional complex having a reactive group (Rx) attached to an oligonucleotide (horizontal line) is dispensed. In a first step, the reactive group in each compartment is reacted with a reactant, in a second step a codon oligonucleotide and a splint is added together with a ligase to ligate covalently the codon oligonucleotide to the reacted nascent bifunctional complex, and in a third step the ligation product is recovered. The content of the wells may subsequently be combined and used as a library of bifunctional complexes or recycled for another round of reaction and addition of tag.

Figure 14:
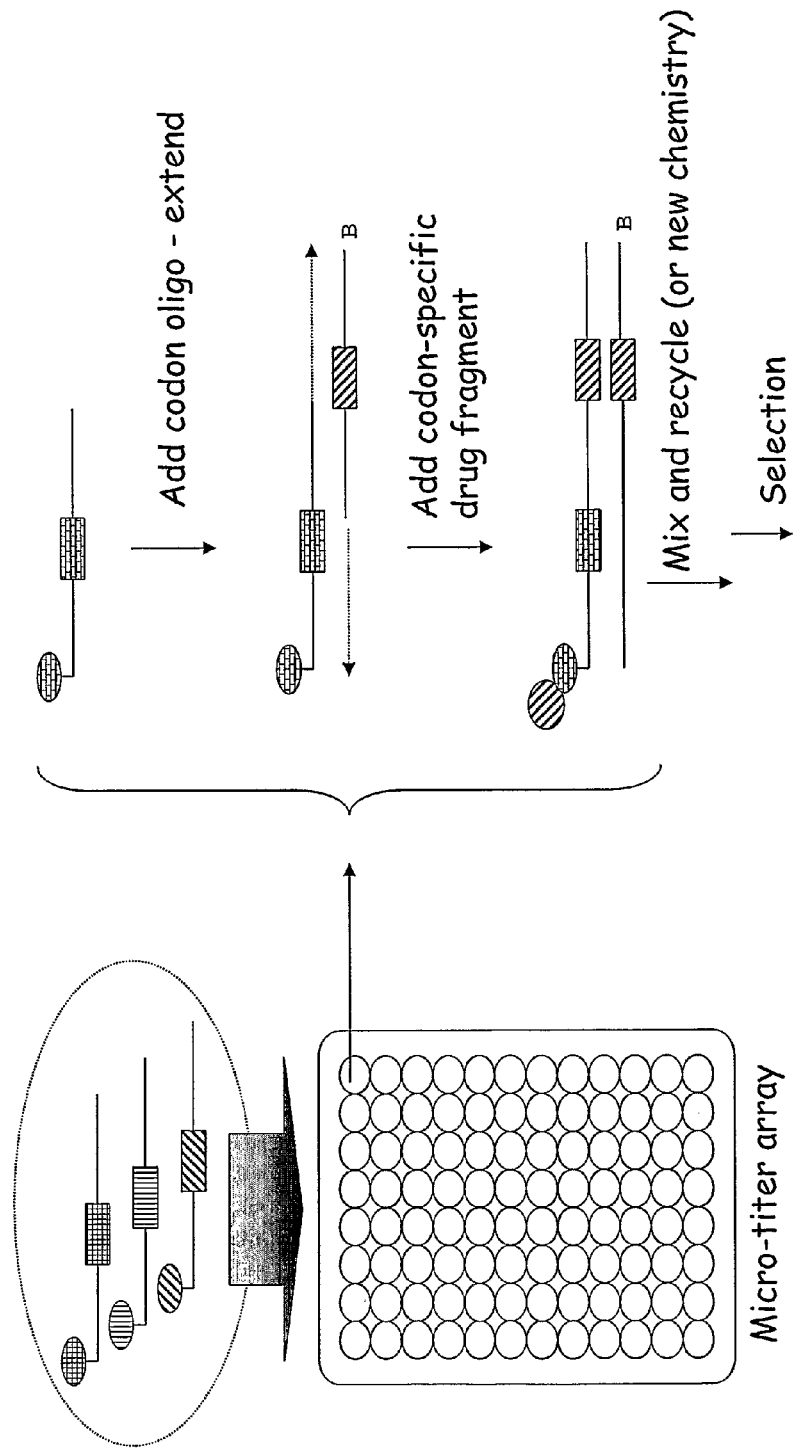
FIG. 14 discloses a library generation method using polymerase encoding.

FIG. 14 discloses the use of the library produced in accordance FIG. 13, or any other library having a coding part and display molecule part, in a further round. Initially, the combined contents of the wells from the embodiment of FIG. 13 are dispensed in separate wells. Then an anti-codon oligonucleotide having a binding region which is complementary to the binding region of the nascent bifunctional molecule is added under hybridisation conditions, i.e. conditions which favour the assembly of the hybridisation product between the nascent bifunctional complex and the anti-codon oligonucleotide. Subsequently, or simultaneously with the addition of the anti-codon oligonucleotide, a polymerase, a collection of dNTP (usually, dATP, dGTP, dCTP, and dTTP), and appropriate salts and buffer are added to provide for an extension to occur. The extension (dotted arrow) transcribe the anti-codon to the identifier, thus attaching a tag that encodes the identity of the reactant subsequently reacted at the chemical reaction site. The anti-codon oligonucleotide is connected to a biotin (B) to allow for removal of the oligonucleotide.

Figure 15:
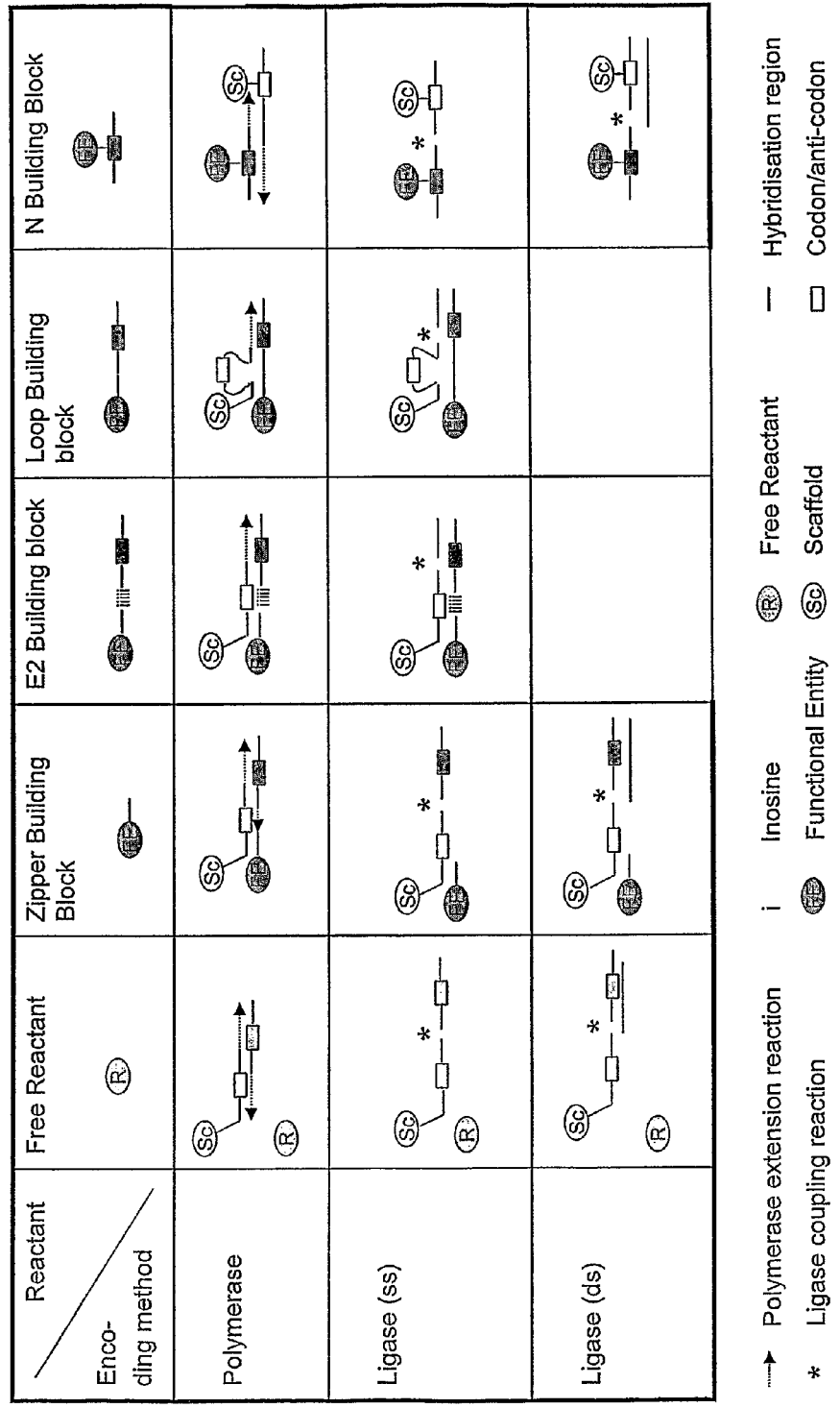
FIG. 15 discloses various embodiments for single encoding methods.

FIG. 15 discloses a scheme of various encoding methods combined with a collection of reactants. All the combinations are in according the invention.

Free Reactant/Polymerase Encoding:

A nascent bifunctional complex comprises a scaffold (=chemical reaction site) comprising a reactive group and an oligonucleotide part comprising a codon identifying the scaffold. The codon is associated with an oligonucleotide binding region capable of forming a hybridisation product with a complementing binding region of an anti-codon oligonucleotide. The hybridisation product is subjected to an extension reaction, in which the scaffold oligonucleotide is extended over the anti-codon, thereby providing the scaffold oligonucleotide with a codon. Subsequent, simultaneously with or prior to the extension reaction, a free reactant coded for by the anti-codon is reacted with the scaffold.

Zipper Building Block/Polymerase:

A nascent bifunctional complex comprises a scaffold (=chemical reaction site) comprising a reactive group and an oligonucleotide part comprising a codon identifying the scaffold. The codon is associated with two oligonucleotide binding region capable of forming a hybridisation product with a complementing binding region of an anti-codon oligonucleotide and a complementing binding region of the reactant. The hybridisation product is subjected to an extension reaction, in which the scaffold oligonucleotide is extended over the anti-codon, thereby providing the scaffold oligonucleotide with a codon. Subsequent, simultaneously with or prior to the extension reaction, a functional entity coded for by the anti-codon is reacted with the scaffold. The selection of polymerase may determine the order of reaction and encoding as some polymerase, such as Sequenase, displaces the binding region attached to the functional entity, while other polymerases, like Taq polymerase, do not perform the displacement of the binding region. When a zipper building block is used a close proximity between the scaffold and the functional entity is obtained thereby promoting a reaction to take place.

E2 Building Block/Polymerase Encoding:

A nascent bifunctional complex comprises a chemical scaffold and an oligonucleotide part comprising the codon identifying the scaffold. The oligonucleotide part comprises two binding region on each sides of the codon. An E2 building block anneals to the scaffold oligonucleotide such that the functional entity comes in close proximity as to the scaffold and a double helix is formed just before the anti-codon, thus enable a polymerase to recognize the double helix as a binding area. Applying appropriate conditions and substrates enable the extension of the identifier oligonucleotide over the anti-codon, thus transcribing the genetic information of the function entity to the identifier. Opposing the scaffold codon is a stretch of universal binding nucleotides, such as inosine. Use of an E2 building block allows for one-pot synthesis of a library.

Loop Building Block/Polymerase Encoding:

A nascent bifunctional complex comprises a chemical scaffold and an oligonucleotide part comprising the codon identifying the scaffold. The oligonucleotide part comprises two binding region on each sides of the codon. A loop building block anneals to the scaffold oligonucleotide such that the functional entity comes in close proximity as to the scaffold and a double helix is formed just before the anti-codon, thus enable a polymerase to recognize the double helix as a binding area. Applying appropriate conditions and substrates enable the extension of the identifier oligonucleotide over the anti-codon, thus transcribing the genetic information of the function entity to the identifier. As no sequence on the building block complements the scaffold codon sequence, this codon sequence loops out. Use of a loop building block allows for one-pot synthesis of a library.

N Building Block/Polymerase Encoding:

A nascent bifunctional complex comprises a chemical scaffold attached to a scaffold codon through a linker. On one or each side of the codon a binding region is present. An N building block comprises a binding region which is complementary to the scaffold binding region and an anti-codon. A functional entity is attached to the codon or a binding region. Under hybridisation conditions the complementary binding regions hybridise and a polymerase extends in both directions, thereby transferring the genetic information of the anti-codon to the oligonucleotide covalently connected to the scaffold. Before, after or simultaneously with the extension reaction, the reaction between the functional entity and the scaffold may take place. Usually, the functional entity is attached to the anti-codon oligonucleotide via a cleavable linker so as to allow for transfer of the functional entity to the scaffold structure.

Free Reactant/Ligase:

A scaffold entity is attached to an oligonucleotide comprising a codon. The scaffold oligonucleotide further comprises a priming site to which a codon oligonucleotide is ligated. The ligation is performed by a ligase. The ligation can take place in a single stranded or double stranded form. In the single stranded form, a 3' OH (or 5'-phosphate) of the scaffold oligonucleotide is ligated to a 5'-phosphate (or 3'-OH) of the codon oligonucleotide. In the double stranded form, an oligonucleotide complementing the ends of the scaffold and codon oligonucleotides, respectively, is used and designed so that the ends abuts each other. Optionally, the ligation occurs between two double stranded oligonucleotides, i.e. a double stranded scaffold oligonucleotide with an over hang ("sticky end") is ligated to a double stranded codon oligonucleotide provided with a complementing overhang. The type of ligation depends on the selected enzyme. Usually, the double stranded ligation is preferred because the reaction is faster due to the guiding effect of the oligonucleotide complementing the ends. The complementing oligonucleotide is also referred to herein as the splint oligonucleotide. Following, preceding, or simultaneously with the ligation of the codon oligonucleotide to the scaffold oligonucleotide a reaction between the free reactant and the scaffold takes place.

Zipper Building Block/Ligase:

A scaffold entity is attached to an oligonucleotide comprising a codon and binding region between the scaffold and the codon. The scaffold oligonucleotide further comprises a priming site to which a codon oligonucleotide is ligated. The ligation is performed by a ligase. The ligation can take place in a single stranded or double stranded form. In the single stranded form, a 3' OH (or 5'-phosphate) of the scaffold oligonucleotide is ligated to a 5'-phosphate (or 3'-OH) of the codon oligonucleotide. In the double stranded form, an oligonucleotide complementing the ends of the scaffold and codon oligonucleotides, respectively, is used and designed so that the ends abuts each other. Optionally, the ligation occurs between two double stranded oligonucleotides, i.e. a double stranded scaffold oligonucleotide with an over hang ("sticky end") is ligated to a double stranded codon oligonucleotide provided with a complementing overhang. The type of ligation depends on the selected enzyme. Usually, the double stranded ligation is preferred because the reaction is faster due to the guiding effect of the oligonucleotide complementing the ends. The complementing oligonucleotide is also referred to herein as the splint oligonucleotide. A zipper building block is a functional entity attached to a binding oligonucleotide. The binding oligonucleotide is complementing the binding region of the scaffold oligonucleotide, thus forming a hybridisation product under hybridisation conditions. Following, preceding, or simultaneously with the ligation of the codon oligonucleotide to the scaffold oligonucleotide a reaction between the functional entity and the scaffold takes place. The use of the binding region on the reactant ensures a close proximity between the functional entity and the scaffold.

E2 Building Block/Ligational Encoding:

Initially is provided a nascent bifunctional complex comprising a scaffold attached to an oligonucleotide, said oligonucleotide comprising a codon and a binding region between the scaffold codon and the scaffold codon. The scaffold oligonucleotide also comprises a priming site to which a codon oligonucleotide can be ligated. The scaffold oligonucleotide is hybridised to an E2 building block which carries a double stranded part. The oligonucleotide complementing the anticodon as ligated to the scaffold oligonucleotide using the E2 building block as a template. Before, after or simultaneously with the ligation a reaction takes place between the functional entity and the scaffold.

Loop Building Block/Ligational Encoding:

A bifunctional complex is provided comprising a scaffold attached to an oligonucleotide, wherein the scaffold oligonucleotide comprises a codon flanked by two binding regions. A loop building block is provided which has binding regions complementing the binding regions of the scaffold oligonucleotide. Upon hybridisation, the codon part of the scaffold oligonucleotide loops out. The loop building block also comprises a double stranded codon part. The oligonucleotide complementing the anti-codon part of the loop building block is ligated to the free binding region of the scaffold oligonucleotide. Before, after or simultaneously with the ligation a reaction takes place between the functional entity and the scaffold.

N Building Block/Ligational Encoding:

A nascent bifunctional complex is initially provided in which a scaffold via a suitable linker is attached the codon identifying said scaffold or attached to a binding region connect to the codon. A building block having a functional entity connected to a codon is the ligated to the scaffold oligonucleotide to connect the scaffold oligonucleotide with functional entity oligonucleotide. The ligation may be performed in a single stranded or in a double stranded state, depending on the particular enzyme selected for the ligation. Subsequently, the functional entity is reacted with the scaffold. In the alternative, the functional entity and the scaffold are reacted prior to ligation of the respective oligonucleotides.

When a round, i.e. a reaction with and a tagging of the nascent bifunctional complex, has been completed in accordance with any of the above encoding methods, a new round maybe in initialized according to any of the above reaction/encoding methods. Thus, the encoding and reaction in a first round may be the same or different in a subsequent second or further round. A single bifunctional complex or a library of complexes may be generated. When a library is contemplated, one-pot-synthesis can be conducted with the building blocks in which a covalent link between the functional entity and the codon/anti-codon is used, i.e. the columns of E2 building block, loop building block, and N building block. Split and mix synthesis can be performed, when no covalent link between the functional entity/reactant and the codon/anti-codon is present, i.e. in the columns indicating the free reactant and the zipper building block.

Figure 16:
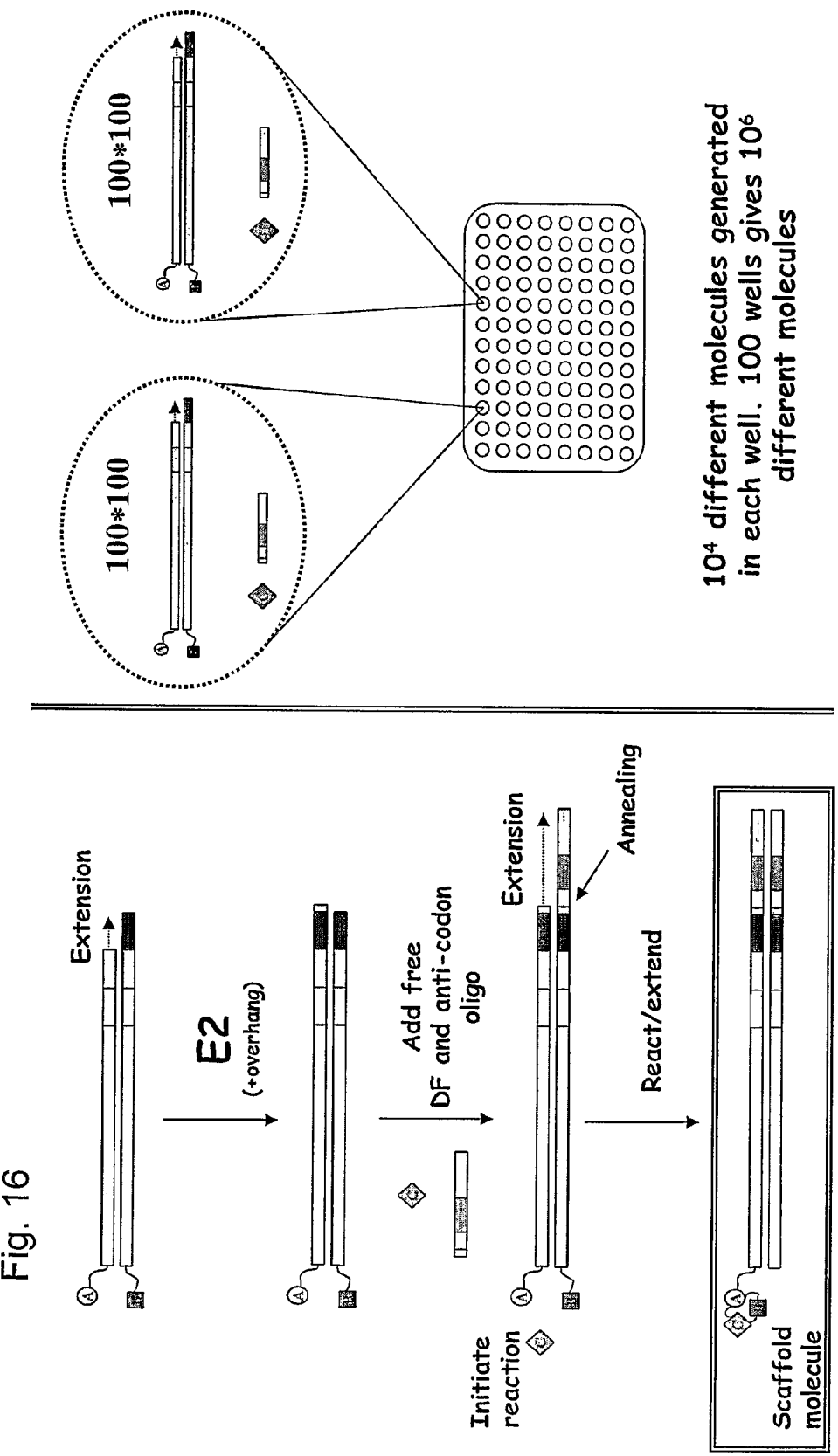
FIG. 16 discloses a double encoding method.

FIG. 16 shows a double encoding method, i.e. a method for encoding two or more reactants in one go. In certain embodiments, the multiple encoding methods allow for multi reaction between reactants and scaffold. Initially, a scaffold connected to an oligonucleotide comprising a hybridisation region, a scaffold codon and a binding region is annealed to an E2 building block. Subsequently, an extension is performed in which the anti-codon of the building block is transferred to the identifier. Several polymerases form an overhang of one or more single stranded nucleotides. This overhang is used in the present invention to attach an anti-codon oligo and allow the polymerase to further extent the identifier oligonucleotide over the anti-codon region of the anti-codon oligonucleotide. The transfer of the information of the anti-codon oligonucleotide allows for encoding a third free reactant C. The annealing between the oligonucleotide carrying A and the oligonucleotide carrying B provide for a close proximity between A and B and thus a high local concentration. Thus, when the free reactant C is added a reaction between the three components is favoured. One advantage of double encoding is that it is possible to exchange solvent, such that the reaction not necessarily must take place in the same solvent as the extension occurs.

To the right is illustrated an example, in which the above method is applied on 100 different scaffold oligonucleotides and 100 building blocks. The hybridisation product between the scaffold oligonucleotides and the building block oligonucleotides is divided into 100 different wells. In each of the wells the extension, addition of anti-codon oligonucleotide and reaction with specific free reactant is allowed. In total $10^6$ different bifunctional molecules are generated.

Figure 17:
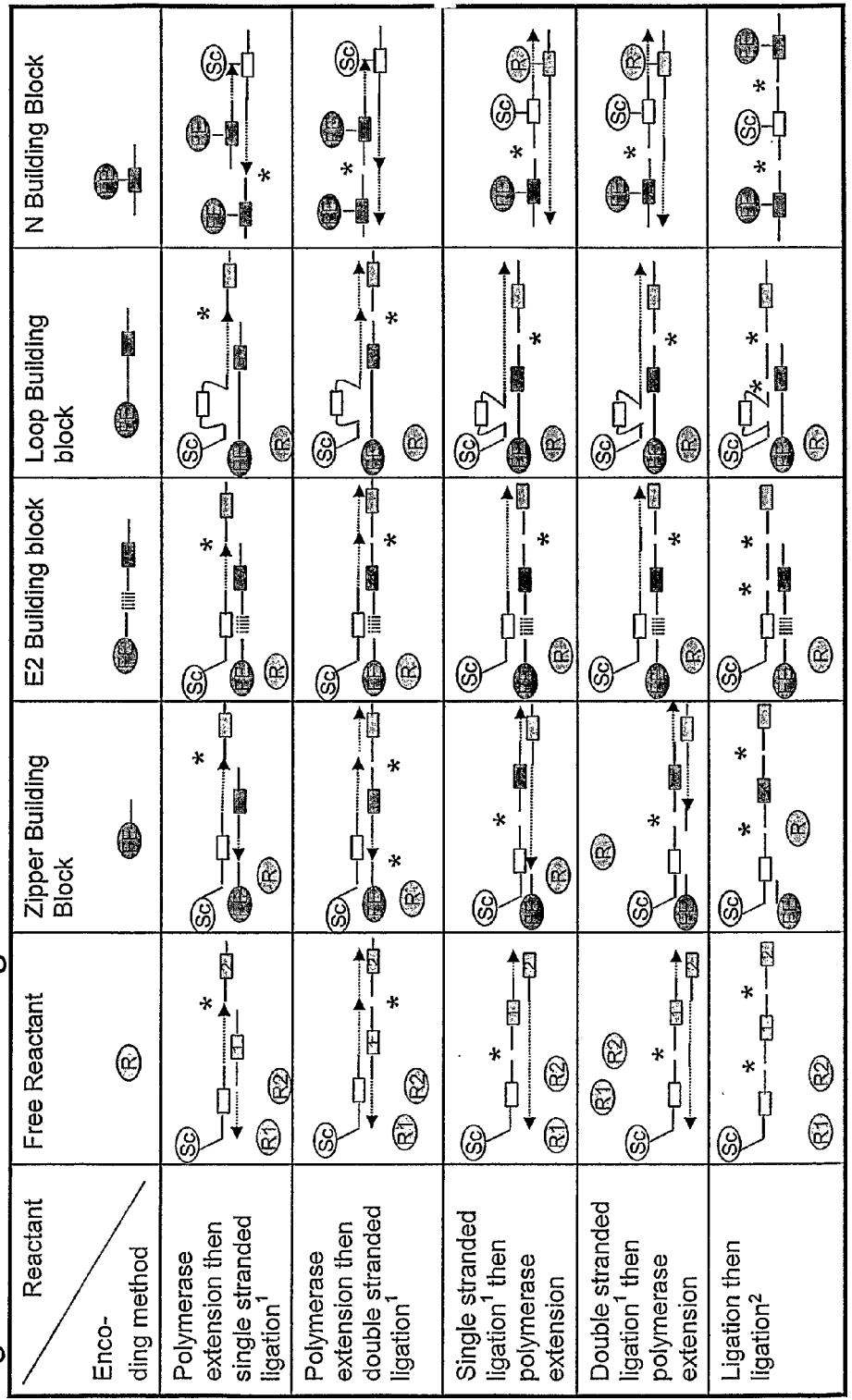
FIG. 17 discloses various double encoding methods.
Figure 18:
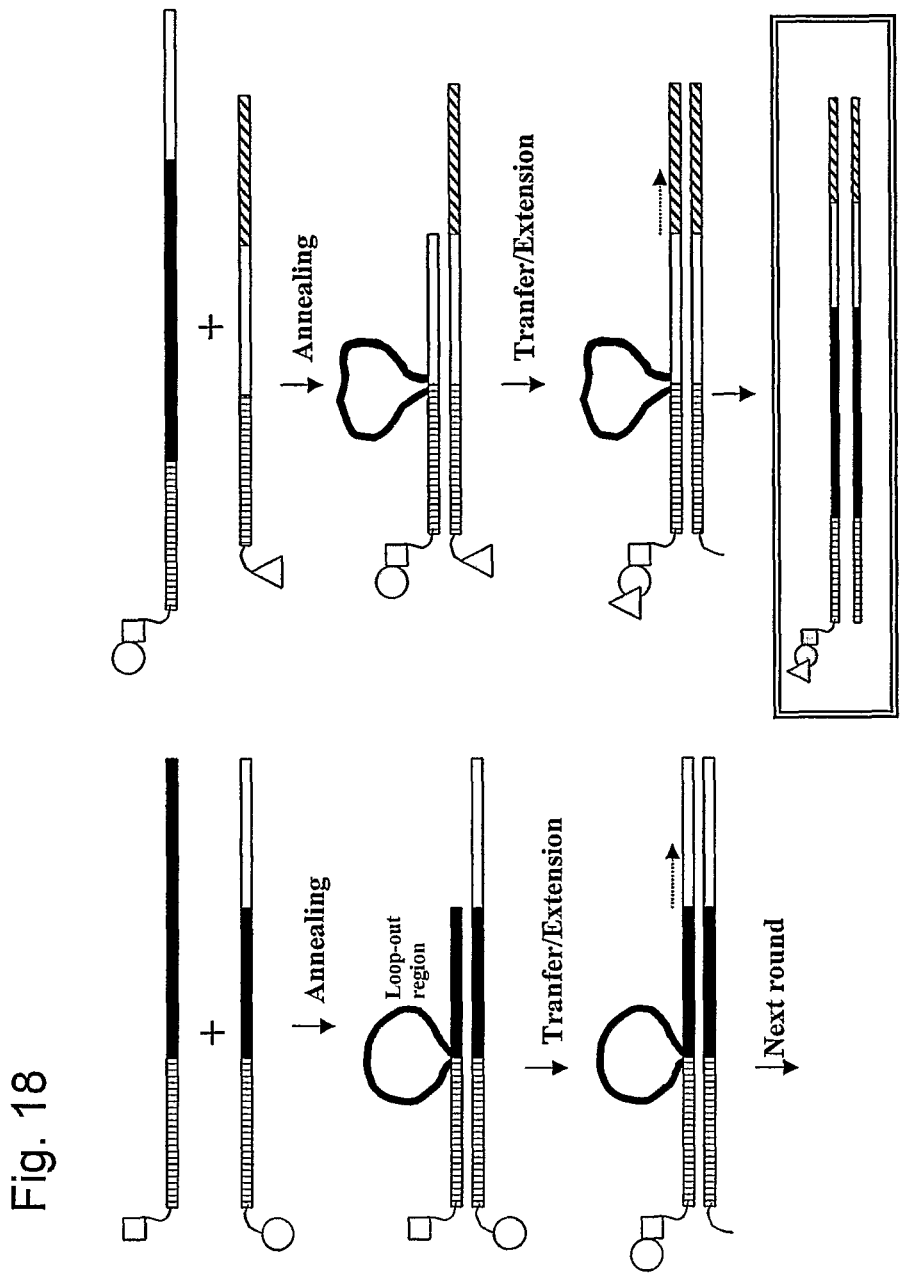
FIG. 18 discloses encoding using an loop building block.
Figure 19:
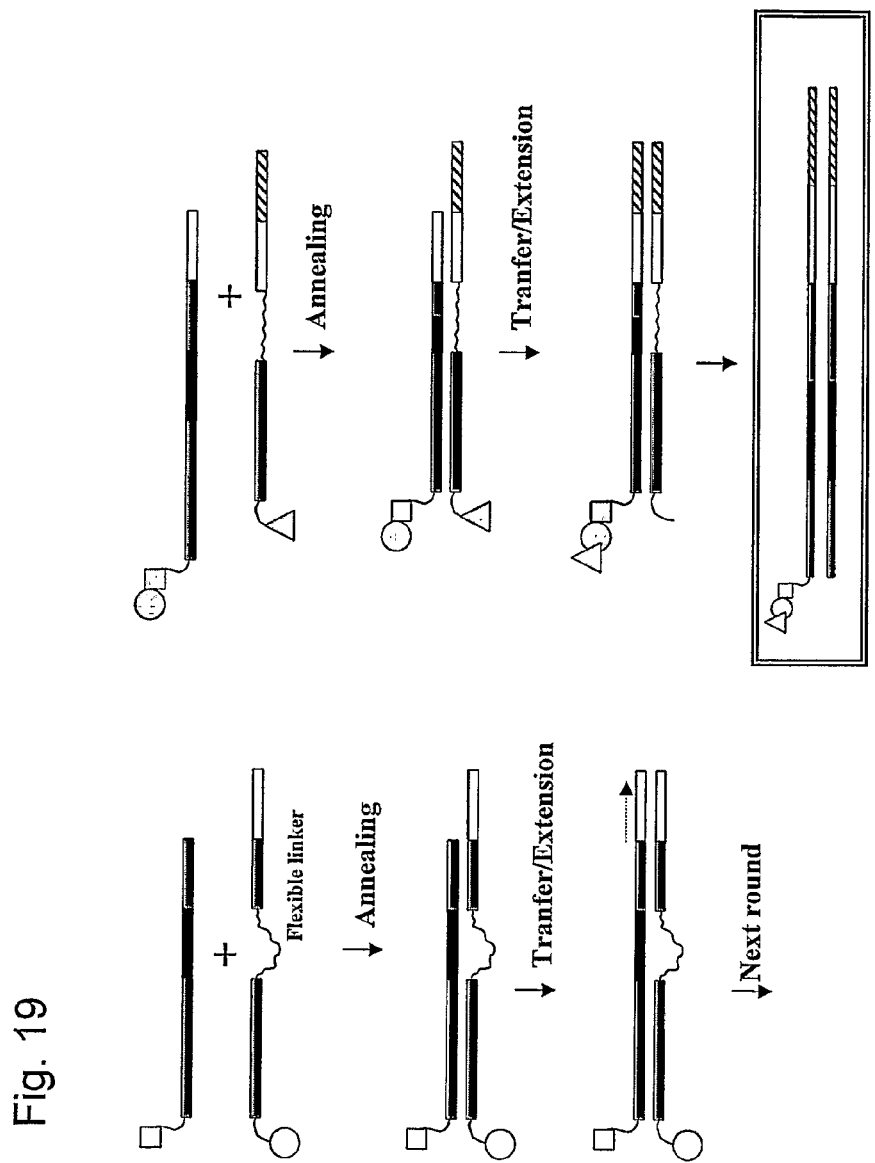
FIG. 19 discloses a method in which a flexible linker is used in the building block.
Figure 20:
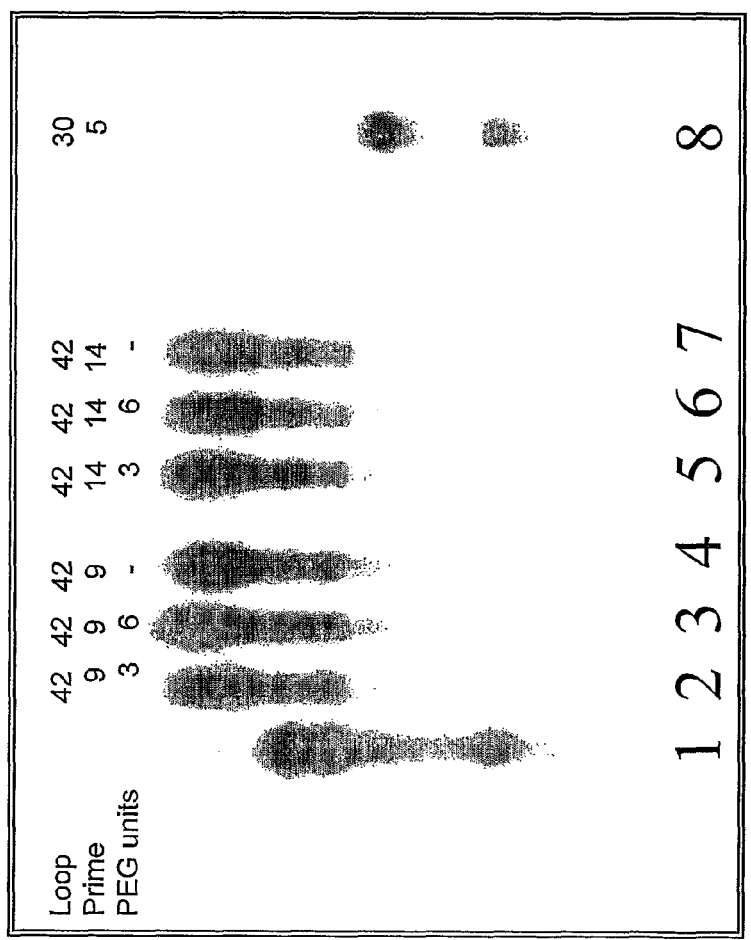
FIG. 20 discloses a gel showing the result of an experiment according to example 6.

FIG. 17 discloses various methods for performing double encoding. In all the examples, the encoding is shown to occur prior to reaction, but it will be within the ambit of the skilled person to perform the reaction first and then the encoding. When a library is contemplated, it is possible to conduct the reaction in a single container (one-pot synthesis) using the N building blocks in combination with any of the encoding methods. For the remaining reactants it is necessary to conduct one or more split-and-mix step. In the combination of the zipper building block, E2 building block, and the loop building block with any of the encoding methods a single split-and-mix step is necessary, whereas two split-and-mix steps are necessary for the free reactant in combination with any encoding method. The scheme makes it possible for the skilled person to select a reaction/encoding method which is useful for a specific reaction. If triple-, quadro-, or multi encoding is contemplated, it is possible to perform such encoding using an embodiment of the double encoding scheme in combination with an embodiment of the single encoding scheme of FIG. 15 one or more times to arrive at an encoding/reaction method that suits the need for a specific chemical reaction.

Figure 21:
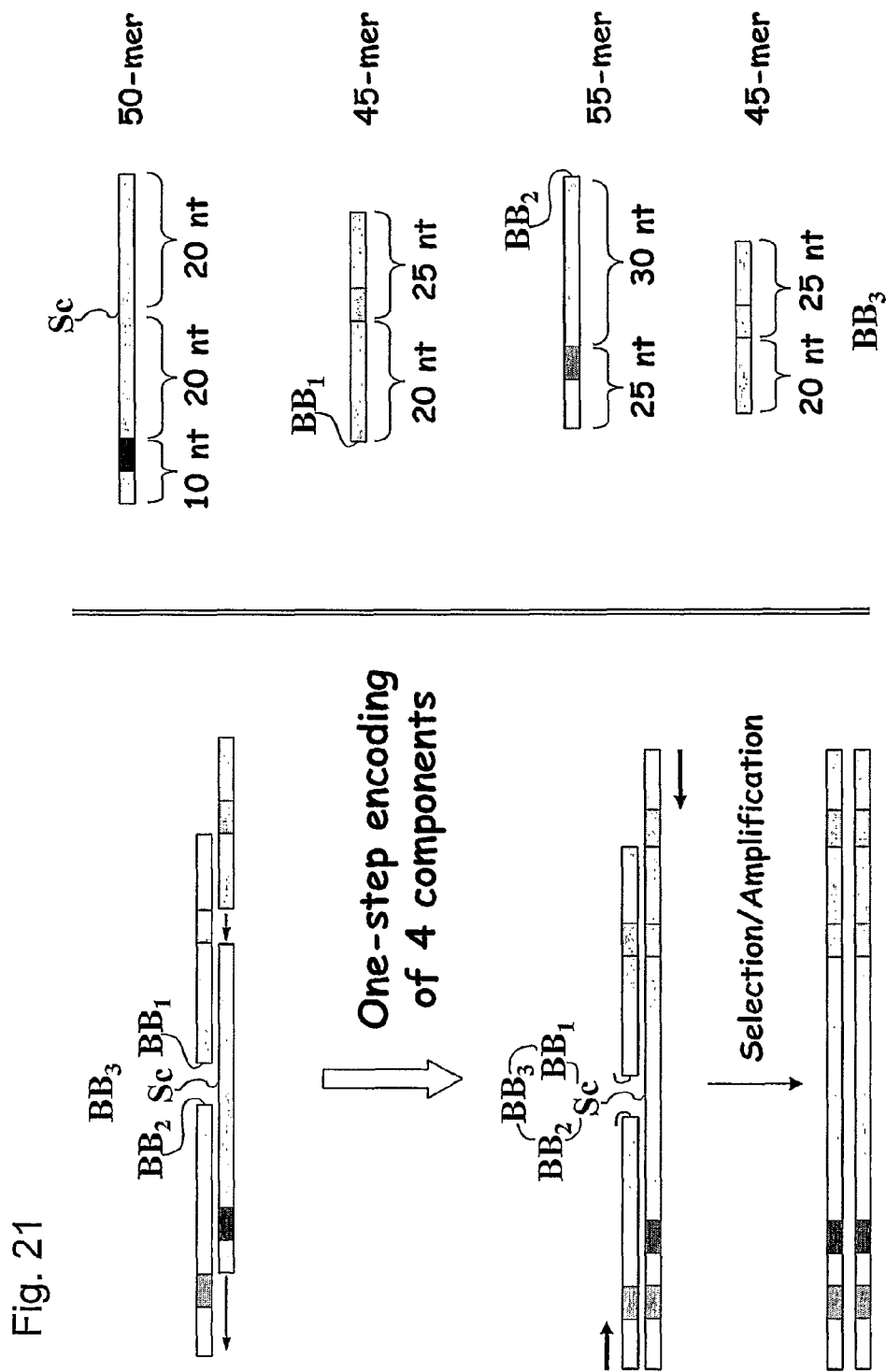
FIG. 21 discloses a triple encoding method.
Figure 22:
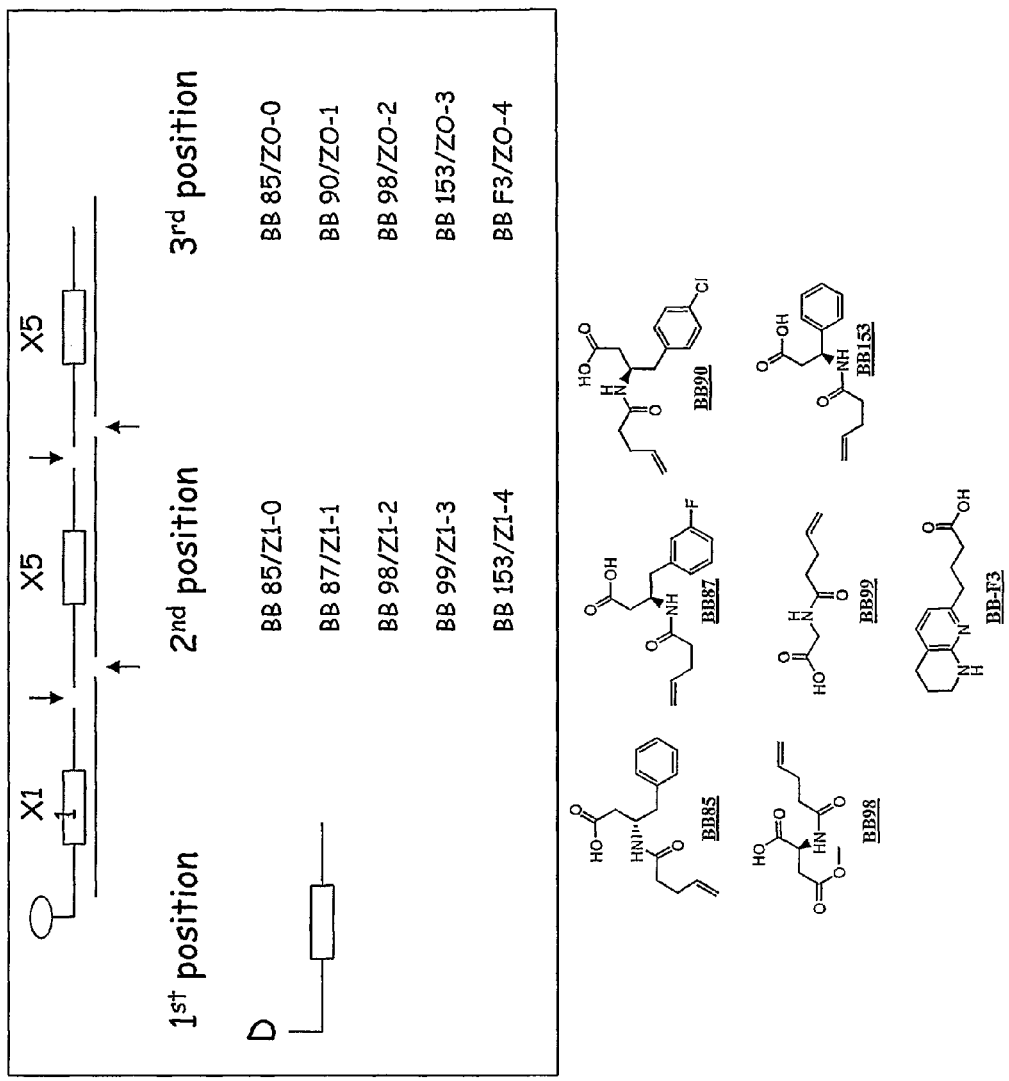
FIG. 22 shows the setup used in example 9.
Figure 23:
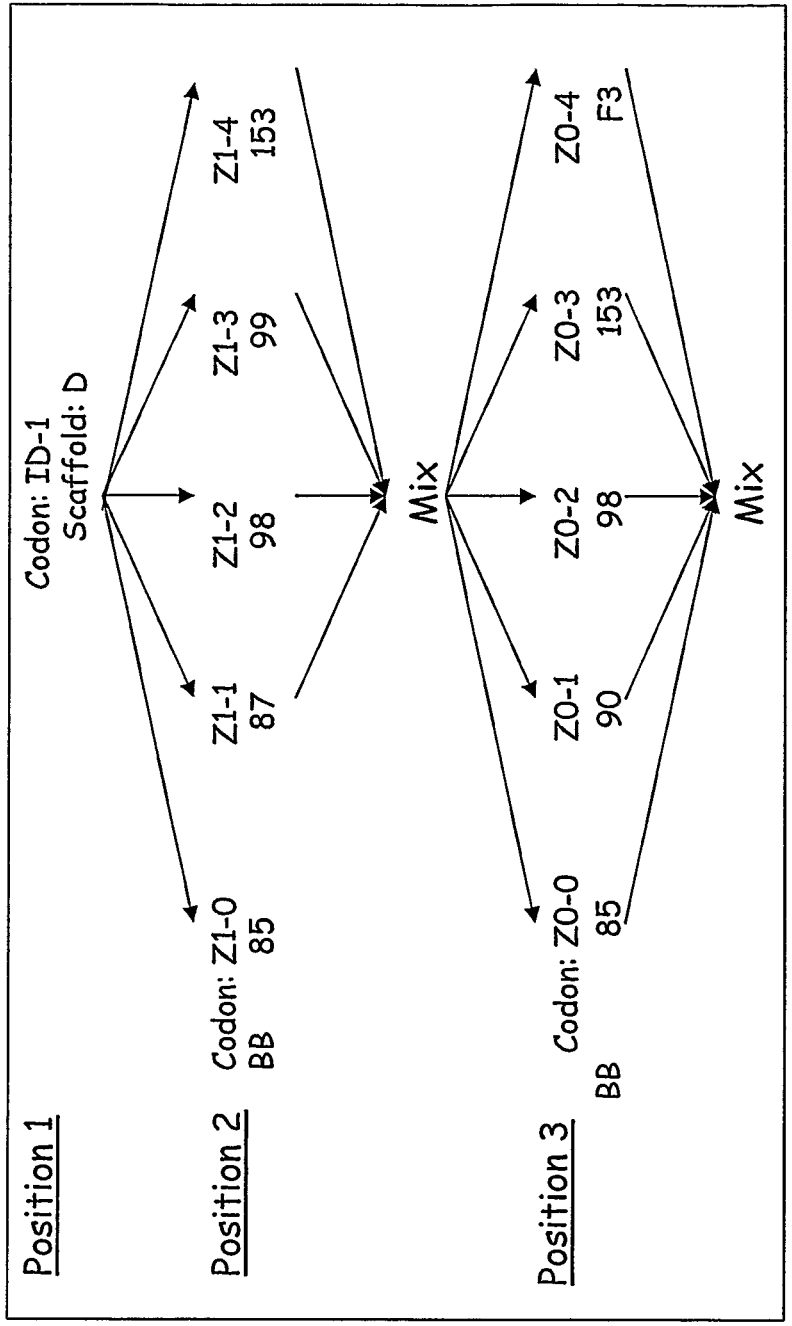
FIG. 23 shows the split-and-mix structure used in example 9.

FIG. 21 discloses a triple encoding method. Initially, a scaffold attached to a scaffold oligonucleotide is provided. The scaffold is attached to a binding region the scaffold oligonucleotide, and the scaffold oligonucleotide is further provided with a codon. The two building blocks of the E2 type is annealed to the scaffold oligonucleotide, thereby bringing the functional entities BB1 and BB2 into close proximity with the scaffold. Simultaneously, prior or subsequent to the addition the building blocks a codon oligonucleotide coding for a third reactant (BB3) is provided which comprises a part complementing a nucleotide sequence of the first building block. The components of the system are allowed to hybridise to each other and a polymerase and a ligase is provided. The polymerase performs an extension where possible and the ligase couples the extended oligonucleotides together so as to form a double stranded product. Following the encoding process, the third reactant is added and conditions are provided which promote a reaction between the scaffold and the reactants. Finally, a selection is used to select reaction products that perform a certain function towards a target. The identifying oligonucleotides of the selected bifunctional complexes are amplified by PCR and identified.

To the right a particular embodiment for carrying out the present invention is indicated. Accordingly, each codon is 5 nucleotides in length and the binding regions flanking the scaffold are 20 nucleotides each. The building blocks designed to hybridise to the binding regions of the scaffold comprises a 20 nucleotide complementing sequence as well as a 5 nucleotide codon.

Figure 24:
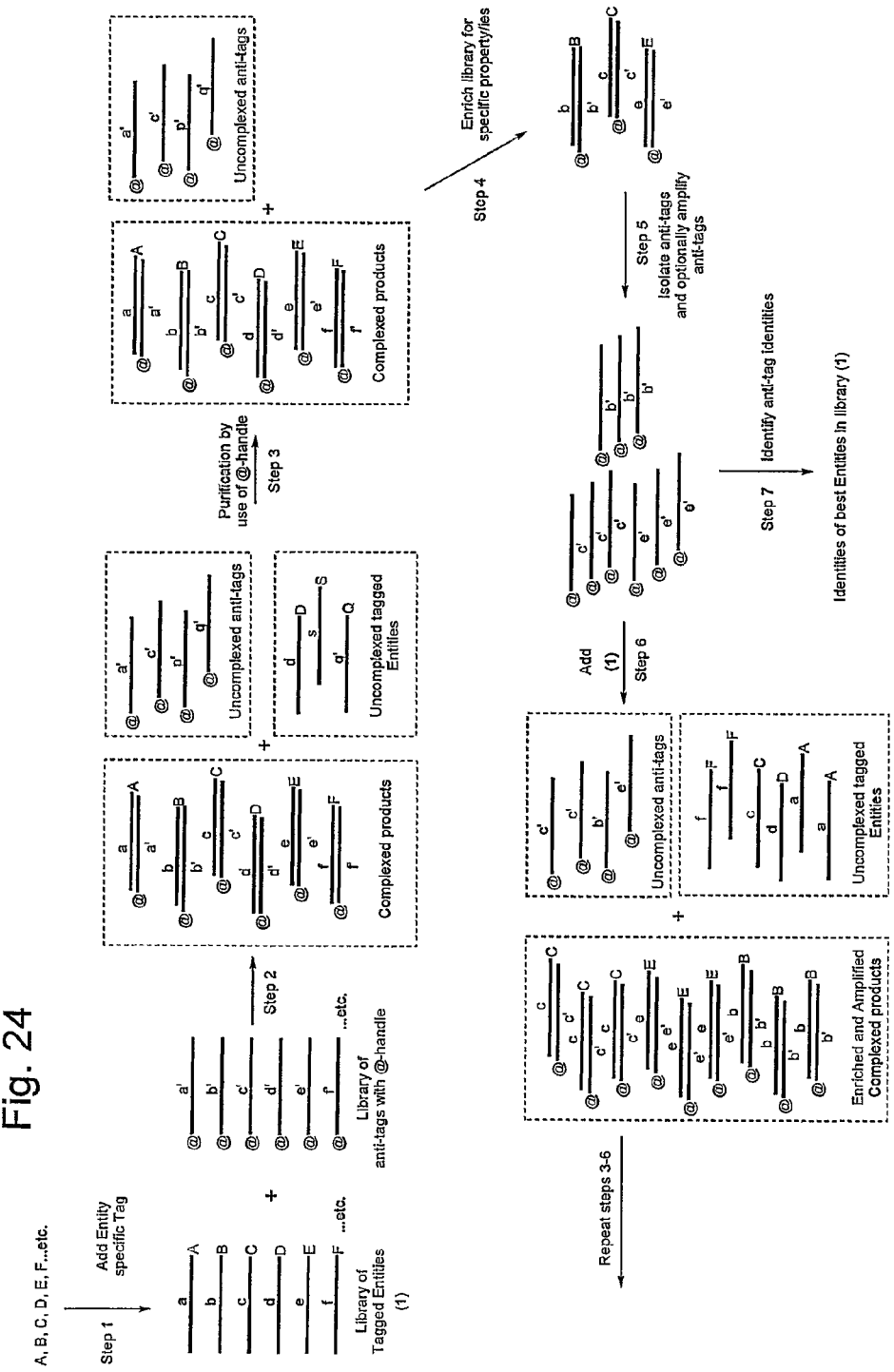
FIG. 24 discloses an embodiment of library enrichment, amplification and identification.

An embodiment of the enrichment method of the present invention is shown on FIG. 24. Initially, each chemical entity (denoted by letters A, B, C, . . . ) in a library is attached to a unique identifier tag (denoted a, b, c, . . . ). The identifier tag comprises information about that particular compound or group of compounds with respect to e.g. structure, mass, composition, spatial position, etc. In a second step, tagged chemical compounds are combined with a set of anti-tag sequences (denoted a', b', c', . . . ). Each anti-tag sequence carries a handle, like biotin, for purification purposes. The anti-tag sequences comprise a segment which is complementary to a sequence of the identifier sequence. The combination of anti-tag sequences and identifier sequences are allowed to form hybridisation products. Optionally, there may be tagged chemical entities present which have not been recognized by an anti-tag. In a third step, the sequences carrying a handle are removed, i.e. the tagged chemical compounds are left in the media while the matter comprising a handle is transferred to a second media. In the event, the handle is biotin it may be transferred to a second media using immobilized streptavidin.

Figure 25:
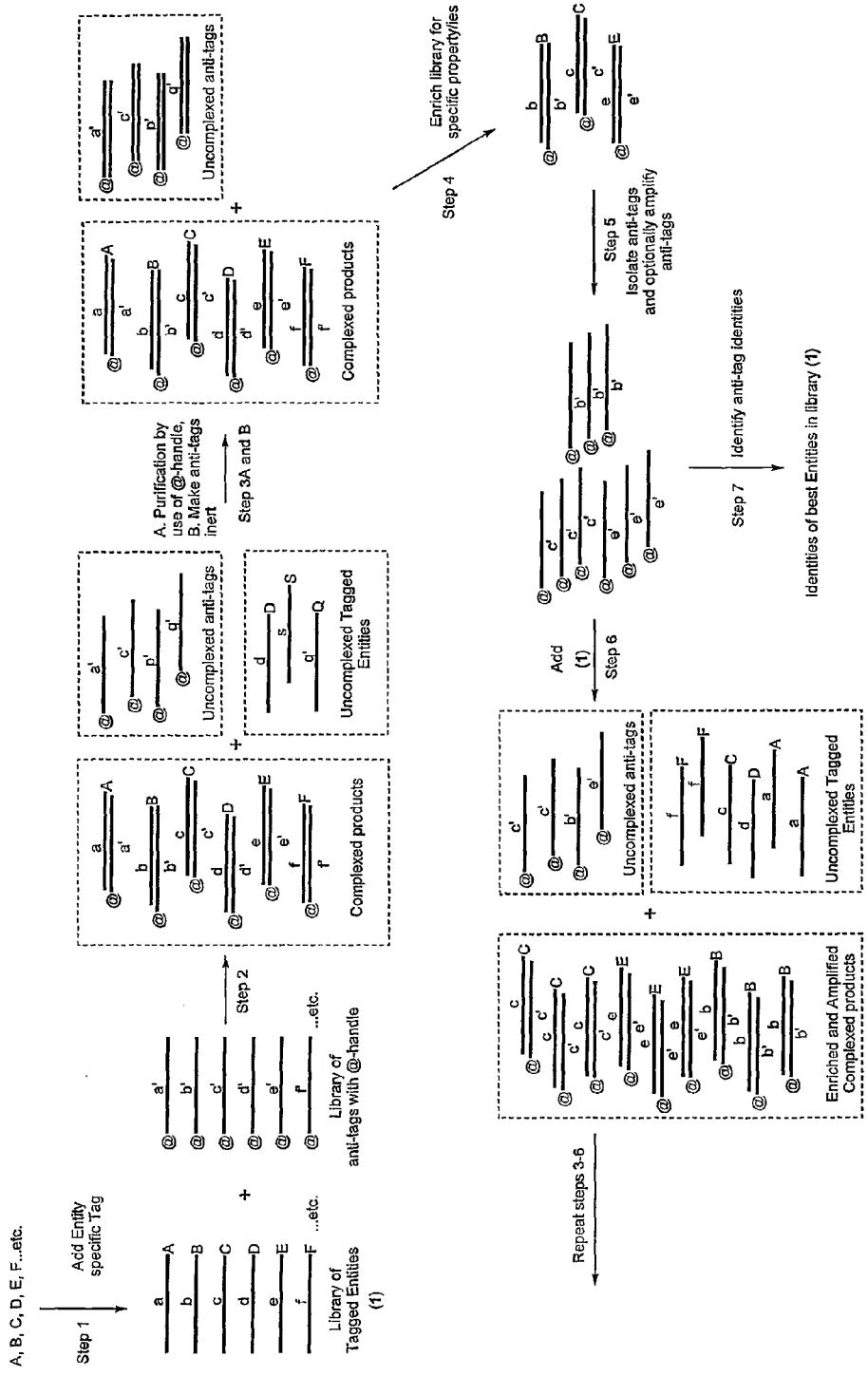
FIG. 25 shows an embodiment in which anti-tag sequences not hybridised to a identifier sequence are made double stranded and thus inert.

The purified matter may comprise anti-tag sequences not hybridised to a cognate sequence. As these anti-tag sequences are not coupled to a chemical compound to be selected for, the enrichment sequences may remain in the media. However, in some applications it may be preferably to make the excess anti-tag sequences double stranded, as illustrated in FIG. 25, because the double helix normally is inert relative to the selection procedure. The excess anti-tag sequences may be transformed into the double helix state by the use of a primer together with a suitable polymerase and nucleotide triphosphates.

The purified fraction is in step 4 is subjected to a selection process. The selection comprises probing for a set of properties, e.g. but not limited to affinity for a specific protein. In such a case, entities which do not bind to the specific protein will be eliminated. Anti-tags complexed to entities binding to the specific protein may be recovered/be isolated through e.g. the use of its purification handle.

In step 5 isolated anti-tags are optionally amplified through the use of PCR or RTPCR.

In step 6, the initial library of tagged entities produced in step 1, may undergo further rounds of complexation and screening, i.e. the anti-tags from step 5 may be added the library of tagged entities of step 1 and then be submitted to step 3, step 4 and step 5. Step 6 may be repeated.

In step 7, the isolated anti-tags of step 5 may be cloned and their identity be revealed. E.g. in the case of DNA, sequencing may be applied whereby the identity of specific entities with selected properties in the library of tagged entities will be revealed.

Figure 26:
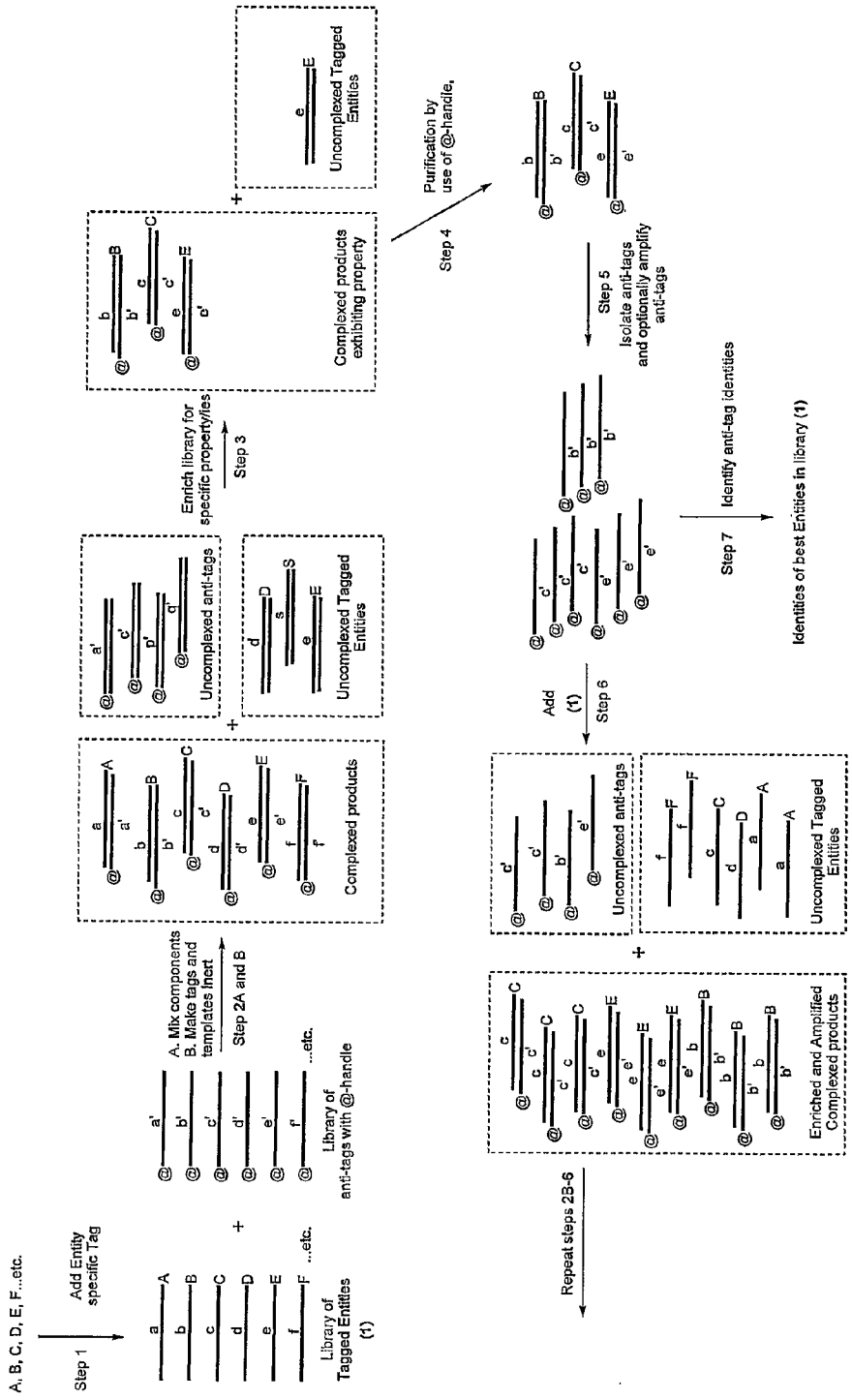
FIG. 26 shows an embodiment in which an enrichment step is before the purification step.

The embodiment shown in FIG. 26 resembles that of FIG. 24 except that the non-complexed components are rendered inert, e.g. if the tags and/or anti-tags are composed of single stranded DNA or RNA, they may be transformed into double stranded DNA, RNA or a hybrid thereof. This may be accomplished by use of a primer, nucleotide triphosphates and a polymerase or transcriptase. Furthermore, the sequence of purification (by use of the purification handle on anti-tags) and probing for properties is changed compared to the method of FIG. 24.

Figure 27:
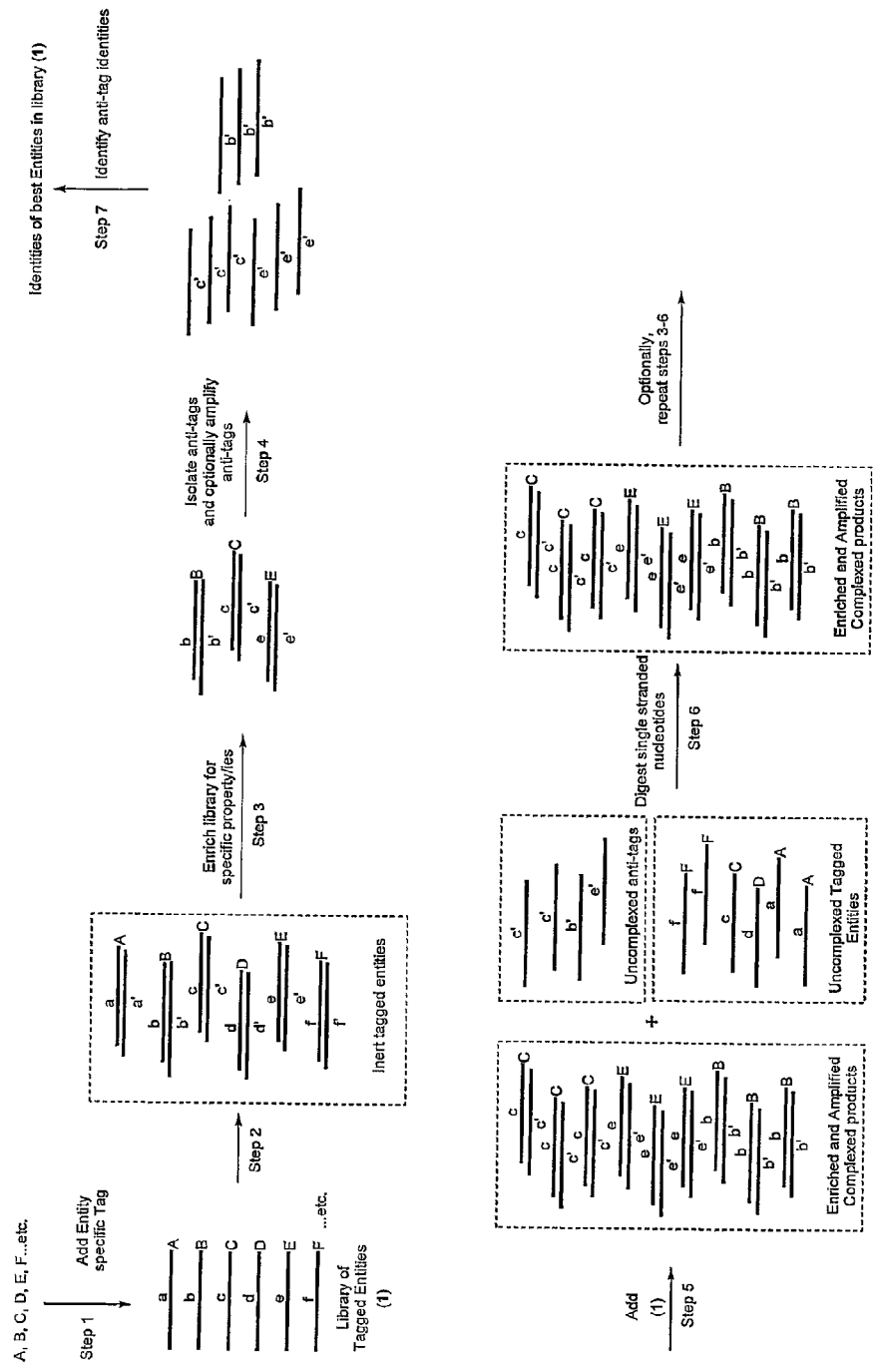
FIG. 27 shows a general principle of library enrichment, amplification, and identification.

In FIG. 27, step 1, a number of entities (denoted by letters A, B, C . . . ), being it mixtures or single compounds are attached to a unique tag more specifically a DNA or RNA sequence or a derivative thereof, holding information on that compound or mixture, such as e.g. structure, mass, composition, spatial information etc.

In step 2, all tags of tagged entities are made double stranded by use of a primer (optionally carrying a @-handle such as e.g. biotin), nucleotide triphosphates and a polymerase or transcriptase. Remaining single stranded DNA or RNA may optionally be digested by use of nucleases.

The mixture, is probed for a set of properties in step 3, e.g. but not limited to affinity for a specific protein. In such a case, entities which do not bind to the specific protein will be eliminated. Anti-tags complexed to entities binding to the specific protein may be recovered/be isolated through e.g. the use of its @-handle.

Isolated anti-tags may optionally be amplified in step 4 through the use of PCR or RTPCR.

In step 5, the library of tagged entities of step 1, may undergo complexation to the isolated and optionally amplified anti-tags of step 3 and 4.

Single stranded components are being digested in step 6 by use of e.g. nucleases. The remaining double stranded subset of the library is optionally subjected to a renewed enrichment of the library according to step 3-6. Steps 3-6 may be repeated as sufficient number of times to obtain an appropriate chemical entity having the desired property.

In step 7, the isolated anti-tags of step 4 can be cloned and their identity be revealed, e.g. in the case of DNA, sequencing may be applied, whereby the identity of specific entities in the library of tagged entities is revealed.

Figure 28:
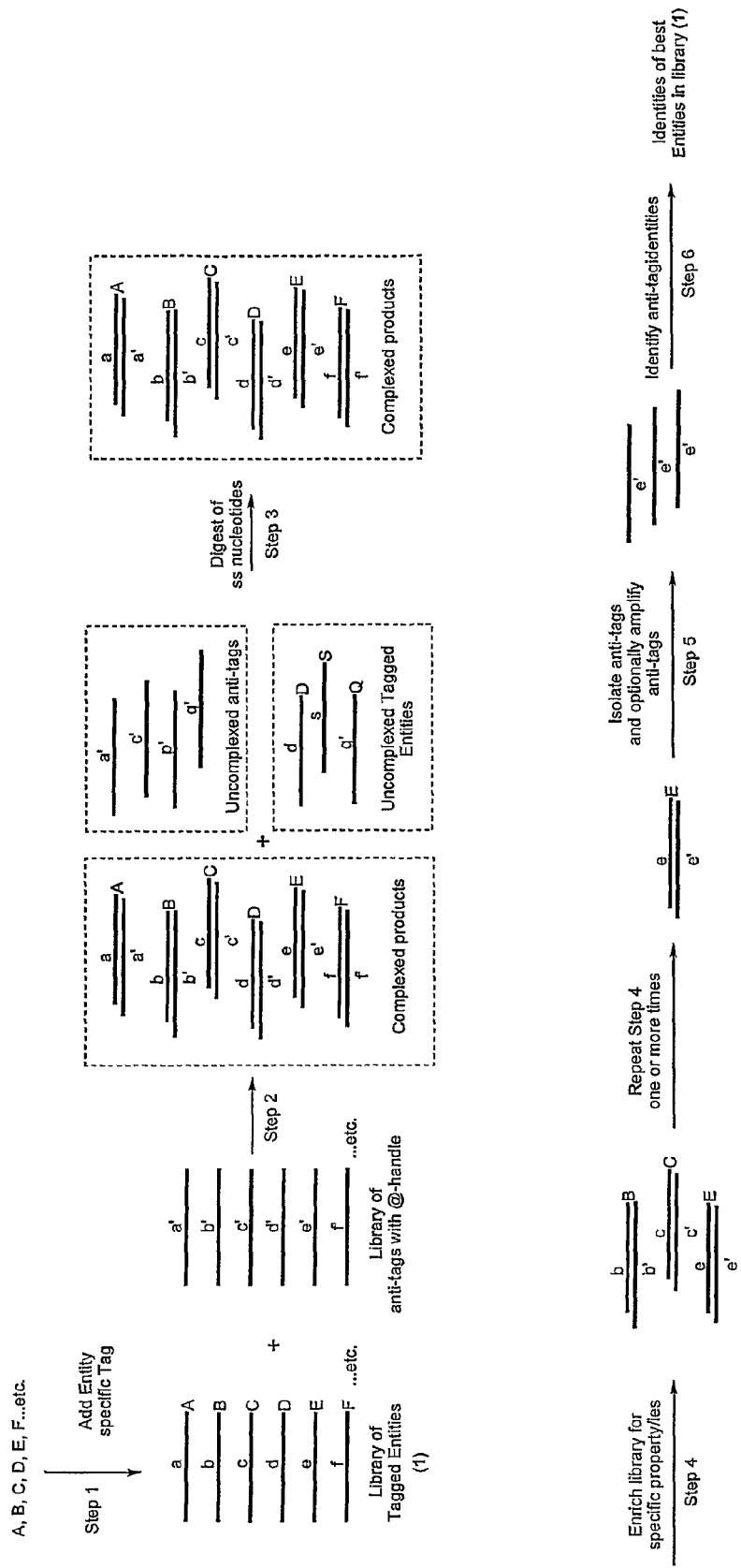
FIG. 28 shows a general principle of library enrichment, amplification, and identification omitting the intermediate amplification step between subsequent enrichment procedures.

FIG. 28 relates to a method involving a digestion of single stranded oligonucleotides. In a first step a number of entities (denoted by letters A, B, C . . . ), being it mixtures or single compounds, are attached to a unique tag, holding information on that compound or mixture, such as e.g. structure, mass, composition, spatial information etc.

In step 2, mixtures of tagged entities are combined with a set of complementary anti-tags. Anti-tags may be, but is not limited to nucleotide derivatives. Anti-tags may optionally carry a @-handle. The tag and the anti-tags are allowed to form a complex. The complexation may be, but is not limited to hybridization. Some anti-tags will not form a complex with a tagged entity and some tagged entities will not form a complex with an anti-tag.

Non-complexed components is digested in step 3 using e.g. nucleases when the tags and/or anti-tags are composed of DNA or RNA or hybrids thereof.

The mixture of step 3, is probed for a set of properties in step 4, e.g. but not limited to affinity for a specific protein. In such a case, entities which do not bind to the specific protein will be eliminated. Anti-tags complexed to entities binding to the specific protein may be recovered/be isolated through e.g. the use of its @handle. Step 4 may be repeated one or more times.

Isolated anti-tags may optionally be amplified through the use of PCR or RTPCR as illustrated in step 5. Anti-tags may then also be used as described in FIGS. 24-27.

The isolated anti-tags may be cloned and their identity be revealed in step 6, e.g. in the case of DNA, sequencing may be applied, whereby the identity of specific entities in the library of tagged entities will be revealed.

Figure 29:
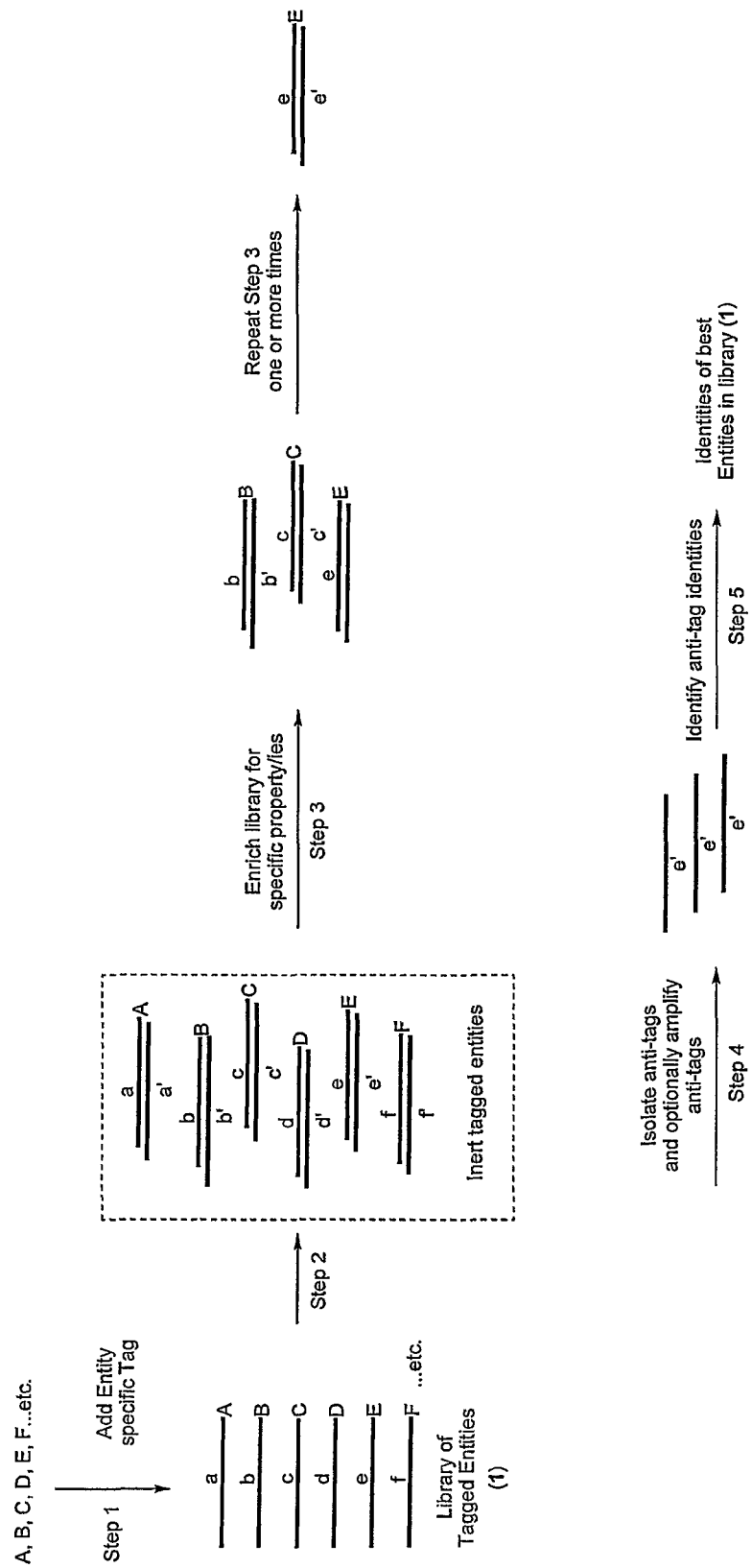
FIG. 29 shows a general principle of library enrichment, amplification, and identification in which the initial single stranded library is made double stranded prior to enrichment.

According to FIG. 29, step 1, a number of entities (denoted by letters A, B, C . . . ), being it mixtures or single compounds, are attached to a unique tag more specifically a DNA or RNA sequence or a derivative thereof, holding information on that compound or mixture, such as e.g. structure, mass, composition, spatial information etc.

All tags of tagged entities are made double stranded in step 2 by use of a primer (optionally carrying a @-handle such as e.g. biotin), nucleotide triphosphates and a polymerase or transcriptase. Remaining single stranded DNA or RNA may optionally be digested by use of e.g. nucleases.

In step 3, the mixture is probed for a set of properties, e.g. but not limited to affinity for a specific protein. In such a case, entities which do not bind to the specific protein will be eliminated. Anti-tags complexed to tags having appended entities binding to the specific protein may be recovered/be isolated through e.g. the use of its @-handle. Step 3 may be repeated one or more times.

According to step 4, isolated anti-tags may optionally be amplified through the use of PCR or RTPCR. Anti-tags may then also be used as described in FIGS. 24-27.

The isolated anti-tags may be cloned in step 5 and their identity be revealed, e.g. in the case of DNA, sequencing may be applied. Whereby, the identity of specific entities in the library of tagged entities will be revealed.

Figure 30:
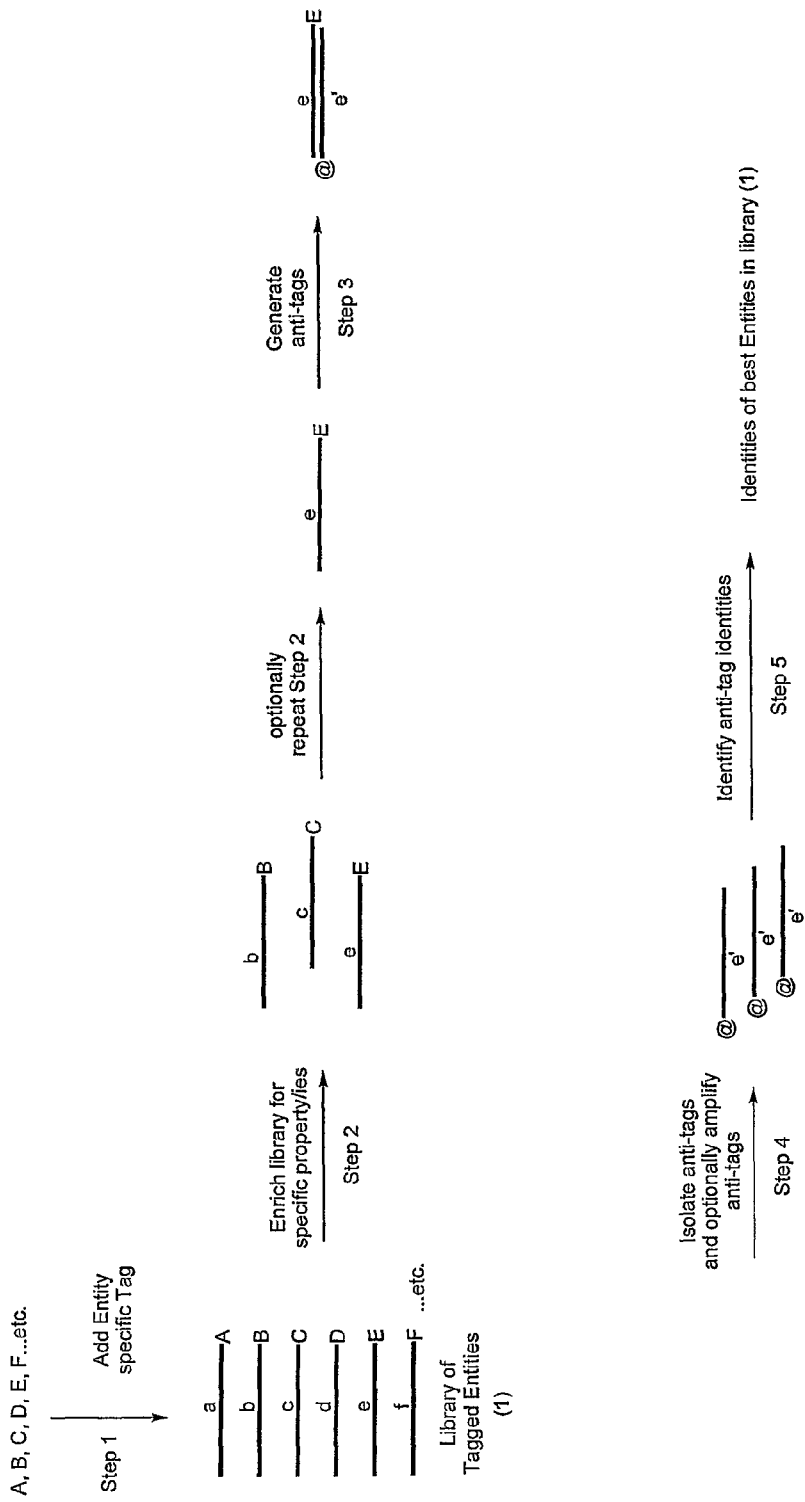
FIG. 30 shows a general principle for library enrichment, in which the anti-tag is not formed until after the one and more enrichment processes.

FIG. 30, step 1, produces a number of entities (denoted by letters A, B, C . . . ), being it mixtures or single compounds which are attached to a unique tag more specifically a DNA or RNA sequence or a derivative thereof, holding information on that compound or mixture, such as e.g. structure, mass, composition, spatial information etc.

In step 2, the mixture is probed for a set of properties, e.g. but not limited to affinity for a specific protein. In such a case, entities which do not bind to the specific protein will be eliminated. Step 2 may be repeated.

All tags of tagged entities are made double stranded in step 3 by use of a primer (optionally carrying a @-handle such as e.g. biotin), nucleotide triphosphates and a polymerase or transcriptase. Remaining single stranded DNA or RNA may optionally be digested by use of e.g. nucleases.

Anti-tags complexed to tags of entities binding to the specific protein may be recovered/be isolated in step 4 through e.g. the use of its @-handle. Anti-tags may optionally be amplified through the use of PCR or RTPCR. Anti-tags may then also be used as described in FIGS. 24-27.

The isolated anti-tags may be cloned in step 5 and their identity be revealed, e.g. in the case of DNA, sequencing may be applied, whereby, the identity of specific entities in the library of tagged entities is revealed.

FIG. 31A shows the result of polyacrylamide gel electrophoresis of the sample created in example 13, the result of annealing identifier oligo E57 with zipper building block E32 and anti-codon oligonucleotide CD-M-8-01720001 (with anti-codon sequence Anti-Codon 1) (lane 2) and of annealing the same identifier oligo with E32 and anti-codon oligo E60 (with anti-codon sequence Anti-codon X) (lane 3).

FIG. 31B shows the result of polyacrylamide gel electrophoresis of the sample in which E58 is annealed to zipper building block CX-1 and anti-codon oligo CD-M-8-0172-0001, and E58 to E32 and E60. This time a reactant on the zipper building block was cross linked to the display molecule in the identifier oligonucleotide.

Figure 32:
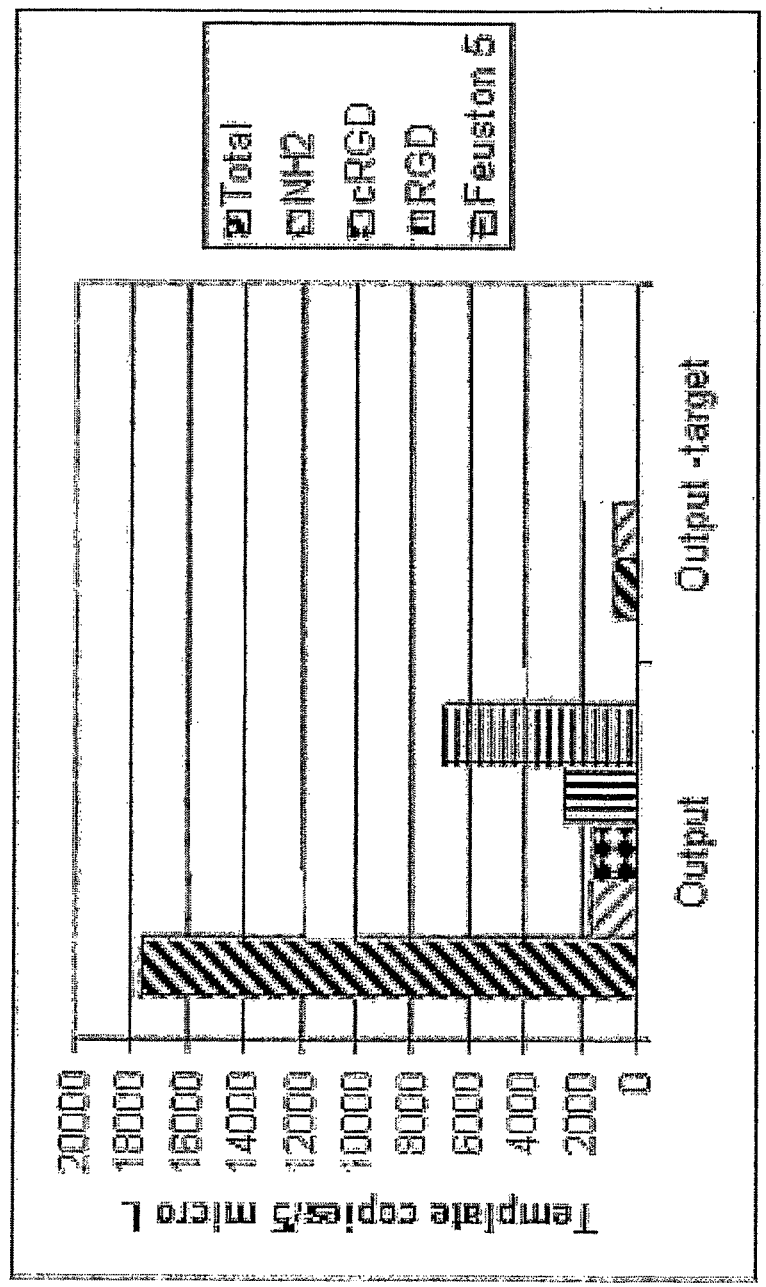
FIG. 32 shows the result of the experiment reported in Example 14.
Figure 33:
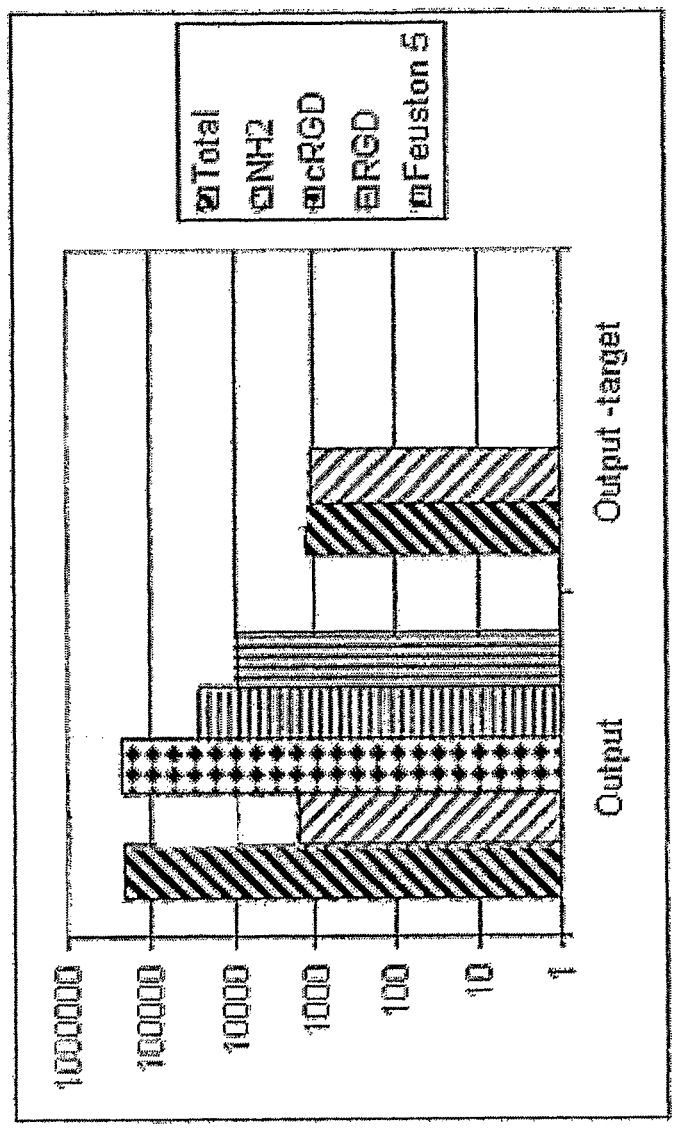
FIG. 33 shows the result of the experiment reported in Example 14.

FIGS. 32 and 33 are more fully discussed in Example 14.
FIGS. 34-47 are more fully discussed in examples 1-5, 7-9.

EXAMPLES

Example 1

Loading of a Scaffold onto Identifier Molecules

An amino-modifier C6 5'-labeled identifier oligo (5'-X-TCGTAACGACTGAATGACGT-3', (SEQ ID NO: 5) wherein X may be obtained from Glen research, cat. #10-1039-90) was loaded with a peptide scaffold (Cys-Phe-Phe-Lys-Lys-Lys, CFFKKK, SEQ ID NO: 6) using SPDP activation (see below). The SPDP-activation of amino-oligo was performed using 160 µl of 10 nmol oligo in 100 mM Hepes-KOH, pH=7.5, and 40 µl 20 mM SPDP and incubation for 2 h at 30° C. The activated amino-oligo was extracted 3 times with 500 µl EtOAc, dried for 10 min in a speed-vac and purified using micro bio-spin column equilibrated with 100 mM Hepes-KOH. The loading of scaffold was then performed by adding 10 µl of 100 mM attachment entity and incubating overnight at 30° C.

Figure 34:
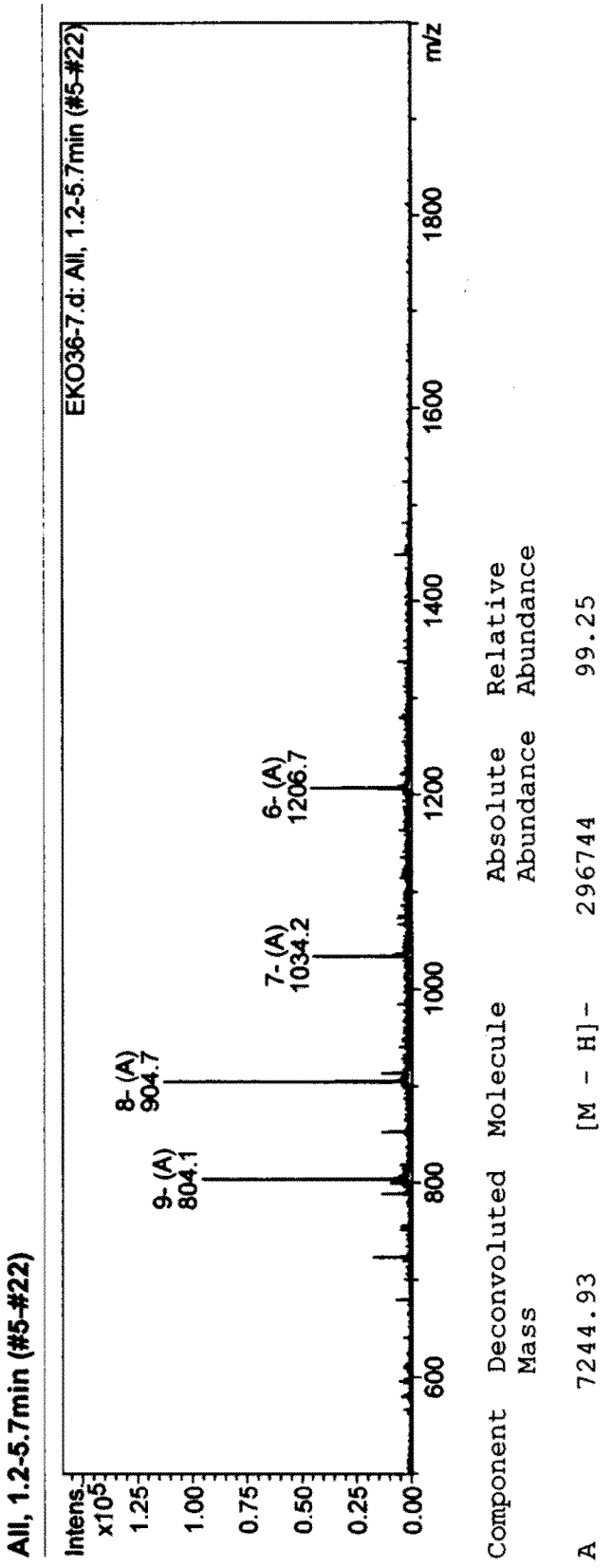
FIG. 34 is a mass spectrogram showing the observed mass (7244.93 Da) for the sample of example 1.

The loaded identifier oligo was precipitated with 2 M $NH_4OAc$ and 2 volume 96% ethanol for 15 min at 80° C. and then centrifuged for 15 min at 4° C. and 15.000 g. The pellet was re-suspended in water and the precipitation was repeated. Wash of the oligo-pellet was done by adding 100 µl of 70% ethanol and then briefly centrifuged. The oligo was re-dissolved in 50 µl $H_2O$ and analysed by MS. The MS analysis was performed after 100 pmol oligo in 10 µl water was treated with 10 µl of ion exchanger resin and incubated minimum 2 h at 25° C. on a shaker. After incubation the resin was removed by centrifugation and 15 µl of the supernatant was mixed with 7 µl of water, 2 µl of piperidine and imidazole (each 625 mM) and 24 µl acetonitrile. The sample was analysed using a mass spectroscopy instrument (Bruker Daltonics, Esquire 3000plus). The observed mass, as can be seen in FIG. 34, was 7244.93 Da, which correspond well with the calculated mass, 7244.00 Da. This experimental data exemplify the possibility to load scaffolds onto identifier oligonucleotides. This loaded identifier molecule can be used to receive functional entities from building blocks. This particular scaffold harbours three identical reactive groups, i.e. the amine group of the lycin side chain, and can therefore be transferred with one, two, or three functional entities, which is capable of reacting with the amine groups.

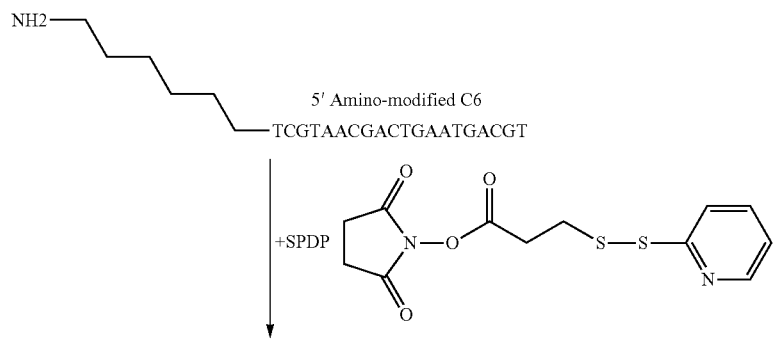

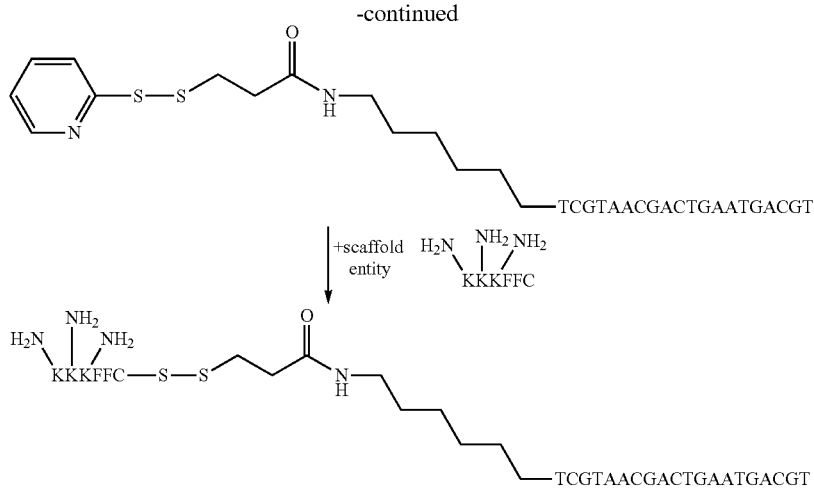

In the above figure, the DNA sequence is SEQ ID NO:5 and the peptide sequence (which, in the figure, is in reverse order, C-terminal to N-terminal is SEQ ID NO:6.

Example 2

Loading of Functional Entities onto Building Blocks

Loading of functional entities onto building block molecules can be done using a thiol-oligo (see below). An Biotin 5' labeled and thio-modifier C6 S—S (obtainable from Glen Research, cat #10-1936-90) 3'-labeled building block oligo (5'-BTGCAGACGTCATTCAGTCGTTACGA-3' SEQ ID NO: 7) was converted to an NHS-oligo using NHM.

10 nmol oligo was dried in speed-vac, re-dissolved in 50 µl 100 mM DTT, 100 mM sodium-phosphate pH 8.0 and incubated at 37° C. for 1 hour. The thiol-oligo was then purified using micro bio-spin column equilibrated with 100 mM Hepes-KOH, pH 7.5. The thiol-oligo was converted to NHS-oligo by adding 100 mM NHM in 100 mM Hepes-KOH pH. 7.5. The sample was incubated at 25° C. over night. The NHS-oligo was then purified using bio-spin column equilibrated with MS-grade $H_2O$.

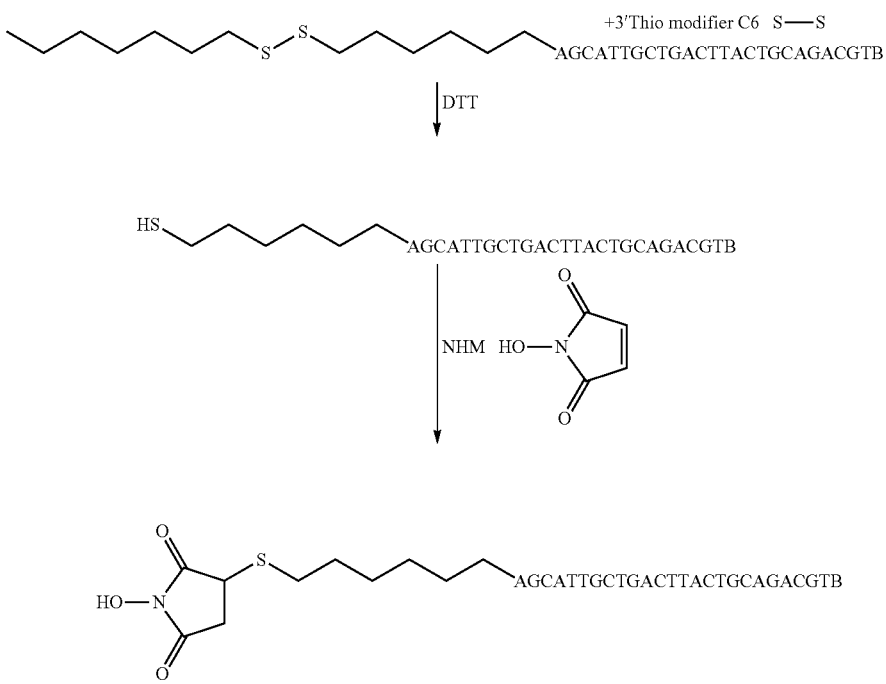

Calculated MS: 8372.1

In the above figure, the DNA sequence is SEQ ID NO:7.

Figure 35:
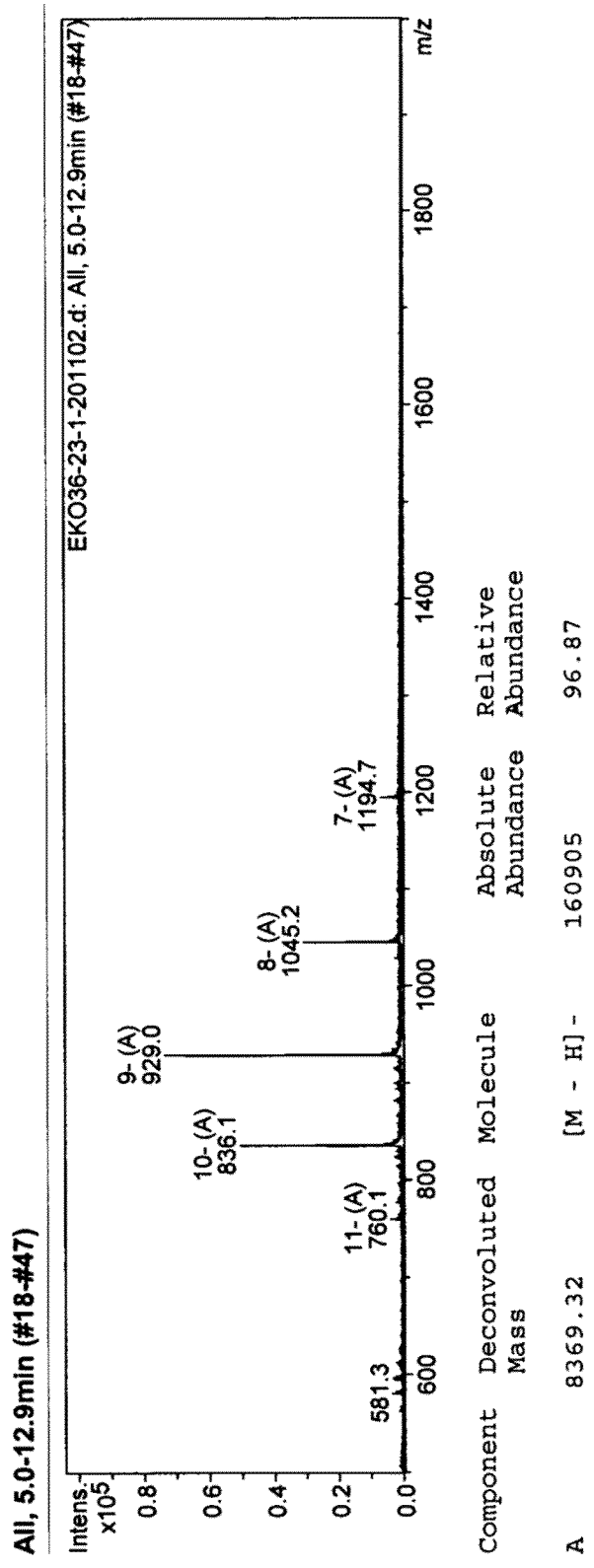
FIG. 35 is a mass spectrogram showing the observed mass (8369.32 Da) for the sample of example 2.
Figure 36:
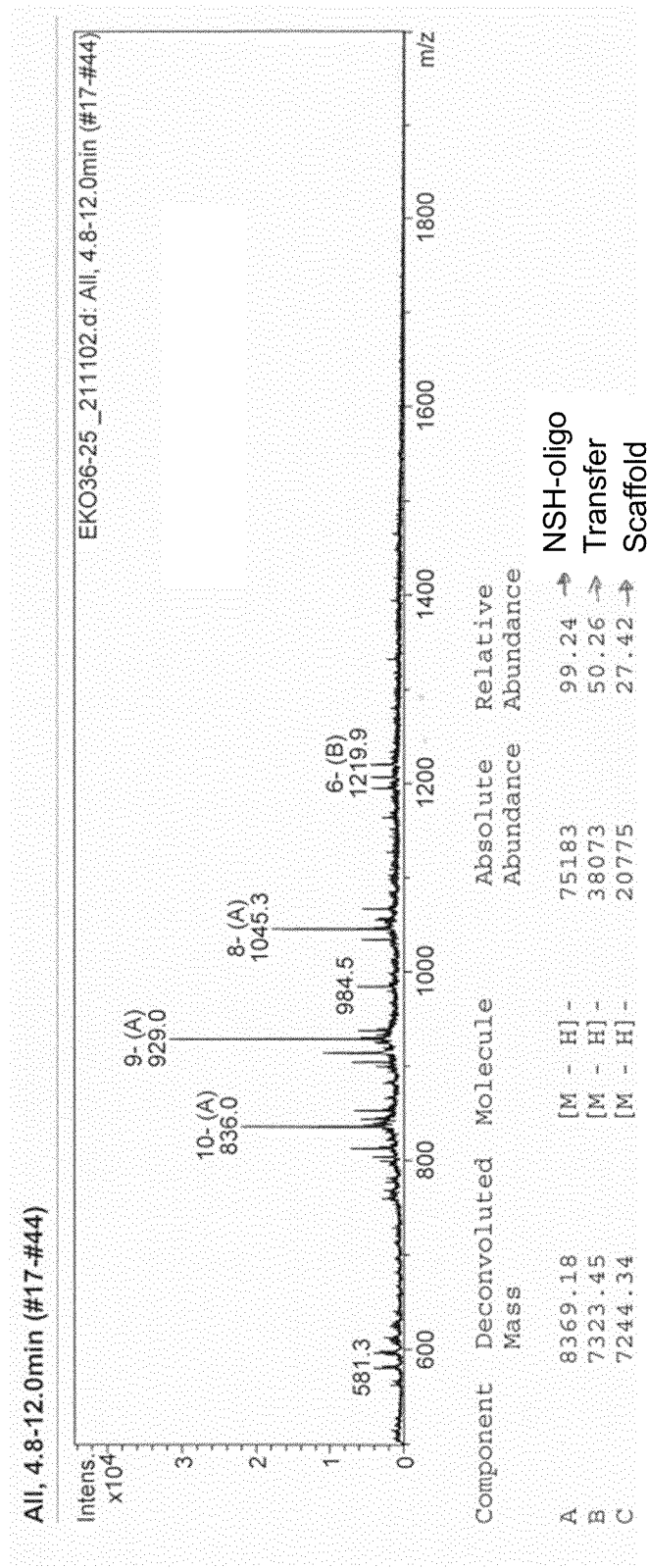
FIG. 36 is a mass spectrogram showing the observed mass (7323.45 Da) for the first sample of example 3.
Figure 37:
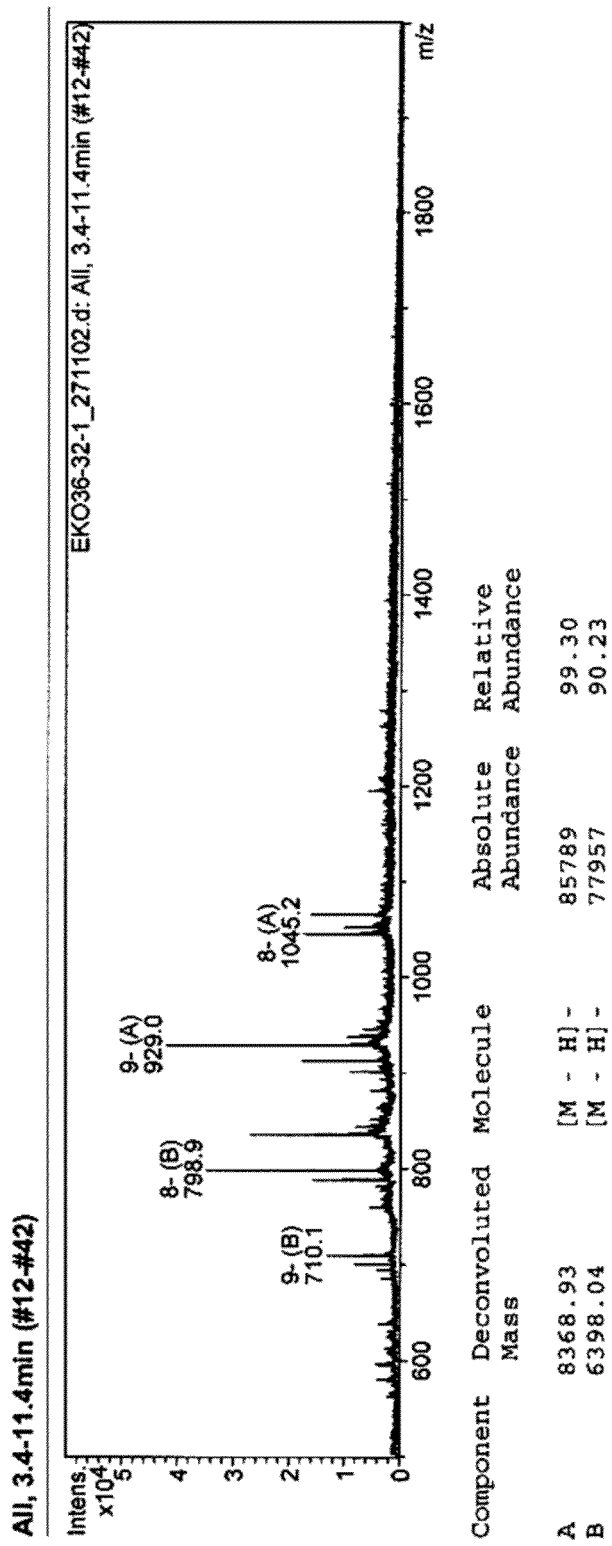
FIG. 37 is a mass spectrogram showing the observed mass (6398.04 Da) for the second sample of example 3.
Figure 38:
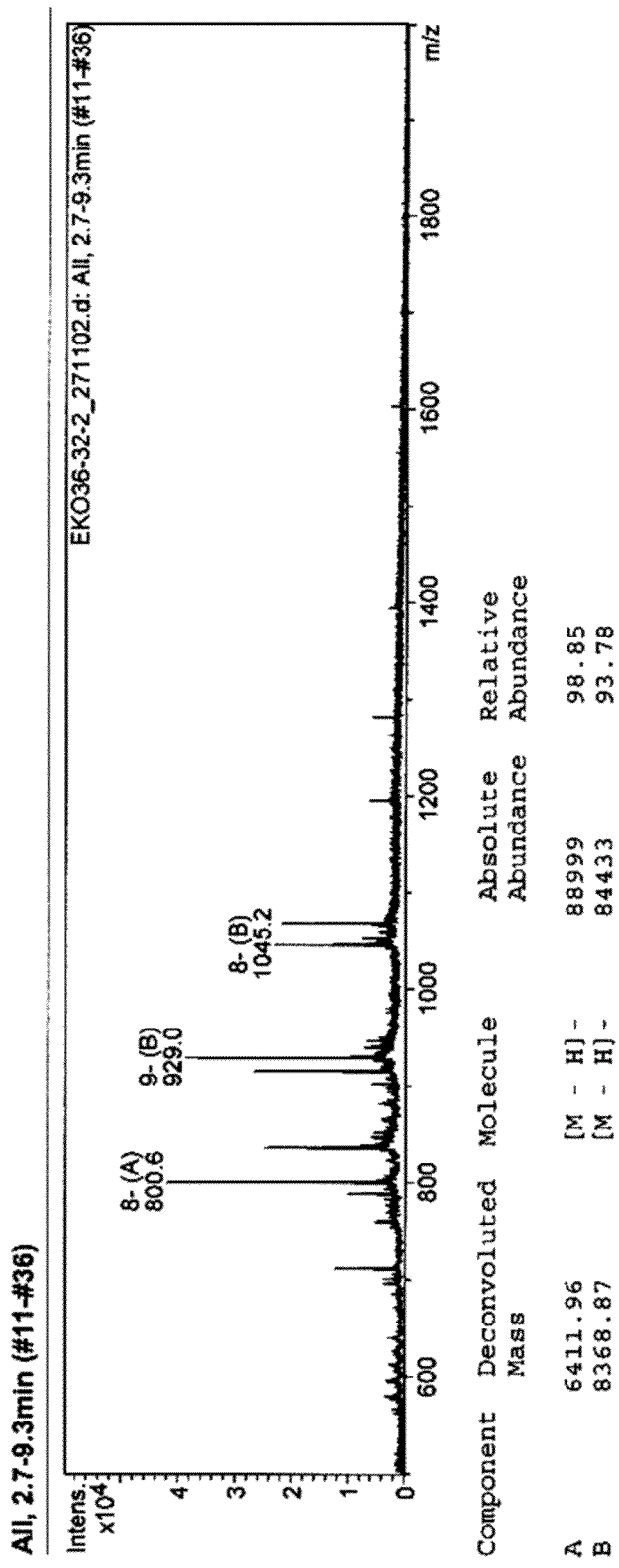
FIG. 38 is a mass spectrogram showing the observed mass (6411.96 Da) for the third sample of example 3.

The MS analysis was performed after 100 pmol oligo in 10 µl water was treated with 10 µl of ion exchanger resin and incubated minimum 2 h at 25° C. on a shaker. After incubation the resin was removed by centrifugation and 15 µl of the supernatant was mixed with 7 µl of water, 2 µl of piperidine and imidazole (each 625 mM) and 24 µl acetonitrile. The sample was analysed using a mass spectroscopy instrument (Bruker Daltonics, Esquire 3000plus). The observed mass as can be seen in FIG. 35 was 8369.32, which correspond well with the calculated mass, 8372.1. The experimental data exemplify the possibility to convert the attachment entity on building block oligonucleotides. This product can later be used to attach transferable functional entities.

The NHS-oligo was then used to load functional entities. EDC activation of the functional entity (4-pentynoic acid) was performed mixing 50 µl of 200 mM functional entity in DMF with 50 µl of 200 mM EDC in DMF and incubated for 30 min at 25° C. on a shaker. The loading was then performed using 1 nmol NHS-oligo lyophilized in a speed-vac and 10 µl of the activated building block (see below). This was incubated at 25° C. for 5 min and then mixed with 30 µl 100 mM MES pH. 6.0. The loaded NHS-oligo was purified using bio-spin column equilibrated with 100 mM MES pH 6.0. The loaded building block oligo is then used immediately for the transfer reaction without any MS analysis. This is due to the unstable structure of the functional entity during the conditions used for the MS measurements.

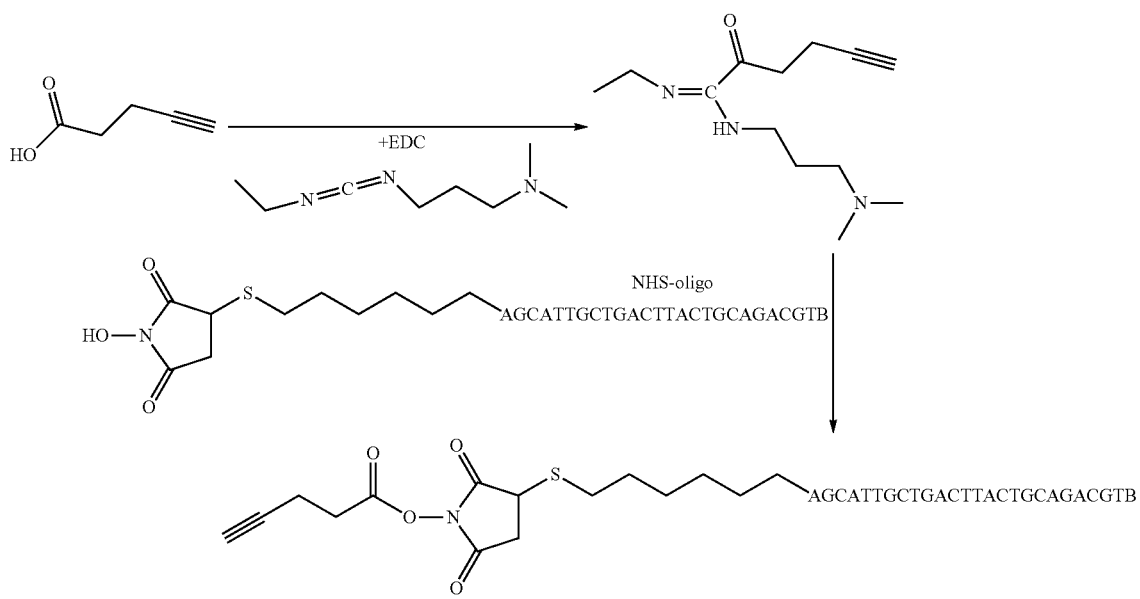

In the above Figure, the DNA sequence is SEQ ID NO:7.

This experiment exemplifies a complete loading of a functional entity onto a building block molecule ready for transfer to an recipient reactive group when annealed to the complementary identifier molecule.

Another example of a functional entity that can be loaded as described above onto a building block is a 5-hexynoic acid as shown below. Again, no MS analysis was performed on this compound due to the unstable structure of the functional entity in the conditions used in the MS measurements.

Building group R1:

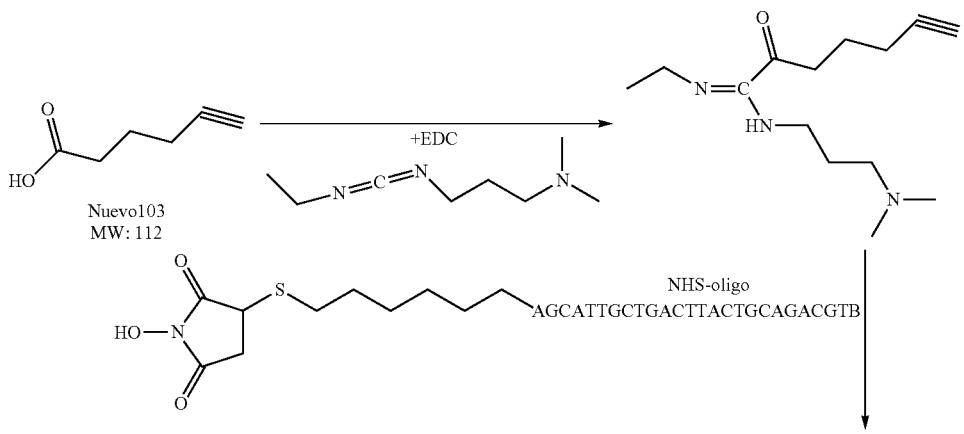

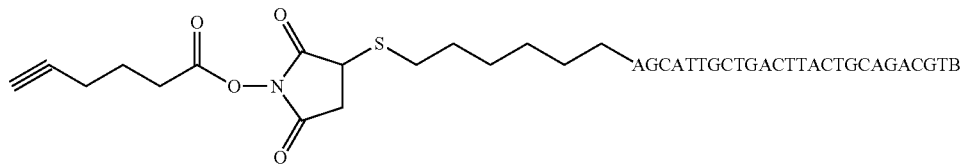

In the above figure, the DNA sequence is SEQ ID NO:7

Example 3

Transfer of Functional Entities from the Building Block to the Identifier Molecule The attachment entity (AE) in the following experiments are either a scaffold, e.g. the peptide, CFFKKK (SEQ ID NO: 134), loaded on an identifier as prepared in Example 1 or a recipient reactive group exemplified by an amino modified oligonucleotide used as starting material in Example 1. These attachment entities allow transfer of three or one functional entities, respectively.

The identifier used in this experiment is an identifier oligonucleotide loaded with CFFKKK as described in Example 1. The functional entity (FE) in this experiment is the 4-Pentynoic acid, the loading of which was described in Example 2. The identifier molecule loaded with the scaffold is annealed to the loaded building block molecule to bring the attachment entity and the functional entity in close proximity. The annealing is directed by the identifier region in the identifier molecule and the complementary sequence in the building block molecule.

```
AE-TCGTAACGACTGAATGACGT   (SEQ ID NO: 5)
              +
FE-AGCATTGCTGACTTACTGCAGACGTB (SEQ ID NO: 7)
```

-continued
```
AE-TCGTAACGACTGAATGACGT   (SEQ ID NO: 5)
FE-AGCATTGCTGACTTACTGCAGACGTB (SEQ ID NO: 7)
```

After the annealing step between the identifier and building block molecules, the transfer reaction takes place where the functional entity is transferred to the identifier molecule.

The annealing was performed using 600 pmol of the building block and 400 μmol identifier molecules in 0.1 M MES buffer at 25° C. in a shaker for 2 hours. The reactive part (functional entity) of the building block was transferred to the one of the amino group on the attachment entity on the identifier molecule during the annealing (see below). After annealing the sample was purified by micro-spin gel filtration and analyzed by MS. The sample was prepared for MS analysis using equal amount of sample (about 100 pmol) and ion exchanger resin and incubated minimum 2 h at 25° in a shaker. After incubation the resin was centrifuged down and 15 μl of the supernatant was added 7 μl of water, 2 μl of piperidine and imidazole (each 625 mM) and 24 ul acetonitrile. The sample was analysed on a Mass Spectroscopy instrument (Bruker Daltonics, Esquire 3000plus). The observed mass (see FIG. 36) was 7323.45 Da, which correspond well with the calculated mass, 7324.00 Da. Thus, the MS spectrum of the identifier molecule after the transfer reaction shows a mass corresponding to the transferred functional entity on the identifier molecule.

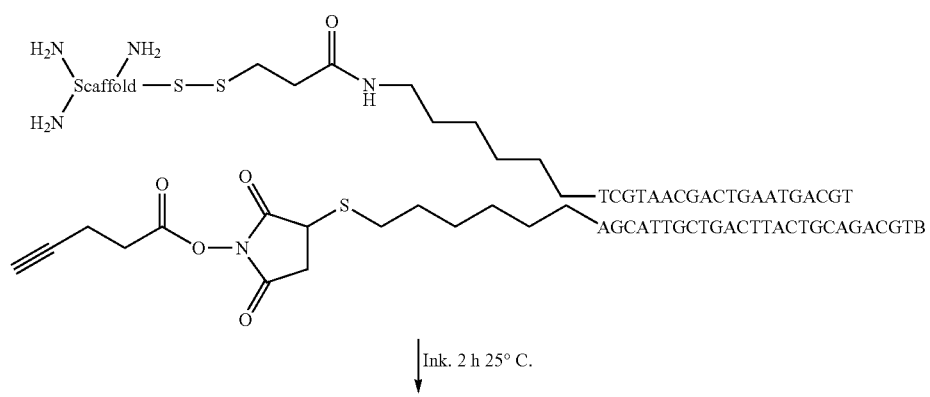

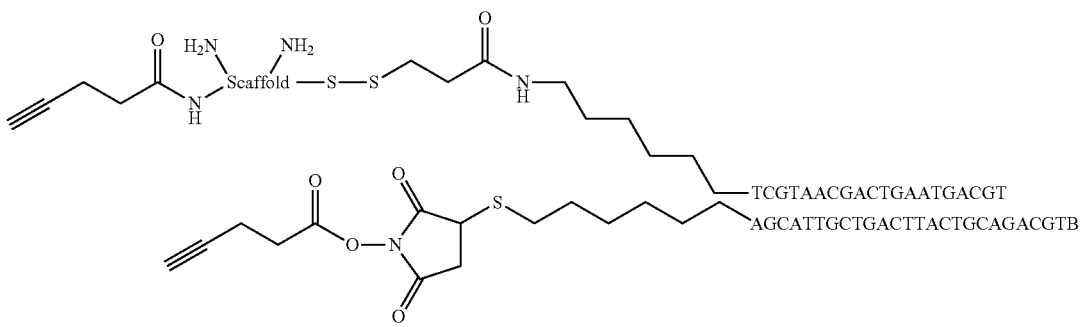

In the above figure, the first sequence is SEQ ID NO:5 and the second is SEQ ID NO:7.

Another example of transfer of functional entity is shown below using the amino oligo directly as the AE on the identifier molecule. The functional entity on the building block molecule used in this experiment was 4-pentynoic acid, as disclosed in example 2.

The annealing was performed using 500 pmol of the building block and the identifier molecules in 0.1 M MES buffer and incubating the mixture at 25° C. in a shaker for 2 hours. The reactive part (functional entity) of the building block was transfer to the amino group on the identifier molecule during the annealing (see below). After annealing and transfer the sample was purified by micro-spin gel filtration and analyzed by MS. The sample was prepared for MS analysis using equal amount of sample (about 100 pmol) and ion exchanger resin and incubated minimum 2 h at 25° in a shaker. After incubation the resin was removed by centrifugation and 15 μl of the supernatant was added 7 μl of water, 2 μl of piperidine and imidazole (each 625 mM) and 24 ul acetonitrile.

In the above figure, in both the starting materials and the products, the first sequence is SEQ ID NO:5 and the second is SEQ ID NO:7.

The sample was analysed on a Mass Spectroscopy instrument (Bruker Daltonics, Esquire 3000plus). The observed mass was 6398.04 Da, which correspond well with the calculated mass, 6400.00 Da. Thus, the MS spectra of the identifier molecule after transfer of the functional entity show a mass corresponding to the transferred functional entity on the identifier molecule. This example shows that functional entities can be transferred using this setup of a building block molecule and an identifier molecule.

Another example of transfer of functional entity is shown below using the amino oligo directly as the identifier molecule. The functional entity used in this experiment was 5-Hexynoic acid, prepared as shown in example 2.

The annealing was performed using 500 pmol of the building block and 500 pmol of the identifier molecules in 0.1 M

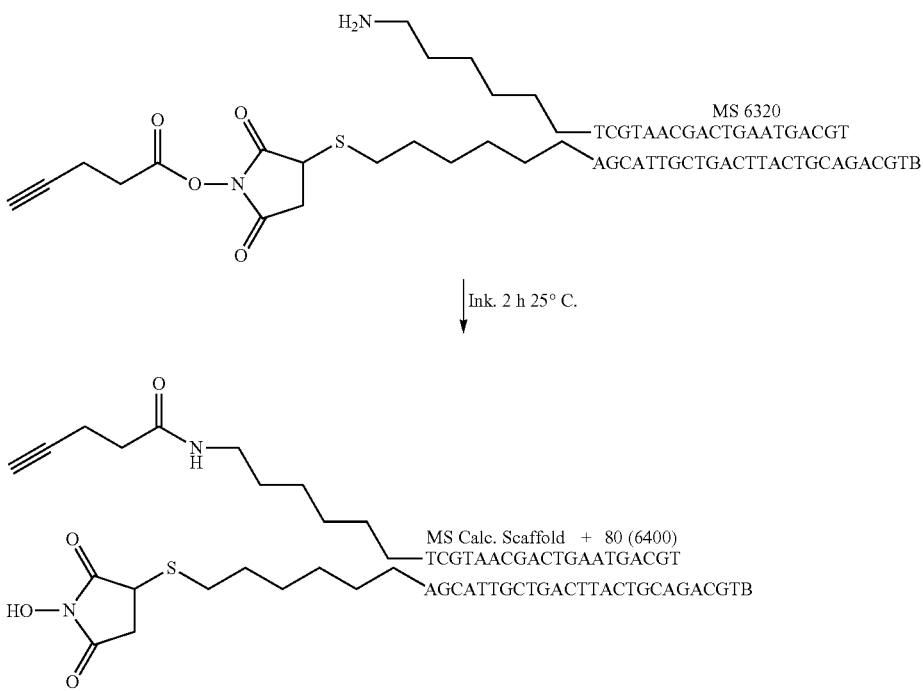

MES buffer incubated at 25° C. in a shaker for 2 hours. The reactive part (functional entity) of the building block was transferred to the amino group on the identifier molecule (see below). After annealing and transfer the sample was purified by micro-spin gel filtration and analyzed by MS. The sample was prepared for MS analysis using equal amount of sample (about 100 pmol) and ion exchanger resin and incubated minimum 2 h at 25° C. in a shaker. After incubation the resin was removed by centrifugion and 15 µl of the supernatant was added 7 µl of water, 2 µl of piperidine and imidazole (each 625 mM) and 24 ul acetonitrile.

molecule is extended in order to transfer the unique codon, that identifies the transferred functional entity, to the identifier molecule. This is accomplished by adding a suitable polymerase and a polymerase buffer containing the wild type nucleotides (dATP, dTTP, dCTP, dGTP). This will extend the identifier molecule in the 3'-end towards the end of the 5'-end of the building block molecule. The extension of the identifier molecule to transfer the unique anticodon(s) is preferably performed after the transfer of the FE as shown below.

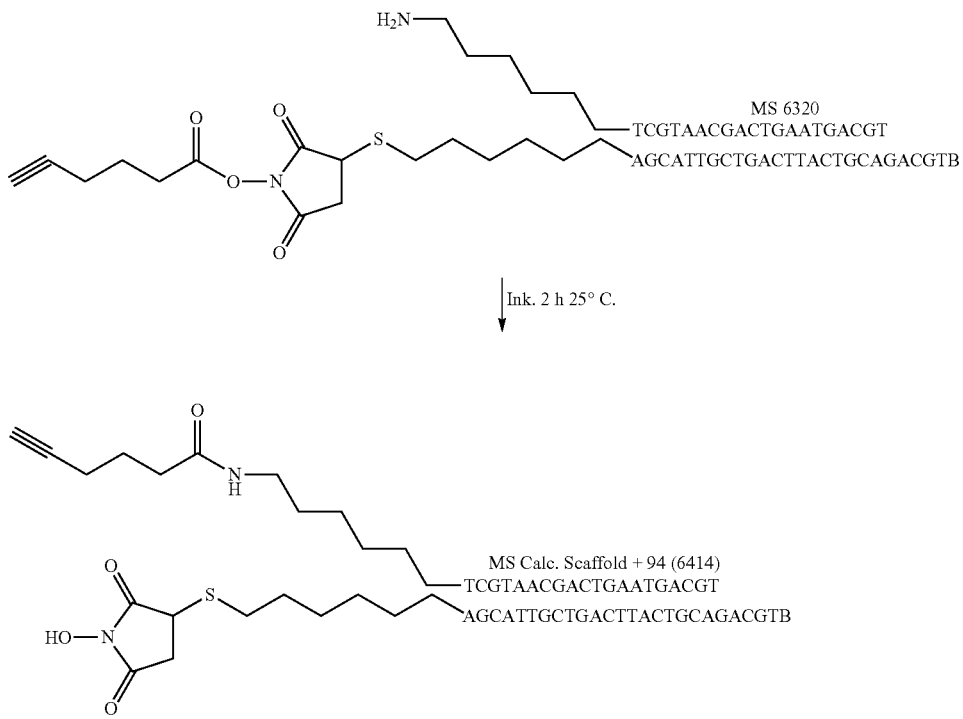

In the above figure, in both the starting materials and the products, the first sequence is SEQ ID NO:5 and the second is SEQ ID NO:7.

The sample was analysed on a Mass Spectroscopy instrument (Bruker Daltonics, Esquire 3000plus). The observed mass was 6411.96 Da, which correspond well with the calculated mass, 6414 Da. Thus, the MS spectra of the identifier molecule after transfer of the functional entity show a mass corresponding to the transferred functional entity onto the identifier molecule. This example shows that functional entities can be transferred using this setup of a building block molecule and an identifier molecule.

Example 4

Extension of the Identifier Molecule to Transfer Unique Codons

After the transfer of the functional entity (FE) to the attachment entity (AE) on the identifier molecule, the identifier

```
FE-AE-TCGTAACGACTGAATGACGT         (SEQ ID NO: 5)
   -AGCATTGCTGACTTACTGCAGACGTB     (SEQ ID NO: 7)
                    ↓
FE-AE-TCGTAACGACTGAATGACGTCTGCT    (SEQ ID NO: 166)
   -AGCATTGCTGACTTACTGCAGACGTB     (SEQ ID NO: 7)
```

The extension was performed using 15 units Taq polymerase in a buffer containing 0.4 mM of each nucleotide in an extension buffer (20 mM HEPES-KOH, 40 mM KCl, 8 mM $MgCl_2$, pH=7.4). After the extension reaction the sample was analyzed using MS. The MS analysis was performed using about 100 pmol purified extension mixture in a half volume of ion exchanger resin and incubated minimum 2 h at 25° C. in a shaker. After incubation the resin was removed by centrifugation and 15 µl of the supernatant was mixed with 7 µl of water, 2 µl of piperidine and imidazole (each 625 mM) and 24 µl acetonitrile. The sample was analysed on a Mass Spectroscopy instrument (Bruker Daltonics, Esquire 3000plus).

Figure 39:
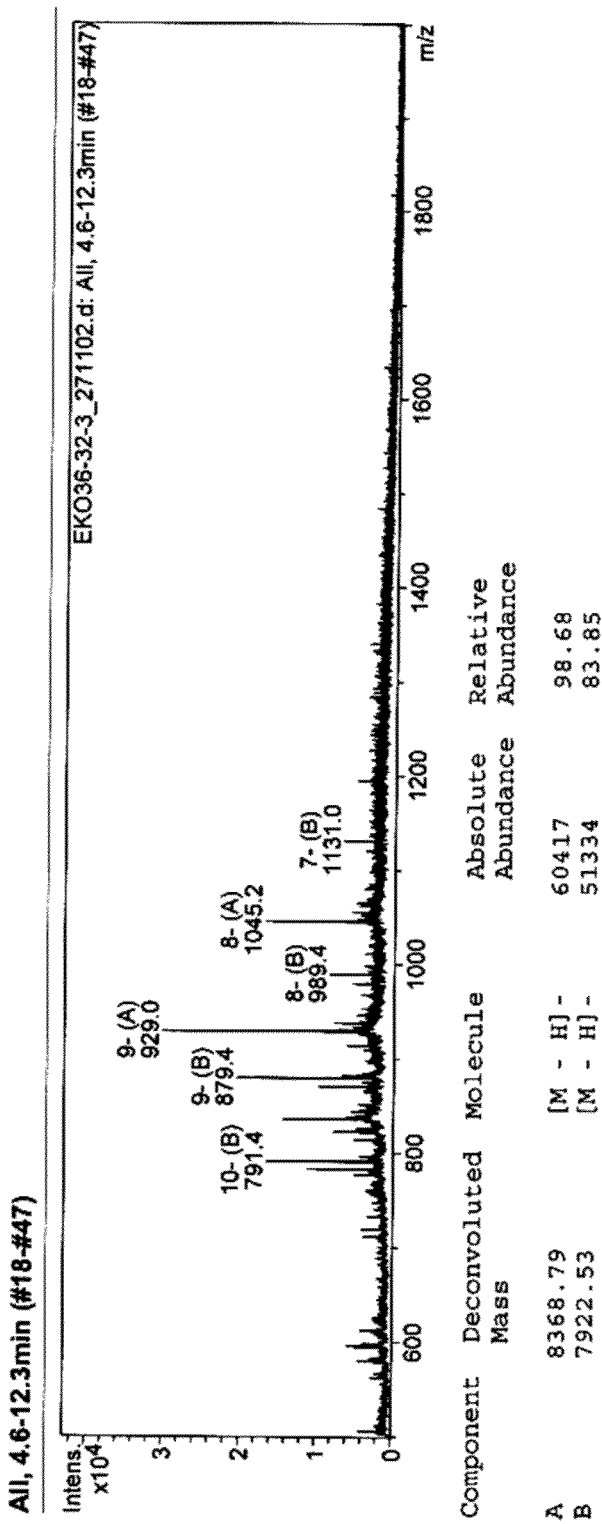
FIG. 39 is a mass spectrogram showing the observed mass (7922.53 Da) for the first sample of Example 4.

The MS data for extension on the identifier molecule with a transferred 4-Pentynoic acid is shown FIG. 39.

The observed mass was 7922.53 Da, which correspond well with the calculated mass, 7924.00 Da. The MS spectra of the identifier molecule after the transfer reaction of the functional entity and extension reaction of the encoding region (the unique codon) showed a mass corresponding to the transferred functional entity and the extension on the identifier molecule. This example shows that functional entities can be transferred using this setup with a longer building block molecule than the identifier molecule and that the identifier molecule can be extended using a polymerase after the transfer process. This shows the possibility to transfer both the functional entity and the unique codon from the same building block to an identifier molecule.

Figure 40:
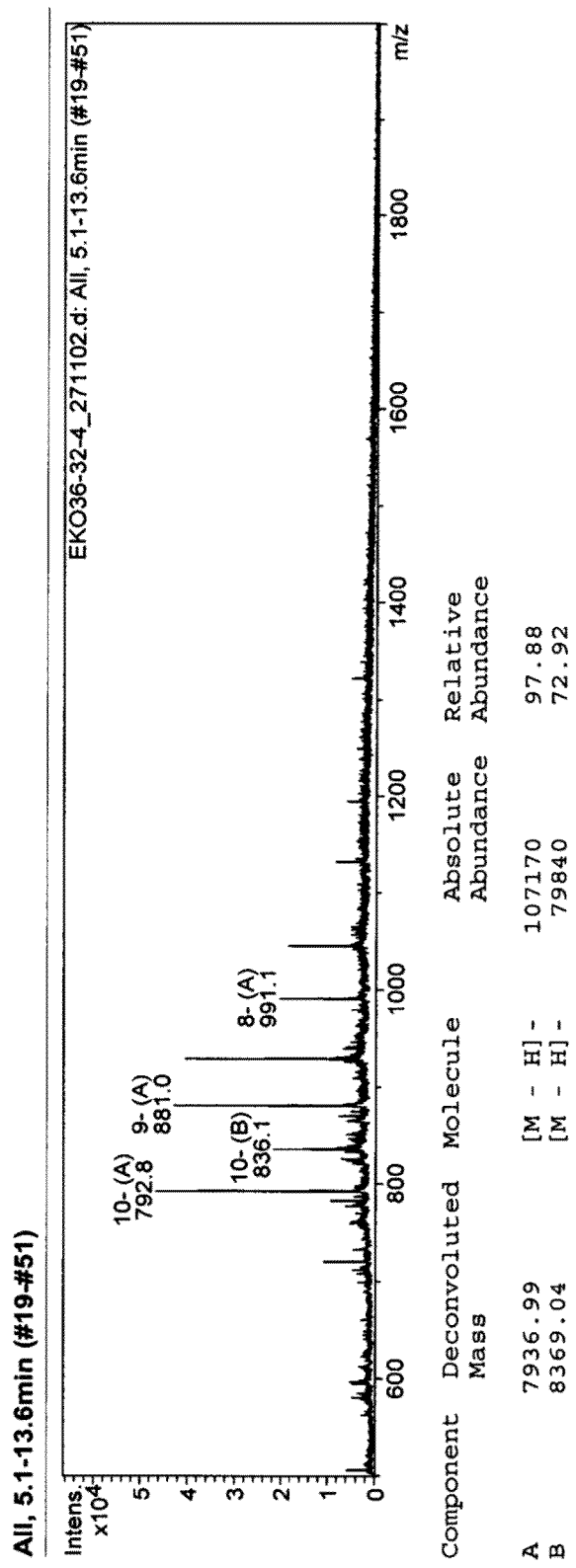
FIG. 40 is a mass spectrogram showing the observed mass (7936.99 Da) for the second sample of example 4.
Figure 41:
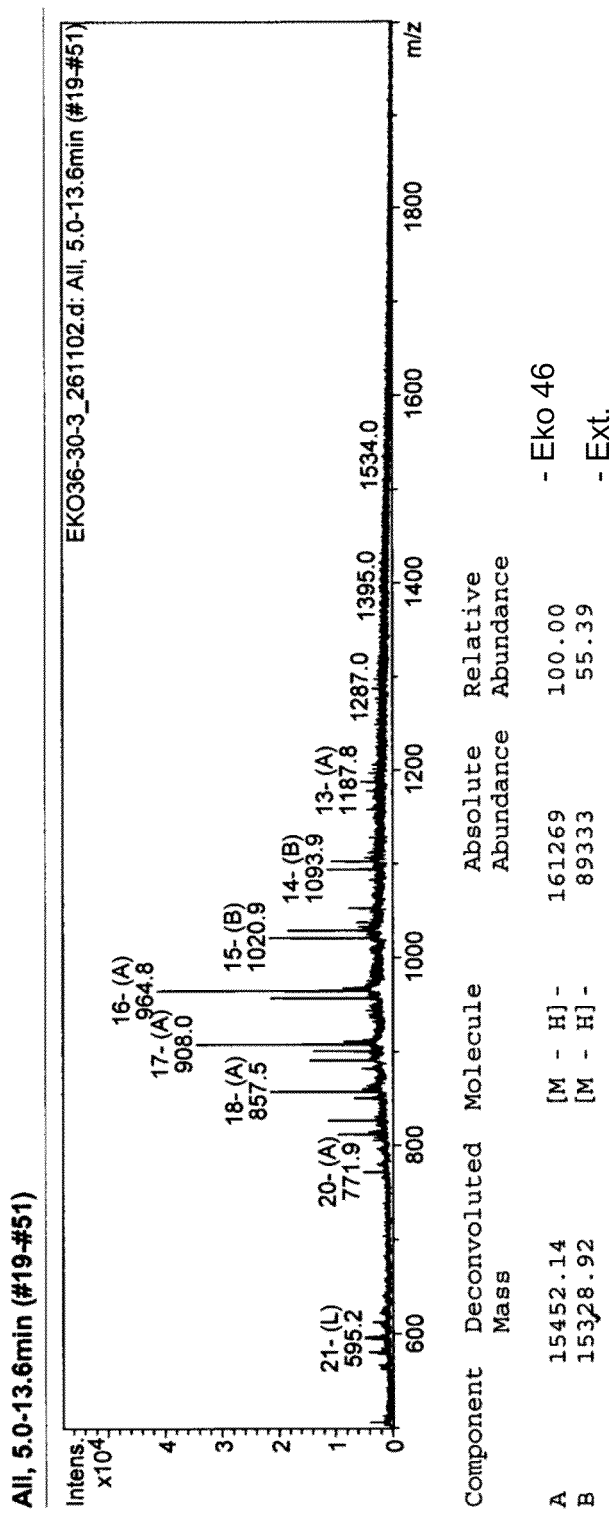
FIG. 41 is a mass spectrogram showing the observed masses or the template (15452.14 Da) and the extended primer (15328.92 Da) in the first experiment of example 5.
Figure 42:
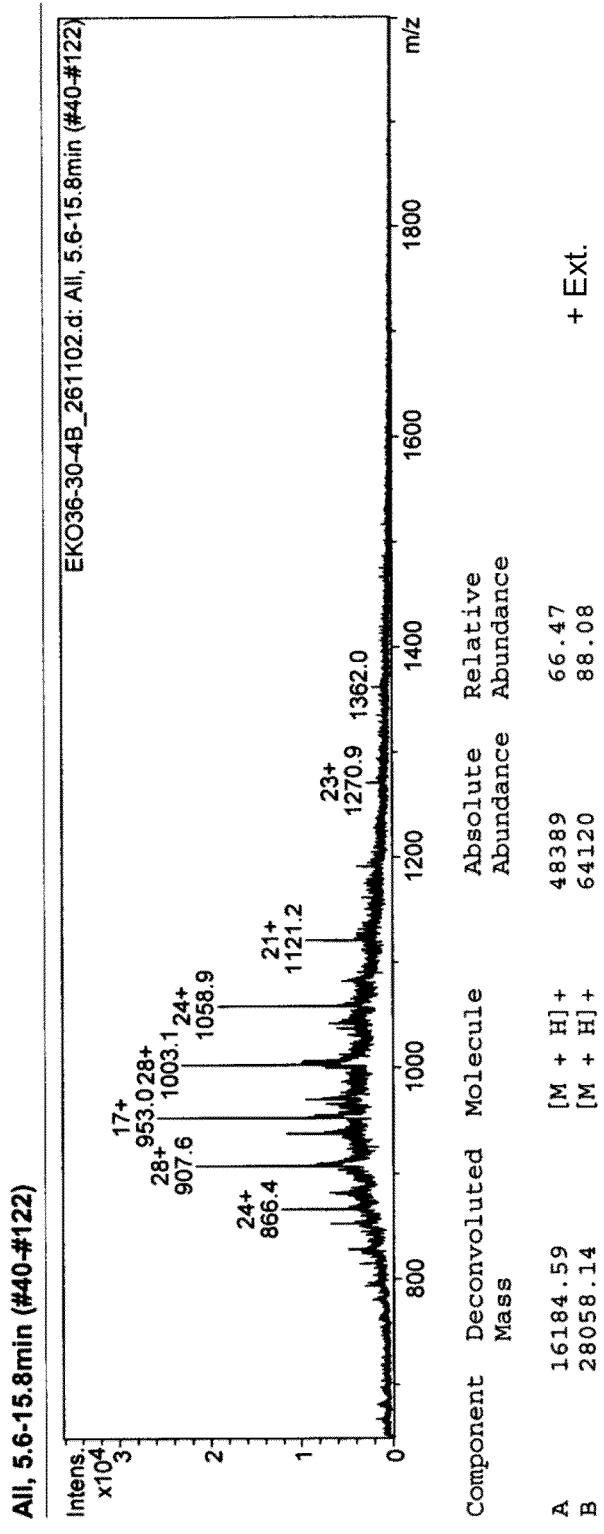
FIG. 42 is a mass spectrogram showing the observed mass for the extended primer (28058.14 Da) for the second experiment of example 5.
Figure 43:
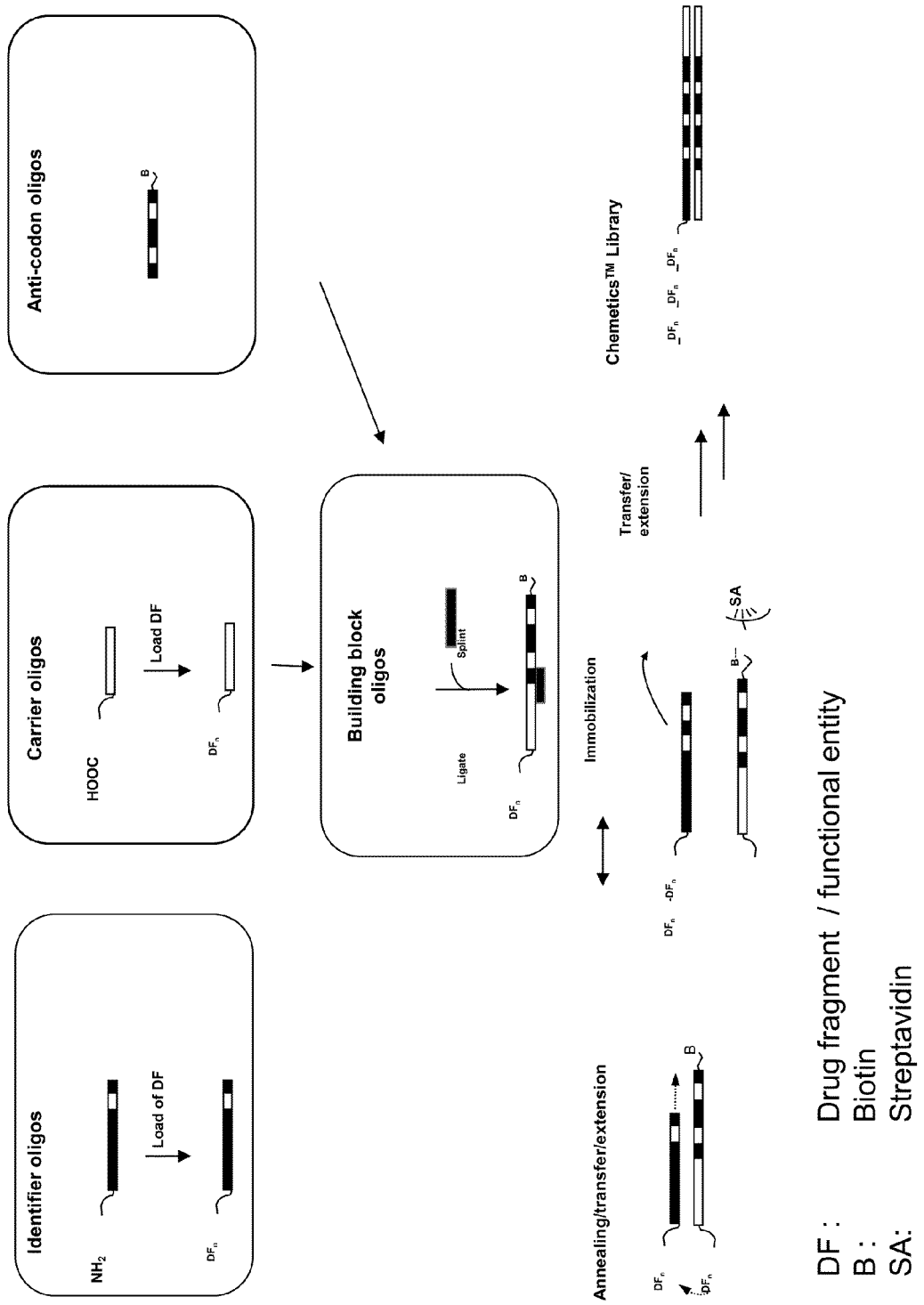
FIG. 43 is a flow chart for the production of one embodiment of a library of bifunctional complexes, as set forth in Example 7. DF: Drug fragment/functional entity; B: Biotin; SA: Streptavidin.
Figure 44:
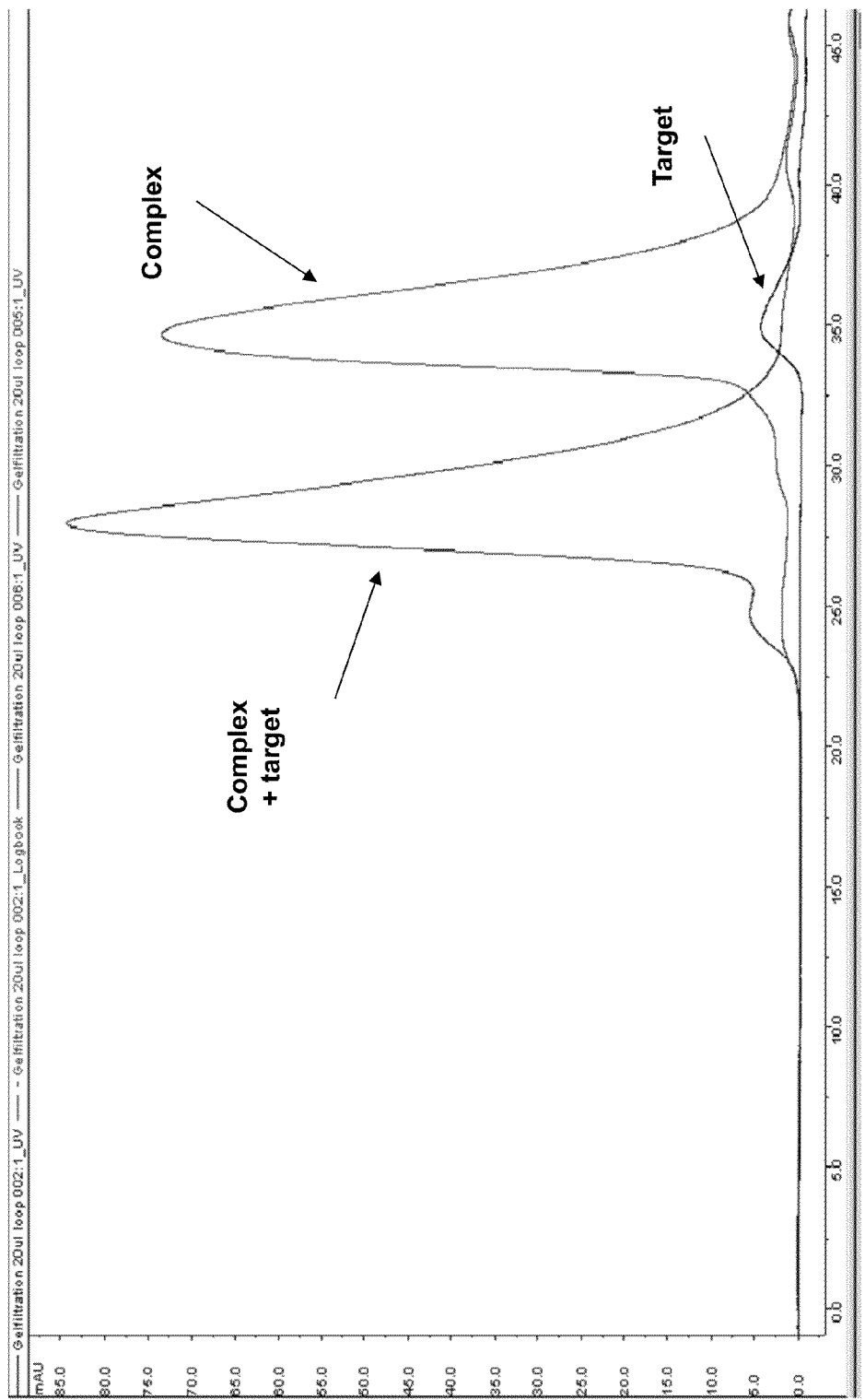
FIG. 44 shows the retention time of the complex of Example 8 on a size-exclusion column.
Figure 45:
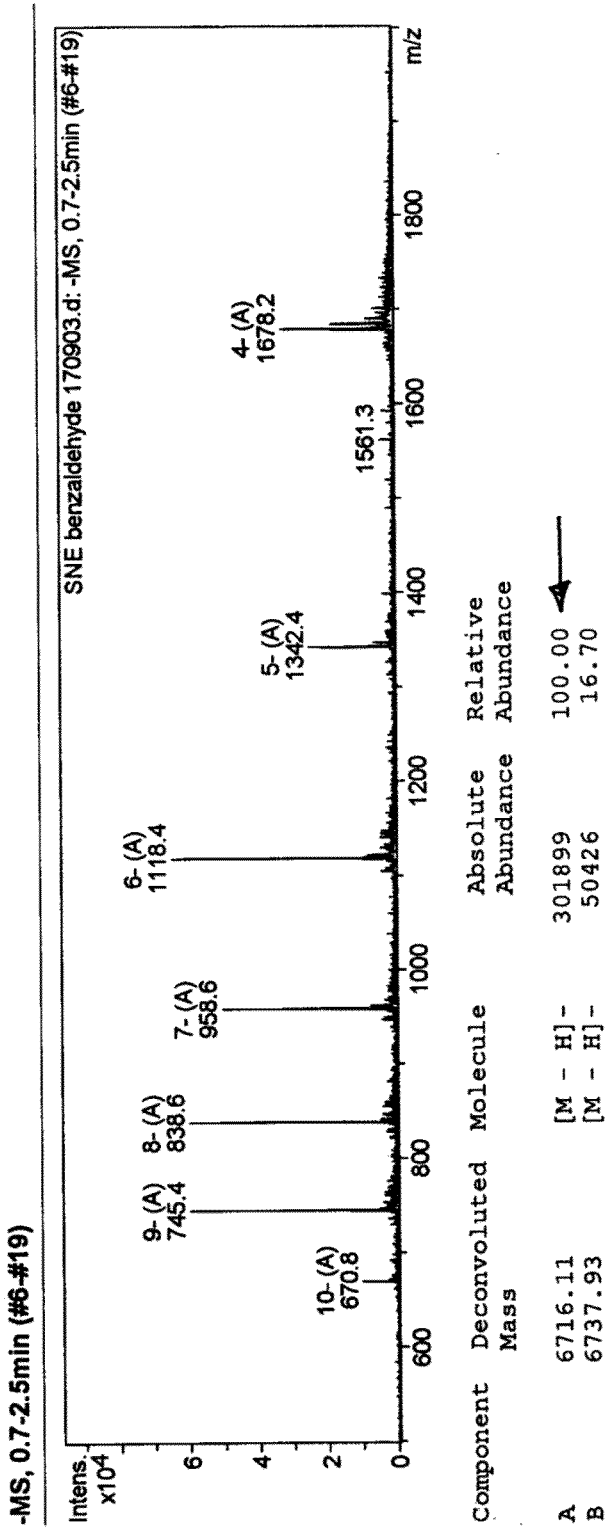
FIG. 45 is a mass spectrogram showing the observed mass (66716.11 Da) for the loaded oligo in Example 9, section 9.1.
Figure 46:
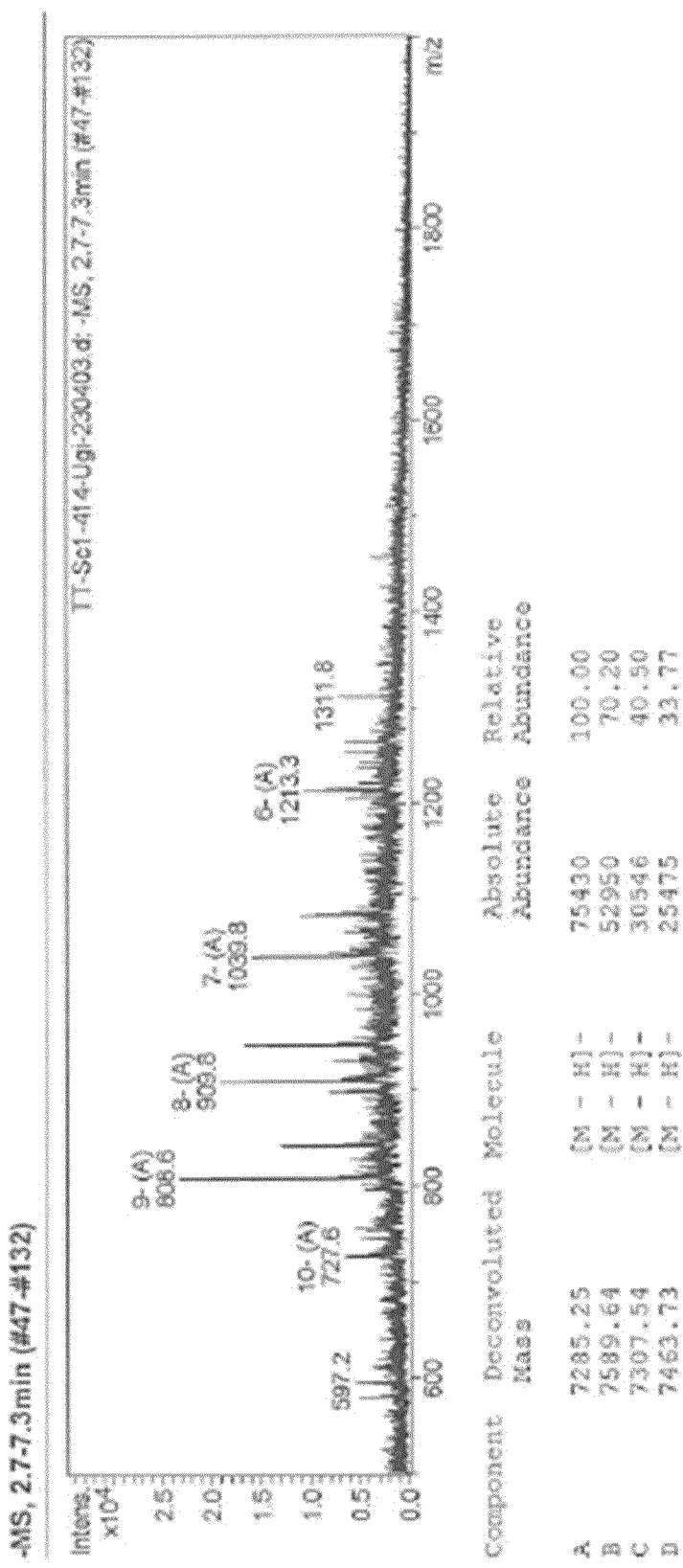
FIG. 46 is a mass spectrogram showing the observed masses for the starting benzaldehyde loaded L1 oligo (A) and the UGI product (B) in Example 9, section 9.2.
Figure 47:
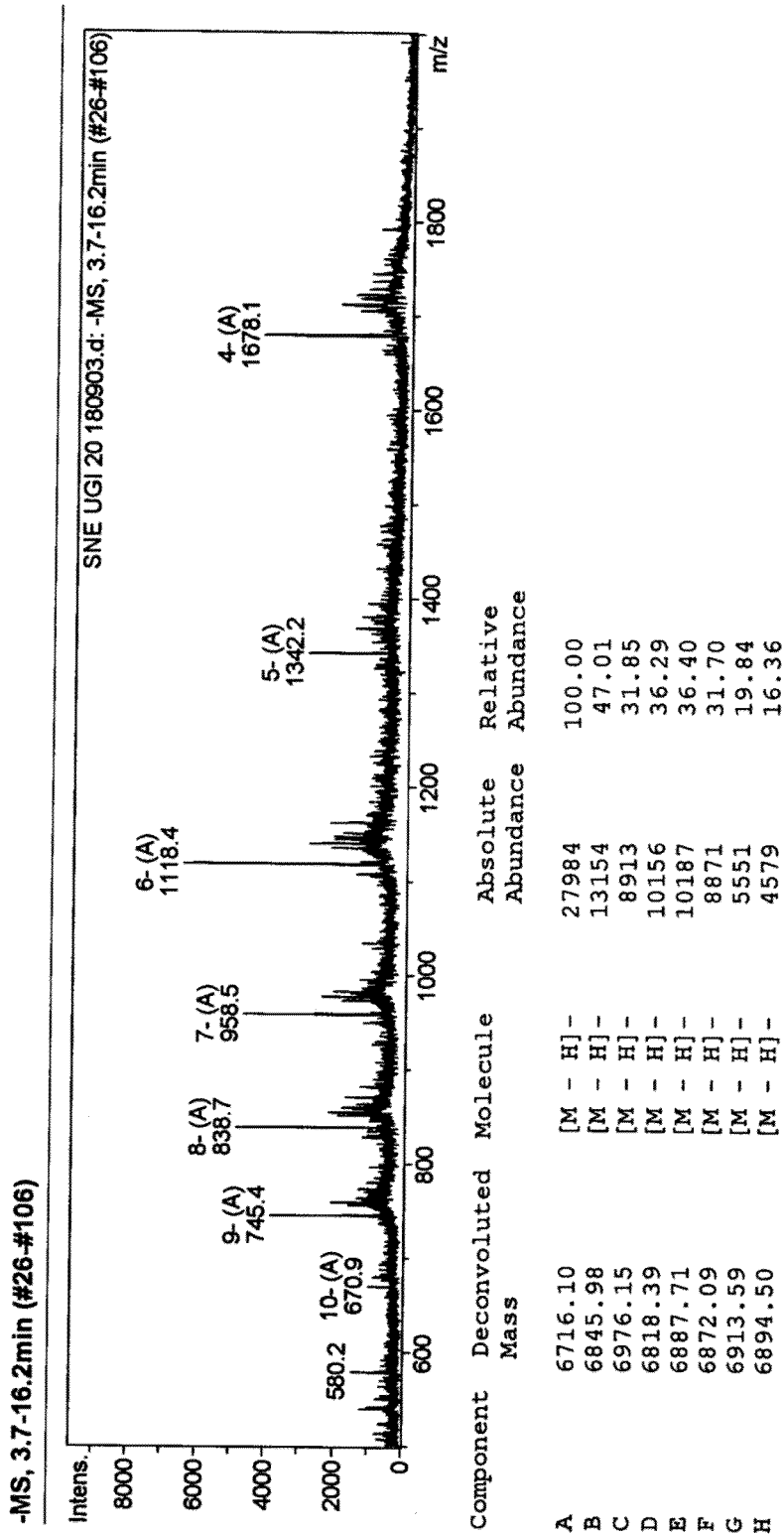
FIG. 47 is a mass spectrogram showing the observed masses for the starting benzaldehyde loaded L1 oligo (A), dilcetopiperazine (B), UGI product (C) and amine product (H) in Example 9, section 9.3.

Another example showing transfer and extension is for the building block with the functional entity 5-Hexynoic acid. The MS data for extension on the identifier molecule with a transferred 5-Hexynoic acid is shown in FIG. 40.

The observed mass was 7936.99 Da, which correspond well with the calculated mass, 7938.00 Da. The MS spectra of the identifier molecule after transfer reaction of the functional entity and extension reaction of the encoding region (the unique codon) showed a mass corresponding to the transferred functional entity and the extension on the identifier molecule. This example also shows that functional entities can be transferred using this setup with a longer building block molecule than the identifier molecule and the identifier molecule can be extended using a polymerase after the transfer process. This exemplifies the possibility to transfer both the functional entity and the unique codon from one building block molecule to one identifier molecule.

Example 5

Library Design

The identifier molecule can be designed to operate optimal under various conditions. However, it should contain a few elements that are vital for the function. The identifier molecule should comprise of a sequence that can anneal to the building block and an attachment entity that can accommodate various functional entities. Below is an example on how an identifier molecule can be designed in the extension region. The region that becomes extended during each step of transfer and encoding can be designed using various approaches. Importantly, there must be a base-pair match between the building block and the identifier to allow efficient extension using a polymerase. This can be accomplished using either a region that is constant, the binding region as described in FIG. 3 (A), or a region that allow binding to any given sequence, also shown in FIG. 3 (B). A combination of these to approaches can also be used.

The first step in the extension process needs no special binding region due to the match of the identifier and the building block molecules (step 1 shown below). However, the subsequently steps needs a binding region sufficient complementary to the identifier molecule to allow for hybridisation because the enzyme, preferably a polymerase must be able to bind to the douplex and perform an extension. The example below shows four steps in the encoding procedure. This process of extension can be continued to obtain the suitable number of transfer of building blocks. The binding region in this example contains 6 nucleotides, but this can be varied dependent on the design of the building blocks.

A possibility to accommodate the possible mismatches in the previous anticodon is to use universal nucleobases, i.e. a nucleobases with the ability to base pair with more than one of the natural nucleobases. A possible base is inosine which can form base pairs with cytidine, thymidine, and adenosine (although the inosine:adenosine pairing presumably does not fit quite correctly in double stranded DNA, so there may be an energetic penalty to pay when the helix bulges out at this purine:purine pairing). In principle, any design that allows extension of the unique codons is possible to use

The invention claimed is:

1. A method for obtaining a library comprising bifunctional complexes, wherein each complex comprises a display molecule part and coding part, said method comprising the steps of:
   (a) reacting a nascent bifunctional complex comprising a chemical reaction site and a priming site at the chemical reaction site with one or more reactants; and
   (b) reacting the priming site with one or more tags identifying the one or more reactants, the reaction being catalyzed by an enzyme;
   wherein steps (a) and (b) provide an intermediate bifunctional complex having a modified chemical reaction site containing a structural entity formed from the nascent bifunctional complex and the one or more reactants and a modified priming site containing the one or more tags;
   (c) reacting the intermediate bifunctional complex with one or more additional reactants at the modified reactant site and one or more additional tags identifying the one or more additional reactants at the modified priming site using the methods of steps (a) and (b);
   (d) optionally repeating step (c) as many times as desired; and
   (e) obtaining a library of different bifunctional complexes; wherein the library is produced using split and mix methods, and
   wherein the coding part comprises an identifier oligonucleotide comprising tags identifying the reactants which have participated in the formation of the display molecule, and a reactant and the tag identifying the reactant are not linked prior to their reaction with the chemical reaction site and the priming site, respectively, of the nascent bifunctional complex.

2. The method of claim 1, wherein the bifunctional complexes comprise a reaction product and an identifier oligonucleotide comprising tags identifying the reactants which have participated in the formation of the reaction product.

3. The method of claim 1, wherein the sequence of the tags of the identifier oligonucleotide of the bifunctional complex is used to decipher the structure of the reactants that have participated in the formation of the display molecule.

4. The method of claim 1, wherein the order of the tags determines the order of incorporation of reactants into the display molecule.

5. The method of claim 1, wherein a single reactant is reacted with the chemical reaction site in a reaction cycle, said reaction cycle further comprising adding a single tag identifying the reactant with the priming site wherein one or more enzymes catalyzes the addition of the tag.

6. The method of claim 1, wherein multiple reactants are reacted with the chemical reaction site in a reaction cycle, said reaction cycle further comprising adding multiple respective tags identifying the reactants with the priming site wherein one or more enzymes catalyzes the addition of the tags.

7. The method of claim 1, wherein the bifunctional complex is prepared by sequentially adding a tag and reacting a reactant.

8. The method of claim 1, wherein the chemical reaction site comprises a single reactive group.

9. The method of claim 1, wherein the chemical reaction site comprises a scaffold having one or more reactive groups attached.

10. The method of claim 9, wherein there is provided a scaffold "X" linked to a tag "x" identifying said scaffold, wherein a reactant "A" is reacted with scaffold "X", said reaction resulting in "A" being linked to "X", and wherein a tag "a" is added to the scaffold tag "x".

11. The method of claim 9, wherein the scaffold is selected from the group consisting of benzodiazepines, steroids, hydantoins, piperazines, diketopiperazines, morpholines, tropanes, cumarines, quinolines, indoles, furans, pyrroles, oxazoles, amino acid precursors, and thiazoles.

12. The method of claim 1, wherein the chemical reaction site comprises multiple reactive groups capable of reacting with one or more reactants.

13. The method of claim 12, wherein at least one of the multiple reactive groups is selected from the group consisting of hydroxyl groups, carboxylic acid groups, aldehyde groups, thiol groups, isocyanate groups, amine groups, ester groups, thioester groups, alkylating agents and acylating agents.

14. The method of claim 1, wherein a reactant among the one or more reactants comprises a reactive group or an activatable reactive group precursor.

15. The method of claim 1, wherein the reaction of a reactant and the chemical reaction site takes place in the presence of a further reactant mediating a connection between the reactant and the chemical reaction site.

16. The method of claim 1, wherein the reactant among the one or more reactants is a precursor for a structural entity incorporated into the display molecule.

17. The method of claim 1, wherein the number of reactive groups of the one or more reactants is from one to ten.

18. The method of claim 17, wherein the one or more reactive groups include an amino group.

19. The method of claim 1, wherein the display molecule comprises a polymer or a scaffold, and a reactant featuring only one reactive group is used in the end positions of the polymer or the scaffold.

20. The method of claim 1, wherein the display molecule comprises a polymer or a scaffold, and a reactant having two reactive groups is used for the formation of the body part of a polymer or scaffolds capable of being reacted further.

21. The method of claim 1, wherein two or more reactive groups are present on a scaffold in the form of a core structure, and different molecules of the scaffold are reacted with different reactants thereby generating different, scaffolded display molecules.

22. The method of claim 21, wherein reactants reacting with the scaffold contain one, two or several reactive groups capable of forming a connection with the scaffold.

23. The method of claim 1, wherein the nascent bifunctional complex further comprises a linking moiety, connecting the chemical reaction site and the priming site.

24. The method of claim 23, wherein the linking moiety of the nascent bifunctional complex comprises information relating to the identity of the chemical reaction site.

25. The method of claim 23, wherein the linking moiety is a nucleic acid sequence to which a complementing oligonucleotide can hybridise.

26. The method of claim 23, wherein the linking moiety is attached to the chemical reaction site via a spacer comprising a selectively cleavable linker.

27. The method of claim 26, wherein the selectively cleavable linker is cleaved and the display molecule is detached from the identifier oligonucleotide of the bifunctional complex after the formation of a final bifunctional complex.

28. The method of claim 26, wherein the selectively cleavable linker is cleaved by electromagnetic radiation.

29. The method of claim 27, wherein the bifunctional complex comprises a selectively cleavable linker capable of being cleaved by electromagnetic radiation, wherein said bifunctional complex is selected from the group consisting of

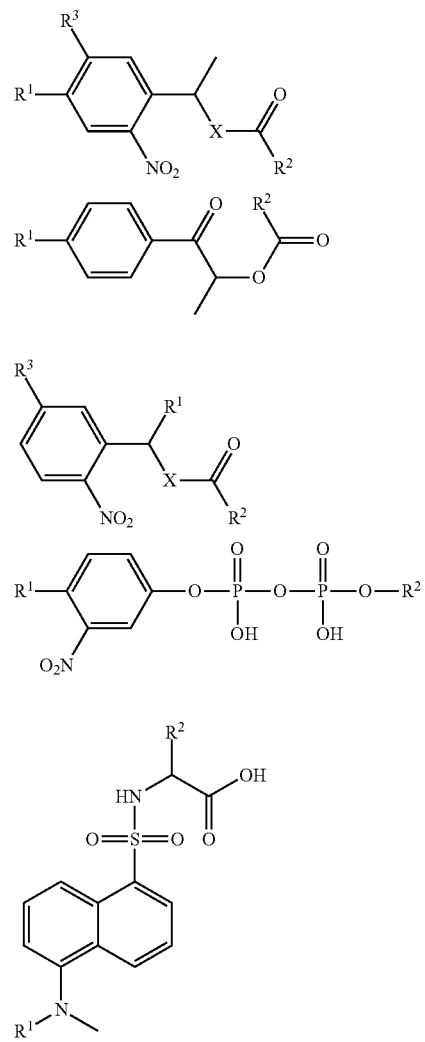

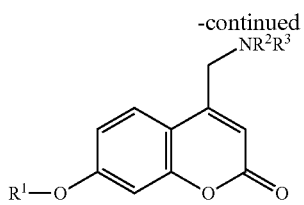

wherein $R^1$ and $R^2$ are selected from the group consisting of a display molecule and an identifier oligonucleotide comprising tags identifying the reactants which have participated in the formation of the display molecule;

wherein $R^3$ is H or $OCH^3$; and wherein X is O or NH.

30. The method of claim 1, wherein the identifier oligonucleotide comprises 3, 4, 5, or more tags.

31. The method of claim 1, wherein the priming site comprises one, two, or more nucleotides, to which a complementing oligonucleotide can hybridise.

32. The method of claim 31, wherein the priming site comprises a 3'-OH or 5'-phosphate group of a nucleotide.

33. The method of claim 1, wherein all tags of the identifier oligonucleotide are attached using an enzymatically catalysed reaction.

34. The method of claim 1, wherein the tags are unique tags.

35. The method of claim 1, wherein the identifier oligonucleotide of the bifunctional complex comprises a double stranded oligonucleotide in order to reduce reaction between the oligonucleotide and the reactants.

36. The method of claim 1, wherein the identifier oligonucleotide of the bifunctional complex is amplifiable.

37. The method of claim 1, wherein the nucleotides of the identifier oligonucleotide are selected from DNA and RNA.

38. The method of claim 1, wherein the nucleotides of the identifier oligonucleotide are composed of a nucleobase moiety and a backbone unit, wherein the backbone unit is composed of a sugar moiety and an internucleoside linker.

39. The method of claim 38, wherein at least one nucleobase moiety is a naturally occurring nucleobase and at least one other nucleobase moiety is a non-naturally occurring nucleobase moiety.

40. The method of claim 38, wherein the nucleobase is selected from the group consisting of purine heterocycles, pyrimidine heterocycles and heterocyclic analogues and tautomers thereof.

41. The method of claim 39, wherein the nucleobase is selected from the group consisting of adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine and inosine.

42. The method of claim 40, wherein the nucleobase is selected from the group consisting of adenine, guanine, thymine, cytosine, 5-methylcytosine and uracil.

43. The method of claim 38, wherein the backbone units of the identifier oligonucleotide are selected independently from the group consisting of

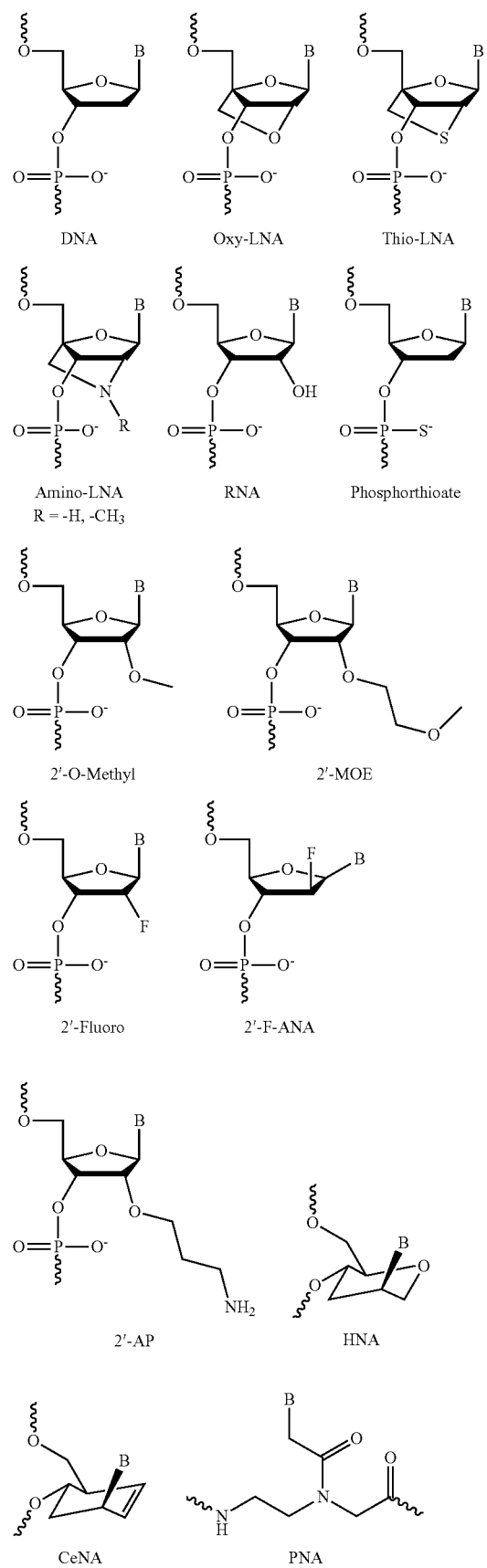

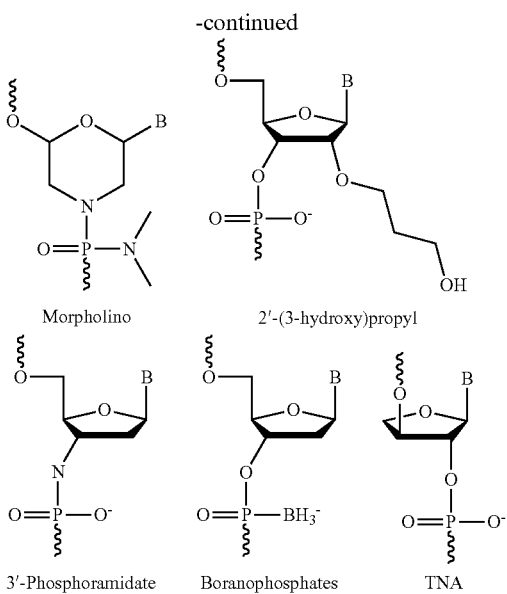

wherein B denotes a nucleobase.

44. The method of claim 38, wherein the sugar moiety of the backbone unit is a pentose.

45. The method of claim 44, wherein the pentose is selected from the group consisting of ribose, 2'-deoxyribose, 2'-O-methyl-ribose, 2'-fluor-ribose, and 2'-4'-O-methylene-ribose (LNA).

46. The method of claim 44 or 45, wherein the nucleobase of the nucleotide is attached to the 1' position of the pentose.

47. The method of claim 38, wherein the internucleoside linker linking two neighbouring nucleotides of the identifier oligonucleotide is selected from the group consisting of phosphodiester bonds, phosphorothioate bonds, methylphosphonate bonds, phosphoramidate bonds, phosphotriester bonds and phosphodithioate bonds.

48. The method of claim 38, wherein the identifier oligonucleotide comprises naturally occurring nucleosides of the DNA and RNA family connected through phosphodiester linkages.

49. The method of claim 48, wherein the deoxynucleosides are selected from the group consisting of deoxyadenosine, deoxyguanosine, deoxythymidine, and deoxycytidine, and wherein the nucleosides are selected from adenosine, guanosine, uridine, cytidine, and inosine.

50. The method of claim 1, wherein each tag codes for different reactants and wherein the structure of the display molecule is deduced by taking into account different attachment chemistries, steric hindrance and deprotection of orthogonal protection groups.

51. The method of claim 1, wherein individual tags are distinguished from each other by only a single nucleotide.

52. The method of claim 1, wherein two or more differences distinguish a tag from any other tag.

53. The method of claim 1, wherein the length of the tags is 5 nucleotides, and wherein more than 100 nucleotide combinations exist for generating two or more differences between any two tags.

54. The method of claim 1, wherein the tags have from 2 to 100 nucleotides.

55. The method of claim 54, wherein the tags have from 3 to 50 nucleotides.

56. The method of claim 54, wherein the tags have from 4 to 20 nucleotides.

57. The method of claim 54, wherein the tags have from 5 to 15 nucleotides.

58. The method of claim 1, wherein each tag is separated by a binding region of from 1 to 20 nucleotides.

59. The method of claim 58, wherein each binding region identifies the position of a tag in the identifier oligonucleotide.

60. The method of claim 58, wherein the binding regions comprise one or more nucleobases forming three hydrogen bonds to a cognate nucleobase.

61. The method of claim 60, wherein said nucleobases are guanine and cytosine.

62. The method of claim 59, wherein the binding region has a backbone modification selected from the group consisting of 2'-O-methyl substitution of a ribose moiety, 2'-4' O-methylene cyclisation of the ribose moiety (Locked Nucleic Acid; LNA), and peptide nucleic acids (PNA).

63. The method of claim 1, wherein two or more reactants are reacted with the chemical reactive site, and wherein the tags of the identifier oligonucleotide are separated by a binding region.

64. The method of claim 63, wherein the binding region is a substrate recognised by an enzyme selected from a polymerase and a ligase.

65. The method of claim 1, wherein each tag comprises nucleotides identifying a reactant and a framing sequence identifying the synthesis history of the reactant.

66. The method of claim 1, wherein the tags further comprise a flanking region comprising a signal group allowing for detection of the bifunctional complex.

67. The method of claim 66, wherein the flanking regions comprise a detectable label.

68. The method of claim 66, wherein the flanking regions comprise priming sites for PCR amplification.

69. The method of claim 1, wherein the display molecule is the reaction product of two or more reactants with the chemical reaction site.

70. The method of claim 1, wherein the display molecule is the reaction product of more than one reactant and the chemical reaction site of the bifunctional complex.

71. The method of claim 1, wherein the display molecule is a non-polymeric molecule having a molecular weight of less than 1000 Da.

72. The method of claim 1, wherein a first reactant forms an intermediate product upon reaction with the chemical reactive site and a second reactant reacts with the intermediate product to obtain the display molecule, or a precursor thereof.

73. The method of claim 1, wherein two or more reactants react with each other to form an intermediate product and the chemical reactive site reacts with this intermediate product to obtain the display molecule, or a precursor thereof.

74. The method of claim 1, wherein the enzyme used for enzymatic addition of a tag to the priming site is selected from the group consisting of a polymerase, a ligase, and a recombinase.

75. The method of claim 1, wherein the tag is attached to the priming site of a nascent bifunctional complex by using an enzymatic extension reaction.

76. The method of claim 75, wherein the extension reaction is performed by a polymerase or a ligase, or a combination thereof.

77. The method of claim 1, wherein the enzyme is a ligase.

78. The method of claim 77, wherein the substrate for the ligase is an oligonucleotide comprising two or more nucleotides.

79. The method of claim 77, wherein the ligase mediates a single stranded ligation, wherein an oligonucleotide tag is ligated to the nascent bifunctional molecule.

80. The method of claim 79, wherein the single stranded ligation is performed by ligating a 3'—OH group of a first nucleic acid selected from the priming site and the oligonucleotide tag to a 5' phosphate group of a second nucleic acid selected from the priming site and the oligonucleotide tag, with the proviso that the two nucleic acids carry different reactive groups capable of being ligated.

81. The method of claim 77, wherein the ligase mediates a double stranded ligation, wherein the priming site of the nascent bifunctional complex hybridises to a complementing oligonucleotide prior to ligation to an oligonucleotide tag.

82. The method of claim 81, wherein double stranded ligation takes place in the presence of a third oligonucleotide complementing part of the 3' end and part of the 5' end, respectively, of a first and second nucleic acid, said first and second nucleic acids being selected from the priming site and the oligonucleotide tag.

83. The method of claim 77, wherein the ligase is selected from the group consisting of Taq DNA ligase, T4 DNA ligase, T4 RNA ligase, T7 DNA ligase, and E. coli DNA ligase.

84. The method of claim 81 or 82, wherein the double stranded oligonucleotide to be ligated has blunt ends, and wherein a T4 RNA ligase is used for ligating said blunt ends.

85. The method of claim 81 or 82, wherein the double stranded oligonucleotide to be ligated has sticky ends, and wherein a Taq DNA ligase is used for ligating said sticky ends.

86. The method of claim 77, wherein a combination of polymerase transcription and ligational coupling of hybridised and complementary oligonucleotides is used for generating a double stranded identifier oligonucleotide.

87. The method of claim 86, wherein a gap in an otherwise double stranded identifier oligonucleotide is initially filled-in by a polymerase and then ligated by a ligase to an upstream oligonucleotide to produce an exclusively double stranded identifier oligonucleotide.

88. The method of claim 1, wherein the enzyme reactions are conducted in aqueous solvent, and wherein at least some reactions between a reactant and the chemical reaction site are carried out in an organic solvent.

89. The method of claim 88, wherein no lyophilization step is included in the method, and wherein appropriate reaction conditions are obtained by adding a solvent to the aqueous solvent.

90. The method of claim 89, wherein the added solvent is miscible with the aqueous solvent, wherein the addition of the solvent produces a homogeneous reaction solvent.

91. The method of claim 1, wherein the display molecule of a nascent bifunctional complex is protected by protection groups.

92. The method of claim 1, wherein the reactive groups of the chemical reaction site are initially in an activatable pro-form, wherein the activatable pro-form reactive groups are activated prior to reaction with a reactant.

93. The method of claim 92, wherein the activatable pro-form reactive groups are protected with a group preventing reaction with a reactant.

94. The method of claim 1, wherein the nascent bifunctional complexes are provided in separate reaction compartments and wherein the reaction between the chemical reaction site and one or more reactants and reaction of the priming site with the one or more tags are performed in the separate reaction compartments.

95. The method of claim 94, wherein the nascent bifunctional complexes provided in each separate reaction compartment are identical.

96. The method of claim 94, wherein the nascent bifunctional complexes provided in each separate reaction compartment are different.

97. The method of claim 94, wherein the nascent bifunctional complexes differ at the chemical reaction site and wherein each of the nascent bifunctional complexes comprises a tag identifying the structure of the chemical reaction site.

98. The method of claim 94, wherein the reactants applied in each separate reaction compartment are identical.

99. The method of claim 94, wherein the reactants applied in each separate reaction compartment are different.

100. The method of claim 94, wherein the reaction conditions in each separate reaction compartment are the same.

101. The method of claim 94, wherein the reaction conditions in each separate reaction compartment are different.

102. The method of claim 94, wherein the nascent bifunctional complex is reacted with more than a single reactant.

103. The method of claim 94, wherein two or more reaction compartments are pooled together after the formation in each reaction compartment of a bifunctional complex and subsequently split into an array of further reaction compartments for a subsequent round of reaction.

104. The method of claim 103 comprising more than one round of bifunctional complex synthesis, wherein the reaction product of a preceding synthesis round is used as a nascent bifunctional complex in a subsequent synthesis round for obtaining a library of different bifunctional complexes each comprising a display molecule and an identifier oligonucleotide comprising tags identifying the reactants which have participated in the formation of individual display molecules.

105. The method of claim 104, wherein the separate reaction compartments are mixed together and split into further reaction compartments between each round of synthesis.

106. The method of claim 103, wherein two or more reactant reactions occur before a tag is added to the priming site.

107. The method of claim 104, wherein the last round of synthesis of the bifunctional complex includes the incorporation of an oligonucleotide comprising a priming site.

108. The method of claim 94, wherein the library contains from $10^5$ to $10^8$ different bifunctional complexes.

109. The method of claim 94, wherein the library contains from $10^5$ to $10^{10}$ different bifunctional complexes.

110. The method of claim 1, wherein a bicyclic product is formed by the reaction between a) the nascent bifunctional complex comprising one or more chemical reaction sites and b) one or more reactants.

111. The method of claim 1, wherein the enzyme reactions are conducted in aqueous solvent, and wherein at least some reactions between a) a reactant and the chemical reaction site are carried out in water.

112. The method of claim 1, wherein a covalently linked bifunctional complex is formed.

113. The method of claim 1, wherein a branched product is formed.

114. The method of claim 1, wherein a linear product is formed.

115. The method of claim 94 comprising the further step of identifying, from the library of different bifunctional complexes, one or more display molecule(s) having a predetermined property, wherein the method for identifying the one or more display molecule(s) comprises the steps of a) subjecting the library of bifunctional complexes produced by the method of claim 113 to a selection condition, wherein one or more display molecules having said predetermined property is partitioned from the remainder of the bifunctional complexes of the library, and b) identifying the one or more display molecules having said predetermined property by decoding the identifier oligonucleotide of the partitioned one or more bifunctional complexes.

116. The method of claim 115, wherein the partitioned display molecules are partitioned by a method involving one or more of the steps of plastic binding, nitrocellulose filter binding, column chromatography, filtration, affinity chromatography and centrifugation.

117. The method of claim 115, wherein the identifier oligonucleotide of the bifunctional complex is in single stranded form.

118. The method of claim 115, wherein the identifier oligonucleotide of the bifunctional complex is in double stranded form.

119. The method of claim 115, wherein the selection condition involves the step of contacting the library of bifunctional complexes with a target selected from the group consisting of a protein, a peptide, a carbohydrate, a polysaccharide, a glycoprotein, a hormone, a receptor, an antigen, an antibody, a virus, a substrate, a metabolite, a transition state analog, a cofactor, an inhibitor, a drug, a dye, a nutrient, a growth factor, a cell, a tissue, an angiotensin converting enzyme, a renin, a cyclooxygenase, a 5-lipoxygenase, an IIL-10 converting enzyme, a cytokine receptor, a PDGF receptor, a type II inosine monophosphate dehydrogenase, a β-lactamase, a fungal cytochrome P-450, a bradykinin, a neutrophil elastase, a HIV protein, a nucleocapsid, VEGF, bFGF, TGFβ, KGF, PDGF, thrombin, theophylline, caffeine, substance P, IgE, sPLA2, red blood cells, glioblastomas, fibrin clots, PBMCs, hCG, lectins, selectins, cytokines, ICP4, and complement proteins, wherein bifunctional complexes having an affinity for the target are partitioned form the remainder of the library by removing non-binding bifunctional complexes from the bifunctional complexes having an affinity for the target, and subsequently eluting under more stringent selection conditions bifunctional complexes having an affinity for said target.

120. The method of claim 115, wherein the identifier oligonucleotide of the partitioned bifunctional complexes is cleaved from the display molecule after the removal of the non-binding bifunctional complexes.

121. The method of claim 120, wherein the identifier oligonucleotide of the partitioned bifunctional complexes is recovered and decoded for identifying the respective display molecules.

122. The method of claim 115, wherein a single round of selection against a specific target is followed by amplification of the partitioned bifunctional complexes variants.

123. The method of claim 122, wherein the selected bifunctional complex variants are separately tested in an assay.

124. The method of claim 115, wherein more selection rounds against a specific target are followed by amplification of the partitioned bifunctional complexes variants.

125. The method of claim 124, wherein several selection rounds employ increased stringency conditions.

126. The method of claim 125, wherein an amplification of the selected complex is performed in between each selection step.

127. The method of any of claim 122 and 126, wherein the tags of the identifier oligonucleotide are amplified using PCR and primers generating two unique cut-sites.

128. The method of claim 127, wherein the cut-sites are used for multimerization of the tags by cloning the tags of the identifier oligonucleotide into a suitable vector for sequencing.

129. The method of claim 127, wherein the PCR product resulting from the amplification is cloned directly into a suitable vector using TA cloning.

130. The method of claim 127, wherein the PCR product resulting from the amplification is introduced to a microarray in order to identify the display molecule.

131. The method of claim 115 comprising the further step of identifying, from the library of different bifunctional complexes, one or more display molecule(s) having a predetermined property, wherein the method for identifying the one or more display molecule(s) comprises the steps of a. partitioning the library of different bifunctional complexes, and b. identifying reaction product(s) having the predetermined property by decoding the oligonucleotide tags of the bifunctional complex.

132. A method for obtaining a library of different bifunctional complexes each comprising a display molecule part and an identifier oligonucleotide part, said method comprising the steps of i) providing a nascent bifunctional complex comprising a chemical reaction site capable of receiving one or more reactants and a priming site capable of receiving one or more tags, ii) reacting the chemical reaction site with one or more reactants, and reacting the priming site with respective tag(s) identifying the reactant(s), wherein one or more enzymes catalyze the reaction;

wherein steps (ii) and (iii) provide an intermediate bifunctional complex having a modified chemical reaction site containing a structural entity formed from the nascent bifunctional complex and the one or more reactants and a modified priming site containing the one or more tags;

reacting the intermediate bifunctional complex with one or more additional reactants at the modified reactant site and one or more additional tags identifying the one or more additional reactants at the modified priming site using the methods of steps (ii) and (iii);

optionally repeating step (iv) as many times as desired; and obtaining a library of different bifunctional complexes;

vii) subjecting the library of different bifunctional complexes to a partitioning condition, viii) partitioning a display molecule, or a subset of display molecules, having a predetermined property from the remainder of the library, ix) selecting a display molecule, or a subset of display molecules, having said predetermined property, x) identifying display molecule(s) having said predetermined property by decoding the identifier oligonucleotide of the bifunctional complex, and xi) reacting the partitioned bifunctional complex(es) one or more times with further reactant(s) and reacting said bifunctional complexes with respective identifying tag(s), thereby generating a further library of different bifunctional complexes comprising a reaction product and an identifier oligonucleotide comprising tags identifying the reactants which have participated in the formation of the reaction product.

133. The method of claim 94,
wherein a plurality of nascent bifunctional complexes each comprising a chemical reaction site and a priming site capable of receiving a tag is provided,
wherein the chemical reaction site of one or more bifunctional complexes is reacted with one or more reactants,
wherein respective tag(s) identifying the reactant(s) are reacted with the priming site of the bifunctional complexes, wherein one or more enzymes catalyzes the reaction,
wherein the library of different bifunctional complexes is subjected to a partitioning condition,
wherein display molecules having a predetermined property are partitioned from the remainder of the library,
wherein display molecules having said predetermined property are selected, wherein display molecules having said predetermined property are identified by decoding the identifier oligonucleotide of each of the bifunctional complexes.

134. The method of claim 1 wherein at least one enzymatic addition of a tag is performed using an enzyme with ligase activity.

135. The method of claim 1 wherein at least one enzymatic addition of a tag is performed using a DNA ligase.

136. The method of claim 1 wherein at least one enzymatic addition of a tag is performed in aqueous solution.

137. The method of claim 1 wherein at least one enzymatic addition of a tag is performed in a mixture of an aqueous solvent and a non-aqueous solvent.

138. The method of claim 1 wherein at least one reaction with a reactant is performed with the nascent bifunctional complex immobilized on a solid support and at least one other reaction with a reactant is performed with the nascent bifunctional complex not so immobilized.

139. The method of claim 1 wherein the library comprises from $10^5$ to $10^{20}$ different bifunctional complexes.

140. The method of claim 1, wherein the bifunctional complex is prepared by simultaneously adding a tag and reacting a reactant.

141. The method of claim 119, wherein the HIV protein is selected from the group consisting of tat, rev, gag, int, and RT.

* * * * *